(12) United States Patent
Andrews et al.

(10) Patent No.: US 8,865,726 B2
(45) Date of Patent: Oct. 21, 2014

(54) SUBSTITUTED PYRAZOLO[1,5-A]PYRIMIDINE COMPOUNDS AS MTOR INHIBITORS

(75) Inventors: Steven W. Andrews, Boulder, CO (US); Kevin Ronald Condroski, Wallingford, CT (US); Lisa A. De Meese, Chandler, AZ (US); Jay Bradford Fell, Boulder, CO (US); John P. Fischer, Boulder, CO (US); John A. Josey, Dallas, TX (US); Kevin Koch, Boulder, CO (US); Yvan Le Huerou, Boulder, CO (US); Gregory F. Miknis, Broomfield, CO (US); Martha E. Rodriguez, Lafayette, CO (US); George T. Topalov, Superior, CO (US); Eli M. Wallace, Richardson, TX (US); Rui Xu, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 243 days.

(21) Appl. No.: 13/393,767

(22) PCT Filed: Sep. 3, 2010

(86) PCT No.: PCT/US2010/047856
§ 371 (c)(1),
(2), (4) Date: Mar. 1, 2012

(87) PCT Pub. No.: WO2011/029027
PCT Pub. Date: Mar. 10, 2011

(65) Prior Publication Data
US 2012/0178715 A1 Jul. 12, 2012

Related U.S. Application Data

(60) Provisional application No. 61/239,473, filed on Sep. 3, 2009, provisional application No. 61/305,210, filed on Feb. 17, 2010.

(51) Int. Cl.
*C07D 487/04* (2006.01)
*A61K 31/519* (2006.01)
*A61P 35/00* (2006.01)

(52) U.S. Cl.
CPC .................. *C07D 487/04* (2013.01)
USPC ...................... 514/259.3; 544/281

(58) Field of Classification Search
CPC ..................... C07D 487/04; A61K 31/519
USPC ...................... 544/281; 514/259.3
See application file for complete search history.

(56) References Cited

FOREIGN PATENT DOCUMENTS

| EP | 1873157 A1 | 1/2008 |
|---|---|---|
| WO | 2008/037477 A1 | 4/2008 |
| WO | 2010/0118207 A1 | 10/2010 |

OTHER PUBLICATIONS

International Search Report Corresponding to Related PCT Application No. PCT/US2010/047856, mailing date May 11, 2010.

*Primary Examiner* — Susanna Moore
(74) *Attorney, Agent, or Firm* — Viksnins Harris & Padys PLLP; Sarah S. Mastous

(57) ABSTRACT

Compounds of Formula I: and salts thereof in which $R^1$, $R^2$, $R^{2a}$, $R^3$, n, X and ring B have the meanings given in the specification, are inhibitors of mTOR and are useful in the treatment of diseases which are sensitive to inhibition of mTOR, such as cancers.

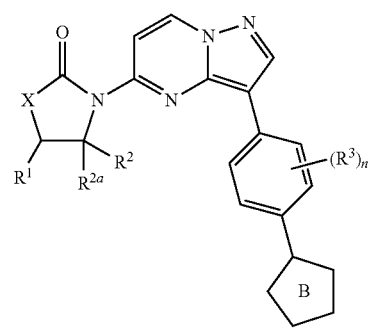

45 Claims, No Drawings

SUBSTITUTED PYRAZOLO[1,5-A]PYRIMIDINE COMPOUNDS AS MTOR INHIBITORS

The present invention relates to novel compounds, to pharmaceutical compositions comprising the compounds, to processes for making the compounds, and to the use of the compounds in therapy. More particularly, it relates to certain substituted pyrazolo[1,5-a]pyrimidine compounds which are inhibitors of mammalian Target Of Rapamycin (mTOR) kinase, and which are useful in the treatment of cancer.

mTOR is a serine/threonine enzyme belonging to the phosphatidylinositol (PI) kinase-related kinase (PIKK) family of protein kinases. mTOR resides in cells in at least two functional multiprotein complexes, mTOR complex 1 (mTORC1) and mTOR complex 2 (mTORC2). A prominent role in promoting cellular translation is well established for mTORC1, and the mTORC1 pathway has been shown to regulate a wide range of cellular functions including translation, transcription, mRNA turnover, protein stability, actin cytoskeleton reorganization and autophagy (Jacinto and Hall, Nature Reviews Molecular and Cell Biology, 2005, 4, 117-126). The recently identified mTORC2 phosphorylates the serine/threonine kinase AKT, thereby increasing its activity. In addition, this second complex has been shown to modulate the activity of multiple other factors associated with cell growth and survival including certain isoforms of protein kinase C, the serum and glucocorticoid kinases and the HIF2a transcription factor.

The PI3K/AKT signaling cascade, which lies upstream of mTOR, has been shown to be deregulated in certain cancers. The positive regulation of AKT by mTORC2 implicates mTOR as acting both upstream and downstream of AKT and its diverse and complex roles in cancer cell growth, survival, and resistance to chemotherapy. In addition, evidence has linked mTOR with cell cycle regulation (from G1 to S-phase), and has shown that inhibition of mTOR results in inhibition of these regulatory events.

Generally, investigators have explored the physiological and pathological roles of mTOR inhibition with the macrolide antibiotic rapamycin (sirolimus) and related rapamycin analogues ('rapalogs') based on their specificity for mTOR as an intracellular target. Rapamycin and its analog everolimus (RAD001 or Certican™) have been approved for immunosuppression and drug eluting stents. Recently, these mTOR inhibitors have been receiving interest as agents for cancer treatment, as they possess antiproliferative and antitumor activity as single agents both in vitro and in vivo in solid tumors and demonstrate synergistic activity with conventional chemotherapy (Yap, et al, Curr. Opin. Pharmacol., 2008, 8, 303-412). Recently, two rapamycin analogues, everolimus and temsirolimus, were approved for the treatment of advanced renal cell carcinoma. However, recent data suggests that rapamycin displays variable inhibitory actions on mTOR signaling functions. In particular, rapamycin and rapalogs are specific and allosteric inhibitors of mTORC1, as such they do not directly inhibit mTORC2 (Yu, et al., Cancer Res. 2009, 69(15), OF1-OF9). In addition, these compounds are ineffective at inhibiting TORC1's ability to modulate 4E-BP1, a factor critical to cellular proliferation and transformation. Finally, rapamycin has been shown to abrogate certain negative feedback loops controlling the PI3K/AKT pathway leading to their enhanced activation. Therefore, the rapamycin mechanism of action may not be sufficient for achieving a broad and robust anticancer effect.

mTOR also plays a key role in tumor angiogenesis. Recent studies show that mTOR controls VEGF production by cancer cells through effects on the expression of HIF1-α and HIF1-β, which are subunits of hypoxia-inducible factor (HIF), a master transcription factor modulating the expression of angiogenic factors (Faivre et al., Nat. Rev. Drug Disc., 2006, 5, 671-688). There is also evidence that endothelial cell proliferation is stimulated by vascular endothelial cell growth factor (VEGF) activation of the PI3K-Akt-mTOR signaling pathway (Dancey, Expert Opinion on Investigational Drugs, 2005, 14, 313-328). Therefore, tumor angiogenesis may depend on mTOR kinase signaling in two ways, through hypoxia-induced synthesis of VEGF by tumor and stromal cells, and through VEGF stimulation of endothelial proliferation and survival through PI3K-Akt-mTOR signaling. These findings suggest that mTOR kinase represents an attractive therapeutic target for treatment of the various forms of cancer comprising solid tumors such as carcinomas and sarcomas and the leukemias and lymphoid malignancies.

Recent studies have revealed a role for mTOR kinase in other diseases (Easton & Houghton, Expert Opinion on Therapeutic Targets, 2004, 8, 551-564). Rapamycin has been demonstrated to be a potent immunosuppressant by inhibiting antigen-induced proliferation of T cells, B cells and antibody production (Sehgal, Transplantation Proceedings, 2003, 35, 7S-14S) and thus mTOR kinase inhibitors may also be useful immunosuppressives. Furthermore, the Rapamycin analogue, everolimus, can reduce the severity and incidence of cardiac allograft vasculopathy (Eisen et al., New England Journal of Medicine, 2003, 349, 847-858). Elevated mTOR kinase activity has been associated with cardiac hypertrophy, which is of clinical importance as a major risk factor for heart failure and is a consequence of increased cellular size of cardiomyocytes (Tee & Blenis, Seminars in Cell and Developmental Biology, 2005, 16, 29-37). Thus mTOR kinase represents an attractive target for the treatment of a wide variety of diseases in addition to cancer.

Several classes of small molecule inhibitors of mTOR and dual inhibitors of mTOR/PI3K said to be useful for treating cancer are known (Yap et al., Curr. Opin. Pharmacol., 2008, 8, 303-412; Cancer Res., 2009, 69, OF1-OF9). Several mTOR kinase inhibitors have been reported and demonstrated utility as anti-cancer agents in preclinical animal models (Maria et al., Mol. Cancer. Ther. 2008, 7 (7), 1851-1863; Liu, et al., Mol. Cancer. Ther. 2009, 8 (8), 2204-2210; Yu, et al., Cancer Res. 2009, 69 (15), 6232-6240; Cao, et al., British Journal of Cancer 2009, 100, 1267-1276; García-Martínez, et al., Biochem. J., 2009, 421(1), 29-42).

Pyrazolo[1,5-a]pyrimidine compounds are known. For example, International Publication WO 2008/037477 discloses a 3-phenyl-5-(piperidin-1-yl)pyrazolo[1,5-a]pyrimidine derivative having the structure:

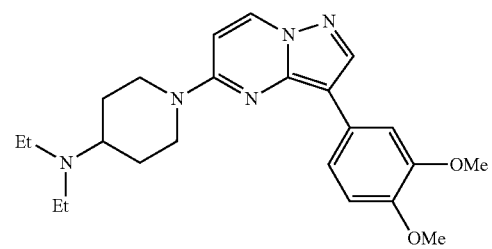 [SMILES: CCN(CC)C1CCN(c2ccn3ncc(-c4ccc(OC)c(OC)c4)c3n2)CC1]

which is disclosed to be an inhibitor of PI3K and/or mTOR.

International Publication WO 2005/063755 discloses a 5-(3-phenylpyrazolo[1,5-a]pyrimidin-5-yl)-1,2,4-oxadiazole derivative having the structure:

as a CRF receptor antagonist for use in treating stress-related disorders.

It has now been found that certain pyrazolo[1,5-a]pyrimidine compounds bearing a heteroaryl-substituted phenyl group at the 3-position and an optionally substituted cyclic urea or oxazolidinone group at the 5-position, are inhibitors of mTOR and are useful for treating disorders and diseases sensitive to inhibition of mTOR, such as proliferative diseases, for example cancer.

Accordingly, one embodiment of this invention provides a compound of the general Formula I:

or a salt thereof, wherein:

$R^1$ is H, (1-6C)alkyl or trifluoromethyl;

$R^{2a}$ is H or methyl;

$R^2$ is H, (1-6C)alkyl, a 3-6 membered cycloalkyl ring, hetCyc$^4$, Ar$^2$CH$_2$—, (3-6C cycloalkyl)CH$_2$—, Ar$^3$, hetAr$^1$, hetAr$^2$, (1-3C alkoxy)(1-3C)alkyl, or a 2-oxo-1,2-dihydropyridinyl ring optionally substituted with (1-6C)alkyl;

or $R^1$ and $R^2$ together with the atoms to which they are attached form a 5-6 membered carbocyclic ring optionally fused to a benzo ring;

each $R^3$ is independently selected from halogen and (1-6C) alkyl;

n is 0, 1 or 2;

ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH;

X is O or NR$^4$;

$R^4$ is H, (1-6C)alkyl, (1-6C)hydroxyalkyl, (1-6C)dihydroxyalkyl, [(1-6C)alkoxy](1-6C)alkyl-, [(1-6C)alkoxy]-[(1-6C)alkoxy]-(1-6C)alkyl-, Ar$^1$CH$_2$—, hetCyc$^1$, hetCyc$^2$ (1-2C)alkyl- or hetCyc$^3$(1-2C)alkyl-;

Ar$^1$ is phenyl optionally substituted with one or more substituents independently selected from (1-6C)alkoxy, halogen, (1-6C)alkyl and CF$_3$;

hetCyc$^1$ is a carbon-linked 4-6 membered azacyclic ring optionally substituted with a substituent selected from (1-6C) alkyl;

hetCyc$^2$ is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo;

hetCyc$^3$ is a bridged 8-membered heterocyclic ring having a ring nitrogen atom and optionally having a ring oxygen atom;

hetCyc$^4$ is a 5-6 membered heterocyclic ring having a ring heteroatom selected from N and O;

Ar$^2$ is phenyl optionally substituted with one or more halogen atoms;

Ar$^3$ is phenyl optionally substituted with one or more substituents independently selected from halogen, (1-6C)alkoxy, hetCyc$^5$, (1-6C)alkyl and CF$_3$;

hetCyc$^5$ is a 6 membered heterocyclic ring having 1-2 ring nitrogen atoms;

hetAr$^1$ is pyridyl optionally substituted with one or more substituents independently selected from halogen, CF$_3$, (1-6C)alkyl and (1-6C)alkoxy; and hetAr$^2$ is a 5-membered heteroaryl having 1-2 ring heteroatoms independently selected from N and S and optionally substituted with (1-6C)alkyl.

Formula I includes compounds of the general Formula IA:

or salts thereof, wherein:

$R^1$ is H, (1-6C)alkyl or trifluoromethyl;

$R^2$ is H, (1-6C)alkyl, phenyl, pyridyl, or a 5-6 membered cycloalkyl ring;

or $R^1$ and $R^2$ together with the atoms to which they are attached form a 5-6 membered carbocyclic ring;

$R^{2a}$ is hydrogen;

$R^3$ is halogen or (1-6C)alkyl;

n is 0 or 1;

ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH;

X is O or NR$^4$;

R⁴ is H, (1-6C)alkyl, (1-6C)hydroxyalkyl, (1-6C)dihydroxyalkyl, [(1-6C)alkoxy](1-6C)alkyl, [(1-6C)alkoxy]-[(1-6C)alkoxy]-(1-6C)alkyl, Ar¹CH₂—, hetCyc¹, hetCyc²(1-2C)alkyl- or hetCyc³(1-2C)alkyl-;

Ar¹ is phenyl optionally substituted with (1-6C)alkoxy;

hetCyc¹ is a carbon-linked 4-6 membered azacyclic ring optionally substituted with a substituent selected from (1-6C)alkyl;

hetCyc² is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo; and hetCyc³ is a bridged 8-membered heterocyclic ring having a ring nitrogen atom and optionally having a ring oxygen atom.

In certain embodiments, R¹ is hydrogen.

In certain embodiments, R¹ is (1-6C)alkyl. In certain embodiments, R¹ is (1-4C)alkyl. A particular example includes methyl.

In certain embodiments, R¹ is CF₃.

In certain embodiments, R² is hydrogen.

In certain embodiments, R² is (1-6C)alkyl. In certain embodiments, R² is (1-4C)alkyl. Particular examples include methyl, ethyl, propyl, isopropyl and isobutyl.

In certain embodiments, R² is hetCyc⁴. In certain embodiments, hetCyc⁴ is a 5-membered heterocyclic ring having a ring heteroatom selected from N and O. In certain embodiments, hetCyc⁴ is a 6 membered heterocyclic ring having a ring heteroatom selected from N and O. Examples include piperidinyl and tetrahydropyranyl rings.

In certain embodiments, R² is Ar²CH₂—, wherein Ar² is optionally substituted with one or more halogen atoms. A particular example of Ar²CH₂— is benzyl.

In certain embodiments, R² is (3-6C cycloalkyl)CH₂—. A particular example is cyclopropylmethyl.

In certain embodiments, R² is Ar³, wherein Ar³ is phenyl optionally substituted with one or more substituents independently selected from halogen, (1-6C)alkoxy, hetCyc⁵, (1-6C)alkyl and CF₃. In certain embodiments Ar³ is phenyl optionally substituted with one or more substituents independently selected from halogen, (1-6C)alkoxy and hetCyc⁵. In certain embodiments, Ar³ is phenyl optionally substituted with one or more substituents independently selected from fluoro, chloro, methoxy and piperazinyl. In certain embodiments, Ar³ is phenyl optionally substituted with one or two of said substituents.

Particular examples of R² when represented by Ar³ include phenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl, 3-chloro-4-fluorophenyl, 2-methoxyphenyl, 4-methoxyphenyl and 2-(piperazin-1-yl)phenyl.

In certain embodiments, R² is phenyl.

In certain embodiments, R² is hetAr¹, wherein hetAr¹ is pyridyl optionally substituted with one or more substituents independently selected from halogen, CF₃, (1-6C)alkyl and (1-6C)alkoxy. In certain embodiments, R² is pyridyl optionally substituted with one or more substituents independently selected from fluoro, chloro, CF₃, methyl and methoxy. In certain embodiments, R² is pyridyl optionally substituted with one or two of said substituents.

Examples of R² when represented by hetAr¹ include pyrid-2-yl, pyrid-3-yl, 6-methylpyrid-2-yl, 6-methylpyrid-3-yl, 5-fluoropyrid-2-yl, 5-chloropyridy-2-yl, 5-methylpyrid-2-yl, 6-methoxypyrid-2-yl, 5-fluoro-6-methylpyrid-2-yl, 4-methyl-5-fluoropyrid-2-yl and 5-trifluoromethylpyrid-2-yl, 4-methylpirid-2-yl, and 3-fluoro-6-methylpyrid-2-yl.

In certain embodiments, R² is pyridyl optionally substituted with fluoro.

In certain embodiments, R² is pyridyl, for example pyrid-2-yl.

In certain embodiments, R² is hetAr², wherein hetAr² is a 5-membered heteroaryl having 1-2 ring heteroatoms independently selected from N and S, wherein hetAr² is optionally substituted with (1-6C)alkyl. Examples include a thiazolyl ring optionally substituted with a substituent selected from (1-6C)alkyl, such as a methyl group. Particular examples of R² when represented by hetAr² include 4-methylthiazol-2-yl and 2-methylthiazol-4-yl.

In certain embodiments, R² is a 3-6 membered cycloalkyl ring. In certain embodiments, R² is cyclopropyl, cyclopentyl or cyclohexyl.

In certain embodiments, R² is a 5-6 membered cycloalkyl ring. In certain embodiments, R² is cyclohexyl.

In certain embodiments, R² is (1-3C alkoxy)(1-3C)alkyl. Examples include 2-methoxymethyl, ethoxymethyl and 1-methoxyethyl.

In certain embodiments, R² is a 2-oxo-1,2-dihydropyridinyl ring optionally substituted with (1-6C)alkyl. Examples of alkyl substituents include methyl and ethyl. A particular example of R² is 1-ethyl-2-oxo-1,2-dihydropyridin-3-yl having the structure:

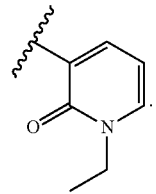 [SMILES: *c1cccn(CC)c1=O]

In certain embodiments, R² is selected from methyl, ethyl, propyl, isopropyl, isobutyl, piperidinyl, tetrahydropyranyl, benzyl, cyclopropylmethyl, phenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl, 3-chloro-4-fluorophenyl, 2-methoxyphenyl, 4-methoxyphenyl, 2-(piperazin-1-yl)phenyl, pyrid-2-yl, pyrid-3-yl, 6-methylpyrid-2-yl, 6-methylpyrid-3-yl, 5-fluoropyrid-2-yl, 5-chloropyridy-2-yl, 5-methylpyrid-2-yl, 6-methoxypyrid-2-yl, 5-fluoro-6-methylpyrid-2-yl, 4-methyl-5-fluoropyrid-2-yl, 5-trifluoromethylpyrid-2-yl, 4-methylpyrid-2-yl, 1-ethyl-2-oxo-1,2-dihydropyridin-3-yl and 3-fluoro-6-methylpyrid-2-yl, 4-methylthiazol-2-yl, 2-methylthiazol-4-yl, cyclopropyl, cyclopentyl, cyclohexyl, 2-methoxymethyl, ethoxymethyl and 1-methoxyethyl.

In certain embodiments, R¹ and R² together with the atoms to which they are attached form a 5-6-membered carbocyclic ring. In certain embodiments, R¹ and R² together with the atoms to which they are attached form a 5-6-membered carbocyclic ring which is fused with a benzo ring.

Examples of the ring at the 5 position of the pyrazolopyrimidine ring when R¹ and R² together with the atoms to which they are attached form a 5- or 6-membered carbocyclic ring includes the structures:

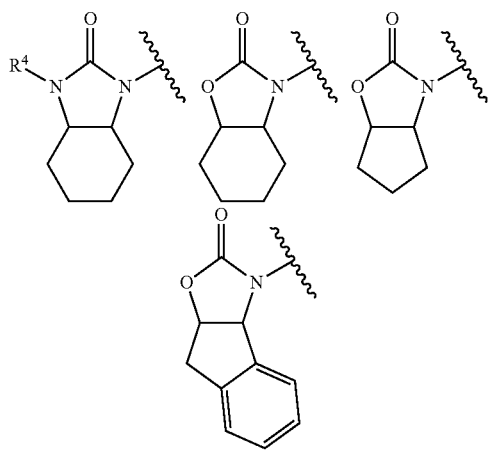

including the cis- and trans-ring fused isomers thereof.

In certain embodiments, the ring at the 5 position of the pyrazolopyrimidine ring when $R^1$ and $R^2$ together with the atoms to which they are attached form a 5- or 6-membered carbocyclic ring includes the structures:

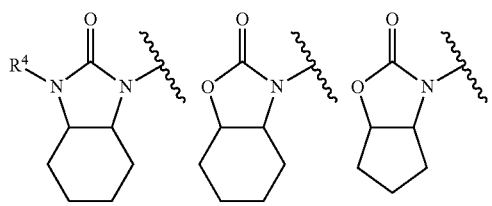

including the cis- and trans-ring fused isomers thereof.

In certain embodiments, $R^{2a}$ is hydrogen.

In certain embodiments, $R^{2a}$ is methyl.

In certain embodiments, X is oxygen, such that the ring at the 5 position of the pyrazolopyrimidine ring is an oxazolidinone ring.

In certain embodiments when X is oxygen, $R^1$ is hydrogen, (1-6C)alkyl or $CF_3$.

In certain embodiments when X is oxygen, $R^1$ is H, Me or $CF_3$.

In certain embodiments when X is oxygen, $R^1$ is H.

In certain embodiments when X is oxygen, $R^2$ is H, (1-6C) alkyl, a 3-6 membered cycloalkyl ring, $hetCyc^4$, $Ar^2CH_2$—, (3-6C cycloalkyl)$CH_2$—, $Ar^3$, $hetAr^1$, $hetAr^2$, or (1-3C alkoxy)(1-3C)alkyl.

In certain embodiments when X is oxygen, $R^2$ is hydrogen, (1-6C)alkyl, phenyl or pyridyl.

In certain embodiments when X is oxygen, $R^2$ is hydrogen.

In certain embodiments when X is oxygen, $R^2$ is Me.

In certain embodiments when X is oxygen, $R^1$ and $R^2$ together with the atoms to which they are attached form a 5-6 membered carbocyclic ring. In certain embodiments when X is oxygen, $R^1$ and $R^2$ together with the atoms to which they are attached form a 5-6 membered carbocyclic ring which is fused to a benzo ring.

In certain embodiments the ring at the 5-position of the pyrazolopyrimidine core of Formula I when X is oxygen includes the structures:

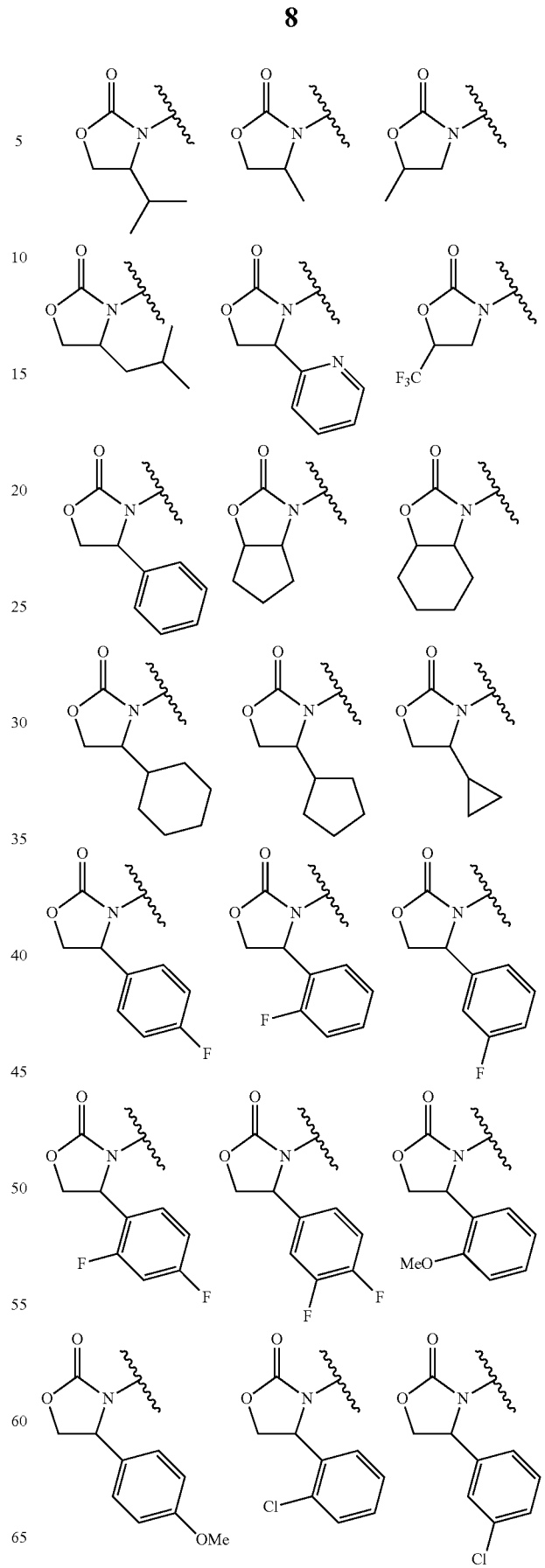

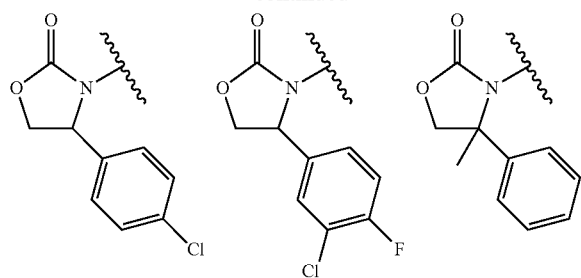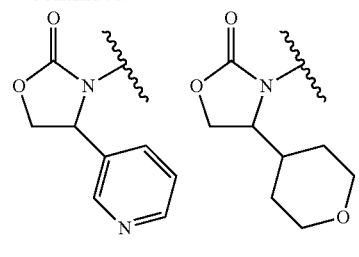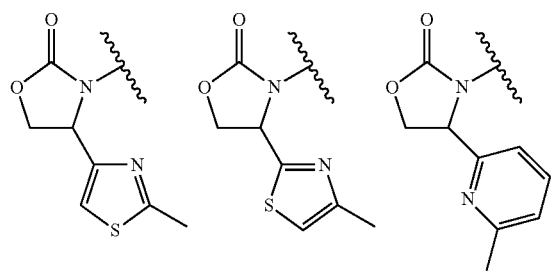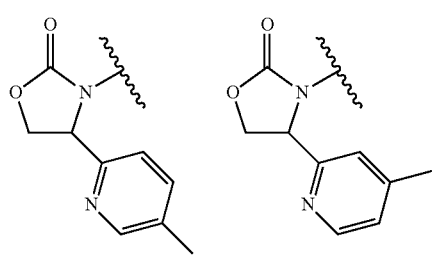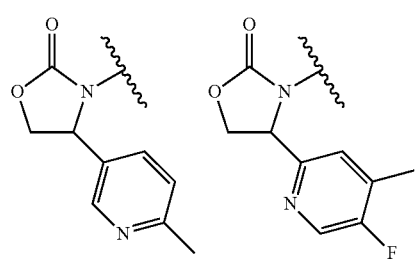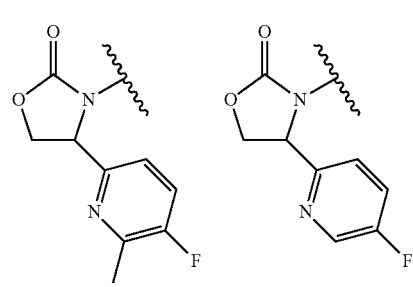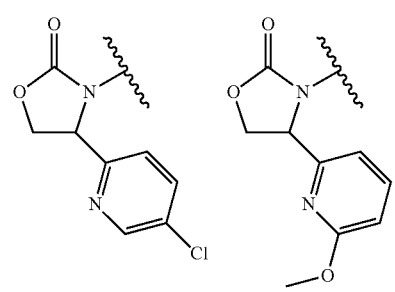
In certain embodiments the ring at the 5-position of the pyrazolopyrimidine core of Formula I when X is oxygen includes the structures:
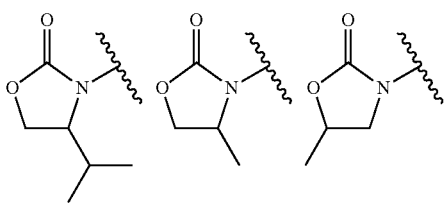

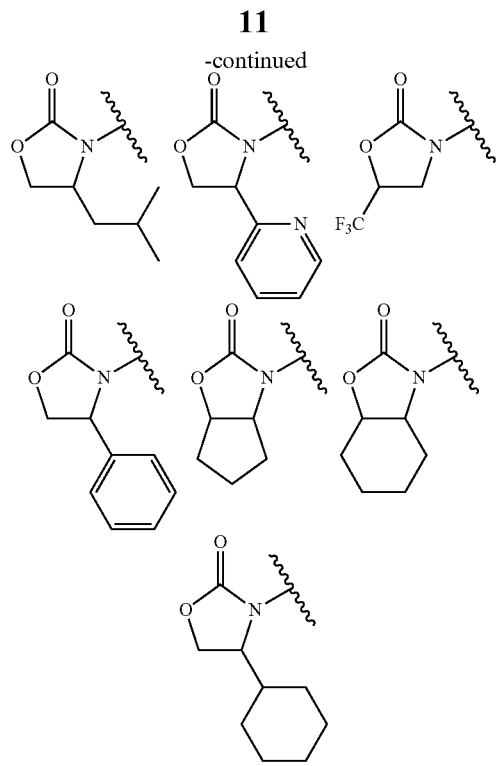

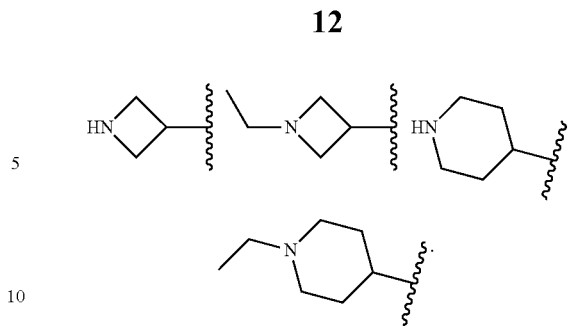

In certain embodiments, X is NR⁴, such that the ring at the 5 position of the pyrazolopyrimidine ring is a cyclic urea group.

In certain embodiments, R⁴ is hydrogen.

In certain embodiments, R⁴ is (1-6C)alkyl. In certain embodiments, R⁴ is (1-4C)alkyl. A particular example of R⁴ is methyl.

In certain embodiments, R⁴ is (1-6C)hydroxyalkyl or (1-6C)dihydroxyalkyl. In certain embodiments, R⁴ is (1-6C)hydroxyalkyl or (2-6C)dihydroxyalkyl. Particular examples include HOCH₂CH₂—, HOCH₂CH₂CH₂—, and HOCH₂CH(OH)CH₂—.

In certain embodiments, R⁴ is [(1-6C)alkoxy](1-6C)alkyl. Particular examples include methoxyethyl, ethoxyethyl, isopropoxyethyl, methoxypropyl, ethoxypropyl and isopropoxypropyl.

In certain embodiments, R⁴ is [(1-6C)alkoxy]-[(1-6C)alkoxy]-(1-6C)alkyl. A particular example is methoxyethoxyethyl.

In certain embodiments, R⁴ is Ar¹CH₂—, wherein Ar¹ is phenyl optionally substituted with one or more substituents independently selected from (1-6C)alkoxy, halogen, (1-6C)alkyl and CF₃.

In certain embodiments, R⁴ is Ar¹CH₂—, where Ar¹ is phenyl optionally substituted with (1-6C)alkoxy, for example methoxy. Particular examples of R⁴ include benzyl and 4-methoxybenzyl.

In certain embodiments, R⁴ is hetCyc¹ or hetCyc²(1-2C)alkyl.

In certain embodiments, R⁴ is hetCyc¹, where hetCyc¹ is a carbon-linked 4-6 membered azacyclic ring optionally substituted with a substituent selected from (1-6C)alkyl, for example methyl, ethyl, propyl, isopropyl, butyl, isobutyl or t-butyl. Examples include azetidinyl, pyrrolidinyl and piperidinyl rings optionally substituted with (1-6C)alkyl. As used herein, the term "carbon-linked" means that the azacyclic ring is bonded to the nitrogen of the NR⁴ group through a carbon atom in the azacyclic ring. Particular example of hetCyc¹ include the structures:

In certain embodiments, R⁴ is hetCyc²(1-2C)alkyl. Examples of hetCyc² groups include piperidinyl, piperazinyl, morpholinyl, and pyrrolidinyl rings optionally substituted with a substituent selected from (1-6C)alkyl, OH, (1-6C)alkoxy, halogen and oxo. Examples of substituents include methyl, ethyl, isopropyl, OH, OMe, F and oxo. In certain embodiments the substituents include methyl, ethyl, OH, OMe, F and oxo. Particular example of R⁴ when represented by hetCyc²(1-2C)alkyl include the structures:

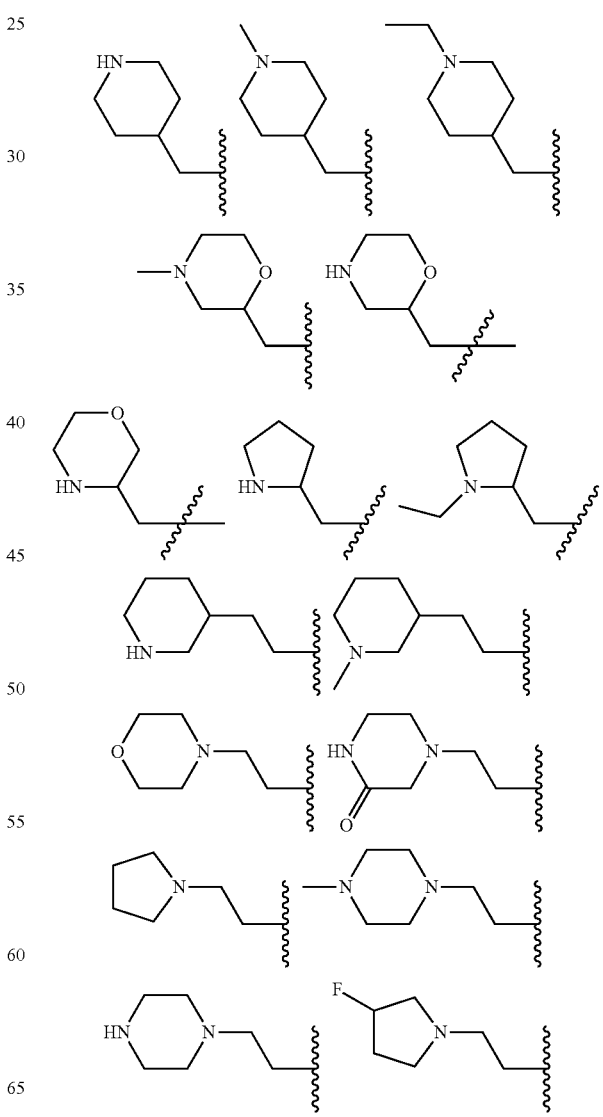

-continued

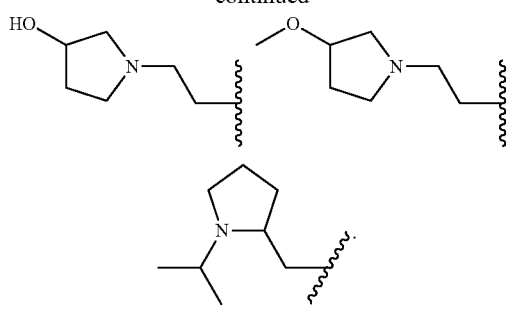

In certain embodiments, $R^4$ is hetCyc$^3$(1-2C)alkyl, where hetCyc$^3$ is a bridged 8-membered heterocyclic ring having a ring nitrogen atom and optionally having a ring oxygen atom. An example of hetCyc$^3$ is a 8-oxa-3-azabicyclo[3.2.1]octane ring. A particular example of $R^4$ when represented by hetCyc$^3$(1-2C)alkyl is the structure:

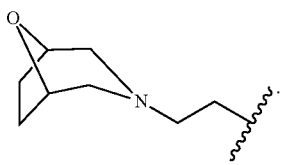 [SMILES: *CCN1CC2CCC(C1)O2]

In certain embodiments when X is $NR^4$, $R^1$ is selected from H and (1-6C)alkyl.

In certain embodiments when X is $NR^4$, $R^1$ is H.

In certain embodiments when X is $NR^4$, $R^1$ is (1-6C)alkyl. In certain embodiments $R^1$ is Me.

In certain embodiments when X is $NR^4$, $R^2$ is (1-6C)alkyl. A particular example is isopropyl.

In certain embodiments when X is $NR^4$, $R^{2a}$ is H.

In certain embodiments when X is $NR^4$, $R^{2a}$ is Me.

In certain embodiments when X is $NR^4$, $R^1$ and $R^2$ together with the atoms to which they are attached form a 6-membered carbocyclic ring.

Particular examples of the cyclic urea group at the 5-position of the pyrazolopyrimidine ring of Formula I include the structures:

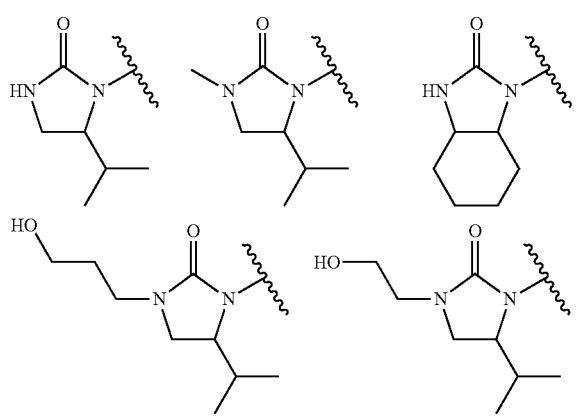

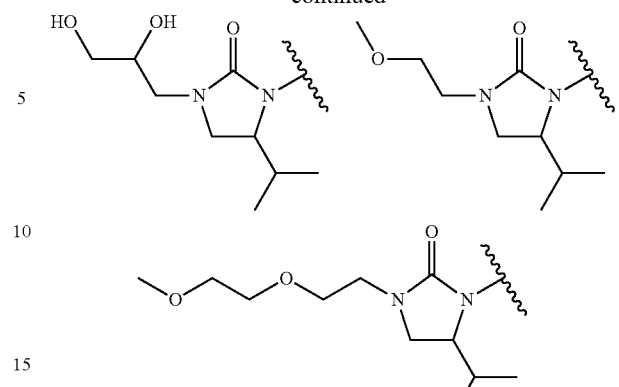

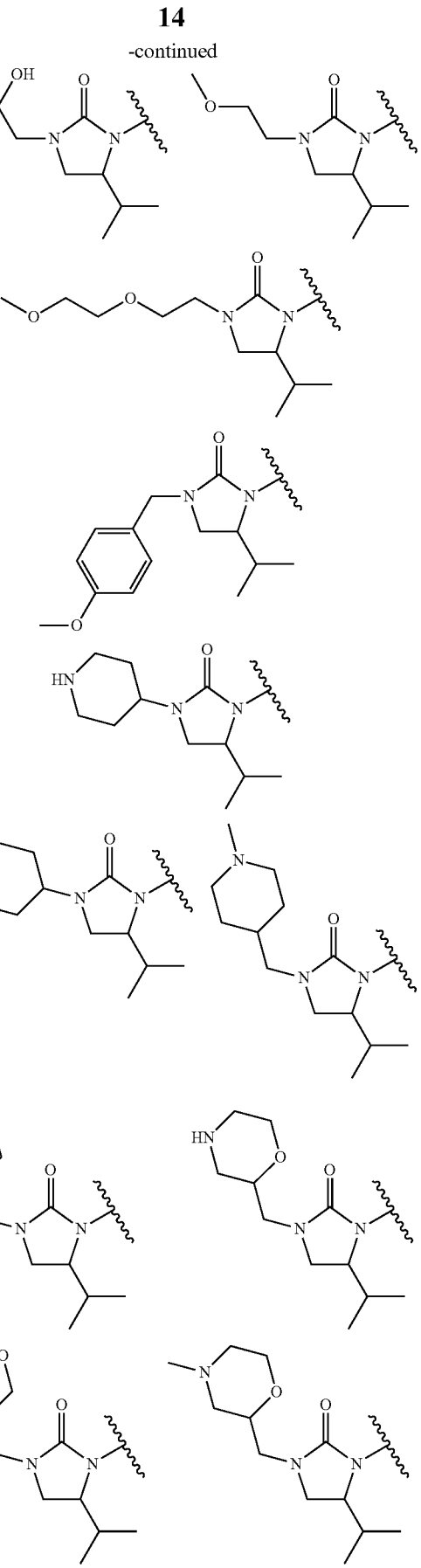

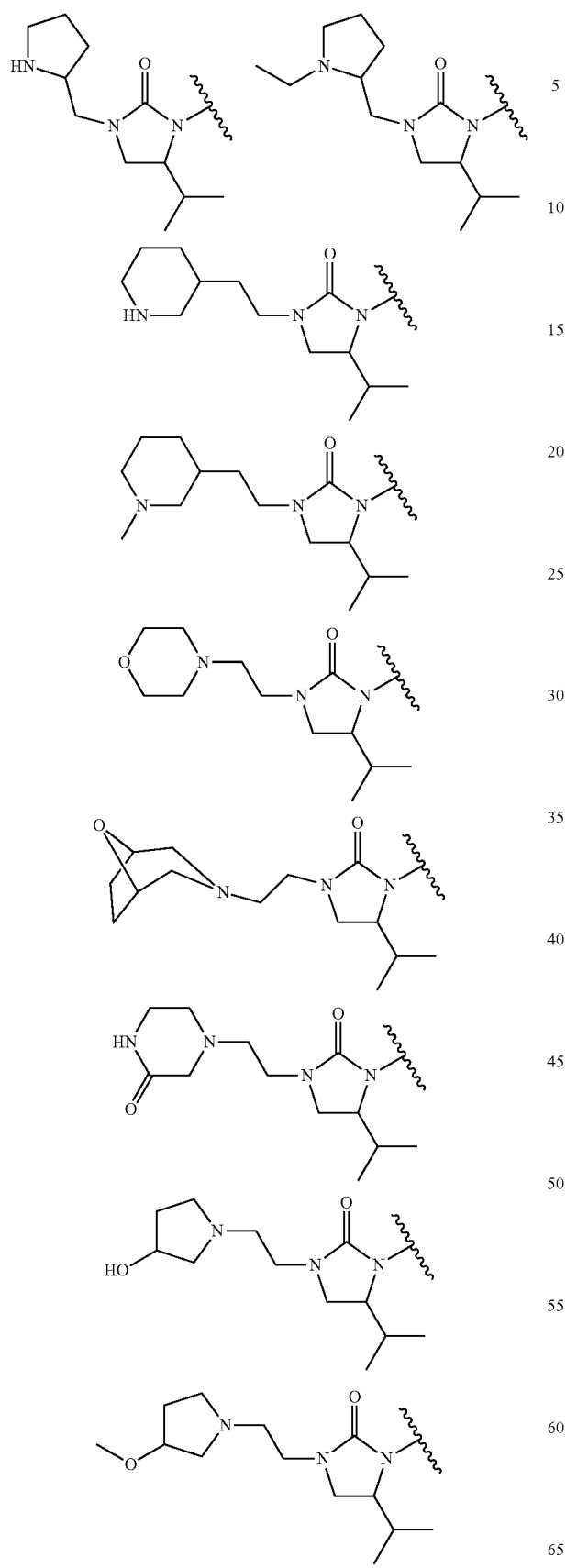
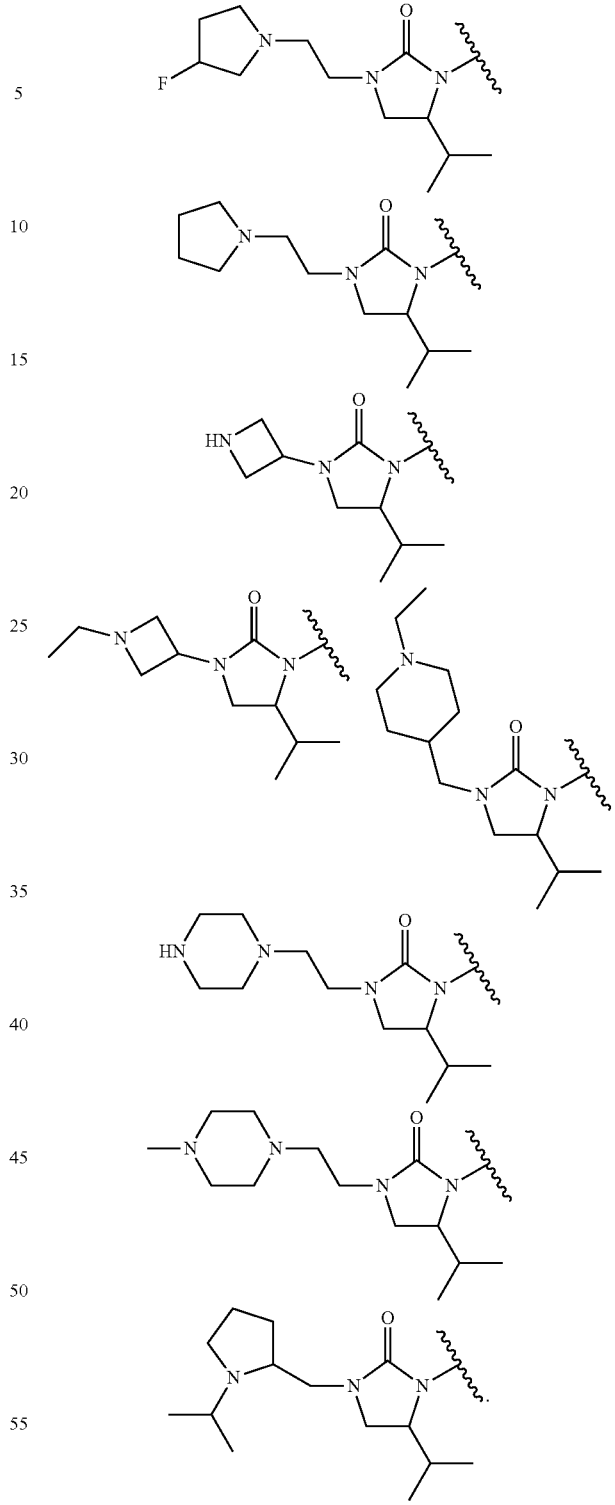

Referring now to ring B of Formula I, in certain embodiments, ring B is a heteroaryl ring selected from imidazolyl, triazolyl, oxadiazolyl, thiadiazolyl and pyrazolyl, wherein said heteroaryl ring is optionally substituted with a substituent selected from (1-6C)alkyl, $NH_2$, (1-6C hydroxyalkyl)NH—, $(HO)_2P(=O)OCH_2$—, (1-6C)hydroxyalkyl, and (1-6C alkyl)COOH. In other embodiments, ring B is a heteroaryl ring selected from imidazolyl, triazolyl, oxadiazolyl, and thiadiazolyl, wherein said ring is optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH. Examples of substituents on ring B include NH$_2$, methyl, —NHCH$_2$CH$_2$OH, CH$_2$CH$_2$OH, CH$_2$COOH, CH$_2$CH$_2$COOH, and —CH$_2$OP(=O)(OH)$_2$.

In certain embodiments, ring B is an imidazoyl ring optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH. In certain embodiments, ring B is an imidazoyl.

In certain embodiments, ring B is a triazolyl ring optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH. In certain embodiments, ring B is triazolyl optionally substituted with a substituent selected from Me, HOCH$_2$CH$_2$—, (HO)$_2$P(=O)OCH$_2$—, and CH$_2$C(=O)H.

In certain embodiments, ring B is an oxadiazolyl ring optionally substituted with a substituent selected from (1-6C)alkyl, NH$_2$, (1-6C hydroxyalkyl)NH— and (1-6C)hydroxyalkyl. n certain embodiments, ring B is oxadiazolyl optionally substituted with —NHCH$_2$CH$_2$OH or NH$_2$.

In certain embodiments, ring B is a thiadiazolyl ring optionally substituted with a substituent selected from (1-6C)alkyl, NH$_2$, (1-6C hydroxyalkyl)NH— and (1-6C)hydroxyalkyl. In certain embodiments, ring B is thiadiazolyl optionally substituted with NH$_2$.

In certain embodiments, ring B is a pyrazolyl ring optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH. In certain embodiments, ring B is pyrazolyl.

Particular examples of ring B include the structures:

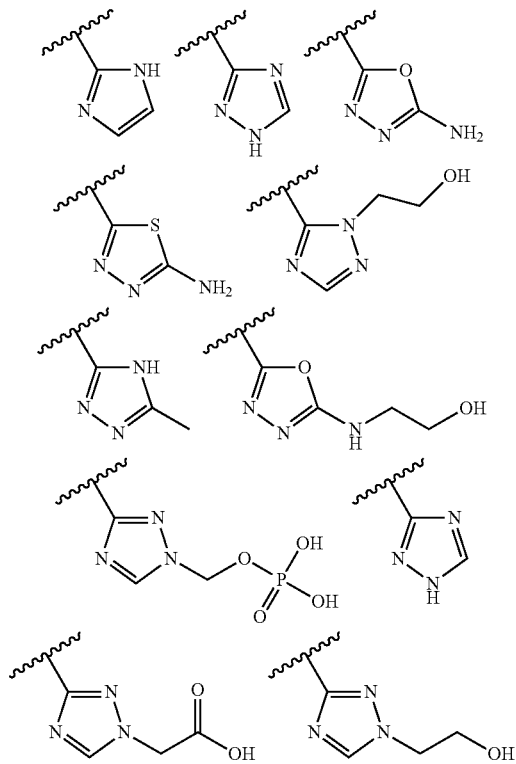

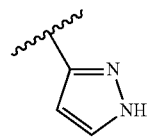

and tautomers thereof.

Additional examples of ring B include the structures:

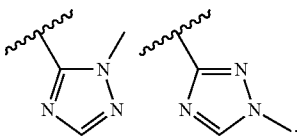

Referring to the R$^3$ group on the phenyl ring of Formula I, in certain embodiments, n is 0. In certain embodiments, n is 1. In certain embodiments, n is 2. In certain embodiments, R$^3$ is at the 2 position of the phenyl ring relative to the position of ring B. In certain embodiments, R$^3$ is at the 3 position of the phenyl ring relative to the position of ring B.

In certain embodiments, R$^3$ is halogen. Particular examples include fluoro and chloro.

In certain embodiments, R$^3$ is (1-6C)alkyl. A particular example is methyl.

Particular examples of the group at the 3-position of the pyrazolopyrimidine ring of Formula I include the structures:

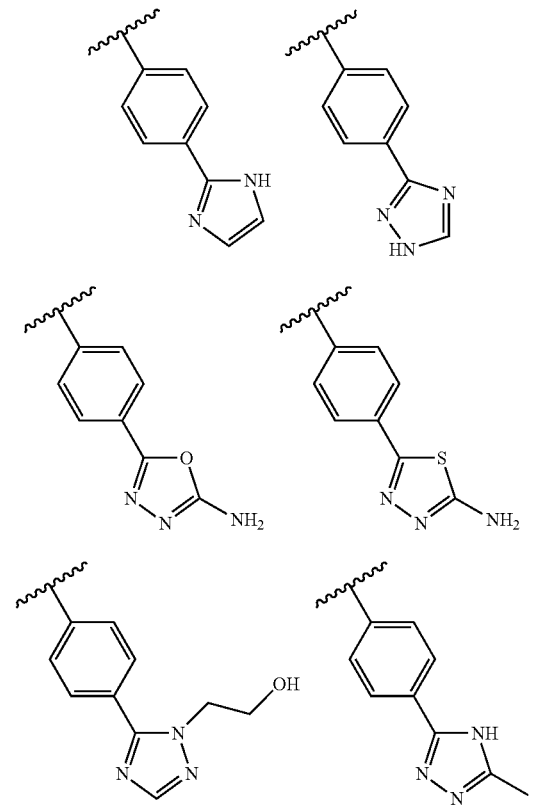

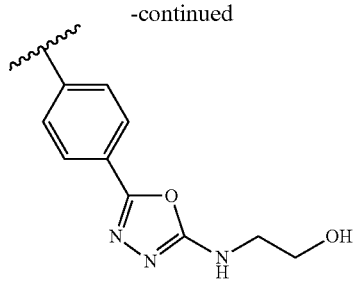

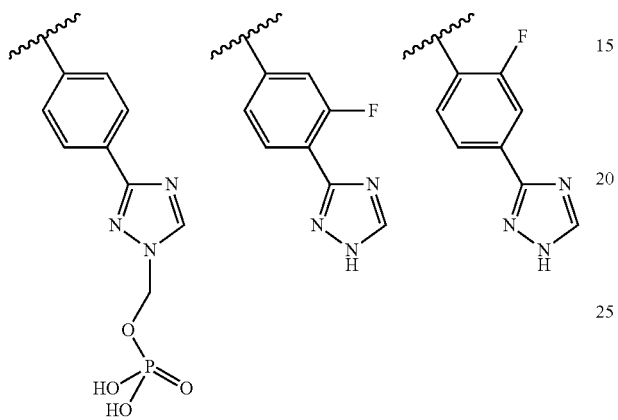

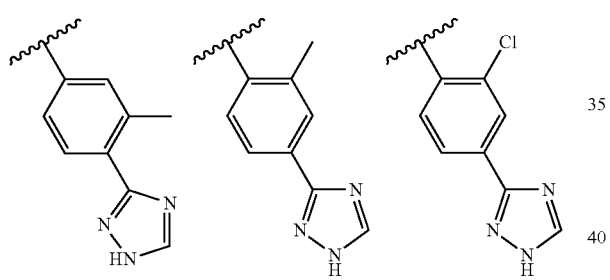

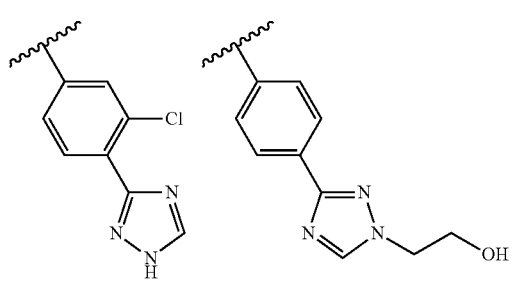

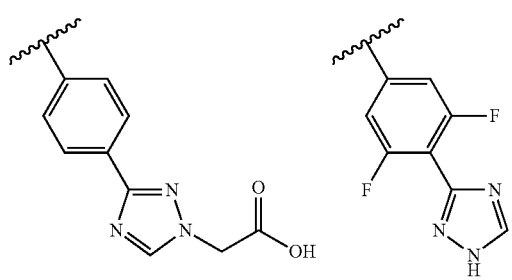

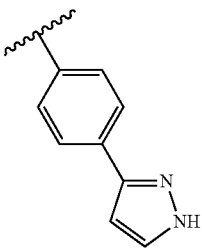

and tautomers thereof.

Additional examples of the group at the 3-position of the pyrazolopyrimidine ring of Formula I include the structures:

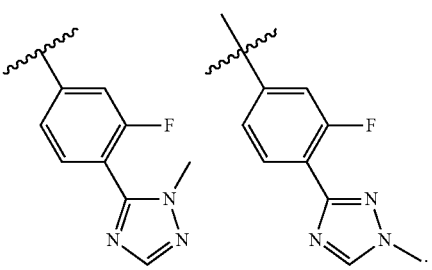 [SMILES: *c1ccc(-c2ncnn2C)c(F)c1 ; *c1ccc(-c2ncn(C)n2)c(F)c1]

In certain embodiments, the group at the 3-position of the pyrazolopyrimidine ring includes the above structures and tautomers thereof with the exception of the structure:

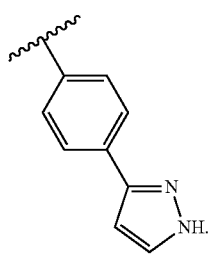 [SMILES: *c1ccc(-c2cc[nH]n2)cc1]

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In one embodiment, the $R^2$ group of a compound of Formula I has the absolute configuration shown in Formula Ia:

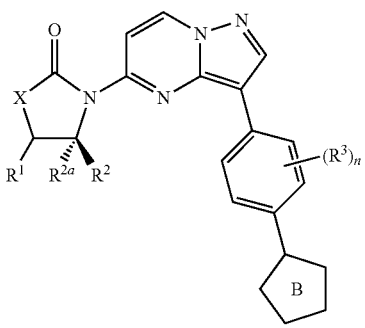

It will also be appreciated that certain compounds of Formula I may be used as intermediates for further compounds of Formula I.

Formula I includes compound of Formula Ib wherein:
X is NR⁴;
R¹ is H, (1-6C)alkyl or trifluoromethyl;
R²ᵃ is H or methyl;
R² is H, (1-6C)alkyl, hetCyc⁴, Ar²CH₂—, (3-6C cycloalkyl)CH₂—, Ar³, hetAr¹, hetAr², a 3-6 membered cycloalkyl ring, or (1-3C alkoxy)(1-3C)alkyl;
hetCyc⁴ is a 5-6 membered heterocyclic ring having a ring heteroatom selected from N and O;
Ar² is phenyl optionally substituted with one or more halogen atoms;
Ar³ is phenyl optionally substituted with one or more substituents independently selected from halogen, (1-6C)alkoxy, hetCyc⁵, (1-6C)alkyl and CF₃;
hetCyc⁵ is a 6 membered heterocyclic ring having 1-2 ring nitrogen atoms;
hetAr¹ is pyridyl optionally substituted with one or more substituents independently selected from halogen, CF₃, (1-6C)alkyl and (1-6C)alkoxy;
hetAr² is a 5-membered heteroaryl having 1-2 ring heteroatoms independently selected from N and S, wherein hetAr² is optionally substituted with (1-6C)alkyl;
each R³ is independently selected from halogen and (1-6C)alkyl;
n is 0, 1 or 2;
ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, NH₂, (1-6C hydroxyalkyl)NH—, (HO)₂P(=O)OCH₂—, (1-6C)hydroxyalkyl, and (1-6C alkyl)COOH;
R⁴ is H, (1-6C)alkyl, (1-6C)hydroxyalkyl, (1-6C)dihydroxyalkyl, [(1-6C)alkoxy](1-6C)alkyl, [(1-6C)alkoxy]-[(1-6C)alkoxy]-(1-6C)alkyl, Ar¹CH₂—, hetCyc¹, hetCyc²(1-2C)alkyl- or hetCyc³(1-2C)alkyl-;
Ar¹ is phenyl optionally substituted with one or more substituents independently selected from (1-6C)alkoxy, halogen, (1-6C)alkyl and CF₃;
hetCyc¹ is a carbon-linked 4-6 membered azacyclic ring optionally substituted with a substituent selected from (1-6C)alkyl;
hetCyc² is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo; and hetCyc³ is a bridged 8-membered heterocyclic ring having a ring nitrogen atom and optionally having a ring oxygen atom.

In certain embodiments of Formula Ib, Ring B is an imidazolyl, triazolyl, oxadiazolyl, thiadiazolyl or pyrazolyl ring optionally substituted with a substituent selected from (1-6C)alkyl, NH₂, (1-6C hydroxyalkyl)NH—, (HO)₂P(=O)OCH₂—, (1-6C)hydroxyalkyl, and (1-6C alkyl)COOH.

Formula Ib include also compound of Formula Ib-1 wherein:
X is NR⁴;
R¹ is hydrogen;
R²ᵃ is hydrogen;
R² is (1-6C)alkyl;
each R³ is independently selected from halogen and (1-6C)alkyl;
n is 0, 1 or 2;
R⁴ is H, (1-6C)alkyl, (1-6C)hydroxyalkyl, (1-6C)dihydroxyalkyl, [(1-6C)alkoxy](1-6C)alkyl, [(1-6C)alkoxy]-[(1-6C)alkoxy]-(1-6C)alkyl, Ar¹CH₂—, hetCyc¹, hetCyc²(1-2C)alkyl- or hetCyc³(1-2C)alkyl-;
Ar¹ is phenyl optionally substituted with one or more substituents independently selected from (1-6C)alkoxy, halogen, (1-6C)alkyl and CF₃;
hetCyc¹ is a carbon-linked 4-6 membered azacyclic ring optionally substituted with a substituent selected from (1-6C)alkyl;
hetCyc² is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo;
hetCyc³ is a bridged 8-membered heterocyclic ring having a ring nitrogen atom and optionally having a ring oxygen atom; and
ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, NH₂, (1-6C hydroxyalkyl)NH—, (HO)₂P(=O)OCH₂—, (1-6C)hydroxyalkyl, and (1-6C alkyl)COOH.

In certain embodiments of Formula Ib-1, Ring B is an imidazolyl, triazolyl, oxadiazolyl, thiadiazolyl or pyrazolyl ring optionally substituted with a substituent selected from (1-6C)alkyl, NH₂, (1-6C hydroxyalkyl)NH—, (HO)₂P(=O)OCH₂—, (1-6C)hydroxyalkyl, and (1-6C alkyl)COOH.

Compounds of Formula I include compounds of Formula Ic, wherein:
X is O;
R¹ is H, (1-6C)alkyl or trifluoromethyl;
R²ᵃ is H or methyl;
R² is H, (1-6C)alkyl, hetCyc⁴, Ar²CH₂—, (3-6C cycloalkyl)CH₂—, Ar³, hetAr¹, hetAr², a 3-6 membered cycloalkyl ring, (1-3C alkoxy)(1-3C)alkyl or a 2-oxo-1,2-dihydropyridinyl ring optionally substituted with (1-6C)alkyl;
hetCyc⁴ is a 5-6 membered heterocyclic ring having a ring heteroatom selected from N and O;
Ar² is phenyl optionally substituted with one or more halogen atoms;
Ar³ is phenyl optionally substituted with one or more substituents independently selected from halogen, (1-6C)alkoxy, hetCyc⁵, (1-6C)alkyl and CF₃;
hetCyc⁵ is a 6 membered heterocyclic ring having 1-2 ring nitrogen atoms;

hetAr¹ is pyridyl optionally substituted with one or more substituents independently selected from halogen, $CF_3$, (1-6C)alkyl and (1-6C)alkoxy;

hetAr² is a 5-membered heteroaryl having 1-2 ring heteroatoms independently selected from N and S, wherein hetAr² is optionally substituted with (1-6C)alkyl;

each $R^3$ is independently selected from halogen and (1-6C) alkyl;

n is 0, 1 or 2; and ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, $NH_2$, (1-6C hydroxyalkyl)NH—, $(HO)_2P(=O)OCH_2$—, (1-6C)hydroxyalkyl and (1-6C alkyl)COOH.

In certain embodiments of Formula Ic, Ring B is an imidazolyl, triazolyl, oxadiazolyl, thiadiazolyl or pyrazolyl ring optionally substituted with a substituent selected from (1-6C) alkyl, $NH_2$, (1-6C hydroxyalkyl)NH—, $(HO)_2P(=O)OCH_2$—, (1-6C)hydroxyalkyl, and (1-6C alkyl)COOH.

In certain embodiments of Formula Ic, Ring B is imidazolyl, triazolyl, oxadiazolyl or thiadiazolyl optionally substituted with a substituent selected from $NH_2$, methyl, —$NHCH_2CH_2OH$, $CH_2CH_2OH$, $CH_2COOH$, $CH_2CH_2COOH$, and —$CH_2OP(=O)(OH)_2$.

Formula Ic includes compounds of Formula Ic-1 wherein:

X is O;

$R^1$ is hydrogen;

$R^{2a}$ is hydrogen;

$R^2$ is selected from methyl, ethyl, propyl, isopropyl, isobutyl, piperidinyl, tetrahydropyranyl, benzyl, cyclopropylmethyl, phenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl, 3-chloro-4-fluorophenyl, 2-methoxyphenyl, 4-methoxyphenyl, 2-(piperazin-1-yl)phenyl, pyrid-2-yl, pyrid-3-yl, 6-methylpyrid-2-yl, 6-methylpyrid-3-yl, 5-fluoropyrid-2-yl, 5-chloropyridy-2-yl, 5-methylpyrid-2-yl, 6-methoxypyrid-2-yl, 5-fluoro-6-methylpyrid-2-yl, 4-methyl-5-fluoropyrid-2-yl, 5-trifluoromethylpyrid-2-yl, 4-methylpyrid-2-yl, 1-ethyl-2-oxo-1,2-dihydropyridin-3-yl, 3-fluoro-6-methylpyrid-2-yl, 4-methylthiazol-2-yl, 2-methylthiazol-4-yl, cyclopropyl, cyclopentyl, cyclohexyl, 2-methoxymethyl, ethoxymethyl and 1-methoxyethyl;

each $R^3$ is independently selected from halogen and (1-6C) alkyl;

n is 0, 1 or 2; and ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, $NH_2$, (1-6C hydroxyalkyl)NH—, $(HO)_2P(=O)OCH_2$—, (1-6C)hydroxyalkyl and (1-6C alkyl)COOH.

In certain embodiments of Formula Ic-1, Ring B is an imidazolyl, triazolyl, oxadiazolyl, thiadiazolyl or pyrazolyl ring optionally substituted with a substituent selected from (1-6C)alkyl, $NH_2$, (1-6C hydroxyalkyl)NH—, $(HO)_2P(=O)OCH_2$—, (1-6C)hydroxyalkyl and (1-6C alkyl)COOH.

In certain embodiments of Formula Ic-1, Ring B is imidazolyl, triazolyl, oxadiazolyl or thiadiazolyl optionally substituted with a substituent selected from $NH_2$, methyl, —$NHCH_2CH_2OH$, $CH_2CH_2OH$, $CH_2COOH$, $CH_2CH_2COOH$, and —$CH_2OP(=O)(OH)_2$.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I. Particular examples of salts include acid addition salts such as HCl and trifluoroacetic acid salts, including the mono- and di-addition salts thereof. Further examples of salts include sodium salts, including disodium salts.

It will further be appreciated that the compounds of Formula I and their salts may be isolated in the form of solvates, and accordingly that any such solvate is included within the scope of the present invention.

The compounds of Formula I also include compounds that differ only in the presence of one or more isotopically enriched atoms. For example, compounds of the invention include compounds wherein one or more hydrogen atoms are replaced by deuterium or tritium, or one or more carbon atoms are replaced by a $^{13}C$— or $^{14}C$-enriched carbon are within the scope of this invention.

The terms "(1-6C)alkyl" and "(1-4C)alkyl" as used herein refers to saturated linear or branched-chain monovalent hydrocarbon radicals of one to six carbon atoms, or one to four carbon atoms, respectively. Examples include, but are not limited to, methyl, ethyl, 1-propyl, 2-propyl, 1-butyl, 2-methyl-1-propyl, 2-butyl, 2-methyl-2-propyl, pentyl, and hexyl.

The term "(1-6C) alkoxy" as used herein refers to saturated linear or branched-chain monovalent radicals of one to six carbon atoms, respectively, wherein the radical is on the oxygen atom. Examples include methoxy and ethoxy.

The term "(1-6C)hydroxyalkyl" as used herein refer to saturated linear or branched-chain monovalent hydrocarbon radicals of one to six carbon atoms, respectively, wherein one of the hydrogen atoms is replaced with an OH group.

The terms "(1-6C)dihydroxyalkyl" "(2-6C)dihydroxyalkyl" as used herein refer to saturated linear or branched-chain monovalent hydrocarbon radicals of one to six carbon atoms or two to six carbon atoms, respectively, wherein two of the hydrogen atoms are replaced with an OH group, provided that two OH groups are not on the same carbon.

The term "3-6 membered cycloalkyl" refers to a fully saturated monocyclic hydrocarbon group containing 3-6 carbons, respectively, per ring.

The term "(1-3C alkoxy)(1-3C)alkyl" as used herein refer to saturated linear or branched-chain monovalent hydrocarbon radicals of one to three carbon atoms, respectively, wherein one of the hydrogen atoms is replaced with a (1-3C alkoxy) group, such as a methoxy (MeO—) group.

The term "(1-6C hydroxyalkyl)NH" as used herein refers to a primary alkylamino group, wherein the radical is on the nitrogen and the alkyl portion is a saturated linear or branched-chain monovalent hydrocarbon radicals of one to six carbon atoms, respectively, wherein one of the hydrogen atoms is replaced with an OH group.

The term "(1-6C alkyl)COOH" as used herein refers to a saturated linear or branched-chain monovalent hydrocarbon radicals of one to six carbon atoms, respectively, wherein one of the hydrogen atoms is replaced with a COOH group.

The term "[(1-6C)alkoxy](1-6C)alkyl-" as used herein refers to saturated linear or branched-chain monovalent radicals of one to six carbon atoms, wherein one of the hydrogen atoms is replaced by a (1-6C alkoxy) group as defined herein.

The term "[(1-6C)alkoxy]-[(1-6C)alkoxy]-(1-6C)alkyl-" as used herein refers to a [(1-6C)alkoxy](1-6C)alkyl group as defined above, wherein one of the hydrogen atoms of the (1-6C)alkoxy portion is replaced with a (1-6C)alkoxy group. An example includes $CH_3OCH_2OCH_2$—.

The term "halogen" includes fluoro, chloro, bromo and iodo.

According to another aspect, the present invention provides a process for the preparation of a compound of Formula I or a salt thereof as defined herein which comprises:

(a) coupling a corresponding compound having the formula II

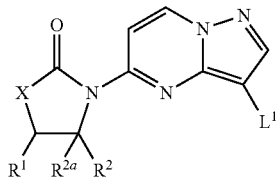

II where X, R$^1$, R$^2$ and R$^{2a}$ are as defined for Formula I and L$^1$ is a leaving atom, with a corresponding compound having the formula III

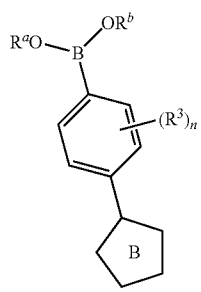

III where R$^3$, n and ring B are as defined for Formula I or ring B is an optionally protected derivative thereof, R$^a$ and R$^b$ are H or (1-6C)alkyl, or R$^a$ and R$^b$ together with the atoms to which they are connected form a 5-6 membered ring optionally substituted with 1-4 substituents selected from (1-3C alkyl), wherein said coupling takes place in the presence of a palladium catalyst and base and optionally in the presence of a ligand; or (b) for a compound of Formula I where X is O, coupling a corresponding compound having the formula IV

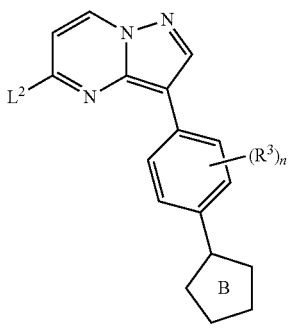

IV where R$^3$, n and ring B are as defined for Formula I, or ring B is a protected derivative thereof, and L$^2$ is a leaving group or atom, with a corresponding compound having the formula V

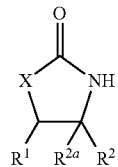

V where X is O and R$^1$, R$^2$ and R$^{2a}$ are as defined for Formula I, in the presence of a base; or (c) for a compound of Formula I where ring B is a thiadiazolyl ring substituted with NH$_2$, cyclizing a corresponding compound having the formula VI

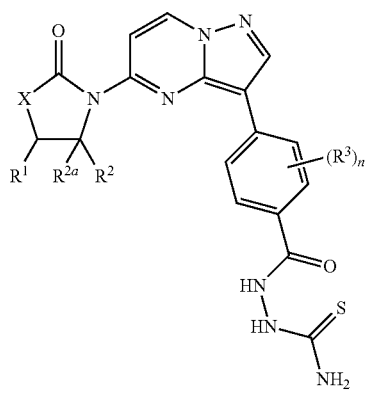

VI where X, R$^1$, R$^2$, R$^{2a}$ R$^3$ and n are as defined for Formula I and when X is NR$^4$ then R$^4$ is optionally an amine-protected derivative thereof, in the presence of triphenylphosphine and a base; or (d) for a compound of Formula I where ring B is a triazolyl ring optionally substituted with (1-6C)alkyl, cyclizing a corresponding compound having the formula VII

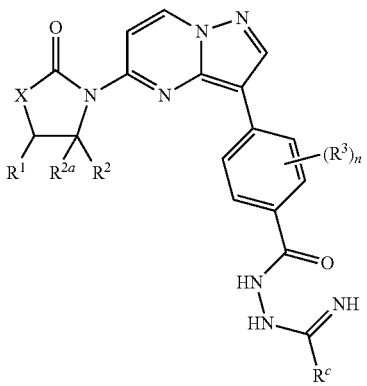

VII where R$^1$, R$^2$, R$^{2a}$, R$^3$, n, and X are as defined for Formula I and R$^c$ is (1-6C alkyl), and when X is NR$^4$ then R$^4$ is optionally an amine-protected derivative thereof, in the presence of triphenylphosphine and a base; or (e) for a compound of Formula I where ring B is an oxadiazolyl ring optionally substituted with (1-6C hydroxyalkyl)NH—, cyclizing a corresponding compound having the formula VIII

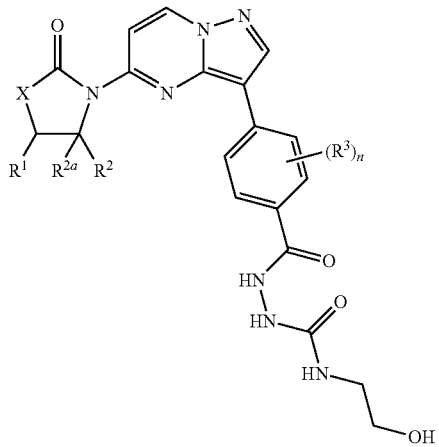

where X, $R^1$, $R^2$, $R^{2a}$, $R^3$ and n are as defined for Formula I, and when X is $NR^4$ then $R^4$ is optionally an amine-protected derivative thereof, in the presence of triphenylphosphine and a base; or (f) for a compound of Formula I where X is $NR^4$ and $R^{2a}$ is hydrogen, cyclizing a corresponding compound of formula IX

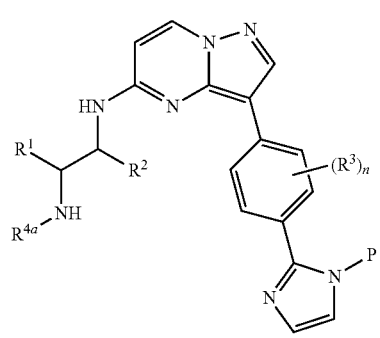

where $R^1$, $R^2$, $R^3$ and n are as defined for Formula I and $R^{4a}$ is as defined for $R^4$ or is an alcohol-protected or nitrogen-protected derivative thereof, in the presence of a carbonylating reagent, and a base; or (g) for a compound of Formula I where X is $NR^4$ and $R^4$ is hetCyc$^1$, hetCyc$^2$(1-2C)alkyl or hetCyc$^3$(1-2C)alkyl wherein each of hetCyc$^1$, hetCyc$^2$ and hetCyc$^3$ contains a ring nitrogen atom substituted with (1-6C)alkyl, reacting a corresponding compound having the formula X

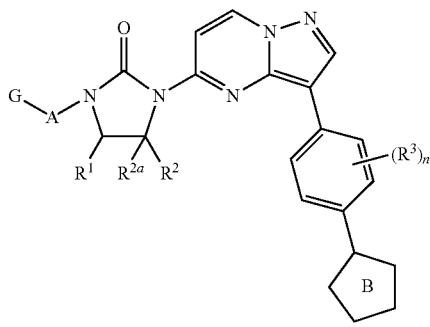

where $R^1$, $R^2$, $R^{2a}$, $R^3$, n and Ring B are as defined for Formula I, A is a bond or (1-2C)alkyl and G is hetCyc$^{1a}$, hetCyc$^{2a}$ or hetCyc$^{3a}$ each of which contains an unsubstituted ring nitrogen atom, with a corresponding compound having the formula (1-5C alkyl)C(=O)H in the presence of a reducing agent; or (h) for a compound of Formula I where X is $NR^4$, coupling a corresponding compound having the formula XI

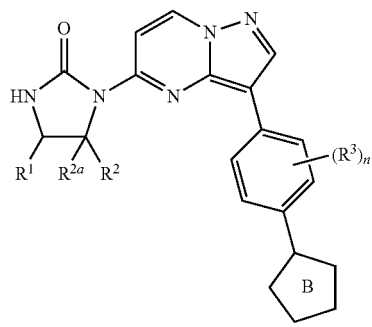

where $R^1$, $R^2$, $R^{2a}$, $R^3$, n and Ring B are as defined for Formula I, with a corresponding compound having the formula $R^4$-$L^3$, where $L^3$ is a leaving group or atom, in the presence of a base;

(i) for a compound of Formula I where X is $NR^4$, and $R^4$ has the formula

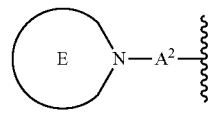

where ring E is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo, or ring E is a bridged 8-membered heterocyclic ring having a ring nitrogen atom and optionally having a ring oxygen atom, and $A^2$ is (2-3C alkyl), reacting a corresponding compound having the formula XII

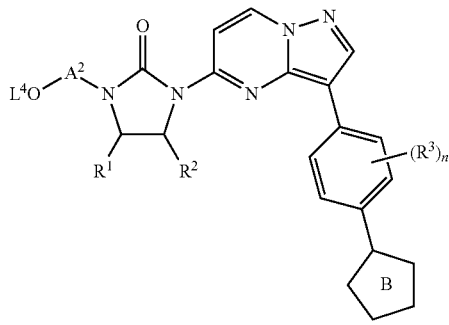

where $R^1$, $R^2$, $R^3$, $A^2$, n and ring B are as defined for Formula I and $L^4$ is a leaving group, with a compound having the formula

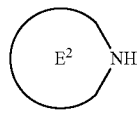

where ring $E^2$ is as defined for ring E; or (j) for a compound of Formula I where ring B is an imidazolyl or triazolyl ring substituted with $(HO)_2P(=O)OCH_2—$, reacting a corresponding compound where ring B is an unsubstituted imidazolyl or triazolyl ring with di(1-4C alkyl)-chloromethylphosphate in the presence of a base; and optionally removing any protecting groups and forming a salt if desired.

The amine protecting group described in any of the above methods may be any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC), and [2-(trimethylsilyl)ethoxy]methyl (SEM).

Referring to method (a), compounds of Formula II where X is $NR^4$ and $R^4$ is H can be prepared by cyclizing a corresponding compound having the formula IIA

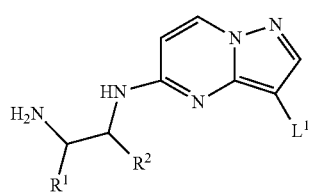

in the presence of a carbonylating agent, such as phosgene, trichloromethyl chloroformate, bis(trichloromethyl) carbonate or di(1H-imidazol-1-yl)methanone. The leaving atom $L^1$ may be, for example a halogen atom such as Br or I. Compounds of Formula II where X is oxygen can be prepared by coupling a compound having the formula IIB

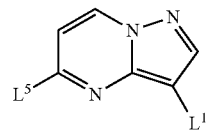

where $L^5$ is a leaving group or atom, with a corresponding compound having the formula

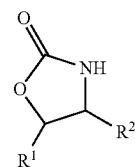

where $R^1$ and $R^2$ are as defined for Formula I. The leaving group $L^5$ may be, for example, an alkylsulfonyloxy group or an arylsulfonyloxy group, such as a mesylate or a tosylate group. Alternatively, the leaving atom $L^5$ may be a halogen such as Cl.

In embodiments where X is $NR^4$ and $R^1$ and $R^2$ together with the atoms to which they are attached form a 6-membered ring, the compounds of Formula II may be prepared by coupling a compound having the formula

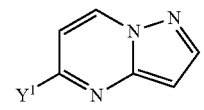

where $Y^1$ is a leaving atom such as Cl, or a leaving group such as mesylate or tosylate, with cyclohexan-1,2-diamine followed by cyclization with a carbonylating agent such as phosgene, trichloromethyl chloroformate, bis(trichloromethyl) carbonate or di(1H-imidazol-1-yl)methanone and subsequent treatment with N-bromosuccinimide.

With continued reference to method (a), suitable palladium catalysts include $Pd(PPh_3)_4$, $Pd_2(dba)_3$, $Pd(OAc)_2$, and $Pd(PPh_3)_2Cl_2$. Suitable ligands include XPHOS, DIPHOS or rac-BINAP. The base may be, for example, an alkali metal carbonate, hydroxide, alkoxide or acetate, such as for example cesium carbonate, sodium carbonate, potassium carbonate, sodium hydroxide, sodium tert-butoxide or potassium acetate. Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C.

Compounds of the formula III can be prepared by reacting the corresponding bromide derivative with a reagent having the formula $B(OR^a)(OR^b)$. Examples of $B(OR^a)(OR^b)$ include boronic acid (i.e., where $R^a$ and $R^b$ are both hydrogen), and boronic esters. Examples of boronic esters include dioxaborolanes (i.e., where $R^a$ and $R^b$ together with the atoms to which they are attached form an optionally substituted 5-membered ring) and dioxaborinanes (i.e., where $R^a$ and $R^b$ together with the atoms to which they are attached form an optionally substituted 6-membered ring). A particular example of a dioxoborinane is 4,4,4',4',5,5,5',5'-octamethyl-2,2'-bi(1,3,2-dioxaborolane) (also known as bis(pinacoloato)diboron). A particular example of a compound of formula III is the structure IIIA:

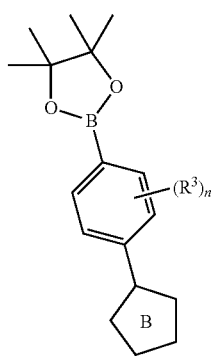

IIIA which can be prepared by reacting the corresponding bromide derivative with pinacol diborane in the presence of a palladium (II) catalyst (e.g., $PdCl_2$-dppf-DCM), and a base (e.g., an alkali metal carbonate, hydroxide, alkoxide or acetate), and optionally in the presence of a ligand, such as 1,1'-bis(diphenylphosphino)ferrocene (dppf).

Referring to method (b), the leaving group $L^2$ may be an alkylsulfonyl or arylsulfonyl group, for example, a triflate group, or an arylsulfonyloxy group or an alkylsulfonyloxy group, such as a mesylate or a tosylate group. Alternatively, $L^2$ may be a leaving atom such as Cl. Suitable bases include alkali metal hydrides such as NaH, alkali metal amine bases such as lithium diisopropylamide and silicon-containing alkali metal amides (e.g., sodium hexamethyldisilazide or lithium hexamethyldisilazide). Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C. Compounds of formula IV may be prepared in a manner analogous to that of method (a).

Referring to methods (c), (d) and (e), suitable bases include amine bases such as triethylamine and diisopropylethylamine. In certain embodiments, the triphenylphosphine reagent is used in the form of a polystyrene-bound $PPh_3$ resin (sold as $PS—PPh_3$ by Biotage Systems). The reaction is conveniently performed at temperatures ranging from ambient temperature to about 100° C., for example at 40-60° C. Suitable solvents include neutral solvents, for example acetonitrile, THF or $CCl_4$.

Compounds of formula VI can be prepared by coupling a corresponding compound having the formula VIA

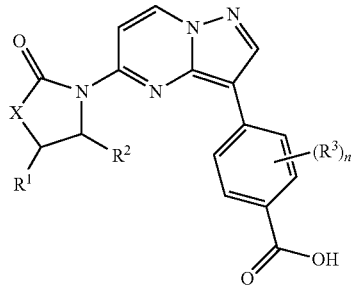

VIA with a compound having the structure:

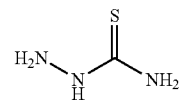

in the presence of an activating agent such as 1-ethyl-3-(3'-dimethylaminopropyl)carbodiimide (EDCI), dicyclohexylcarbodiimide (DCC), carbonyl diimidazole (CDI) or benzotriazole-1-yl-oxy-tris-pyrrolidino-phosphonium hexafluorophosphate (PyBOP).

Compounds of formula VII can be prepared by reacting the corresponding benzoic acid derivative with hydrazine, followed by coupling the resulting benzohydrazide derivative with ethyl acetimidate in the presence of an amine base.

Compounds of formula VIII can be prepared by reacting a corresponding compound of formula VIIIA

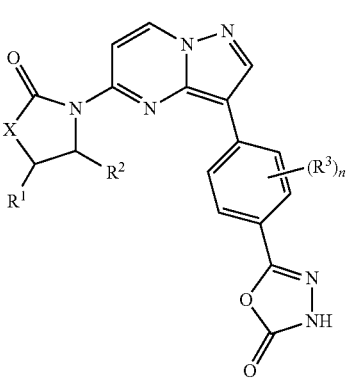

VIIIA with 2-aminoethanol. Compounds of formula VIIIA can be prepared by reacting the corresponding benzohydrazide derivative with di(1H-imidazol-1-yl)methanone.

Referring to method (f), examples of carbonylating reagents include trichloromethyl chloroformate, phosgene, bis(trichloromethyl)carbonate and di(1H-imidazol-1-yl)methanone. Suitable bases include amine bases such as triethylamine and diisopropylethylamine. Compounds of formula IX can be prepared by reacting a corresponding compound of formula IxA

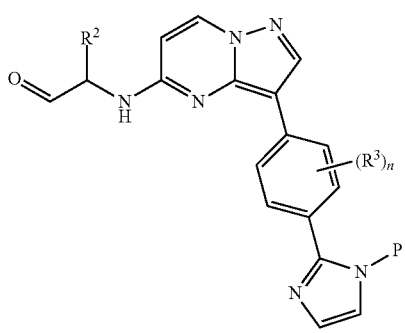

IXA where P is an amine protecting group, with a compound having the formula $NH_2R^a$ in the presence of a reducing agent, such as $Na(OAc)_3BH$. Suitable amino protecting groups include $CH_2OCH_2CH_2SiMe_3$ and t-butyloxycarbonyl (BOC).

Referring to method (g), suitable reducing agents include $Na(OAc)_3BH$ and $NaCNBH_3$. Suitable solvents include neutral solvents such as acetonitrile, THF, and dichloroethane.

Referring to method (h), the leaving atom $L^3$ may be a halogen, for example iodide or bromide. Alternatively, $L^3$ may be a leaving group such as an alkylsulfonoxy or arylsulfonoxy group, such as methylsulfonoxy. Suitable bases include alkali metal hydrides such as sodium hydride or potassium hydride, and silicon-containing alkali metal amide such as sodium hexamethyldisilazide and lithium hexamethyldisilazide.

Referring to method (i), the leaving group $L^4$ may be an alkylsulfonate or arylsulfonate, such as a tosylate group.

The compounds of Formulas II, IV, VI, VII, VIII, IX, X, XI, and XII are also believed to be novel and are provided as further aspects of this invention.

Compounds of Formula I are inhibitors of mTOR and are useful for treating disorders and diseases sensitive to inhibition of mTOR, such as proliferative diseases, for example cancer. The ability of compounds of the invention to act as inhibitors of mTOR may be demonstrated by the assay described in Example A.

It has further been found that certain representative compounds of Formula I are selective for mTOR relative to PI3K.

Compounds of Formula I may be of therapeutic value for treatment of the various forms of cancer, including solid tumors such as carcinomas and sarcomas and liquid tumors such as the leukemias and lymphoid malignancies.

In particular, compounds of Formula I may be useful for treatment of, for example, cancers such as: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast: invasive breast carcinomas (invasive ductal carcinoma and invasive lobular carcinoma), etc.; and Adrenal glands: neuroblastoma.

Compounds of Formula I may be administered alone as a sole therapy or can be administered in addition with one or more other substances and/or treatments that work by the same or a different mechanism of action. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to compositions of the present invention may be, for example, surgery, radiotherapy, chemotherapy, signal transduction inhibitors and/or monoclonoal antibodies.

Accordingly, the compounds of Formula I may be administered in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

As used herein, the term treatment includes prophylaxis as well as treatment of a preexisting condition.

Accordingly, another embodiment of this invention provides a method of treating cancer in a mammal, comprising administering to said mammal one or more compounds of Formula I or a pharmaceutically acceptable salt thereof in an amount effective to treat or prevent said cancer.

The phrase "effective amount" means an amount of compound that, when administered to a mammal in need of such treatment, is sufficient to (i) treat or prevent a particular disease, condition, or disorder such as described herein, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove together with a pharmaceutically acceptable diluent or carrier.

According to another embodiment, the present invention provides a compound of Formula I or a pharmaceutically acceptable salt thereof, for use in the treatment of cancer in a mammal.

According to a further aspect, the present invention provides the use of a compound of Formula I or a pharmaceutically acceptable salt thereof, in the treatment of cancer in a mammal.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM, methylene chloride), toluene, dimethyl formamide (DMF) and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Examples

Example A mTOR Kinase Assay

The ability of compounds of Formula I to inhibit mTOR was determined in a radioactive filtration assay that measures the transfer of radiolabeled phosphate from [$\gamma$-$^{33}$P]ATP to the protein substrate 4E-BP1. Compounds were first prepared at 50× the top dose of 10,000 nM and serially diluted 3-fold in DMSO to give ten dose dilution series. Assays were conducted in 96-well polypropylene U-bottom plates in 40 μL (final volume) assay mixtures that contained 50 mM K$^+$HEPES, pH 7.5, 1 mM EGTA, 0.005% Tween-20, 10 mM MnCl$_2$, 2.5 mM DTT, 2% DMSO (final concentration with compound), 10 μM [$\gamma$-$^{33}$P]ATP (50 μCi/mL), 5 μM 4E-BP1 and 5 nM mTOR, which was added last to initiate the assay. Each plate contained appropriate high (uninhibited) and low (prequenched) controls as well as a reference compound. Incubations were carried out at 22° C. for 45 minutes, after which the reaction was stopped by the addition of 100 μL aliquots of 25% TCA. The precipitated, radiolabeled product was captured onto a glass fiber filter plate using a cell harvester, and following the addition of 35 μL aliquots of scintillation cocktail to each well, the phosphorylated 4E-BP1 was quantitated by counting in a microplate scintillation counter. Raw counts were converted to percent of control (POC) values, and the IC$_{50}$'s were determined by fitting a standard 4-parameter logistic model to the dose response curves. An IC$_{50}$ is defined as the concentration of inhibitor that gives 50 POC.

Table 1 provides averaged IC$_{50}$ values for compounds of the invention when tested in this assay.

TABLE 1

| Example # | mTOR enzyme IC$_{50}$ (nM) |
| --- | --- |
| 1 | 2.4 |
| 2 | 23.2 |
| 3 | 58.1 |
| 4 | 2.5 |
| 5 | 4.8 |
| 6 | 2.0 |
| 7 | 15.9 |
| 8 | 12.3 |
| 9 | 6.5 |
| 10 | 6.6 |
| 11 | 6.1 |
| 12 | 18.9 |
| 13 | 46.0 |
| 14 | 8.2 |
| 15 | 1.7 |
| 16 | 1.5 |
| 17 | 5.2 |
| 18 | 9.5 |
| 19 | 18.3 |
| 20 | 2.7 |

TABLE 1-continued

| Example # | mTOR enzyme IC$_{50}$ (nM) |
|---|---|
| 21 | 17.7 |
| 22 | 12.3 |
| 23 | 48.2 |
| 24 | 27.7 |
| 25 | 2.5 |
| 26 | 4.7 |
| 27 | 9.4 |
| 28 | 8.3 |
| 29 | 68.6 |
| 30 | 9.8 |
| 31 | 19.4 |
| 32 | 26.8 |
| 33 | 20.7 |
| 34 | 7.5 |
| 35 | 5.1 |
| 36 | 8.0 |
| 37 | 16.3 |
| 38 | 20.4 |
| 39 | 27.6 |
| 40 | 72.7 |
| 41 | 16.3 |
| 42 | 22.4 |
| 43 | 59.1 |
| 44 | 40.6 |
| 45 | 51.2 |
| 46 | 37.0 |
| 47 | 29.7 |
| 48 | 7.6 |
| 49 | 11.5 |
| 50 | 22.4 |
| 51 | 42.7 |
| 52 | 5.8 |
| 53 | 19.2 |
| 54 | 21.5 |
| 55 | 19.2 |
| 56 | 2.8 |
| 57 | 279 |
| 58 | 189 |
| 59 | 2046 |
| 60 | 21.7 |
| 61 | 3.5 |
| 62 | 1.6 |
| 63 | 56.7 |
| 64 | 4.2 |
| 65 | 16.1 |
| 66 | 31.3 |
| 67 | 21.9 |
| 68 | 7.5 |
| 69 | 49.2 |
| 70 | 7.4 |
| 71 | 2.0 |
| 72 | 1.6 |
| 73 | 11.0 |
| 74 | 14 |
| 75 | 14.9 |
| 76 | 6.4 |
| 77 | 17.1 |
| 78 | 31.7 |
| 79 | 7.8 |
| 80 | 2.3 |
| 81 | 4.5 |
| 82 | 4.4 |
| 83 | 257 |
| 84 | 2.4 |
| 85 | 6.4 |
| 86 | 29.9 |
| 87 | 3.4 |
| 88 | 21.3 |
| 89 | 43.4 |
| 90 | 6.5 |
| 91 | 4.6 |
| 92 | 16.4 |
| 93 | 5.8 |
| 94 | 14.2 |
| 95 | 1.2 |
| 96 | 0.51 |
| 97 | 1.7 |
| 98 | 916 |
| 99 | 88.7 |
| 100 | 593 |
| 101 | 27.2 |
| 102 | 12.2 |
| 103 | 0.87 |
| 104 | 10.1 |
| 105 | 0.51 |
| 106 | 12. |
| 107 | 495 |
| 108 | 5.0 |
| 109 | 0.51 |
| 110 | 2.3 |
| 111 | 36.0 |
| 112 | 2.6 |
| 113 | 1.3 |
| 114 | 2.7 |
| 115 | 2.0 |
| 116 | 9.3 |
| 117 | 12.6 |
| 118 | 1.7 |
| 119 | 20.4 |
| 120 | 15.3 |
| 121 | 6.6 |
| 122 | 7.4 |
| 123 | 10.8 |
| 124 | 11.4 |
| 125 | 2.7 |
| 126 | 7.5 |
| 127 | 0.79 |
| 128 | 2.0 |
| 129 | 2.5 |
| 130 | 4.0 |
| 131 | 25.3 |
| 132 | 1.6 |
| 133 | 14.3 |
| 134 | 4.9 |
| 135 | 49.5 |
| 136 | 6.5 |
| 137 | 4.5 |
| 138 | 12.8 |
| 139 | 11.3 |
| 140 | 3.5 |
| 141 | 859 |
| 142 | 14.5 |
| 143 | 6.3 |
| 144 | 36.9 |

Example B

Cell Viability Assay

Certain compounds of the invention were tested in the following assay to determine the ability of the compounds to inhibit cellular viability. Cells from a variety of established tumor cell lines (PC3, LNCaP, DU145, 22RV1, U87MG, MALME-3M, MiaPaCa-2, A459, MDA-MD-231, HCT-116, NCI—H460, MOLT-3, MOLT-4, GDM-1, HL-60, THP-1, MO7e, K562, MOLM-13, MV4-11 and HEL) were plated in Costar 3904 96-well plates, in growth medium, at a density that allowed for logarithmic growth over the period of the assay, and incubated at 37° C., 5% $CO_2$ overnight. The following day, compounds were added to the cells, at a final DMSO concentration of 0.5%. The concentrations of the compounds were typically varied over the range of 0.1-50,000 nM. Plates were then incubated as above. After a 72-96 hour incubation, 20 μL resazurin solution (Cell Titer Blue, Promega G8081) was added to all wells and the plates incubated for a further period of time. Viable cells convert resazurin to resorufin, a fluorescent end-product. The fluorescent signal was determined in a fluorescent plate reader at 560 nm excitation/590 nm emission. The POC (percent of uninhibited control signal) was determined for each well, and the IC$_{50}$ for inhibition of viability was determined employing a standard 4-parameter logistical curve fitted to the values obtained.

Certain compounds of the invention when tested in this assay were found to be active, that is, certain compounds had IC$_{50}$ values less than 200 nM when tested in this model.

Example C

Tumor Growth Inhibition Study

Certain compounds of the invention were tested in the following assay to determine the ability of the compounds to inhibit tumor growth in vivo. PC3-NCI, U87MG or NCI—H460 cells were grown as tumors in nude mice by subcutaneous injection of the cells into right or left flank of the animals. Once the tumors had reached appropriate size (~200 mm$^3$), compounds were dosed by oral gavage throughout the course of the study. Tumor volume was measured daily or every other day using electronic calipers, and calculated as volume=(length×width2)/2.

Certain compounds of the invention when tested in this assay were found to be active, that is, certain compounds inhibited tumor growth greater that 50% as compared to control tumors.

Preparative Examples

Preparation A

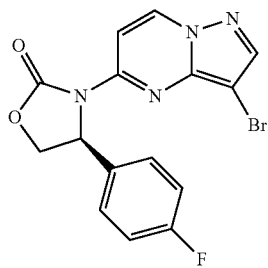 [SMILES: O=C1OC[C@H](c2ccc(F)cc2)N1c1ccn2ncc(Br)c2n1]

(S)-3-(3-bromopyrazolo[1,5-a]pyrimidin-5-yl)-4-(4-fluorophenyl)oxazolidin-2-one

Step 1: To a solution of (S)-2-amino-2-(4-fluorophenyl) ethanol hydrochloride (2.0 g, 10 mmol) in water (50 mL) cooled to 0° C. was added potassium hydroxide (3.5 g, 63 mmol) followed by THF (50 mL) and the reaction was stirred for 20 minutes at 0° C. Bis(trichloromethyl) carbonate (3.1 g, 10 mmol) was added as a solid and the reaction was stirred at 0° C. for 2 hours. The reaction was poured into ethyl acetate (200 mL) and the organic layer was washed with HCl (1N, 30 mL), NaOH (1N, 30 mL) and brine (30 mL), dried over MgSO$_4$ and concentrated under vacuum to give (S)-4-(4-fluorophenyl)oxazolidin-2-one (1 g, 53%).

Step 2: To a solution of (S)-4-(4-fluorophenyl)oxazolidin-2-one (0.43 g, 2.4 mmol) in DMF (10 mL) was added sodium hydride (0.095 g, 2.4 mmol) and the reaction stirred at ambient temperature for 30 minutes. 3-Bromo-5-chloropyrazolo[1,5-a]pyrimidine (0.50 g, 2.2 mmol) was added and the reaction was stirred for 2 hours at ambient temperature. The reaction mixture was poured into water (100 mL) and extracted into ether (2×100 mL). The organic layer was washed with brine (2×20 mL), dried over MgSO$_4$ and concentrated under vacuum. The crude material was purified by silica gel chromatography, eluting with 2% EtOAc/DCM to yield (S)-3-(3-bromopyrazolo[1,5-a]pyrimidin-5-yl)-4-(4-fluorophenyl)oxazolidin-2-one (0.35 g, 43%).

Example 1

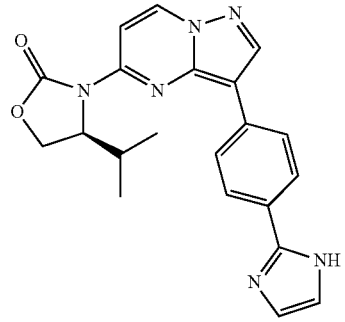 [SMILES: CC(C)[C@H]1COC(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-4-isopropyloxazolidin-2-one Step 1: To a solution of dry EtOH (500 mL) was added sodium (22.1 g, 481 mmol) under a cold water bath. After complete dissolution, 1H-pyrazol-3-amine (40.0 g, 481 mmol) and 1,3-dimethylpyrimidine-2,4(1H,3H)-dione (101 g, 722 mmol) were added. The reaction mixture was heated at reflux for 4 hours. After cooling, the white solid was collected by filtration, washed with cold EtOH and dried under vacuum. The crude solid was suspended in minimum amount of water and the pH of the solution was adjusted to 5 by dropwise addition of acetic acid. The precipitated solid was collected by filtration, re-dissolved in MeOH and concentrated by rotary evaporation to azeotrope any remaining water to afford pyrazolo[1,5-a]pyrimidin-5-ol (34.3 g, 53%).

Step 2: A mixture of pyrazolo[1,5-a]pyrimidin-5-ol (17.0 g, 126 mmol) in POCl$_3$ (100 mL) was heated at reflux for 3 hours. After cooling, the reaction was concentrated under vacuum. To the residue was added dichloromethane. The organic phase was carefully washed with saturated aqueous NaHCO$_3$ solution, dried and concentrated. The crude product was purified by passing through a short silica gel pad eluting with 50% EtOAc in hexane to give 5-chloropyrazolo[1,5-a] pyrimidine (13.1 g, 68%).

Step 3: To a solution of 5-chloropyrazolo[1,5-a]pyrimidine (2.30 g, 15.0 mmol) in dichloromethane (100 mL) was added N-bromosuccinimide (2.67 g, 15.0 mmol) and the mixture allowed to stir at ambient temperature for 1 hour. The reaction mixture was poured into water, extracted with dichloromethane, and dried over sodium sulfate. The crude product was purified by column chromatography, eluting with 1% MeOH/dichloromethane and afforded 1.50 g (45%) of 3-bromo-5-chloropyrazolo[1,5-a]pyrimidine as a light yellow solid.

Step 4: To a solution of 3-bromo-5-chloropyrazolo[1,5-a] pyrimidine (5.30 g, 22.8 mmol) and (S)-4-isopropyloxazolidin-2-one (4.42 g, 34.2 mmol) in dry DMF (100 mL) at ambient temperature was added sodium hydride (0.821 g, 34.2 mmol) and the solution stirred for 12 hours. Saturated aqueous NH$_4$Cl solution was added and the solids were collected by filtration. Purification of the crude material by column chromatography, eluting with 1% MeOH/dichloromethane afforded 5.30 g (71%) of (S)-3-(3-bromopyrazolo[1,5-a]pyrimidin-5-yl)-4-isopropyloxazolidin-2-one as a yellow solid. LCMS (APCI+) m/z 325, 327 [M+H]⁺.

Step 5: To a solution of 4-bromobenzonitrile (80.0 g, 440 mmol) in MeOH (800 mL) was added NaOMe (20.1 mL, 87.9 mmol). The mixture was allowed to stir at ambient temperature for 5.5 hours. 2,2-Dimethoxyethanamine (61.6 mL, 571 mmol) was added followed by acetic acid (50.3 mL, 879 mmol). The reaction mixture was heated to 50° C. for 1 hour and then cooled to ambient temperature. MeOH (200 mL) and HCl (200 mL, 1200 mmol) were added, and the reaction mixture was heated to 65° C. for 18 hours. The reaction mixture was then concentrated, and washed with 1:1 H₂O:Et₂O (2000 mL). The pH of the aqueous layer was adjusted to pH=9 with 6 N NaOH. The resulting solid was filtered and dried to give 2-(4-bromophenyl)-1H-imidazole (20.0 g, 20%). LCMS (APCI+) m/z 223, 224 [M+H]⁺.

Step 6: To a solution of 2-(4-bromophenyl)-1H-imidazole (15.0 g, 67.2 mmol) in DMF (150 ml) at 0° C. was added NaH (60% dispersion in mineral oil, 3.90 g, 97.5 mmol). The mixture was stirred at 0° C. for 1 hour and (2-(chloromethoxy)ethyl)trimethylsilane (14.8 mL, 84.0 mmol) was added. The resulting solution was allowed to warm from 0° C. to ambient temperature while stirring over 24 hours. The reaction mixture was diluted with 1:1 brine:H₂O (500 mL), extracted with EtOAc (3×200 mL), dried over sodium sulfate, filtered and concentrated to an oil. Purification of the oil by column chromatography, eluting with 10-50% EtOAc/Hexane, afforded 2-(4-bromophenyl)-1-((2-(trimethylsilyl)ethoxy)methyl)-1H-imidazole as a light orange oil, (17.1 g, 70%). LCMS (APCI+) m/z 353, 355 [M+H]⁺.

Step 7: A mixture of 2-(4-bromophenyl)-1-((2-(trimethylsilyl)ethoxy)methyl)-1H-imidazole (17.1 g, 47.0 mmol), DPPF (0.703 g, 2.82 mmol), PdCl₂-dppf-dichloromethane (1.41 g, 5.64 mmol), potassium acetate (8.33 g, 141 mmol), 4,4,4',4',5,5,5',5'-octamethyl-2,2'-bi(1,3,2-dioxaborolane) (35.8 g, 141 mmol) in dioxane (200 mL) under N₂ was heated at 90° C. for 18 hours. The crude product was filtered through a pad of Celite, washed with saturated NaHCO₃, brine, dried over MgSO₄, filtered, and concentrated. Purification of the crude material by column chromatography, eluting with 30% EtOAc/Hexane, afforded 2-(4-(4,4,5,5-tetramethyl-1,3,2-dioxaborolan-2-yl)phenyl)-1-((2-(trimethylsilyl)ethoxy)methyl)-1H-imidazole as a light orange oil (13.8 g, 47%). LCMS (APCI+) m/z 401 [M+H]⁺.

Step 8: To a sealed tube was added (S)-3-(3-bromopyrazolo[1,5-a]pyrimidin-5-yl)-4-isopropyloxazolidin-2-one (2.5 g, 7.69 mmol), 2-(4-(4,4,5,5-tetramethyl-1,3,2-dioxaborolan-2-yl)phenyl)-1-((2-(trimethylsilyl)ethoxy)methyl)-1H-imidazole (4.62 g, 11.5 mmol), dioxane (76.9 mL, 7.69 mmol) and 2.0M Na₂CO₃ (11.5 mL, 23.1 mmol). The mixture was degassed by bubbling N₂ through the solution. Pd₂dba₃ (0.704 g, 0.769 mmol) and dicyclohexyl(2',4',6'-triisopropylbiphenyl-2-yl)phosphine (0.367 g, 0.769 mmol) were added and the vessel was sealed under a N₂ atmosphere. The mixture was heated at 90° C. for 72 hours. The reaction mixture was diluted with H₂O (150 mL) and EtOAc (150 mL), separated, and the aqueous layer was further extracted with EtOAc. The combined organic extracts were washed with brine, dried (Na₂SO₄), filtered and concentrated. Purification of the crude material by normal phase chromatography, eluting with 0-4% (9:1 MeOH:NH₄OH)/dichloromethane, provided (S)-4-isopropyl-3-(3-(4-(1-((2-(trimethylsilyl)ethoxy)methyl)-1H-imidazol-2-yl)phenyl)pyrazolo[1,5-a]pyrimidin-5-yl)oxazolidin-2-one as a bright yellow-orange foamy solid, 2.09 g (52%). LCMS (APCI+) m/z 519 [M+H]⁺.

Step 9: (S)-4-isopropyl-3-(3-(4-(1-((2-(trimethylsilyl)ethoxy)methyl)-1H-imidazol-2-yl)phenyl)pyrazolo[1,5-a]pyrimidin-5-yl)oxazolidin-2-one (2.09 g, 4.03 mmol) was dissolved in dichloromethane (20 mL) and trifluoroacetic acid (25 mL) was added and the mixture allowed to stir at ambient temperature for 12 hours. The reaction mixture was concentrated and the residue partitioned between saturated aqueous NaHCO₃ (50 mL) and EtOAc (100 mL). The aqueous layer was washed with EtOAc. The combined organic extracts were washed with brine, dried (Na₂SO₄), filtered and concentrated to give a light yellow solid. Purification of the crude material by column chromatography, eluting with a gradient of 0-4% (9:1 MeOH/NH₄OH)/EtOAc, provided (S)-3-(3-(4-(1H-imidazol-2-yl)phenyl)pyrazolo[1,5-a]pyrimidin-5-yl)-4-isopropyloxazolidin-2-one as a yellow solid (961.3 mg, 61%). LCMS (APCI+) m/z 389 [M+H]⁺; ¹H NMR (400 MHz, CDCl₃) δ 8.57 (d, J=7.8 Hz, 1H), 8.39 (s, 1H), 8.04 (d, J=8.6 Hz, 2H), 8.03 (d, J=7.8 Hz, 1H), 7.89 (d, J=8.6 Hz, 2H), 7.19 (s, 2H), 4.95-4.91 (m, 1H), 4.36-4.45 (m, 2H), 2.83-2.91 (m, 1H), 1.04 (d, J=7.0 Hz, 3H), 0.92 (d, J=7.0 Hz, 3H).

Example 2

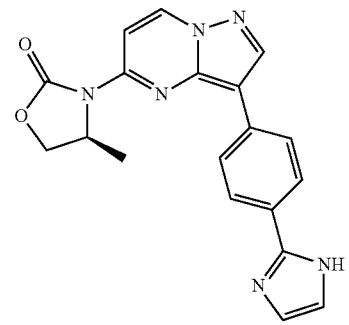 [SMILES: C[C@H]1COC(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-4-methyloxazolidin-2-one Step 1: A mixture of pyrazolo[1,5-a]pyrimidin-5-ol (Example 1, Step 1, 28.3 g, 210 mmol) and N-bromosuccinimide (37.3 g, 210 mmol) in dichloromethane (200 mL) and DMF (300 mL) was stirred at ambient temperature for 17 hours. The reaction mixture was concentrated and the product was precipitated using Et₂O. The solids were collected by filtration and dried to afford 3-bromopyrazolo[1,5-a]pyrimidin-5-ol (40.4 g, 90%). LCMS (APCI−) m/z 211, 213 [M−H]⁻.

Step 2: 3-(4-(1-((2-(trimethylsilyl)ethoxy)methyl)-1H-imidazol-2-yl)phenyl)pyrazolo[1,5-a]pyrimidin-5-ol (0.190 g, 10%) was prepared by the procedure described in Example 1, Step 8, substituting 3-bromopyrazolo[1,5-a]pyrimidin-5-ol (1.00 g, 4.60 mmol) for 3-bromo-5-chloropyrazolo[1,5-a]pyrimidine. LCMS (APCI+) m/z 408 [M+H]⁺.

Step 3: A mixture of 3-(4-(1-((2-(trimethylsilyl)ethoxy)methyl)-1H-imidazol-2-yl)phenyl)pyrazolo[1,5-a]pyrimidin-5-ol (15.0 mg, 0.0368 mmol), tosyl chloride (7.0 mg, 0.0368 mmol) and NEt₃ (5.13 µL, 0.037 mmol) in dioxane (2 mL) was heated at 80° C. for 18 hours. Additional portions of tosyl chloride (7.0 mg, 0.037 mmol) and NEt₃ (5.1 µL, 0.037 mmol) were added and the mixture continued to heat at 80° C. for 12 hours. The cooled reaction mixture was poured into EtOAc and extracted with 10% HCl. The organic extract was dried (Na$_2$SO$_4$), filtered, and concentrated. Purification of the crude material by column chromatography, eluting with 1-2% MeOH/dichloromethane, afforded 3-(4-(1-((2-(trimethylsilyl)ethoxy)methyl)-1H-imidazol-2-yl)phenyl)pyrazolo[1,5-a]pyrimidin-5-yl 4-methylbenzenesulfonate as a brown-yellow film (19.0 mg, 92%). LCMS (APCI+) m/z 562 [M+H]$^+$.

Step 4: A solution of (S)-4-methyloxazolidin-2-one (9.0 mg, 0.089 mmol) in dry DMF (0.5 mL) was cooled to 0° C. Sodium hexamethyldisilazide (0.089 mL, 0.089 mmol) was added and the resulting yellow solution stirred for 10 minutes before addition of a solution of 3-(4-(1-((2-(trimethylsilyl)ethoxy)methyl)-1H-imidazol-2-yl)phenyl)pyrazolo[1,5-a]pyrimidin-5-yl 4-methylbenzenesulfonate (20.0 mg, 0.0356 mmol) in DMF (0.5 mL). The mixture was then brought to ambient temperature prior to heating at 80° C. for 1 hour. The cooled reaction mixture was poured into saturated aqueous NH$_4$Cl and extracted with EtOAc. The combined organic extracts were dried over sodium sulfate, filtered and concentrated. Purification of the crude material by column chromatography, eluting with 1-2% MeOH/dichloromethane afforded the protected intermediate which was taken up in dichloromethane (1 mL). Trifluoroacetic acid (3 mL) was added and the mixture stirred at ambient temperature for 12 hours. The reaction mixture was concentrated, washed with saturated aqueous NaHCO$_3$, extracted into ethyl acetate, dried over sodium sulfate, filtered and concentrated. Purification of the crude material by column chromatography, eluting with 2-4% MeOH/dichloromethane, afforded (S)-3-(3-(4-(1H-imidazol-2-yl)phenyl)pyrazolo[1,5-a]pyrimidin-5-yl)-4-methyloxazolidin-2-one as a light yellow solid (1 mg, 8%). LCMS (APCI+) m/z 361 [M+H]$^+$; $^1$H NMR (400 MHz, DMSO-d$_6$) δ 8.82 (d, J=7.8 Hz, 1H), 8.54 (s, 1H), 8.17 (d, J=8.6 Hz, 2H), 7.97 (d, J=7.8 Hz, 1H), 7.91 (d, J=8.6 Hz, 2H), 7.14 (s, 2H), 5.06-5.13 (m, 1H), 4.65 (t, J=8.2 Hz, 1H), 4.21-4.24 (m, 1H), 1.66 (d, J=6.2 Hz, 3H).

Example 3

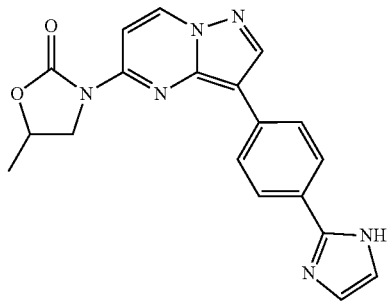 [SMILES: CC1CN(c2ccn3ncc(-c4ccc(-c5ncc[nH]5)cc4)c3n2)C(=O)O1]

3-(3-(4-(1H-imidazol-2-yl)phenyl)pyrazolo[1,5-a]pyrimidin-5-yl)-5-methyloxazolidin-2-one Step 1: 5-Methyl-3-(pyrazolo[1,5-a]pyrimidin-5-yl)oxazolidin-2-one (0.170 g, 48%) was prepared by the procedure described in Example 1, Step 4, substituting 5-methyloxazolidin-2-one (0.494 g, 4.88 mmol) for (S)-4-isopropyloxazolidin-2-one and 5-chloropyrazolo[1,5-a]pyrimidine (0.250 g, 1.63 mmol) for 3-bromo-5-chloropyrazolo[1,5-a]pyrimidine.

Step 2: 3-(3-Bromopyrazolo[1,5-a]pyrimidin-5-yl)-5-methyloxazolidin-2-one (0.129 g, 55%) was prepared from 5-methyl-3-(pyrazolo[1,5-a]pyrimidin-5-yl)oxazolidin-2-one (0.171 g, 0.784 mmol) by the procedure described in Example 1, Step 3.

Step 3: 5-Methyl-3-(3-(4-(1-((2-(trimethylsilyl)methyl)-1H-imidazol-2-yl)phenyl)pyrazolo[1,5-a]pyrimidin-5-yl)oxazolidin-2-one (50.0 mg, 47%) was prepared from 3-(3-bromopyrazolo[1,5-a]pyrimidin-5-yl)-5-methyloxazolidin-2-one (65.0 mg, 0.220 mmol) by the procedure described in Example 1, Step 8. LCMS (APCI+) m/z 491 [M+H]

Step 4: 3-(3-(4-(1H-Imidazol-2-yl)phenyl)pyrazolo[1,5-a]pyrimidin-5-yl)-5-methyloxazolidin-2-one (14.0 mg, 38%) was prepared from 5-methyl-3-(3-(4-(1-((2-(trimethylsilyl)ethoxy)methyl)-1H-imidazol-2-yl)phenyl)pyrazolo[1,5-a]pyrimidin-5-yl)oxazolidin-2-one (50.0 mg, 0.100 mmol) by the procedure described in Example 1, Step 9. LCMS (APCI+) m/z 361 [M]$^+$; $^1$H NMR (400 MHz, DMSO-d$_6$) δ 9.08 (d, J=7.4 Hz, 1H), 8.73 (s, 1H), 8.17 (d, J=8.6 Hz, 2H), 7.99 (d, J=8.6 Hz, 2H), 7.87 (d, J=7.8 Hz, 1H), 7.25 (s, 1H), 7.03 (s, 1H), 4.90-4.98 (m, 1H), 4.51 (q, J=6.1 Hz, 1H), 3.94 (q, J=6.0 Hz, 0H), 1.51 (d, J=6.2 Hz, 3H).

Example 4

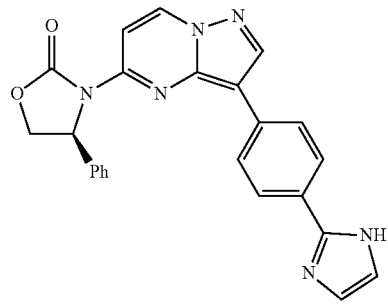 [SMILES: O=C1OC[C@H](c2ccccc2)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-4-phenyloxazolidin-2-one Step 1: (S)-4-Phenyl-3-(pyrazolo[1,5-a]pyrimidin-5-yl)oxazolidin-2-one (0.423 g, 77%) was prepared by the procedure described in Example 1, Step 4, substituting (S)-4-phenyloxazolidin-2-one (0.638 g, 3.91 mmol) for (S)-4-isopropyloxazolidin-2-one and 5-chloropyrazolo[1,5-a]pyrimidine (0.300 g, 1.95 mmol) for 3-bromo-5-chloropyrazolo[1,5-a]pyrimidine.

Step 2: (S)-3-(3-Bromopyrazolo[1,5-a]pyrimidin-5-yl)-4-phenyloxazolidin-2-one (0.423 g, 78%) was prepared from (S)-4-phenyl-3-(pyrazolo[1,5-a]pyrimidin-5-yl)oxazolidin-2-one (0.423 g, 1.51 mmol) by the procedure described in Example 1, Step 3.

Step 3: A solution containing (S)-3-(3-bromopyrazolo[1,5-a]pyrimidin-5-yl)-4-phenyloxazolidin-2-one (0.100 g, 0.278 mmol), 2-(4-(4,4,5,5-tetramethyl-1,3,2-dioxaborolan-2-yl)phenyl)-1-((2-(trimethylsilyl)ethoxy)methyl)-1H-imidazole (0.334 g, 0.835 mmol) and 2M Na$_2$CO$_3$ (0.418 mL, 0.835 mmol) in dioxane (10 mL) was degassed with argon. Dicyclohexyl(2',4',6'-triisopropylbiphenyl-2-yl)phosphine (13.3 mg, 0.0278 mmol) and Pd$_2$(dba)$_3$ (6.5 mg, 0.028 mmol), were added and the solution was degassed again with argon. The reaction vessel was sealed and heated to 80° C. for 18 hours. The cooled reaction mixture was partitioned between ethyl acetate and brine. The organic layer was dried over sodium sulfate, filtered, and concentrated. Purification of the crude material by column chromatography, eluting with 1-5% MeOH/dichloromethane afforded the protected intermediate which was taken up in dichloromethane (2 mL). Trifluoroacetic acid (2 mL) was added and the mixture stirred at ambient temperature for 12 hours. The reaction mixture was concentrated, washed with saturated aqueous NaHCO$_3$, extracted into ethyl acetate, dried over sodium sulfate, filtered and concentrated. Purification of the crude material by column chromatography, eluting with 2-4% MeOH/dichloromethane, afforded (S)-3-(3-(4-(1H-imidazol-2-yl)phenyl)pyrazolo[1,5-a]pyrimidin-5-yl)-4-phenyloxazolidin-2-one as a light yellow solid, 14 mg (12%). LCMS (APCI+) m/z 423 [M+H]$^+$; $^1$H NMR (400 MHz, DMSO-d$_6$) δ 9.10 (d, J=7.8 Hz, 1H), 8.65 (s, 1H), 7.93 (d, J=7.8 Hz, 1H), 7.91 (d, J=8.6 Hz, 2H), 7.78 (d, J=8.6 Hz, 2H), 7.44-7.50 (m, 5H), 7.22 (s, 2H), 5.94-5.98 (m, 1H), 4.93 (t, J=8.6 Hz, 1H), 4.23-4.27 (m, 1H).

Example 5

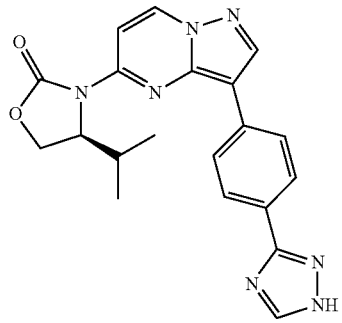 [SMILES: CC(C)[C@H]1COC(=O)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-isopropyloxazolidin-2-one Step 1: A suspension of 4-bromobenzamide (9.50 g, 47.5 mmol) in 1,1-dimethoxy-N,N-dimethylmethanamine (17.2 mL, 47.5 mmol) in a round bottom flask topped with a short path distillation head was placed in a preheated sand bath at 122° C. The reaction mixture was allowed to stir at this temperature for 1.5 hours, during which time the MeOH that was formed was collected from the distillation condenser. Upon cooling solids were formed and collected by vacuum filtration affording (E)-4-bromo-N-((dimethylamino)methylene)benzamide as a pale yellow solid (9.38 g, 77%) which was used directly in the next step without further purification. LCMS (APCI+) m/z 255, 257 [M+H]$^+$.

Step 2: To a solution of hydrazine hydrate (1.96 mL, 40.4 mmol) in acetic acid (91.9 mL, 36.8 mmol) was added (E)-4-bromo-N-((dimethylamino)methylene)benzamide (9.38 g, 36.8 mmol) and the mixture stirred at 90° C. for 1.5 hours. The reaction mixture was concentrated to about 10 mL and diluted with ether (50 mL). The resulting white solid was collected by vacuum filtration, rinsing with excess ether, and dried to afford 5-(4-bromophenyl)-1H-1,2,4-triazole (5.48 g, 66%) which was carried on without further purification. LCMS (APCI+) m/z 224, 226 [M+H]$^+$.

Step 3: To a solution of 5-(4-bromophenyl)-1H-1,2,4-triazole (5.40 g, 24.1 mmol) in DMF (48.2 mL, 24.1 mmol) at 0° C. was carefully added NaH (1.16 g, 28.9 mmol). The resultant mixture was stirred for 30 minutes prior to the addition of (2-(chloromethoxy)ethyl)trimethylsilane (6.38 mL, 36.2 mmol). The reaction mixture was stirred 0° C. for 15 minutes before removal of the ice bath and the mixture was allowed to warm to ambient temperature stirring for 2 hours. The reaction mixture was diluted with H$_2$O (150 mL) and extracted with EtOAc (2×200 mL). The combined organic extracts were washed with brine, dried (Na$_2$SO$_4$), filtered and concentrated to provide 10.09 g as a pale yellow oil which solidified upon standing. Purification by normal phase chromatography on silica eluting with 0-50% EtOAc/Hexanes provided 3-(4-bromophenyl)-1-((2-(trimethylsilyl)ethoxy)methyl)-1H-1,2,4-triazole and 5-(4-bromophenyl)-1-((2-(trimethylsilyl)ethoxy)methyl)-1H-1,2,4-triazole (7.94 g, 93%) as a mixture of two regioisomers. LCMS (APCI+) m/z 354, 356 [M+H]$^+$.

Step 4: In a sealed tube, a mixture of 3-(4-bromophenyl)-1-((2-(trimethylsilyl)ethoxy)methyl)-1H-1,2,4-triazole and 5-(4-bromophenyl)-1-((2-(trimethylsilyl)ethoxy)methyl)-1H-1,2,4-triazole (5.00 g, 14.1 mmol), DPPF (0.469 g, 0.847 mmol), PdCl$_2$dppf-dichloromethane (1.38 g, 1.69 mmol), potassium acetate (4.15 g, 42.3 mmol) and 4,4,4',4',5,5,5',5'-octamethyl-2,2'-bi(1,3,2-dioxaborolane) (7.17 g, 28.2 mmol) in dioxane (141 mL) was heated at 90° C. under N$_2$ for 18 hours. The crude product was filtered through a pad of Celite, washed with saturated NaHCO$_3$, brine, dried over MgSO$_4$, filtered, and concentrated. Purification of the crude material by column chromatography, eluting with 0-30% EtOAc/Hexanes, afforded 3-(4-(4,4,5,5-tetramethyl-1,3,2-dioxaborolan-2-yl)phenyl)-1-((2-(trimethylsilyl)ethoxy)methyl)-1H-1,2,4-triazole and 5-(4-(4,4,5,5-tetramethyl-1,3,2-dioxaborolan-2-yl)phenyl)-1-((2-(trimethylsilyl)ethoxy)methyl)-1H-1,2,4-triazole (5.55 g, 98%) as a mixture of two regioisomers. LCMS (APCI+) m/z 402 [M+H]$^+$.

Step 5: To a sealed tube was added (S)-3-(3-bromopyrazolo[1,5-a]pyrimidin-5-yl)-4-isopropyloxazolidin-2-one (Example 1, Steps 1-4; 3.00 g, 9.23 mmol), 3-(4-(4,4,5,5-tetramethyl-1,3,2-dioxaborolan-2-yl)phenyl)-1-((2-(trimethylsilyl)ethoxy)methyl)-1H-imidazole and 5-(4-(4,4,5,5-tetramethyl-1,3,2-dioxaborolan-2-yl)phenyl)-1-((2-(trimethylsilyl)ethoxy)methyl)-1H-imidazole as a mixture of regioisomers (5.55 g, 13.8 mmol), dioxane (92.3 mL, 9.23 mmol) and 2.0M Na$_2$CO$_3$ (13.8 mL, 27.7 mmol). The mixture was degassed by bubbling N$_2$ through the solution. Pd$_2$ dba$_3$ (0.845 g, 0.923 mmol) and dicyclohexyl(2',4',6'-triisopropylbiphenyl-2-yl)phosphine (0.440 g, 0.923 mmol) were added and the vessel was sealed under a N$_2$ atmosphere. The mixture was heated at 90° C. for 39 hours. The reaction mixture was diluted with H$_2$O (200 mL) and EtOAc (200 mL), separated, and the aqueous layer was further extracted with EtOAc (1×200 mL, 1×100 mL). The combined organic extracts were washed with brine, dried (Na$_2$SO$_4$), filtered and concentrated. Purification of the crude material by normal phase chromatography, eluting with 0-2% MeOH/dichloromethane, provided (S)-4-Isopropyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-isopropyl-3-(3-(4-(1-((2-(trimethylsilyl)ethoxy)methyl)-1H-1,2,4-triazol-5-yl)phenyl)pyrazolo[1,5-a]pyrimidin-5-yl)oxazolidin-2-one (4.07 g, 76%) as a mixture of two regioisomers. LCMS (APCI+) m/z 520 [M+H]$^+$.

Step 6: A mixture of (S)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-isopropyl-3-(3-(4-(1-((2-(trimethylsilyl)ethoxy)methyl)-1H-1,2,4-triazol-5-yl)phenyl)pyrazolo[1,5-a]pyrimidin-5-yl)oxazolidin-2-one (2.37 g, 4.25 mmol) was dissolved in dichloromethane (12 mL) and trifluoroacetic acid (22.5 mL) was added and the mixture allowed to stir at ambient temperature for 6 hours. The reaction mixture was concentrated and the residue partitioned between saturated aqueous NaHCO$_3$ (100 mL) and EtOAc (100 mL). The aqueous layer was washed with EtOAc (2×100 mL). The combined organic extracts were washed with brine, dried (Na$_2$SO$_4$), filtered and concentrated to give a golden yellow solid. Purification of the crude material by column chromatography, eluting with a gradient of Hexanes to 50% EtOAc/Hexanes to 0-2% (9:1 MeOH/NH$_4$OH)/EtOAc provided (S)-3-(3-(4-(1H-1,2,4-triazol-3-yl)phenyl)pyrazolo[1,5-a]pyrimidin-5-yl)-4-isopropyloxazolidin-2-one (1.30 g, 78%) as a yellow crystalline solid. LCMS (APCI+) m/z 390 [M+H]$^+$; $^1$H NMR (400 MHz, DMSO-d6) δ 9.11 (d, J=7.8 Hz, 1H), 8.77 (s, 1H), 8.37 (bs, 1H), 8.22 (d, J=8.6 Hz, 2H), 8.05 (d, J=8.6 Hz, 2H), 7.89 (d, J=7.4 Hz, 1H), 4.95-4.99 (m, 1H), 4.52 (d, J=6.2 Hz, 2H), 2.74-2.82 (m, 1H), 1.07 (d, J=7.0 Hz, 3H), 0.87 (d, J=6.6 Hz, 3H).

Example 6

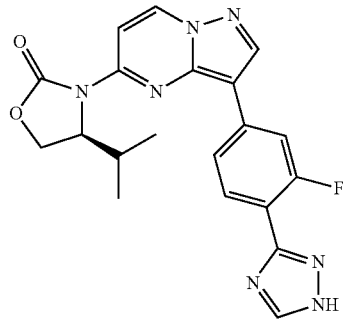 [SMILES: CC(C)[C@H]1COC(=O)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-isopropyloxazolidin-2-one Step 1: A solution of 4-bromo-2-fluorobenzonitrile (1.00 g, 5.00 mmol), trifluoroacetic acid (3.5 mL, 45 mmol), and sulfuric acid (3.5 mL, 66 mmol) was stirred at ambient temperature for 4 hours, at 30° C. for 15 hours, and at 50° C. for 6 hours. After cooling to 0° C., water (20 mL) was added, and the resulting suspension was stirred at 0° C. for 1.5 hours. The solids were collected by vacuum filtration, rinsed with excess water, and dried to afford 4-bromo-2-fluorobenzamide (0.956 g, 88%) as an off-white solid which was carried on without further purification.

Step 2: A suspension of 4-bromo-2-fluorobenzamide (0.929 g, 4.26 mmol) in 1,1-dimethoxy-N,N-dimethylmethanamine (1.66 mL, 11.7 mmol) in a round bottom flask topped with a short path distillation head was heated to 100-100° C. The resulting solution was allowed to stir at this temperature for 3.5 hours, during which time the MeOH that was formed was collected from the distillation condenser. Heptane (5 mL) was added dropwise and the resulting suspension was cooled to 0-5° C. The solids were collected by vacuum filtration, rinsed with excess heptane, and dried to afford (E)-4-bromo-N-((dimethylamino)methylene)-2-fluorobenzamide (1.111 g, 96%) as an off-white solid which was carried on without further purification.

Step 3: Hydrazine (0.14 mL, 4.4 mmol) was added to a solution of (E)-4-bromo-N-((dimethylamino)methylene)-2-fluorobenzamide (1.105 g, 4.046 mmol) in acetic acid (11 mL). The resulting white suspension was heated to 95-100° C. The resulting solution was stirred at 95-100° C. for 2 hours. The reaction mixture was cooled to ambient temperature and the acetic acid was azeotropically removed in vacuo with multiple additions of heptane. Heptane (10 mL) was added to the residue. The resulting suspension was cooled to 0-5° C. and stirred for 1 hour. The solids were collected by vacuum filtration, rinsed with excess heptane, and dried to afford 5-(4-bromo-2-fluorophenyl)-1H-1,2,4-triazole (1.116 g, 114%) as an off-white solid which was carried on without further purification.

Step 4: To a solution of 5-(4-bromo-2-fluorophenyl)-1H-1,2,4-triazole (0.976 g, 4.03 mmol) in DMF (10 mL) at 0° C. was added NaH (60% dispersion in mineral oil, 0.24 g, 6.0 mmol). The mixture was stirred at 0° C. for 30 minutes and (2-(chloromethoxy)ethyl)trimethylsilane (1.2 mL, 6.8 mmol) was added. The resulting suspension was stirred at 0° C. for 30 minutes, then allowed to warm and stir at ambient temperature for 1.5 hours. The reaction mixture was diluted with H$_2$O (20 mL) and extracted twice with EtOAc (15 mL, 10 mL). The combined organic extracts were washed with H$_2$O (2×15 mL), saturated NaHCO$_3$ solution (15 mL), brine (15 mL), dried over MgSO$_4$, filtered, and concentrated in vacuo to provide a mixture of two regioisomers 3-(4-Bromo-2-fluorophenyl)-1-((2-(trimethylsilyl)ethoxy)methyl)-1H-1,2,4-triazole and 5-(4-bromo-2-fluorophenyl)-1-((2-(trimethylsilyl)ethoxy)methyl)-1H-1,2,4-triazole (1.842 g, 123%) as a light-orange oil which was carried on without further purification.

Step 5: A stirred mixture of 3-(4-bromo-2-fluorophenyl)-1-((2-(trimethylsilyl)ethoxy)methyl)-1H-1,2,4-triazole and 5-(4-bromo-2-fluorophenyl)-1-((2-(trimethylsilyl)ethoxy)methyl)-1H-1,2,4-triazole (1.467 g, 3.940 mmol), dppf (0.109 g, 0.197 mmol), PdCl$_2$dppf-dichloromethane (0.322 g, 0.394 mmol), potassium acetate (1.16 g, 11.8 mmol), and 4,4,4',4',5,5,5',5'-octamethyl-2,2'-bi(1,3,2-dioxaborolane) (1.50 g, 5.91 mmol) in dioxane (22 mL) was degassed by three cycles of vacuum and bubbling N$_2$ through the suspension. The mixture was heated at 90° C. under N$_2$ for 3 hours, cooled and stirred at ambient temperature for 17 hours, heated at reflux for 24 hours, then cooled and stirred at ambient temperature for 48.5 hours. The reaction mixture was diluted with EtOAc (10 mL) and H$_2$O (10 mL), separated, and the aqueous layer extracted with EtOAc (20 mL). The combined organic extracts were washed with saturated NaHCO$_3$ (25 mL), brine (25 mL), dried (MgSO$_4$), filtered and concentrated to an oil. Purification of the crude material by normal phase chromatography, eluting with 20-50% EtOAc/heptane, provided a mixture of two regioisomers 3-(2-Fluoro-4-(4,4,5,5-tetramethyl-1,3,2-dioxaborolan-2-yl)phenyl)-1-((2-(trimethylsilyl)ethoxy)methyl)-1H-1,2,4-triazole and 5-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.862 g, 52%) as a yellow oil.

Step 6: A stirred mixture of 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole and 5-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.144 g, 0.343 mmol), (S)-3-(3-bromopyrazolo[1,5-a]pyrimidin-5-yl)-4-isopropyloxazolidin-2-one (0.083 g, 0.255 mmol), Pd$_2$dba$_3$ (0.012 g, 0.013 mmol), dicyclohexyl(2',4',6'-triisopropylbiphenyl-2-yl)phosphine (0.012 g, 0.025 mmol), 2.0M Na$_2$CO$_3$ (0.39 mL, 0.78 mmol), in dioxane (3 mL) was degassed by three cycles of vacuum and bubbling N₂ through the suspension. The mixture was heated at 80° C. under N₂ for 16.5 hours, then cooled and stirred at ambient temperature for 6 hours. The reaction mixture was diluted with H₂O (3 mL) and EtOAc (3 mL), separated, and the aqueous layer extracted with EtOAc (10 mL). The combined organic extracts were washed with brine (8 mL), dried (MgSO₄), filtered and concentrated to an oil. Purification of the crude material by normal phase chromatography, eluting with 10-50% EtOAc/dichloromethane, provided a mixture of two regioisomers (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.144 g, 105%) as a yellow solid.

Step 7: A mixture of (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.137 g, 0.255 mmol) was dissolved in dichloromethane (0.55 mL). Trifluoroacetic acid (1.1 mL) was added and the mixture allowed to stir at ambient temperature for 18 hours. The reaction mixture was concentrated with multiple dichloromethane additions to give a crude residue. Acetonitrile (5 mL) and 28% aqueous ammonia (3 mL, 44 mmol) were added and the mixture concentrated with multiple acetonitrile additions to a yellow solid. Purification by normal phase chromatography, eluting with 50-100% EtOAc/dichloromethane, provided (S)-3-(3-(3-fluoro-4-(1H-1,2,4-triazol-3-yl)phenyl)pyrazolo[1,5-a]pyrimidin-5-yl)-4-isopropyloxazolidin-2-one (0.032 g, 31%) as a yellow solid. LCMS (APCI+) m/z 408.5 [M+H]⁺; ¹H-NMR (400 MHz, CDCl₃) δ 11.24 (broad s, 1H), 8.61 (d, J=7.8 Hz, 1H), 8.43 (s, 1H), 8.26 (t, J=8.2 Hz, 1H), 8.09 (m, 2H), 8.00 (d×d, J=13.8, 1.0 Hz, 1H), 7.87 (d×d, J=8.4, 1.2 Hz, 1H), 4.99-4.96 (m, 1H), 4.50-4.41 (m, 2H), 2.94-2.86 (m, 1H), 1.10 (d, J=7.0 Hz, 3H), 0.94 (d, J=6.8 Hz, 3H).

Example 7

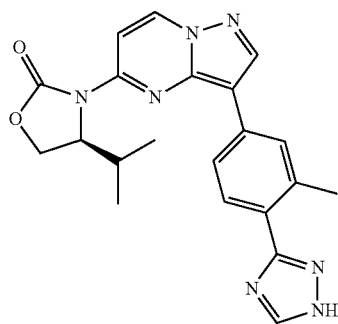 [SMILES: Cc1cc(-c2cnn3ccc(N4C(=O)OC[C@@H]4C(C)C)nc23)ccc1-c1nc[nH]n1]

(S)-4-isopropyl-3-(3-(3-methyl-4-(1H-1,2,4-triazol-3-yl)phenyl)pyrazolo[1,5-a]pyrimidin-5-yl)oxazolidin-2-one Step 1: 4-Bromo-2-methylbenzamide (1.017 g, 93%) was prepared by the procedure described in Example 6, Step 1, substituting 4-bromo-2-methylbenzonitrile (1.00 g, 5.10 mmol) for 4-bromo-2-fluorobenzonitrile, to produce a white solid which was carried on without further purification.

Step 2: (E)-4-bromo-N-((dimethylamino)methylene)-2-methylbenzamide (1.122 g, 91%) was prepared by the procedure described in Example 5, Step 1, using 4-bromo-2-methylbenzamide (0.989 g, 4.62 mmol), to produce an off-white solid which was carried on without further purification.

Step 3: 5-(4-bromo-2-methylphenyl)-1H-1,2,4-triazole (0.871 g, 88.1%) was prepared by the procedure described in Example 5, Step 2, using (E)-4-bromo-N-((dimethylamino)methylene)-2-methylbenzamide (1.117 g, 4.150 mmol), to produce a white solid which was carried on without further purification.

Step 4: A mixture of 3-(4-bromo-2-methylphenyl)-1-((2-(trimethylsilyl)ethoxy)methyl)-1H-1,2,4-triazole and 5-(4-bromo-2-methylphenyl)-1-((2-(trimethylsilyl)ethoxy)methyl)-1H-1,2,4-triazole (1.187 g, 88.6%) was prepared by the procedure described in Example 1, Step 6, using 5-(4-bromo-2-methylphenyl)-1H-1,2,4-triazole (0.864 g, 3.63 mmol), to produce a mixture of two regioisomers as a colorless oil.

Step 5: 3-(2-methyl-4-(4,4,5,5-tetramethyl-1,3,2-dioxaborolan-2-yl)phenyl)-1-((2-(trimethylsilyl)ethoxy)methyl)-1H-1,2,4-triazole and 5-(2-methyl-4-(4,4,5,5-tetramethyl-1,3,2-dioxaborolan-2-yl)phenyl)-1-((2-(trimethylsilyl)ethoxy)methyl)-1H-1,2,4-triazole (0.340 g, 70.0%) were prepared by the procedure described in Example 1, Step 7, using a mixture of 3-(4-bromo-2-methylphenyl)-1-((2-(trimethylsilyl)ethoxy)methyl)-1H-1,2,4-triazole and 5-(4-bromo-2-methylphenyl)-1-((2-(trimethylsilyl)ethoxy)methyl)-1H-1,2,4-triazole (0.433 g, 1.18 mmol), to produce a mixture of two regioisomers as a yellow oil.

Step 6: A mixture of (S)-4-isopropyl-3-(3-(3-methyl-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-isopropyl-3-(3-(3-methyl-4-(1-((2-(trimethylsilyl)ethoxy)methyl)-1H-1,2,4-triazol-5-yl)phenyl)pyrazolo[1,5-a]pyrimidin-5-yl)oxazolidin-2-one (0.289 g, 92.3%) was prepared by the procedure described in Example 1, Step 8, using a mixture of 3-(2-methyl-4-(4,4,5,5-tetramethyl-1,3,2-dioxaborolan-2-yl)phenyl)-1-((2-(trimethylsilyl)ethoxy)methyl)-1H-1,2,4-triazole and 5-(2-methyl-4-(4,4,5,5-tetramethyl-1,3,2-dioxaborolan-2-yl)phenyl)-1-((2-(trimethylsilyl)ethoxy)methyl)-1H-1,2,4-triazole (0.330 g, 0.794 mmol), to produce a mixture of two regioisomers as a yellow oil.

Step 7: (S)-4-isopropyl-3-(3-(3-methyl-4-(1H-1,2,4-triazol-3-yl)phenyl)pyrazolo[1,5-a]pyrimidin-5-yl)oxazolidin-2-one (0.138 g, 64%) was prepared by the procedure described in Example 1, Step 9, using a mixture of (S)-4-isopropyl-3-(3-(3-methyl-4-(1-((2-(trimethylsilyl)ethoxy)methyl)-1H-1,2,4-triazol-3-yl)phenyl)pyrazolo[1,5-a]pyrimidin-5-yl) oxazolidin-2-one and (S)-4-isopropyl-3-(3-(3-methyl-4-(1-((2-(trimethylsilyl)ethoxy)methyl)-1H-1,2,4-triazol-5-yl)phenyl)pyrazolo[1,5-a]pyrimidin-5-yl) oxazolidin-2-one (0.285 g, 0.534 mmol), to produce a yellow solid. LCMS (APCI+) m/z 404.6 [M+H]⁺; ¹H-NMR (400 MHz, CDCl₃) δ 11.40 (broad s, 1H), 8.60 (d, J=7.8 Hz, 1H), 8.41 (s, 1H), 8.22 (s, 1H), 8.05 (d, J=7.8 Hz, 1H), 7.94 (s, 1H), 7.87 (d, J=8.0 Hz, 1H), 7.81 (d, J=8.2 Hz, 1H), 4.97-4.93 (m, 1H), 4.48-4.38 (m, 2H), 2.94-2.87 (m, 1H), 2.65 (s, 3H), 1.07 (d, J=7.0 Hz, 3H), 0.93 (d, J=6.8 Hz, 3H).

Example 8

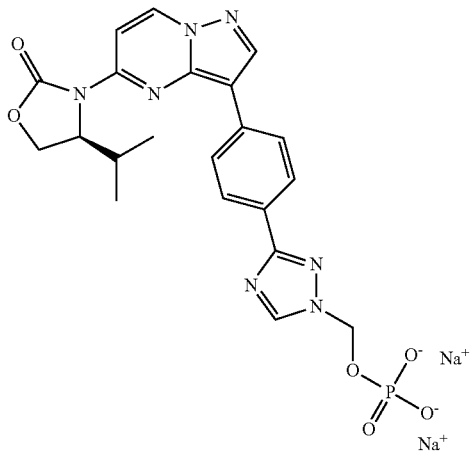 [SMILES: CC(C)[C@H]1COC(=O)N1c1ccn2ncc(-c3ccc(-c4ncn(COP(=O)([O-])[O-])n4)cc3)c2n1 ; [Na+] ; [Na+]]

Bis-sodium (S)-(3-(4-(5-(4-isopropyl-2-oxooxazolidin-3-yl)pyrazolo[1,5-a]pyrimidin-3-yl)phenyl)-1H-1,2,4-triazol-1-yl)methyl phosphate Step 1: To a mixture of (S)-3-(3-(4-(1H-1,2,4-triazol-3-yl)phenyl)pyrazolo[1,5-a]pyrimidin-5-yl)-4-isopropyloxazolidin-2-one (1.72 g, 4.42 mmol), Cs$_2$CO$_3$ (1.58 g, 4.86 mmol) and DMF (40 mL) was added di-tert-butyl chloromethyl phosphate (1.54 g, 5.96 mmol). The reaction mixture was heated at 80° C. for 2 hours. After cooling, the reaction mixture was partitioned between EtOAc and water. The aqueous layer was extracted with EtOAc. The combined organic layers were washed with water and brine, dried and concentrated. The residue was purified by column chromatography (1:1 to 4:1 EtOAc:hexane) to give (S)-di-tert-butyl (3-(4-(5-(4-isopropyl-2-oxooxazolidin-3-yl)pyrazolo[1,5-a]pyrimidin-3-yl)phenyl)-1H-1,2,4-triazol-1-yl)methyl phosphate (0.42 g, 16%). LCMS (APCI+) m/z 612 [M+H]$^+$.

Step 2: To a stirred solution of (S)-di-tert-butyl (3-(4-(5-(4-isopropyl-2-oxooxazolidin-3-yl)pyrazolo[1,5-a]pyrimidin-3-yl)phenyl)-1H-1,2,4-triazol-1-yl)methyl phosphate (420 mg, 0.687 mmol) in dichloromethane (5 mL) was added trifluoroacetic acid dropwise (1 mL) at 0° C. under N$_2$. The reaction mixture was stirred at 0° C. for 1 hour, and then the solvent was evaporated in vacuo. Ether was added to the residue and then decanted. This step was repeated three times. The crude product was suspended in water (8 mL), and the pH was adjusted to 9-9.5 by the addition of 1N NaOH solution. At this point, all the solid dissolved to form a clear solution. i-PrOH (5 mL) was added, and the mixture was heated to reflux. Additional i-PrOH was added until the solution became slightly cloudy. The hot solution was allowed to cool to ambient temperature. The precipitated solid was collected by filtration, washed sequentially with i-PrOH, acetone and ether and dried in vacuo to give (S)-(3-(4-(5-(4-isopropyl-2-oxooxazolidin-3-yl)pyrazolo[1,5-a]pyrimidin-3-yl)phenyl)-1H-1,2,4-triazol-1-yl)methyl phosphate disodium salt as a yellow solid. $^1$H NMR (acid) (400 MHz, DMSO-d$_6$) δ 9.10 (d, J=8.0 Hz, 1H), 8.76 (s, 1H), 8.73 (s, 1H), 8.21 (d, J=8.4 Hz, 2H), 8.05 (d, J=8.4 Hz, 2H), 7.89 (d, J=7.6 Hz, 1H), 5.93 (d, J=10.8 Hz, 2H), 4.95 (m, 1H), 4.52 (d, J=6.0 Hz, 2H), 2.77 (m, 1H), 1.07 (d, 3H), 0.86 (d, 3H); LCMS (APCI+) m/z 500 [M+H]$^+$.

Example 9

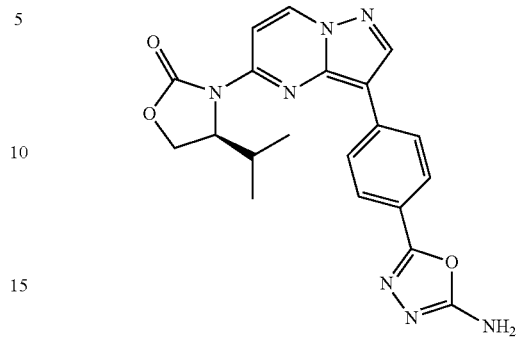

(S)-3-(3-(4-(5-amino-1,3,4-oxadiazol-2-yl)phenyl)pyrazolo[1,5-a]pyrimidin-5-yl)-4-isopropyloxazolidin-2-one Step 1: In a vial, a mixture of (S)-3-(3-bromopyrazolo[1,5-a]pyrimidin-5-yl)-4-isopropyloxazolidin-2-one (Example 1, Step 4; 1.82 g, 5.58 mmol), 4-(4,4,5,5-tetramethyl-1,3,2-dioxaborolan-2-yl)benzoic acid (2.08 g, 8.37 mmol), and 2 M K$_2$CO$_3$ (8.37 mL, 16.7 mmol) in dioxane (20 mL) was degassed by bubbling N$_2$ for 5 minutes. Pd$_2$ dba$_3$ (0.51 g, 0.56 mmol) and XPHOS (0.266 g, 0.558 mmol) were added and the reaction was capped under N$_2$ and heated at 100° C. After 19 hours, the mixture was cooled to ambient temperature, diluted with EtOAc, washed with water and brine, dried over MgSO$_4$, and concentrated under reduced pressure. The crude was purified by silica gel flash column chromatography (0-3% MeOH in dichloromethane) to afford 0.92 g (45%) of (S)-4-(5-(4-isopropyl-2-oxooxazolidin-3-yl)pyrazolo[1,5-a]pyrimidin-3-yl)benzoic acid. LCMS (APCI+) m/z 367.4 [M+H]$^+$.

Step 2: EDCI (2.39 g, 12.45 mmol) was added to a mixture of (S)-4-(5-(4-isopropyl-2-oxooxazolidin-3-yl)pyrazolo[1,5-a]pyrimidin-3-yl)benzoic acid (0.76 g, 2.1 mmol) and HOBT-H$_2$O (0.95 g, 6.226 mmol) in DMF (10 mL) at ambient temperature, and the reaction mixture was stirred for 20 minutes at ambient temperature. A solution of hydrazine hydrate (0.31 mL, 6.2 mmol) in DMF and triethylamine (1.5 mL, 10.38 mmol) were added. The resulting mixture was stirred for 1 hour at ambient temperature. The reaction mixture was diluted with EtOAc, washed with aqueous NH$_4$Cl, NaHCO$_3$, and brine, dried over MgSO$_4$, and concentrated under reduced pressure. The crude was purified by silica gel flash column chromatography (0-5% MeOH in dichloromethane) to afford 0.50 g (64%) of (S)-4-(5-(4-isopropyl-2-oxooxazolidin-3-yl)pyrazolo[1,5-a]pyrimidin-3-yl)benzohydrazide. LCMS (APCI+) m/z 381.4 [M+H]$^+$.

Step 3: To a suspension of (S)-4-(5-(4-isopropyl-2-oxooxazolidin-3-yl)pyrazolo[1,5-a]pyrimidin-3-yl)benzohydrazide (50 mg, 0.131 mmol) in 3 mL of p-dioxane was added cyanogen bromide (30.6 mg, 0.289 mmol) followed by a solution of NaHCO$_3$ (13.3 mg, 0.158 mmol) in 1.5 mL of water. The resulting mixture became a clear tan solution within 3 minutes, and was allowed to stir at ambient temperature for 17 hours. The reaction was diluted with EtOAc, and the organic layer was washed with water and brine. The combined organic layers were dried over MgSO$_4$ and concentrated under reduced pressure. The crude was purified by silica gel flash column chromatography (0-8% MeOH in dichloromethane) to afford 26 mg (49%) of (S)-3-(3-(4-(5-amino-1,3,4-oxadiazol-2-yl)phenyl)pyrazolo[1,5-a]pyrimidin-5-yl)-4-isopropyloxazolidin-2-one. $^1$H NMR (400 MHz, DMSO-$d_6$) δ 9.11 (d, 1H), 8.79 (s, 1H), 8.26 (d, 2H), 7.91 (d, 1H), 7.82 (d, 2H), 7.23 (s, 2H), 4.97 (m, 1H), 4.52 (d, 2H), 2.76 (m, 1H), 1.06 (d, 3H), 0.86 (d, 3H); LCMS (APCI+) m/z 406.4 [M+H]$^+$.

Example 10

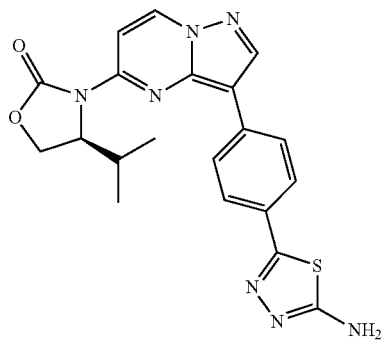 [SMILES: CC(C)[C@H]1COC(=O)N1c1ccn2ncc(-c3ccc(-c4nnc(N)s4)cc3)c2n1]

(S)-3-(3-(4-(5-amino-1,3,4-thiadiazol-2-yl)phenyl)pyrazolo[1,5-a]pyrimidin-5-yl)-4-isopropyloxazolidin-2-one Step 1: EDCI (157 mg, 0.819 mmol) was added to a mixture of (S)-4-(5-(4-isopropyl-2-oxooxazolidin-3-yl)pyrazolo[1,5-a]pyrimidin-3-yl)benzoic acid (Example 9, Step 1; 50 mg, 0.136 mmol) and HOBT-H$_2$O (62.7 mg, 0.409 mmol) in DMF (2 mL) at ambient temperature, and the reaction mixture was stirred for 20 minutes at ambient temperature. 1.0 mL of hydrazinecarbothioamide (12.4 mg, 0.136 mmol) in DMF and triethylamine (95 μL, 0.682 mmol) were added. The resulting mixture was stirred for 1 hour at ambient temperature. The reaction mixture was diluted with EtOAc, washed with aqueous NH$_4$Cl, NaHCO$_3$, and brine, dried over MgSO$_4$, and concentrated under reduced pressure. The crude material was purified by silica gel flash column chromatography (0-5% MeOH in dichloromethane) to afford 20.2 mg (21%) of (S)-2-(4-(5-(4-isopropyl-2-oxooxazolidin-3-yl)pyrazolo[1,5-a]pyrimidin-3-yl)benzoyl)hydrazinecarbothioamide. LCMS (APCI−) m/z 438.4 [M−H]$^+$.

Step 2: To a solution of (S)-2-(4-(5-(4-isopropyl-2-oxooxazolidin-3-yl)pyrazolo[1,5-a]pyrimidin-3-yl)benzoyl)hydrazinecarbothioamide (20.2 mg, 0.029 mmol) in dichloromethane (3 ml) was added PPh$_3$ (22.7 mg, 0.087 mmol), triethylamine (32 μL, 0.231 mmol), and CCl$_4$ (13.3 mg, 0.087 mmol). The reaction mixture was heated to 50° C. for 3 hours. After cooling to ambient temperature the reaction mixture was dissolved in EtOAc, washed with water then brine, dried over MgSO$_4$, and concentrated under reduced pressure. The crude was purified by silica gel flash column chromatography (0-5% 7N NH$_3$-MeOH in dichloromethane). The product was then subjected to preparative plate chromatography (10% MeOH in dichloromethane) to afford 0.9 mg (7%) of (S)-3-(3-(4-(5-amino-1,3,4-thiadiazol-2-yl)phenyl)pyrazolo[1,5-a]pyrimidin-5-yl)-4-isopropyloxazolidin-2-one. $^1$H NMR (400 MHz, CDCl$_3$) δ 8.60 (d, 1H), 8.42 (s, 1H), 8.08 (m, 3H), 7.76 (d, 2H), 4.95 (m, 1H), 4.46 (m, 2H), 2.85 (m, 1H), 1.10 (d, 3H), 0.95 (d, 3H); LCMS (APCI+) m/z 422.5 [M+H]$^+$.

Example 11

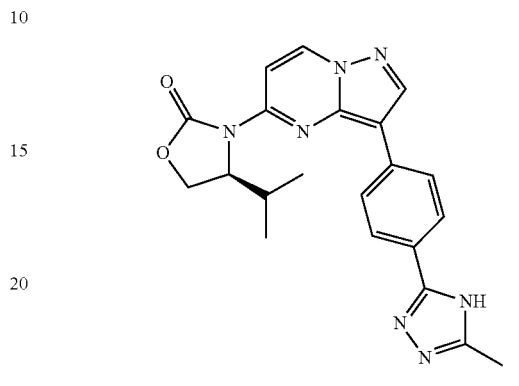

(S)-4-isopropyl-3-(3-(4-(5-methyl-4H-1,2,4-triazol-3-yl)phenyl)pyrazolo[1,5-a]pyrimidin-5-yl)oxazolidin-2-one Step 1: To a stirred suspension of (S)-4-(5-(4-isopropyl-2-oxooxazolidin-3-yl)pyrazolo[1,5-a]pyrimidin-3-yl)benzohydrazide (Example 9, Step 2; 95 mg, 0.25 mmol) in a mixture of THF (2 mL) and DMF (1 mL) at ambient temperature was added ethyl acetimidate HCl salt (37 mg, 0.30 mmol) and triethylamine (45 μL, 0.32 mmol). The reaction mixture was stirred at 0° C. for 2 hours followed by stirring at ambient temperature for 17 hours. The mixture was poured into water, neutralized with dilute aqueous HCl, extracted with EtOAc, dried over MgSO$_4$, and concentrated to afford 40 mg (38%) of (S)—N'-(1-imino ethyl)-4-(5-(4-isopropyl-2-oxooxazolidin-3-yl)pyrazolo[1,5-a]pyrimidin-3-yl)benzohydrazide which was triturated with dichloromethane. LCMS (APCI+) m/z 422.1 [M+H]$^+$.

Step 2: PS-Triphenylphosphine resin (Biotage, catalog No. 800380, 2.28 mmol/g, 0.167 g, 0.38 mmol)triethylamine (0.132 mL, 0.95 mmol), and CCl$_4$ (40 μL, 0.38 mmol) were added to a suspension of (S)—N'-(1-iminoethyl)-4-(5-(4-isopropyl-2-oxooxazolidin-3-yl)pyrazolo[1,5-a]pyrimidin-3-yl)benzohydrazide (40 mg, 0.095 mmol) in dichloromethane (3 mL) and MeCN (3 mL), and the reaction mixture was heated to 50° C. for 2 hours. After cooling to ambient temperature, the mixture was treated with EtOAc, washed with water, dried over MgSO$_4$, concentrated under reduced pressure. The crude was purified by silica gel flash column chromatography (4% MeOH in dichloromethane) to afford 7 mg (18%) of (S)-4-isopropyl-3-(3-(4-(5-methyl-4H-1,2,4-triazol-3-yl)phenyl)pyrazolo[1,5-a]pyrimidin-5-yl)oxazolidin-2-one. $^1$H NMR (400 MHz, CD$_3$OD/CDCl$_3$) δ 8.70 (d, 1H), 8.48 (s, 1H), 8.13 (m, 2H), 8.05 (m, 3H), 5.05 (m, 1H), 4.50 (m, 2H), 2.92 (m, 1H), 2.52 (s, 3H), 1.12 (d, 3H), 0.96 (d, 3H); LCMS (APCI+) m/z 404.3 [M+H]$^+$.

Example 12

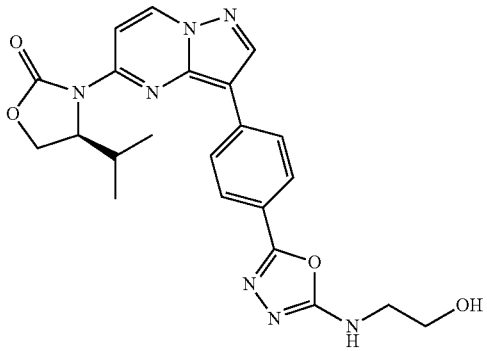 [SMILES: CC(C)[C@H]1COC(=O)N1c1ccn2ncc(-c3ccc(-c4nnc(NCCO)o4)cc3)c2n1]

(S)-3-(3-(4-(5-(2-hydroxyethylamino)-1,3,4-oxadiazol-2-yl)phenyl)pyrazolo[1,5-a]pyrimidin-5-yl)-4-isopropyloxazolidin-2-one Step 1: To a solution of (S)-4-(5-(4-isopropyl-2-oxooxazolidin-3-yl)pyrazolo[1,5-a]pyrimidin-3-yl)benzohydrazide (Example 9, Step 2; 91 mg, 0.239 mmol) in DMF (2 mL) was added di(1H-imidazol-1-yl)methanone (40.7 mg, 0.251 mmol). The reaction mixture was allowed to stir for 1 hour at ambient temperature, then dissolved in EtOAc, washed with water and brine, and concentrated. The resulting solid was suspended in dichloromethane, filtered, washed with dichloromethane, then concentrated to give crude product. The residue was purified by silica gel chromatography (0-5% MeOH in dichloromethane) to afford 42.8 mg (44%) of (S)-5-(4-(5-(4-isopropyl-2-oxooxazolidin-3-yl)pyrazolo[1,5-a]pyrimidin-3-yl)phenyl)-1,3,4-oxadiazol-2(3H)-one. LCMS (APCI+) m/z 407.5 [M+H]+.

Step 2: A suspension of (S)-5-(4-(5-(4-isopropyl-2-oxooxazolidin-3-yl)pyrazolo[1,5-a]pyrimidin-3-yl)phenyl)-1,3,4-oxadiazol-2(3H)-one (42.8 mg, 0.105 mmol) and 2-aminoethanol (19.1 µL, 0.316 mmol) in EtOH (2 mL) was heated to reflux for 22 hours. After the reaction mixture was cooled to ambient temperature, the solvent was removed under reduced pressure. The crude product was flash chromatographed (0-10% MeOH in dichloromethane) to afford 14.4 mg (29%) of (S)—N-(2-hydroxyethyl)-2-(4-(5-(4-isopropyl-2-oxooxazolidin-3-yl)pyrazolo[1,5-a]pyrimidin-3-yl)benzoyl)hydrazinecarboxamide. LCMS (APCI−) m/z 466.5 [M−H]+.

Step 3: To a suspension of (S)—N-(2-hydroxyethyl)-2-(4-(5-(4-isopropyl-2-oxooxazolidin-3-yl)pyrazolo[1,5-a]pyrimidin-3-yl)benzoyl)hydrazinecarboxamide (14.4 mg, 0.031 mmol) in dichloromethane (1 mL) and MeCN (1 mL) was added PS-triphenylphosphine resin (0.054 g, 2.28 mmol/g, 0.123 mmol), triethylamine (44 µL, 0.308 mmol), and CCl4 (12 µL, 0.123 mmol), and the reaction mixture was heated to 50° C. for 4 hours. After the mixture was cooled at ambient temperature, the reaction mixture was treated with EtOAc, washed with water, dried over MgSO4, and concentrated under reduced pressure. The crude was then purified by preparative plate silica gel chromatography (10% MeOH in dichloromethane) to afford 5 mg (35%) of (S)-3-(3-(4-(5-(2-hydroxyethylamino)-1,3,4-oxadiazol-2-yl)phenyl)pyrazolo[1,5-a]pyrimidin-5-yl)-4-isopropyloxazolidin-2-one. 1H NMR (400 MHz, CDCl3) δ 8.60 (d, 1H), 8.43 (s, 1H), 8.08 (m, 3H), 7.92 (d, 2H), 4.96 (m, 1H), 4.44 (m, 2H), 3.94 (t, 2H), 3.65 (m, 2H), 2.88 (m, 1H), 1.09 (d, 3H), 0.95 (d, 3H); LCMS (APCI+) m/z 450.6 [M+H]+.

Example 13

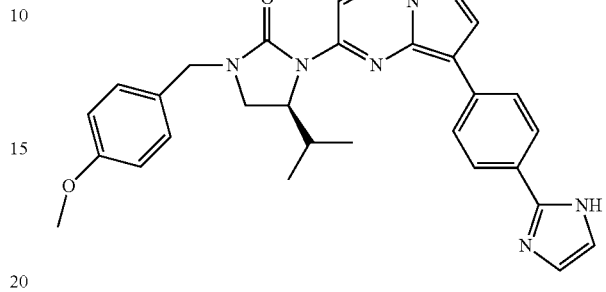

(S)-3-(3-(4-(1H-imidazol-2-yl)phenyl)pyrazolo[1,5-a]pyrimidin-5-yl)-4-isopropyl-1-(4-methoxybenzyl)imidazolidin-2-one Step 1: A solution of (S)-2-(tert-butoxycarbonylamino)-3-methylbutanoic acid (2.50 g, 11.5 mmol), HOBT-H2O (1.76 g, 11.5 mmol) and DIEA (6.01 mL, 34.5 mmol) in THF (50 mL) was cooled to 0° C. HBTU (3.23 g, 13.8 mmol) was added and the mixture stirred at 0° C. for 30 minutes prior to addition of 4-methoxy-benzylamine (2.25 mL, 17.3 mmol). The reaction mixture was allowed to warm slowly to ambient temperature while stirring over 48 hours. The reaction mixture was poured into 10% HCl and extracted with ethyl acetate. The combined organic extracts were dried over sodium sulfate, filtered and concentrated. Purification of the crude material by column chromatography, eluting with 1.5-3% MeOH/dichloromethane afforded (S)-tert-butyl 1-(4-methoxybenzylamino)-3-methyl-1-oxobutan-2-ylcarbamate as a light yellow solid, 2.70 g (70%).

Step 2: A solution of (S)-tert-butyl 1-(4-methoxybenzylamino)-3-methyl-1-oxobutan-2-ylcarbamate (1.50 g, 4.46 mmol) in dichloromethane (15 mL) was cooled to 0° C. Trifluoroacetic acid (2 mL) was added and the mixture stirred at 0° C. for 7 hours. The reaction mixture was concentrated and the residue taken up in dichloromethane and washed with saturated aqueous NaHCO3 solution. The combined organic extracts were dried over sodium sulfate, filtered and concentrated. Purification of the crude material by column chromatography, eluting with 4% MeOH/dichloromethane with 0.1% NH4OH, provided (S)-2-amino-N-(4-methoxybenzyl)-3-methylbutanamide (0.770 g, 73%). LCMS (APCI+) m/z 237 [M+H]+.

Step 3: A solution of (S)-2-amino-N-(4-methoxybenzyl)-3-methylbutanamide (0.770 g, 3.26 mmol) in toluene (20 mL) was cooled to 0° C. BH3—SMe2 (3.58 mL, 7.17 mmol) was added and the mixture heated at reflux for 4 hours. MeOH (5 mL) was added and the solution heated for an additional hour. The cooled reaction mixture was concentrated to about one-third its original volume and added HCl (1M in ether). A thick white precipitate formed which was collected, washed with ether and dried to afford (S)—N1-(4-methoxybenzyl)-3-methylbutane-1,2-diamine dihydrochloride (0.80 g, 83%). LCMS (APCI+) m/z 223 [M+H]+.

Step 4: To a suspension of (S)—N-1-(4-methoxybenzyl)-3-methylbutane-1,2-diamine dihydrochloride (0.740 g, 3.33 mmol) in dioxane (25 mL) at ambient temperature was added N-ethyl-N-isopropylpropan-2-amine (1.16 mL, 6.66 mmol) and CDI (0.648 g, 3.99 mmol). The resultant mixture was heated to 85° C. The cooled reaction mixture was concentrated and the residue taken up in EtOAc, washed with brine. Organic layer was dried over sodium sulfate, filtered, concentrated and purified by column chromatography using 1-5% MeOH/dichloromethane with 0.1% NH$_4$OH to afford (S)-4-isopropyl-1-(4-methoxybenzyl)imidazolidin-2-one as a colorless solid (0.50 g, 60%). LCMS (APCI+) m/z 249 [M+H]$^+$.

Step 5: (S)-4-Isopropyl-1-(4-methoxybenzyl)-3-(pyrazolo[1,5-a]pyrimidin-5-yl)imidazolidin-2-one (0.386 g, 52%) was prepared by the procedure described in Example 1, Step 4, from (S)-4-isopropyl-1-(4-methoxybenzyl)imidazolidin-2-one (0.500 g, 2.01 mmol) and 5-chloropyrazolo[1,5-a]pyrimidine (0.300 g, 1.95 mmol). LCMS (APCI+) m/z 366 [M+H]$^+$.

Step 6: (S)-3-(3-Bromopyrazolo[1,5-a]pyrimidin-5-yl)-4-isopropyl-1-(4-methoxybenzyl)imidazolidin-2-one (0.250 g, 53%) was prepared by the procedure described in Example 1, Step 3, from (S)-4-isopropyl-1-(4-methoxybenzyl)-3-(pyrazolo[1,5-a]pyrimidin-5-yl)imidazolidin-2-one (0.386 g, 1.06 mmol). LCMS (APCI+) m/z 444, 446 [M+H]$^+$.

Step 7: (S)-4-Isopropyl-1-(4-methoxybenzyl)-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (22.0 mg, 16%) was prepared by the procedure described in Example 1, Step 8, from (S)-3-(3-bromopyrazolo[1,5-a]pyrimidin-5-yl)-4-isopropyl-1-(4-methoxybenzyl)imidazolidin-2-one (93.0 mg, 0.209 mmol). LCMS (APCI+) m/z 638 [M+H]$^+$.

Step 8: (S)-3-(3-(4-(1H-Imidazol-2-yl)phenyl)pyrazolo[1,5-a]pyrimidin-5-yl)-4-isopropyl-1-(4-methoxybenzyl)imidazolidin-2-one (1.0 mg, 5%) was prepared by the procedure described in Example 1, Step 9, from (S)-4-isopropyl-1-(4-methoxybenzyl)-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (22.0 mg, 0.0340 mmol). LCMS (APCI+) m/z 508 [M+H]$^+$; $^1$H NMR (400 MHz, CD$_3$OD) δ 8.69 (d, J=7.8 Hz, 1H), 8.47 (s, 1H), 8.19 (d, J=7.8 Hz, 1H), 8.16 (d, J=8.2 Hz, 2H), 7.88 (d, J=8.2 Hz, 2H), 7.28 (d, J=8.2 Hz, 2H), 7.15 (s, 2H), 6.93 (d, J=8.2 Hz, 2H), 4.78-4.82 (m, 1H), 4.57 (d, J=14.4 Hz, 1H), 4.27 (d, J=14.4 Hz, 1H), 3.79 (s, 3H), 3.46 (t, J=9.8 Hz, 1H), 3.25 (dd, J=3.1, 9.8 Hz, 1H), 2.83-2.90 (m, 1H), 1.03 (d, J=7.0 Hz, 3H), 0.72 (d, J=7.0 Hz, 3H).

Example 14

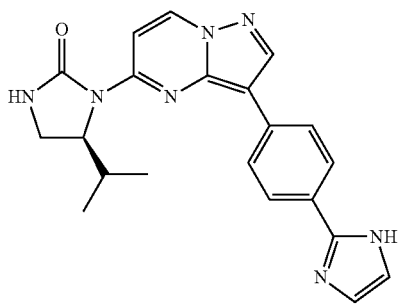 [SMILES: CC(C)[C@H]1CNC(=O)N1c1ccn2ncc(-c3ccc(-c4ncc[nH]4)cc3)c2n1]

(S)-1-(3-(4-(1H-imidazol-2-yl)phenyl)pyrazolo[1,5-a]pyrimidin-5-yl)-5-isopropylimidazolidin-2-one Step 1: A solution of (S)-methyl-2-isocyanato-3-methylbutanoate (4.46 mL, 29.9 mmol) in CHCl$_3$ (50 mL) was added drop-wise to a solution of (2,4-dimethoxyphenyl)methanamine (5.00 g, 29.9 mmol) and NEt$_3$ (8.34 mL, 59.8 mmol) in CHCl$_3$ (100 mL) at ambient temperature. The resultant mixture was heated at 60° C. for 12 hours, then cooled to ambient temperature. The cooled reaction mixture was concentrated to provide (S)-methyl 2-(3-(2,4-dimethoxybenzyl)ureido)-3-methylbutanoate as a white solid, 1.25 g (13%). LCMS (APCI+) m/z 325 [M+H]$^+$.

Step 2: A solution of (S)-methyl 2-(3-(2,4-dimethoxybenzyl)ureido)-3-methylbutanoate (1.00 g, 3.10 mmol) in MeOH (7.5 mL) and NEt$_3$ (0.430 mL, 3.10 mmol) in a sealed vessel was placed in preheated sand bath (at 100° C.) and heated for 18 hours. The cooled reaction mixture was concentrated and the residue was taken up in ether, washed with water, dried over sodium sulfate and filtered. Purification of the crude material by column chromatography, eluting with 1-3% MeOH/dichloromethane, afforded (S)-3-(2,4-dimethoxybenzyl)-5-isopropylimidazolidine-2,4-dione as an ivory colored solid (0.640 g, 71%). LCMS (APCI+) m/z 293 [M+H]$^+$.

Step 3: To a solution of (S)-3-(2,4-dimethoxybenzyl)-5-isopropyl-imidazolidine-2,4-dione (0.550 g, 1.88 mmol) in THF (50 mL) at ambient temperature was added bis(2-methoxyethoxy)aluminumhydride (Red-Al) (2.69 ml, 9.41 mmol) and the resultant mixture heated at reflux for 1 hour. The reaction mixture was cooled to 0° C. and sodium sulfate decahydrate was added portion-wise. The resultant thick emulsion was diluted with THF and filtered through a pad of Celite. The filtrate was concentrated to a clear oil. Purification of the crude material by column chromatography, eluting with 1-5% MeOH/dichloromethane, afforded (S)-1-(2,4-dimethoxybenzyl)-4-isopropylimidazolidin-2-one as a colorless solid (0.329 g, 63%). LCMS (APCI+) m/z 279 [M+H]$^+$.

Step 4: (S)-3-(3-Bromopyrazolo[1,5-a]pyrimidin-5-yl)-1-(2,4-dimethoxy-benzyl)-4-isopropylimidazolidin-2-one (61.0 mg, 30%) was prepared by the procedure described in Example 1, Step 4, from (S)-1-(2,4-dimethoxybenzyl)-4-isopropylimidazolidin-2-one (0.100 g, 0.430 mmol). LCMS (APCI+) m/z 474, 476 [M+H]$^+$.

Step 5: (S)-1-(2,4-Dimethoxybenzyl)-4-isopropyl-3-(3-(4-(1-((2-(trimethyl-silyl)ethoxy)methyl)-1H-imidazol-2-yl)phenyl)pyrazolo[1,5-a]pyrimidin-5-yl)imidazolidin-2-one (32.0 mg, 37%) was prepared by the procedure described in Example 1, Step 8, from (S)-3-(3-bromopyrazolo[1,5-a]pyrimidin-5-yl)-1-(2,4-dimethoxybenzyl)-4-isopropylimidazolidin-2-one (61.0 mg, 0.129 mmol). LCMS (APCI+) m/z 668 [M+H]$^+$.

Step 6: (S)-1-(3-(4-(1H-imidazol-2-yl)phenyl)pyrazolo[1,5-a]pyrimidin-5-yl)-5-isopropylimidazolidin-2-one (1.4 mg, 14%) was prepared by the procedure described in Example 1, Step 9, from (S)-1-(2,4-dimethoxybenzyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (16.0 mg, 0.0240 mmol). LCMS (APCI+) m/z 388 [M+H]$^+$; $^1$H NMR (400 MHz, DMSO-d$_6$) δ 8.68 (d, J=8.2 Hz, 1H), 8.48 (s, 1H), 8.18 (d, J=8.6 Hz, 2H), 8.12 (d, J=7.8 Hz, 1H), 7.90 (d, J=8.6 Hz, 2H), 7.13 (s, 2H), 4.93-4.96 (m, 1H), 3.61 (t, J=9.6 Hz, 1H), 3.45 (dd, J=3.1, 9.8 Hz, 1H), 2.90-2.96 (m, 1H), 1.12 (d, J=7.0 Hz, 3H), 0.94 (d, J=7.0 Hz, 3H).

Example 15

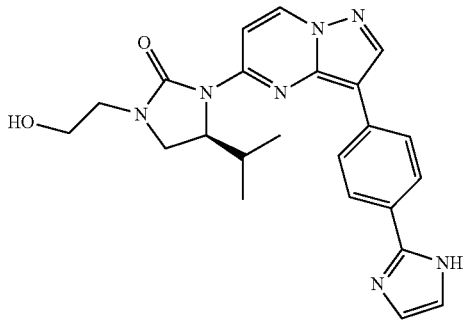 [SMILES: CC(C)[C@H]1CN(CCO)C(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-4-isopropyloxazolidin-2-one Step 1: To a solution of (S)-2-amino-3-methylbutan-1-ol (3.3 g, 32 mmol) in DMF was added 3-bromo-5-chloropyrazolo[1,5-a]pyrimidine (2.5 g, 11 mmol) and N-ethyl-N-isopropylpropan-2-amine (4.2 g, 32 mmol) and the reaction was heated to 100° C. for 4 hours. The reaction mixture was poured into EtOAc and washed with water and brine, dried over magnesium sulfate and concentrated in vacuo to yield (S)-2-(3-bromopyrazolo[1,5-a]pyrimidin-5-ylamino)-3-methylbutan-1-ol (3.2 g, 99%). LCMS (APCI+) m/z 299, 301 [M+H]+.

Step 2: (S)-3-Methyl-2-(3-(4-(1-((2-(trimethylsilyl)ethoxy)methyl)-1H-imidazol-2-yl)phenyl)pyrazolo[1,5-a]pyrimidin-5-ylamino)butan-1-ol (0.77 g, 48%) was prepared by the procedure described in Example 1, Step 8, from (S)-2-(3-bromopyrazolo[1,5-a]pyrimidin-5-ylamino)-3-methylbutan-1-ol (0.97 g, 3.2 mmol). LCMS (APCI+) m/z 493 [M+H]+.

Step 3: To a stirred solution of (S)-3-methyl-2-(3-(4-(1-((2-(trimethylsilyl)ethoxy)methyl)-1H-imidazol-2-yl)phenyl)pyrazolo[1,5-a]pyrimidin-5-ylamino)butan-1-ol (0.41 g, 0.83 mmol) in dichloromethane (6 mL) was added Et3N (0.58 mL, 4.2 mmol) at −15° C. A solution of pyridine-sulfur trioxide complex (0.66 g, 4.2 mmol) in DMSO (6 mL) was added in one portion. After stirring at −15° C. for 30 minutes, the mixture was poured into cold brine solution and extracted with ether. The combined organic extracts were washed with brine, dried and concentrated. The residue was purified by column chromatography (5% MeOH in dichloromethane) to give (S)-3-methyl-2-(3-(4-(1-((2-(trimethylsilyl)ethoxy)methyl)-1H-imidazol-2-yl)phenyl)pyrazolo[1,5-a]pyrimidin-5-ylamino)butanal (0.36 g, 88%). LCMS (APCI+) m/z 491 [M+H]+.

Step 4: To a stirred solution of (S)-3-methyl-2-(3-(4-(1-((2-(trimethylsilyl)ethoxy)methyl)-1H-imidazol-2-yl)phenyl)pyrazolo[1,5-a]pyrimidin-5-ylamino)butanal (27 mg, 0.055 mmol) in DCE (1 mL) was added a solution of 2-(tert-butyldimethylsilyloxy)ethanamine (29 mg, 0.17 mmol) in THF (0.2 mL). The reaction was allowed to stir at ambient temperature for 15 minutes, at which point Na(OAc)3BH was added and the reaction allowed to stir at ambient temperature for 2 hours. The reaction mixture was partitioned between saturated aqueous NaHCO3 and dichloromethane. The aqueous layer was extracted with dichloromethane. The combined extracts were washed with brine, dried and concentrated to give (S)—N1-(2-(tert-butyldimethylsilyloxy)ethyl)-3-methyl-N2-(3-(4-(1-((2-(trimethylsilyl)ethoxy)methyl)-1H-imidazol-2-yl)phenyl)pyrazolo[1,5-a]pyrimidin-5-yl)butane-1,2-diamine. The crude was used in the next step without further purification. LCMS (APCI+) m/z 650.9 [M+H]+.

Step 5: To a stirred solution of (S)—N1-(2-(tert-butyldimethylsilyloxy)ethyl)-3-methyl-N2-(3-(4-(1-((2-(trimethylsilyl)ethoxy)methyl)-1H-imidazol-2-yl)phenyl)pyrazolo[1,5-a]pyrimidin-5-yl)butane-1,2-diamine (0.055 mmol) in dichloromethane (1 mL) was added diisopropylethylamine (0.019 mL, 0.14 mmol). Trichloromethyl chloroformate (0.010 mL, 0.083 mmol) was added dropwise at 0° C. under N2. The reaction mixture was stirred at 0° C. for 30 minutes, then diluted with dichloromethane, washed with aqueous saturated NaHCO3 and brine, dried and concentrated. The residue was purified by silica gel chromatography (dichloromethane:MeOH, 100:1) to give (S)-1-(2-(tert-butyldimethylsilyloxy)ethyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (15 mg, 40% for two steps). LCMS (APCI+) m/z 676.9 [M+H]

Step 6: A solution of (S)-1-(2-(tert-butyldimethylsilyloxy)ethyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (15 mg, 0.022 mmol) in dichloromethane (0.3 mL) and trifluoroacetic acid (0.3 mL) was stirred at ambient temperature for 24 hours. The solvents were evaporated, and the residue was taken up in MeOH. A few drops of 1N LiOH solution was added. The mixture was stirred for 10 minutes. The reaction mixture was diluted with water and extracted with dichloromethane. The combined organic layers were washed with brine, dried and concentrated. The residue was purified by column chromatography (12% MeOH in dichloromethane) to give (S)-3-(3-(4-(1H-imidazol-2-yl)phenyl)pyrazolo[1,5-a]pyrimidin-5-yl)-4-isopropyloxazolidin-2-one (5 mg, 52%) as a pale yellow solid. 1H NMR (400 MHz, CD3OD) δ 8.66 (d, J=7.6 Hz, 1H), 8.47 (s, 1H), 8.18 (d, J=8.4 Hz, 2H), 8.13 (d, J=8.0 Hz, 1H), 7.90 (d, J=8.4 Hz, 2H), 7.16 (s, 2H), 3.2-3.8 (m, 7H), 2.91 (m, 1H), 1.12 (d, 3H), 0.89 (d, 3H). LCMS (APCI+) m/z 432.3 [M+H]

Example 16

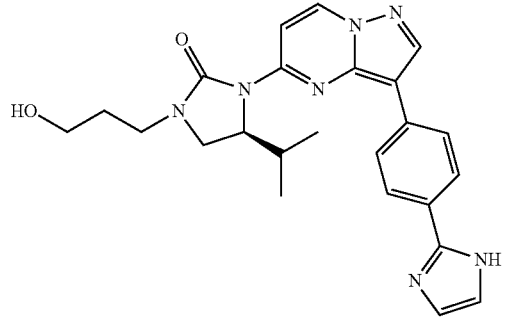 [SMILES: CC(C)[C@H]1CN(CCCO)C(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-1-(3-hydroxypropyl)-4-isopropylimidazolidin-2-one Step 1: (S)—N1-(3-(tert-butyldimethylsilyloxy)propyl)-3-methyl-N2-(3-(4-(1-((2-(trimethylsilyl)ethoxy)methyl)-1H-imidazol-2-yl)phenyl)pyrazolo[1,5-a]pyrimidin-5-yl)butane-1,2-diamine (20 mg, 49%) was prepared by the procedure described in Example 15, Step 4, substituting 3-(tert-butyldimethylsilyloxy)propan-1-amine for 2-(tert-butyldimethylsilyloxy)ethanamine. LCMS (APCI+) m/z 664.3 [M+H]⁺.

Step 2: (S)-1-(3-(tert-Butyldimethylsilyloxy)propyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (19 mg, 91%) was prepared by the procedure described in Example 15, Step 5, from (S)—N1-(3-(tert-butyldimethylsilyloxy)propyl)-3-methyl-N2-(3-(4-(1-((2-(trimethylsilyl)ethoxy)methyl)-1H-imidazol-2-yl)phenyl)pyrazolo[1,5-a]pyrimidin-5-yl)butane-1,2-diamine. LCMS (APCI+) m/z 690.9 [M+H]⁺.

Step 3: (S)-3-(3-(4-(1H-imidazol-2-yl)phenyl)pyrazolo[1,5-a]pyrimidin-5-yl)-1-(3-hydroxypropyl)-4-isopropylimidazolidin-2-one (10 mg, 82%) was prepared by the procedure described in Example 15, Step 6, from (S)-1-(3-(tert-butyldimethylsilyloxy)propyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one. ¹H NMR (400 MHz, CD₃OD) δ 8.67 (d, J=8.0 Hz, 1H), 8.47 (s, 1H), 8.18 (d, J=8.4 Hz, 2H), 8.13 (d, J=7.6 Hz, 1H), 7.90 (d, J=8.4 Hz, 2H), 7.17 (s, 2H), 3.2-3.7 (m, 7H), 2.91 (m, 1H), 1.84 (m, 2H), 1.13 (d, 3H), 0.88 (d, 3H); LCMS (APCI+) m/z 446.7 [M+H]⁺.

Example 17

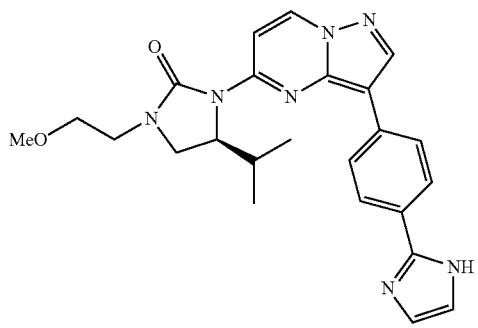 [SMILES: COCCN1C[C@H](C(C)C)N(c2ccn3ncc(-c4ccc(-c5ncc[nH]5)cc4)c3n2)C1=O]

(S)-3-(3-(4-(1H-imidazol-2-yl)phenyl)pyrazolo[1,5-a]pyrimidin-5-yl)-4-isopropyl-1-(2-methoxyethyl)imidazolidin-2-one Step 1: (S)-2-(3-Bromopyrazolo[1,5-a]pyrimidin-5-ylamino)-3-methylbutanal (28 mg, 56%) was prepared by the procedure described in Example 15, Step 3, substituting (S)-2-(3-bromopyrazolo[1,5-a]pyrimidin-5-ylamino)-3-methylbutan-1-ol for (S)-3-methyl-2-(3-(4-(1-((2-(trimethylsilyl)ethoxy)methyl)-1H-imidazol-2-yl)phenyl)pyrazolo[1,5-a]pyrimidin-5-ylamino) butan-1-ol. LCMS (APCI+) m/z 297, 299 [M+H]⁺.

Step 2: (S)—N2-(3-bromopyrazolo[1,5-a]pyrimidin-5-yl)-N1-(2-methoxyethyl)-3-methylbutane-1,2-diamine was prepared by the procedure described in Example 15, Step 4, from (S)-2-(3-bromopyrazolo[1,5-a]pyrimidin-5-ylamino)-3-methylbutanal and 2-methoxyethanamine. LCMS (APCI+) m/z 356, 358 [M+H]⁺.

Step 3: (S)-3-(3-Bromopyrazolo[1,5-a]pyrimidin-5-yl)-4-isopropyl-1-(2-methoxyethyl)imidazolidin-2-one (10 mg, 31% overall yield for Step 2 and Step 3) was prepared by the procedure described in Example 15, Step 5, from (S)—N2-(3-bromopyrazolo[1,5-a]pyrimidin-5-yl)-N1-(2-methoxyethyl)-3-methylbutane-1,2-diamine. LCMS (APCI+) m/z 382, 384 [M+H]⁺.

Step 4: (S)-4-Isopropyl-1-(2-methoxyethyl)-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (15 mg, 48%) was prepared by the procedure described in Example 1, Step 8, from (S)-3-(3-bromopyrazolo[1,5-a]pyrimidin-5-yl)-4-isopropyl-1-(2-methoxyethyl)imidazolidin-2-one. LCMS (APCI+) m/z 576.7 [M+H]⁺.

Step 5: (S)-3-(3-(4-(1H-imidazol-2-yl)phenyl)pyrazolo[1,5-a]pyrimidin-5-yl)-4-isopropyl-1-(2-methoxyethyl)imidazolidin-2-one (9 mg, 78%) was prepared by the procedure described in Example 1, Step 9, from (S)-4-isopropyl-1-(2-methoxyethyl)-3-(3-(4-(1-((2-(trimethylsilyl)ethoxy)methyl)-1H-imidazol-2-yl)phenyl)pyrazolo[1,5-a]pyrimidin-5-yl)imidazolidin-2-one. LCMS (APCI+) m/z 446.7 [M+H]⁺.

Example 18

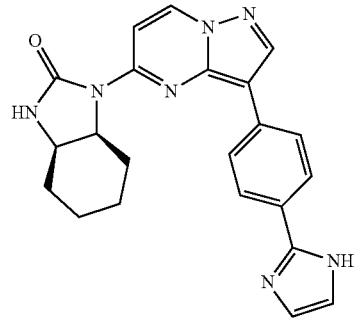 [SMILES: O=C1N[C@@H]2CCCC[C@@H]2N1c1ccn2ncc(-c3ccc(-c4ncc[nH]4)cc3)c2n1]

(3a,7a-cis)-1-(3-(4-(1H-imidazol-2-yl)phenyl)pyrazolo[1,5-a]pyrimidin-5-yl)hexahydro-1H-benzo[d]imidazol-2(3H)-one Step 1: A mixture of 5-chloropyrazolo[1,5-a]pyrimidine (200 mg, 1.30 mmol), cis-cyclohexane-1,2-diamine (297 mg, 2.60 mmol) and diisopropylethylamine (0.794 mL, 4.56 mmol) in NMP (5 mL) was heated at 85° C. for 3 hours. After cooling, dichloromethane (15 mL) was added to the reaction mixture. Trichloromethyl chloroformate (0.39 mL, 3.3 mmol) was added dropwise at 0° C. under N₂. The reaction mixture was stirred at 0° C. for 30 minutes, then diluted with dichloromethane, washed with saturated aqueous NaHCO₃ and brine, dried and concentrated. The residue was purified by column chromatography (1:1 hexanes:EtOAc) to give (3a,7a-cis)-1-(pyrazolo[1,5-a]pyrimidin-5-yl)hexahydro-1H-benzo[d]imidazol-2(3H)-one (80 mg, 24%).

Step 2: (3a,7a-cis)-1-(3-Bromopyrazolo[1,5-a]pyrimidin-5-yl)hexahydro-1H-benzo[d]imidazol-2(3H)-one (20 mg, 19%) was prepared by the procedure described in Example 1, Step 3, from (3a,7a-cis)-1-(pyrazolo[1,5-a]pyrimidin-5-yl)hexahydro-1H-benzo[d]imidazol-2(3H)-one. LCMS (APCI+) m/z 336, 338 [M+H]⁺.

Step 3: (3a,7a-cis)-1-(3-(4-(1-((2-(Trimethylsilyl)ethoxy)methyl)-1H-imidazol-2-yl)phenyl)pyrazolo[1,5-a]pyrimidin-5-yl)hexahydro-1H-benzo[d]imidazol-2(3H)-one (10 mg, 32%) was prepared by the procedure described in Example 1, Step 8, from (3a,7a-cis)-1-(3-bromopyrazolo[1,5-a]pyrimidin-5-yl)hexahydro-1H-benzo[d]imidazol-2(3H)-one. LCMS (APCI+) m/z 530.5 [M+H]⁺.

Step 4: A solution of (3a,7a-cis)-1-(3-(4-(1-((2-(trimethylsilyl)ethoxy)methyl)-1H-imidazol-2-yl)phenyl)pyrazolo[1,5-a]pyrimidin-5-yl)hexahydro-1H-benzo[d]imidazol-2 (3H)-one (10 mg, 0.019 mmol) in dichloromethane (0.3 mL) and trifluoroacetic acid (0.3 mL) was stirred at ambient temperature for 24 hours. The solvents were evaporated. The residue was taken up in MeOH. A few drops of 7N ammonia in MeOH were added. The solvent was evaporated in vacuo. The residue was purified by reverse phase preparative HPLC (5%-95% acetonitrile/water) to give (3a,7a-cis)-1-(3-(4-(1H-imidazol-2-yl)phenyl)pyrazolo[1,5-a]pyrimidin-5-yl)hexahydro-1H-benzo[d]imidazol-2(3H)-one (4 mg, 50%) as a pale yellow solid. LCMS (APCI+) m/z 400.6 [M+H]+.

Example 19

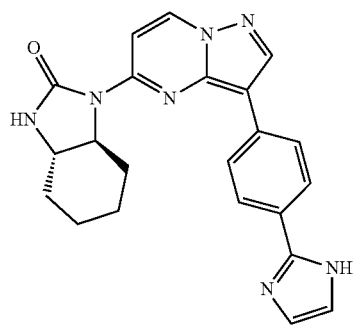 [SMILES: O=C1N[C@H]2CCCC[C@@H]2N1c1ccn2ncc(-c3ccc(-c4ncc[nH]4)cc3)c2n1]

(3aS,7aS)-1-(3-(4-(1H-imidazol-2-yl)phenyl)pyrazolo[1,5-a]pyrimidin-5-yl)hexahydro-1H-benzo[d]imidazol-2(3H)-one Step 1: (3aS,7aS)-1-(3-Bromopyrazolo[1,5-a]pyrimidin-5-yl)hexahydro-1H-benzo[d]imidazol-2(3H)-one (96 mg, 44% overall yield) was prepared by the procedure described in Example 18, Steps 1 and 2, substituting (1S,2S)-cyclohexane-1,2-diamine for cis-cyclohexane-1,2-diamine in Example 18, Step 1. LCMS (APCI+) m/z 336, 338 [M+H]+.

Step 2: (3aS,7aS)-1-(3-(4-(1-((2-(Trimethylsilyl)ethoxy)methyl)-1H-imidazol-2-yl)phenyl)pyrazolo[1,5-a]pyrimidin-5-yl)hexahydro-1H-benzo[d]imidazol-2 (3H)-one (16 mg, 20%) was prepared by the procedure described in Example 1, Step 8, from (3aS,7aS)-1-(3-bromopyrazolo[1,5-a]pyrimidin-5-yl)hexahydro-1H-benzo[d]imidazol-2(3H)-one. LCMS (APCI+) m/z 530 [M+H]+.

Step 3: (3aS,7aS)-1-(3-(4-(1H-Imidazol-2-yl)phenyl)pyrazolo[1,5-a]pyrimidin-5-yl)hexahydro-1H-benzo[d]imidazol-2(3H)-one (6 mg, 50%) was prepared by the procedure described in Example 1, Step 9, from (3aS,7aS)-1-(3-(4-(1-((2-(trimethylsilyl)ethoxy)methyl)-1H-imidazol-2-yl)phenyl)pyrazolo[1,5-a]pyrimidin-5-yl)hexahydro-1H-benzo[d]imidazol-2(3H)-one. LCMS (APCI+) m/z 400.3 [M+H]+.

Example 20

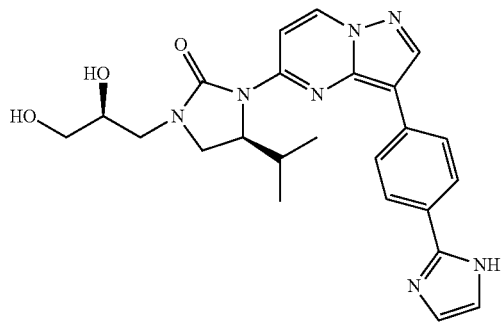 [SMILES: CC(C)[C@H]1CN(C[C@H](O)CO)C(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-1-((S)-2,3-dihydroxypropyl)-4-isopropylimidazolidin-2-one Step 1: (S)—N1-(((S)-2,2-dimethyl-1,3-dioxolan-4-yl)methyl)-3-methyl-N2-(3-(4-(1-((2-(trimethylsilyl)ethoxy)methyl)-1H-imidazol-2-yl)phenyl)pyrazolo[1,5-a]pyrimidin-5-yl)butane-1,2-diamine (32 mg, 65%) was prepared by the procedure described in Example 15, Step 4, substituting (S)-(2,2-dimethyl-1,3-dioxolan-4-yl)methanamine for 2-(tert-butyldimethylsilyloxy)ethanamine. LCMS (APCI+) m/z 606.2 [M+H]+.

Step 2: (S)-1-(((S)-2,2-Dimethyl-1,3-dioxolan-4-yl)methyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one (25 mg, 75%) was prepared by the procedure described in Example 15, Step 5, from (S)—N1-(((S)-2,2-dimethyl-1,3-dioxolan-4-yl)methyl)-3-methyl-N2-(3-(4-(1-((2-(trimethylsilyl)ethoxy)methyl)-1H-imidazol-2-yl)phenyl)pyrazolo[1,5-a]pyrimidin-5-yl)butane-1,2-diamine. LCMS (APCI+) m/z 632.8 [M+H]+.

Step 3: (S)-3-(3-(4-(1H-imidazol-2-yl)phenyl)pyrazolo[1,5-a]pyrimidin-5-yl)-1-((S)-2,3-dihydroxypropyl)-4-isopropylimidazolidin-2-one (14 mg, 77%) was prepared by the procedure described in Example 15, Step 6, from (S)-1-(((S)-2,2-dimethyl-1,3-dioxolan-4-yl)methyl)-4-isopropyl-3-(3-(4-(1-((2-(trimethylsilyl)ethoxy)methyl)-1H-imidazol-2-yl)phenyl)pyrazolo[1,5-a]pyrimidin-5-yl)imidazolidin-2-one. LCMS (APCI+) m/z 462.7 [M+H]+.

Example 21

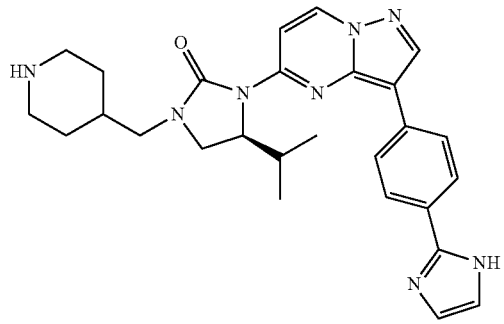 [SMILES: CC(C)[C@H]1CN(CC2CCNCC2)C(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one Step 1: (S)-tert-Butyl 4-((3-methyl-2-(3-(4-(1-((2-(trimethylsilyl)ethoxy)methyl)-1H-imidazol-2-yl)phenyl)pyrazolo[1,5-a]pyrimidin-5-ylamino)butylamino)methyl)piperidine-1-carboxylate (17 mg, 40%) was prepared by the procedure described in Example 15, Step 4, substituting (tert-butyl 4-(aminomethyl)piperidine-1-carboxylate for 2-(tert-butyldimethylsilyloxy)ethanamine. LCMS (APCI+) m/z 689.2 [M+H]+.

Step 2: (S)-tert-Butyl 4-((4-isopropyl-2-oxo-3-(3-(4-(1-((2-(trimethylsilyl)ethoxy)methyl)-1H-imidazol-2-yl)phenyl)pyrazolo[1,5-a]pyrimidin-5-yl)imidazolidin-1-yl)methyl)piperidine-1-carboxylate (15 mg, 85%) was prepared by the procedure described in Example 15, Step 5, from (S)-tert-butyl 4-((3-methyl-2-(3-(4-(1-((2-(trimethylsilyl)ethoxy)methyl)-1H-imidazol-2-yl)phenyl)pyrazolo[1,5-a]pyrimidin-5-ylamino)butylamino)methyl)piperidine-1-carboxylate. LCMS (APCI+) m/z 716.0 [M+H]+.

Step 3: (S)-3-(3-(4-(1H-Imidazol-2-yl)phenyl)pyrazolo[1,5-a]pyrimidin-5-yl)-4-isopropyl-1-(piperidin-4-ylmethyl)imidazolidin-2-one (8 mg, 79%) was prepared by the procedure described in Example 1, Step 9, from (S)-tert-butyl 4-((4-isopropyl-2-oxo-3-(3-(4-(1-((2-(trimethylsilyl)ethoxy)methyl)-1H-imidazol-2-yl)phenyl)pyrazolo[1,5-a]pyrimidin-5-yl)imidazolidin-1-yl)methyl)piperidine-1-carboxylate. LCMS (APCI+) m/z 485.7 [M+H]+.

Example 22

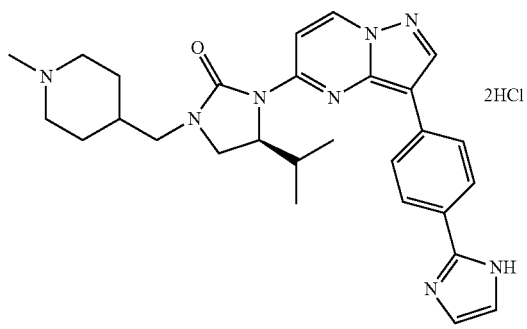 [SMILES: CC(C)[C@H]1CN(CC2CCN(C)CC2)C(=O)N1c1ccn2ncc(-c3ccc(-c4ncc[nH]4)cc3)c2n1]

(S)-3-(3-(4-(1H-imidazol-2-yl)phenyl)pyrazolo[1,5-a]pyrimidin-5-yl)-4-isopropyl-1-((1-methypiperidin-4-yl)methyl)imidazolidin-2-one dihydrochloride To a stirred solution of (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one (Example 21; 2.1 mg, 0.0043 mmol) and formaldehyde (37% aqueous solution, 0.003 mL, 0.04 mmol) in MeCN (0.5 mL) was added NaBH3CN (0.8 mg, 0.42 mmol), and the reaction mixture was stirred at ambient temperature for 1 hour. The reaction mixture was diluted with dichloromethane, washed with saturated aqueous NaHCO3 solution and brine, dried and concentrated. The residue was purified by column chromatography (dichloromethane:7N ammonia in MeOH, 10:1) to give the free base, which was converted to dihydrochloride salt by treatment with 4N HCl in dioxane. LCMS (APCI+) m/z 499.8 [M+H]+.

Example 23

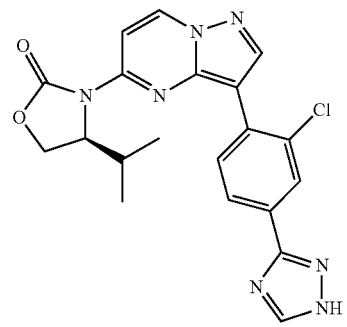 [SMILES: CC(C)[C@H]1COC(=O)N1c1ccn2ncc(-c3ccc(-c4nc[nH]n4)cc3F)c2n1]

(S)-3-(3-(2-chloro-4-(1H-1,2,4-triazol-3-yl)phenyl)pyrazolo[1,5-a]pyrimidin-5-yl)-4-isopropyloxazolidin-2-one Step 1: To a suspension of 4-bromo-3-chlorobenzoic acid (2.00 g, 8.49 mmol) in toluene (10 mL) at ambient temperature was added thionyl chloride (1.85 mL, 25.4 mmol). The reaction mixture was heated at reflux for 20.5 hours, then distilled for 1 hour, collecting 9 mL of distillate. Toluene (10 mL) was added and the reaction was distilled for 30 minutes, collecting 10 mL of distillate. The reaction mixture was cooled to ambient temperature resulting in a suspension. Toluene (10 mL) saturated with ammonia gas was added to the reaction mixture followed by bubbling ammonia gas through the reaction for 10 minutes. The reaction was stirred at ambient temperature for 1 hour. Heptane (10 mL) was added, and the reaction stirred at ambient temperature for 15 minutes, then 0° C. for 1 hour. The solids were collected by vacuum filtration, rinsed with excess heptane, and dried to afford 4-bromo-3-chlorobenzamide (2.327 g, 116.8%) as a white solid which was carried on without further purification.

Step 2: (E)-4-bromo-3-chloro-N-((dimethylamino)methylene)benzamide (2.149 g, 87.5%) was prepared by the procedure described in Example 5, Step 1, substituting 4-bromo-3-chlorobenzamide (1.989 g, 8.483 mmol) for 4-bromobenzamide, to produce a yellow solid which was carried on without further purification.

Step 3: 5-(4-bromo-3-chlorophenyl)-1H-1,2,4-triazole (1.721 g, 99%) was prepared by the procedure described in Example 5, Step 2, substituting (E)-4-bromo-3-chloro-N-((dimethylamino)methylene)benzamide (1.95 g, 6.73 mmol) for (E)-4-bromo-N-((dimethylamino)methylene)benzamide, to produce a light gray solid which was carried on without further purification.

Step 4: 3-(4-bromo-3-chlorophenyl)-1-((2-(trimethylsilyl)ethoxy)methyl)-1H-1,2,4-triazole and 5-(4-bromo-3-chlorophenyl)-1-((2-(trimethylsilyl)ethoxy)methyl)-1H-1,2,4-triazole (2.075 g, 102%) were prepared by the procedure described in Example 1, Step 6, substituting 5-(4-bromo-3-chlorophenyl)-1H-1,2,4-triazole (1.355 g, 5.241 mmol) for 2-(4-bromophenyl)-1H-imidazole, to produce a mixture of two regioisomers as an off-white solid.

Step 5: A mixture of 3-(3-chloro-4-(4,4,5,5-tetramethyl-1,3,2-dioxaborolan-2-yl)phenyl)-1-((2-(trimethylsilyl)ethoxy)

methyl)-1H-1,2,4-triazole and 5-(3-chloro-4-(4,4,5,5-tetramethyl-1,3,2-dioxaborolan-2-yl)phenyl)-1-((2-(trimethylsilyl)ethoxy)methyl)-1H-1,2,4-triazole (1.619 g, 71%) was prepared by the procedure described in Example 1, Step 7, using a mixture of 3-(4-bromo-3-chlorophenyl)-1-((2-(trimethylsilyl)ethoxy)methyl)-1H-1,2,4-triazole and 5-(4-bromo-3-chlorophenyl)-1-((2-(trimethylsilyl)ethoxy)methyl)-1H-1,2,4-triazole (2.039 g, 5.245 mmol), to produce a mixture of two regioisomers as an orange oil.

Step 6: (4S)-3-(3-(2-Chloro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (4S)-3-(3-(2-chloro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.158 g, 57%) were prepared by the procedure described in Example 1, Step 8, using a mixture of 3-(3-chloro-4-(4,4,5,5-tetramethyl-1,3,2-dioxaborolan-2-yl)phenyl)-1-((2-(trimethylsilyl)ethoxy)methyl)-1H-1,2,4-triazole and 5-(3-chloro-4-(4,4,5,5-tetramethyl-1,3,2-dioxaborolan-2-yl)phenyl)-1-((2-(trimethylsilyl)ethoxy)methyl)-1H-1,2,4-triazole (0.295 g, 0.677 mmol), to produce a mixture of two regioisomers as a yellow solid.

Step 7: (4S)-3-(3-(2-Chloro-4-(1H-1,2,4-triazol-3-yl)phenyl)pyrazolo[1,5-a]pyrimidin-5-yl)-4-isopropyloxazolidin-2-one (0.078 g, 65%) was prepared by the procedure described in Example 1, Step 9, using a mixture of (4S)-3-(3-(2-chloro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (4S)-3-(3-(2-chloro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.158 g, 0.285 mmol), to produce a yellow solid. LCMS (APCI+) m/z 424.6 [M+H]+; 1H-NMR (400 MHz, DMSO-$d_6$) δ 14.21 (broad s, 1H), 9.13 (d, J=7.8 Hz, 1H), 8.64 (s, 1H), 8.29 (s, 1H), 8.15 (s, 1H), 8.08 (m, 1H), 8.00 (d×d, J=8.2, 1.5 Hz, 1H), 7.93 (d, J=7.8 Hz, 1H), 4.85-4.81 (m, 1H), 4.45-4.44 (m, 2H), 2.70-2.66 (m, 1H), 0.95 (d, J=7.1 Hz, 3H), 0.84 (d, J=7.0 Hz, 3H).

Example 24

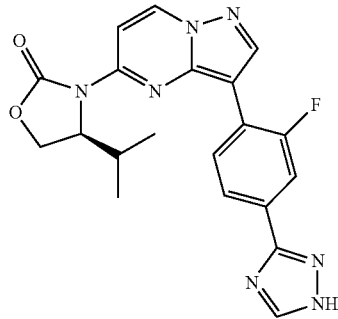

(S)-3-(3-(2-fluoro-4-(1H-1,2,4-triazol-3-yl)phenyl)pyrazolo[1,5-a]pyrimidin-5-yl)-4-isopropyloxazolidin-2-one Step 1: To a suspension of 4-bromo-3-fluorobenzoic acid (1.50 g, 6.85 mmol) in toluene (10 mL) at ambient temperature was added thionyl chloride (1.0 mL, 14 mmol). The reaction mixture was heated at 70° C. for 17 hours, at reflux for 1.5 hours, stirred at ambient temperature for 75 hours, heated at reflux for 18.5 hours, and stirred at ambient temperature for 1 hour. Thionyl chloride (0.25 mL, 3.4 mmol) was added and the reaction mixture was heated at reflux for 3 hours. The reaction was cooled and condensed to an oily solid mixture. Toluene (10 mL), ammonium chloride (0.73 g, 14 mmol) and diisopropylamine (3.6 mL, 21 mmol) were added, and the mixture was stirred at ambient temperature for 17 hours, heated at 50° C. for 5 hours, then cooled to ambient temperature. The reaction mixture was partitioned between EtOAc (10 mL) and $H_2O$ (10 mL), separated, and the aqueous layer further extracted with EtOAc (15 mL). The combined organic extracts were washed with 1N HCl (20 mL), 1N NaOH (20 mL), brine (20 mL), dried ($MgSO_4$), filtered, and concentrated to afford 4-bromo-3-fluorobenzamide (0.938 g, 63%) as a light-yellow solid which was carried on without further purification.

Step 2: (E)-4-Bromo-N-((dimethylamino)methylene)-3-fluorobenzamide (0.737 g, 63%) was prepared by the procedure described in Example 5, Step 1, substituting 4-bromo-3-fluorobenzamide (0.936 g, 4.29 mmol) for 4-bromobenzamide, to produce a light tan solid which was carried on without further purification.

Step 3: 5-(4-Bromo-3-fluorophenyl)-1H-1,2,4-triazole (0.418 g, 65%) was prepared by the procedure described in Example 5, Step 2, using (E)-4-bromo-N-((dimethylamino)methylene)-3-fluorobenzamide (0.730 g, 2.67 mmol), to produce a white solid which was carried on without further purification.

Step 4: 3-(4-Bromo-3-fluorophenyl)-1-((2-(trimethylsilyl)ethoxy)methyl)-1H-1,2,4-triazole and 5-(4-bromo-3-fluorophenyl)-1-((2-(trimethylsilyl)ethoxy)methyl)-1H-1,2,4-triazole (0.595 g, 93%) were prepared by the procedure described in Example 1, Step 6, using 5-(4-bromo-3-fluorophenyl)-1H-1,2,4-triazole (0.415 g, 1.71 mmol), to produce a mixture of two regioisomers as a moist, off-white solid.

Step 5: 3-(3-Fluoro-4-(4,4,5,5-tetramethyl-1,3,2-dioxaborolan-2-yl)phenyl)-1-((2-(trimethylsilyl)ethoxy)methyl)-1H-1,2,4-triazole and 5-(3-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.844 g, 126.0%) were prepared by the procedure described in Example 1, Step 7, using a mixture of 3-(4-bromo-3-fluorophenyl)-1-((2-(trimethylsilyl)ethoxy)methyl)-1H-1,2,4-triazole and 5-(4-bromo-3-fluorophenyl)-1-((2-(trimethylsilyl)ethoxy)methyl)-1H-1,2,4-triazole (0.595 g, 1.60 mmol), to produce a mixture of two regioisomers as a dark amber oil.

Step 6: (4S)-3-(3-(2-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (4S)-3-(3-(2-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.508 g, 80%) were prepared by the procedure described in Example 1, Step 8, using a mixture of 3-(3-fluoro-4-(4,4,5,5-tetramethyl-1,3,2-dioxaborolan-2-yl)phenyl)-1-((2-(trimethylsilyl)ethoxy)methyl)-1H-1,2,4-triazole and 5-(3-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.671 g, 1.60 mmol), to produce a mixture of two regioisomers as a yellow solid.

Step 7: (4S)-3-(3-(2-Fluoro-4-(1H-1,2,4-triazol-3-yl)phenyl)pyrazolo[1,5-a]pyrimidin-5-yl)-4-isopropyloxazolidin-2-one (0.186 g, 48%) was prepared by the procedure described in Example 1, Step 9, using a mixture of (4S)-3-(3-(2-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (4S)-3-(3-(2-fluoro-4-(1-((2-(trimethylsilyl)ethoxy)methyl)-1H-1,2,4-triazol-5-yl)

phenyl)pyrazolo[1,5-a]pyrimidin-5-yl)-4-isopropyloxazolidin-2-one (0.507 g, 0.943 mmol), to produce a yellow solid. LCMS (APCI+) m/z 408.6 [M+H]+; 1H-NMR (400 MHz, DMSO-d6) δ 14.27 (broad s, 1H), 9.16 (d, J=7.8 Hz, 1H), 8.57-8.52 (m, 3H), 7.96-7.85 (m, 3H), 4.97-4.93 (m, 1H), 4.52-4.48 (m, 2H), 2.78-2.71 (m, 1H), 1.05 (d, J=7.1 Hz, 3H), 0.86 (d, J=6.8 Hz, 3H).

Example 25

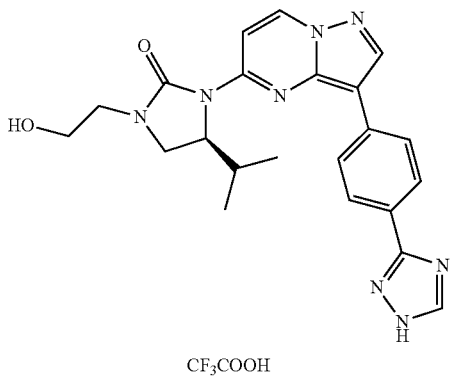 [SMILES: CC(C)[C@H]1CN(CCO)C(=O)N1c1ccn2ncc(-c3ccc(-c4nc[nH]n4)cc3)c2n1 ; "CF3COOH"]

CF3COOH (S)-3-(3-(4-(1H-1,2,4-triazol-3-yl)phenyl)pyrazolo [1,5-a]pyrimidin-5-yl)-1-(2-hydroxyethyl)-4-isopropylimidazolidin-2-one trifluoroacetate Step 1: To a solution of isoindoline-1,3-dione (4.9 g, 34 mmol) in THF cooled to 0° C. was added triphenylphosphine (8.8 g, 34 mmol) and (S)-2-(3-bromopyrazolo[1,5-a]pyrimidin-5-ylamino)-3-methylbutan-1-ol (Example 15, Step 1; 6.7 g, 22 mmol) and the reaction stirred at ambient temperature until all reactants were dissolved. To the reaction was added (E)-diisopropyl diazene-1,2-dicarboxylate (8.2 g, 40 mmol) and the reaction was stirred for 2 hours at ambient temperature. The reaction was concentrated in vacuo and the material chromatographed using 20% EtOAc/dichloromethane as eluent to yield (S)-2-(2-(3-bromopyrazolo[1,5-a]pyrimidin-5-ylamino)-3-methylbutyl)isoindoline-1,3-dione (3.8 g, 40%).

Step 2: To a solution of (S)-2-(2-(3-bromopyrazolo[1,5-a]pyrimidin-5-ylamino)-3-methylbutyl)isoindoline-1,3-dione (3.8 g, 8.9 mmol) in methanol was added methylhydrazine (4.1 g, 89 mmol) and the reaction stirred overnight at ambient temperature. The reaction was concentrated and the residue was purified by chromatography, eluting with 10% MeOH/dichloromethane to 5% MeOH solution containing 7M ammonia/dichloromethane to yield (S)—N2-(3-bromopyrazolo[1,5-a]pyrimidin-5-yl)-3-methylbutane-1,2-diamine (2.2 g, 83%).

Step 3: To a solution of (S)—N2-(3-bromopyrazolo[1,5-a] pyrimidin-5-yl)-3-methylbutane-1,2-diamine (0.75 g, 2.52 mmol) in DMF was added N-ethyl-N-isopropylpropan-2-amine (1.38 ml, 7.55 mmol) and di(1H-imidazol-1-yl)methanone (0.816 g, 5.03 mmol) and the reaction stirred overnight at ambient temperature. The reaction was poured into water and extracted into EtOAc. The combined organic layers were washed with brine, dried over magnesium sulfate and concentrated in vacuo. The crude material was purified by chromatography, eluting with 2% MeOH/dichloromethane, to yield (S)-1-(3-bromopyrazolo[1,5-a]pyrimidin-5-yl)-5-isopropylimidazolidin-2-one (0.48 g, 58%).

Step 4: To a sealed tube was added (S)-1-(3-bromopyrazolo[1,5-a]pyrimidin-5-yl)-5-isopropylimidazolidin-2-one (1.50 g, 4.63 mmol), 3-(4-(4,4,5,5-tetramethyl-1,3,2-dioxaborolan-2-yl)phenyl)-1-((2-(trimethylsilyl)ethoxy)methyl)-1H-1,2,4-triazole (2.51 g, 6.25 mmol), dicyclohexyl(2', 4',6'-triisopropylbiphenyl-2-yl)phosphine (XPHOS) (0.221 g, 0.463 mmol) and Pd2dba3 (0.212 g, 0.231 mmol), dioxane (39 mL) and sodium carbonate (2.0 M solution in water) (6.9 mL, 14 mmol) were added. The reaction mixture was heated to 80° C. overnight under nitrogen. After cooling, the reaction mixture was partitioned between EtOAc and water, and the aqueous layer was extracted once with EtOAc. The combined organic layers were washed with saturated aqueous sodium bicarbonate, brine, dried and concentrated in vacuo. The residue was purified by chromatography using EtOAc as eluent to give (S)-5-isopropyl-1-(3-(4-(1-((2-(trimethylsilyl)ethoxy) methyl)-1H-1,2,4-triazol-3-yl)phenyl)pyrazolo[1,5-a]pyrimidin-5-yl)imidazolidin-2-one (1.35 g, 56%) as a yellow solid.

Step 5: To a solution of (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.23 g, 0.443 mmol) at 0° C. was added sodium hydride (0.0355 g, 0.887 mmol) and the reaction stirred 10 minutes. (2-Bromoethoxy)(tert-butyl)dimethylsilane (0.212 g, 0.887 mmol) was added and the reaction stirred for 2 hours while warming to ambient temperature. The reaction was poured onto water and extracted into EtOAc. The combined organic layers were washed with water, brine, dried over magnesium sulfate and concentrated in vacuo. The crude material was chromatographed using 20% EtOAc/dichloromethane as eluent to yield (S)-1-(2-(tert-butyldimethylsilyloxy)ethyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.18 g, 60%).

Step 6: To a solution of (S)-1-(2-(tert-butyldimethylsilyloxy)ethyl)-4-isopropyl-3-(3-(4-(1-((2-(trimethylsilyl) ethoxy)methyl)-1H-1,2,4-triazol-3-yl)phenyl)pyrazolo[1,5-a]pyrimidin-5-yl)imidazolidin-2-one (0.18 g, 0.27 mmol) in THF was added Tetra-n-butylammonium fluoride (1 mmol, 1 mL, 1M solution in THF) and the reaction was stirred at ambient temperature for 3 hours. The reaction was poured into water and extracted into EtOAc. The combined organic layers were washed with water, brine, dried over magnesium sulfate and concentrated in vacuo. The crude material was chromatographed using 3% MeOH/dichloromethane as eluent to yield (S)-1-(2-hydroxyethyl)-4-isopropyl-3-(3-(4-(1-((2-(trimethylsilyl)ethoxy)methyl)-1H-1,2,4-triazol-3-yl) phenyl)pyrazolo[1,5-a]pyrimidin-5-yl)imidazolidin-2-one (0.15 g, 100%).

Step 7: To (S)-1-(2-hydroxyethyl)-4-isopropyl-3-(3-(4-(1-((2-(trimethylsilyl)ethoxy)methyl)-1H-1,2,4-triazol-3-yl) phenyl)pyrazolo[1,5-a]pyrimidin-5-yl)imidazolidin-2-one (0.18 g, 0.32 mmol) was added trifluoroacetic acid (5 mL) and the reaction was stirred at ambient temperature for 3 hours. The reaction was concentrated in vacuo and the material purified by reverse preparative HPLC to yield the crude product and the corresponding trifluoroacetate ester. To this material was added 1N NaOH/MeOH and the mixture stirred at ambient temperature for 2 hours. The mixture was concentrated in vacuo. The combined crude product was purified by reverse preparative HPLC to give (S)-3-(3-(4-(1H-1,2,4-triazol-3-yl)phenyl)pyrazolo[1,5-a]pyrimidin-5-yl)-1-(2-hydroxyethyl)-4-isopropylimidazolidin-2-one (0.0061 g, 0.014 mmol, 4.4% yield) as the mono TFA salt. LCMS (APCI+) m/z 433 [M+H]+.

Example 26

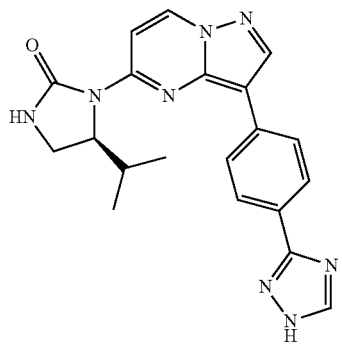 [SMILES: CC(C)[C@H]1CNC(=O)N1c1ccn2ncc(-c3ccc(-c4nc[nH]n4)cc3)c2n1]

(S)-1-(3-(4-(1H-1,2,4-triazol-3-yl)phenyl)pyrazolo[1,5-a]pyrimidin-5-yl)-5-isopropylimidazolidin-2-one A mixture of (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (Example 25, Step 4, 12 mg, 0.023 mmol) and EtOH/6N aqueous HCl (1:2, 0.5 mL total) was heated at reflux for 3 hours. After cooling, the reaction mixture was neutralized by slow addition of saturated aqueous NaHCO₃ solution. The mixture was extracted with dichloromethane, and the combined extracts were washed with brine, dried and concentrated. The residue was purified by column chromatography (12% MeOH in dichloromethane) to give (S)-1-(3-(4-(1H-1,2,4-triazol-3-yl)phenyl)pyrazolo[1,5-a]pyrimidin-5-yl)-5-isopropylimidazolidin-2-one (6 mg, 67%) as a pale yellow solid. LCMS (APCI+) m/z 389 [M+H]+.

Example 27

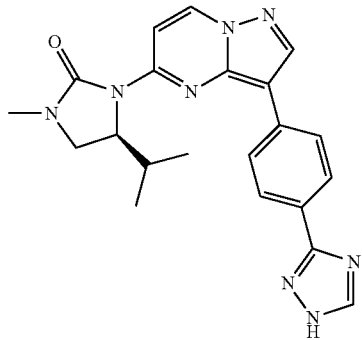 [SMILES: CC(C)[C@H]1CN(C)C(=O)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-isopropyl-1-methylimidazolidin-2-one Step 1: (S)-4-Isopropyl-1-methyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (21 mg, 93%) was prepared by the procedure described in Example 25, Step 5, substituting methyl iodide for (2-bromoethoxy)(tert-butyl)dimethylsilane. LCMS (APCI+) m/z 533 [M+H]+.

Step 2: (S)-3-(3-(4-(1H-1,2,4-Triazol-3-yl)phenyl)pyrazolo[1,5-a]pyrimidin-5-yl)-4-isopropyl-1-methylimidazolidin-2-one (12 mg, 76%) was prepared from (S)-4-Isopropyl-1-methyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one by the procedure described in Example 1, Step 9. LCMS (APCI+) m/z 403 [M+H]+.

Example 28

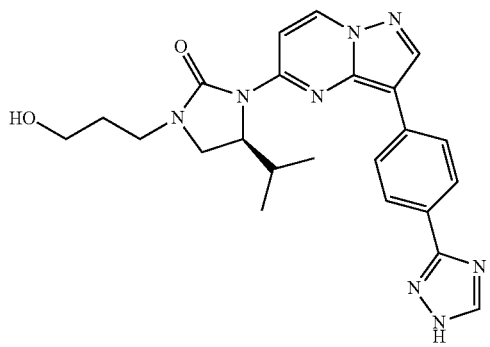 [SMILES: CC(C)[C@H]1CN(CCCO)C(=O)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-1-(3-hydroxypropyl)-4-isopropylimidazolidin-2-one Step 1: (S)-3-(3-Bromopyrazolo[1,5-a]pyrimidin-5-yl)-1-(3-(tert-butyldimethylsilyloxy)propyl)-4-isopropylimidazolidin-2-one (59 mg, 77%) was prepared by the procedure described in Example 25, Step 5, substituting (3-bromopropoxy)(tert-butyl)dimethylsilane for (2-bromoethoxy)(tert-butyl)dimethylsilane, and substituting (S)-1-(3-bromopyrazolo[1,5-a]pyrimidin-5-yl)-5-isopropylimidazolidin-2-one for (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one. LCMS (APCI+) m/z 533 [M+H]+.

Step 2: (S)-1-(3-(tert-Butyldimethylsilyloxy)propyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl) imidazolidin-2-one (39 mg, 48%) was prepared by the procedure described in Example 25, Step 4, from (S)-3-(3-bromopyrazolo[1,5-a]pyrimidin-5-yl)-1-(3-(tert-butyldimethylsilyloxy)propyl)-4-isopropylimidazolidin-2-one. LCMS (APCI+) m/z 692 [M+H]+.

Step 3: (S)-3-(3-(4-(1H-1,2,4-Triazol-3-yl)phenyl)pyrazolo[1,5-a]pyrimidin-5-yl)-1-(3-hydroxypropyl)-4-isopropylimidazolidin-2-one (18 mg, 71%) was prepared by the procedure described in Example 15, Step 6, from (S)-1-(3-(tert-butyldimethylsilyloxy)propyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one. LCMS (APCI+) m/z 447 [M+H]+.

Example 29

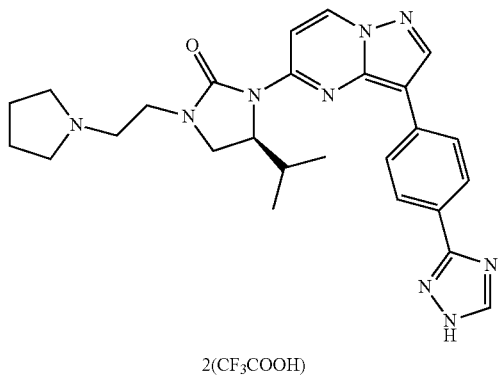 [SMILES: CC(C)[C@H]1CN(CCN2CCCC2)C(=O)N1c1ccn2ncc(-c3ccc(-c4nc[nH]n4)cc3)c2n1 ; "2(CF3COOH)"]

2(CF₃COOH)

(S)-3-(3-(4-(1H-1,2,4-triazol-3-yl)phenyl)pyrazolo[1,5-a]pyrimidin-5-yl)-4-isopropyl-1-(2-(pyrrolidin-1-yl)ethyl)imidazolidin-2-one bis-trifluoroacetate Step 1: To a solution of (S)-1-(2-hydroxyethyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (Example 25, step 6; 0.080 g, 0.142 mmol) in dichloromethane/pyridine (1:1, 10 mL total) was added N-ethyl-N-isopropylpropan-2-amine (0.0520 mL, 0.284 mmol) and 4-methylbenzene-1-sulfonyl chloride (0.136 g, 0.711 mmol). The reaction was stirred overnight at ambient temperature to provide (S)-2-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl) ethyl benzenesulfonate. The crude material was directly in the next reaction (0.102 g, 100%).

Step 2: To the crude (S)-2-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl) ethyl benzenesulfonate from step 1 (5 mL, 0.051 g, 0.071 mmol) was added pyrrolidine (2 mL) and the reaction stirred overnight at ambient temperature. The reaction was concentrated in vacuo and the material taken up in dichloromethane and washed with 1N NaOH. The combined organic layers were concentrated in vacuo and the residue chromatographed using 2% MeOH/dichloromethane to 5% MeOH/dichloromethane to yield (S)-4-isopropyl-1-(2-(pyrrolidin-1-yl)ethyl)-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.041 g, 95%).

Step 3: To the solid (S)-4-isopropyl-1-(2-(pyrrolidin-1-yl)ethyl)-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.040 g, 0.065 mmol) was added 2,2,2-trifluoroacetic acid (0.074 g, 0.65 mmol) and the reaction stirred at ambient temperature for 3 hours. The reaction was next concentrated in vacuo and the material purified by reverse preparative HPLC to yield (S)-4-isopropyl-1-(2-(pyrrolidin-1-yl)ethyl)-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.040 g, 0.065 mmol) as the bis TFA salt; LCMS (APCI+) m/z 486 [M+H]⁺.

Example 30

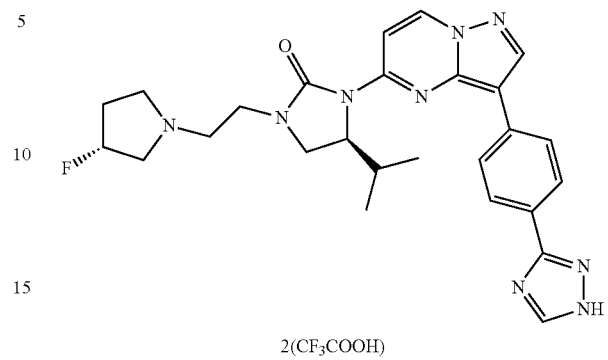

2(CF₃COOH)

(S)-3-(3-(4-(1H-1,2,4-triazol-3-yl)phenyl)pyrazolo[1,5-a]pyrimidin-5-yl)-1-(2-((R)-3-fluoropyrrolidin-1-yl)ethyl)-4-isopropylimidazolidin-2-one bis-trifluoroacetate Step 1: To a solution of (S)-1-(2-hydroxyethyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (Example 25, Step 6; 0.160 g, 0.284 mmol) in pyridine was added 4-methylbenzene-1-sulfonyl chloride (0.136 g, 0.711 mmol) and the reaction stirred overnight at ambient temperature. The reaction was next concentrated in vacuo and the reaction chromatographed using EtOAc as eluent to yield (S)-2-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)ethyl 4-methylbenzenesulfonate (0.14 g, 68.7%).

Step 2: To a solution of (S)-2-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl) ethyl 4-methylbenzenesulfonate (0.070 g, 0.098 mmol) in DMF was added (R)-3-fluoropyrrolidine hydrochloride (0.044 g, 0.49 mmol) and N-ethyl-N-isopropylpropan-2-amine (0.13 g, 0.98 mmol) and the reaction stirred for 4 days at ambient temperature. The reaction was poured into 1N NaOH and the aqueous layer extracted into EtOAc. The organics were washed with water, brine, dried over magnesium sulfate and concentrated in vacuo. The crude material was chromatographed using EtOAc to 3% MeOH/dichloromethane as eluent to yield (S)-1-(2-((R)-3-fluoropyrrolidin-1-yl)ethyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.025 g, 40%).

Step 3: To (S)-1-(2-((R)-3-fluoropyrrolidin-1-yl)ethyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (0.025 g, 0.0394 mmol) was added trifluoroacetic acid (5 mL) and the reaction stirred for 2 hours at ambient temperature. The reaction was concentrated in vacuo and the material purified by reverse preparative HPLC to give (S)-3-(3-(4-(1H-1,2,4-triazol-3-yl)phenyl)pyrazolo[1,5-a]pyrimidin-5-yl)-1-(2-((R)-3-fluoropyrrolidin-1-yl)ethyl)-4-isopropylimidazolidin-2-one (0.0143 g, 0.0284 mmol, 72.0% yield) as the bis TFA salt. LCMS (APCI+) m/z 504 [M+H]⁺.

Example 31

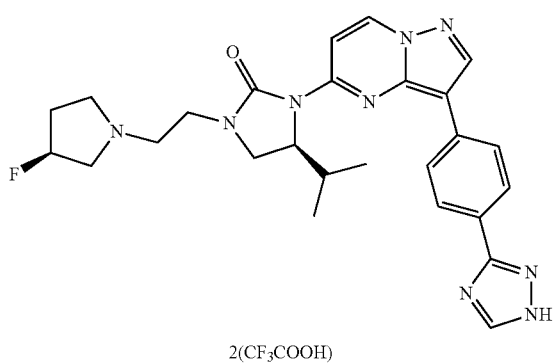 [SMILES: CC(C)[C@H]1CN(CCN2CC[C@H](F)C2)C(=O)N1c1ccn2ncc(-c3ccc(-c4nc[nH]n4)cc3)c2n1 ; "2(CF3COOH)"]

2(CF₃COOH)

(S)-3-(3-(4-(1H-1,2,4-triazol-3-yl)phenyl)pyrazolo[1,5-a]pyrimidin-5-yl)-1-(2-((S)-3-fluoropyrrolidin-1-yl)ethyl)-4-isopropylimidazolidin-2-one bis-trifluoroacetate Prepared according to the method of Example 30, substituting (S)-3-fluoropyrrolidine hydrochloride for (R)-3-fluoropyrrolidine hydrochloride in step 2 (0.0088 g, 0.017 mmol, 37% yield). LCMS (APCI+) m/z 504 [M+H]⁺.

Example 32

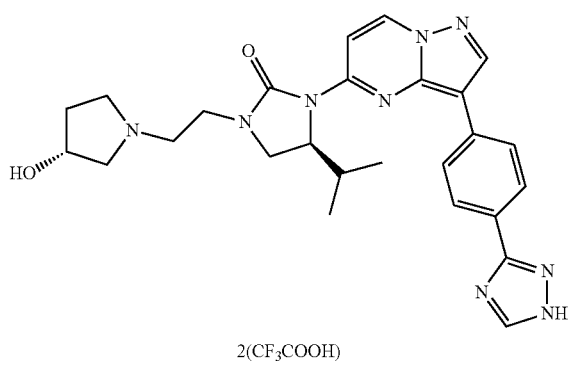 [SMILES: CC(C)[C@H]1CN(CCN2CC[C@@H](O)C2)C(=O)N1c1ccn2ncc(-c3ccc(-c4nc[nH]n4)cc3)c2n1 ; "2(CF3COOH)"]

2(CF₃COOH)

(S)-3-(3-(4-(1H-1,2,4-triazol-3-yl)phenyl)pyrazolo[1,5-a]pyrimidin-5-yl)-1-(2-((R)-3-hydroxypyrrolidin-1-yl)ethyl)-4-isopropylimidazolidin-2-one bis-trifluoroacetate Prepared according to the method of Example 30, substituting (R)-pyrrolidin-3-ol hydrochloride for (R)-3-fluoropyrrolidine hydrochloride in step 2 (0.0075 g, 0.015 mmol, 27% yield). LCMS (APCI+) m/z 502 [M+H]⁺.

Example 33

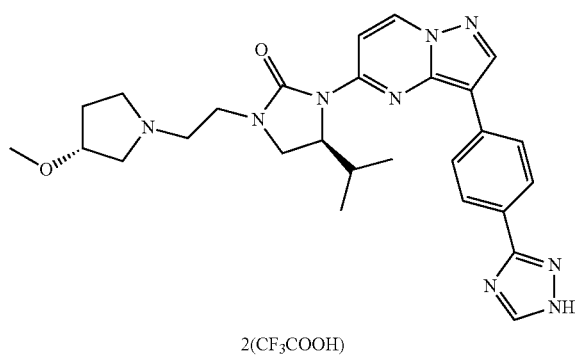 [SMILES: CO[C@@H]1CCN(CCN2C[C@H](C(C)C)N(c3ccn4ncc(-c5ccc(-c6nc[nH]n6)cc5)c4n3)C2=O)C1 ; "2(CF3COOH)"]

2(CF₃COOH)

(S)-3-(3-(4-(1H-1,2,4-triazol-3-yl)phenyl)pyrazolo[1,5-a]pyrimidin-5-yl)-4-isopropyl-1-(2-((R)-3-methoxypyrrolidin-1-yl)ethyl)imidazolidin-2-one bis-trifluoroacetate Prepared according to the method of Example 30, substituting (R)-3-methoxypyrrolidine hydrochloride for (R)-3-fluoropyrrolidine hydrochloride in step 2 (0.0042 g, 0.0081 mmol, 18% yield). LCMS (APCI+) m/z 516 [M+H]⁺.

Example 34

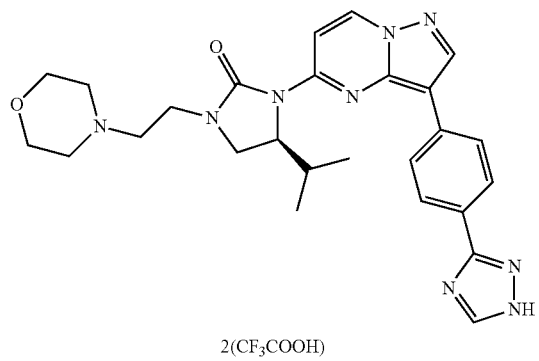 [SMILES: CC(C)[C@H]1CN(CCN2CCOCC2)C(=O)N1c1ccn2ncc(-c3ccc(-c4nc[nH]n4)cc3)c2n1 ; "2(CF3COOH)"]

2(CF₃COOH)

(S)-3-(3-(4-(1H-1,2,4-triazol-3-yl)phenyl)pyrazolo[1,5-a]pyrimidin-5-yl)-4-isopropyl-1-(2-morpholinoethyl)imidazolidin-2-one bis-trifluoroacetate Prepared according to the method of Example 29, substituting morpholine for pyrrolidine in step 2 (9.9 mg, 62.4%). LCMS (APCI+) m/z 502 [M+H]⁺.

Example 35

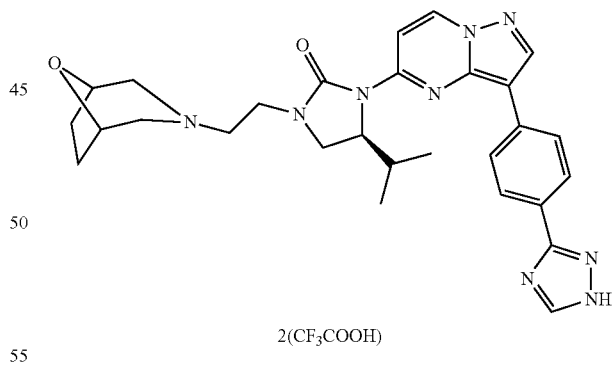

2(CF₃COOH)

(4S)-3-(3-(4-(1H-1,2,4-triazol-3-yl)phenyl)pyrazolo[1,5-a]pyrimidin-5-yl)-1-(2-(8-oxa-3-azabicyclo[3.2.1]octan-3-yl)ethyl)-4-isopropylimidazolidin-2-one bis-trifluoroacetate Prepared according to the method of Example 30, substituting 8-oxa-3-azabicyclo[3.2.1]octane hydrochloride for (R)-3-fluoropyrrolidine hydrochloride in step 2 (0.0017 g, 71% yield). LCMS (APCI+) m/z 528 [M+H]⁺.

Example 36

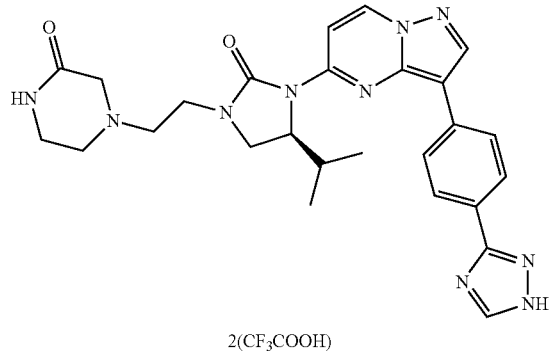 [SMILES: CC(C)[C@H]1CN(CCN2CCNC(=O)C2)C(=O)N1c1ccn2ncc(-c3ccc(-c4nc[nH]n4)cc3)c2n1 ; "2(CF3COOH)"]

2(CF₃COOH)

(S)-4-(2-(3-(3-(4-(1H-1,2,4-triazol-3-yl)phenyl)pyrazolo[1,5-a]pyrimidin-5-yl)-4-isopropyl-2-oxoimidazolidin-1-yl)ethyl)piperazin-2-one bis-trifluoroacetate Prepared according to Example 30, substituting piperazin-2-one for (R)-3-fluoropyrrolidine hydrochloride in step 2 and heating the reaction to 80° C. (0.0081 g, 0.016 mmol, 34% yield). LCMS (APCI+) m/z 515 [M+H]⁺.

Example 37

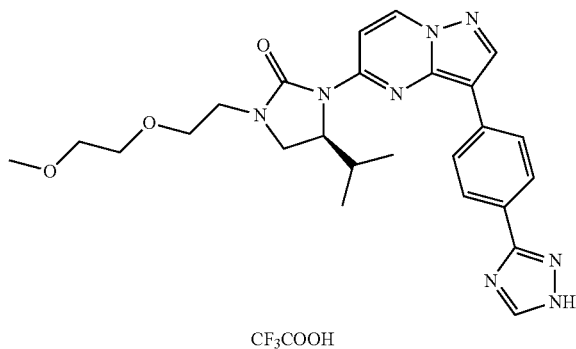 [SMILES: COCCOCCN1C[C@H](C(C)C)N(c2ccn3ncc(-c4ccc(-c5nc[nH]n5)cc4)c3n2)C1=O ; "CF3COOH"]

CF₃COOH (S)-3-(3-(4-(1H-1,2,4-triazol-3-yl)phenyl)pyrazolo[1,5-a]pyrimidin-5-yl)-4-isopropyl-1-(2-(2-methoxyethoxy)ethyl)imidazolidin-2-one trifluoroacetate Prepared according to the method of Example 25, substituting 1-bromo-2-(2-methoxyethoxy)ethane for (2-bromoethoxy)(tert-butyl)dimethylsilane in step 5, Example 25, and omitting step 6 of Example 25 (14 mg, 15%). LCMS (APCI+) m/z 491 [M+H]⁺.

Example 38

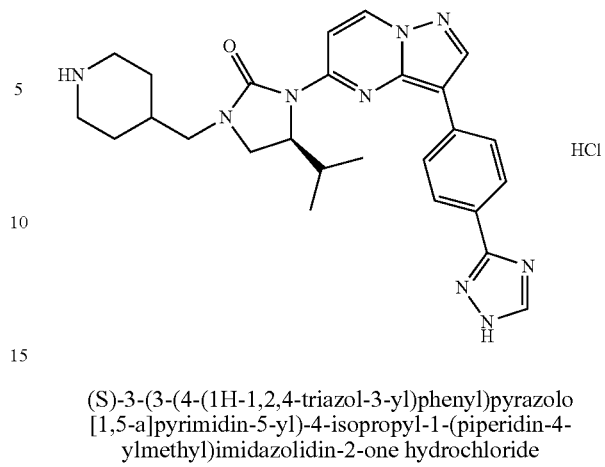

HCl (S)-3-(3-(4-(1H-1,2,4-triazol-3-yl)phenyl)pyrazolo[1,5-a]pyrimidin-5-yl)-4-isopropyl-1-(piperidin-4-ylmethyl)imidazolidin-2-one hydrochloride Step 1: To a stirred solution of (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (Example 25, Step 4; 80 mg, 0.15 mmol) in DMF (1 mL) was added NaH (60% dispersion in mineral oil, 12 mg, 0.31 mmol) at 0° C. under N₂. After stirring at ambient temperature for 30 minutes, a solution of tert-butyl 4-(bromomethyl)piperidine-1-carboxylate (77 mg, 0.28 mmol) in DMF (0.5 mL) was added dropwise. The reaction mixture was heated at 80° C. for 1 hour. After cooling, the reaction mixture was partitioned between EtOAc and water. The aqueous layer was extracted with EtOAc. The combined organic layers were washed with brine, dried and concentrated. The residue was purified by column chromatography (hexane:EtOAc, 1:4) to give (S)-tert-butyl 4-((4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)piperidine-1-carboxylate (99 mg, 90%).

Step 2: A mixture of (S)-tert-butyl 4-((4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)piperidine-1-carboxylate (99 mg, 0.14 mmol) and EtOH/6N aqueous HCl (1:2, 2 mL total) was heated at reflux for 2 hours. After cooling, the reaction mixture was neutralized by slow addition of saturated aqueous NaHCO₃ solution. The mixture was extracted with 10% THF in dichloromethane. The combined extracts were washed with brine, dried and concentrated. The residue was purified by column chromatography (20% 7N ammonia in MeOH/dichloromethane) to give the free base, which was converted to HCl salt (38 mg, 53%) by treatment with 2N HCl in ether. LCMS (APCI+) m/z 486.8 [M+H]⁺.

Example 39

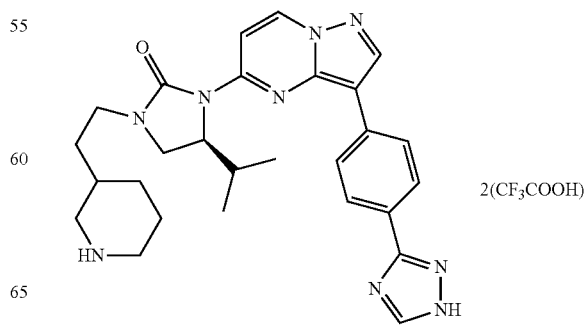

2(CF₃COOH)

(4S)-3-(3-(4-(1H-1,2,4-triazol-3-yl)phenyl)pyrazolo[1,5-a]pyrimidin-5-yl)-4-isopropyl-1-(2-(piperidin-3-yl)ethyl)imidazolidin-2-one bis-trifluoroacetate Prepared according to the method of Example 25, substituting tert-butyl 3-(2-bromoethyl)piperidine-1-carboxylate for (2-bromoethoxy)(tert-butyl)dimethylsilane in step 5 and omitting step 6 (40 mg, 41%). LCMS (APCI+) m/z 500 [M+H]+.

Example 40

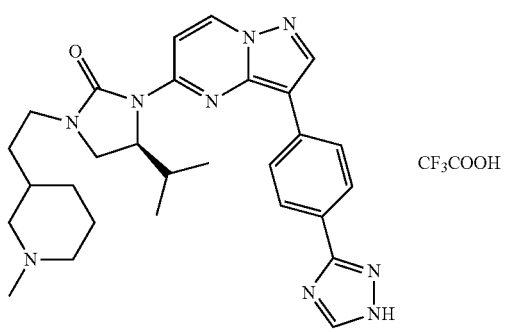 [SMILES: CC(C)[C@H]1CN(CCC2CCCN(C)C2)C(=O)N1c1ccn2ncc(-c3ccc(-c4nc[nH]n4)cc3)c2n1 ; "CF3COOH"]

(4S)-3-(3-(4-(1H-1,2,4-triazol-3-yl)phenyl)pyrazolo[1,5-a]pyrimidin-5-yl)-4-isopropyl-1-(2-(piperidin-3-yl)ethyl)imidazolidin-2-one trifluoroacetate To a solution of (4S)-3-(3-(4-(1H-1,2,4-triazol-3-yl)phenyl)pyrazolo[1,5-a]pyrimidin-5-yl)-4-isopropyl-1-(2-(piperidin-3-yl)ethyl)imidazolidin-2-one bis(2,2,2-trifluoroacetate) (Example 39; 40 mg, 0.055 mmol) in acetonitrile (2 mL) was added formaldehyde (45 mg, 37% solution in water) followed by sodium borohydride and the reaction stirred at ambient temperature for 2 hours. Water (2 mL), was added, and the reaction mixture was concentrated in vacuo. The residue purified by reverse preparative HPLC to give (4S)-3-(3-(4-(1H-1,2,4-triazol-3-yl)phenyl)pyrazolo[1,5-a]pyrimidin-5-yl)-4-isopropyl-1-(2-(piperidin-3-yl)ethyl)imidazolidin-2-one (6.7 mg, 19%) as the mono TFA salt. LCMS (APCI+) m/z 514 [M+H]+.

Example 41

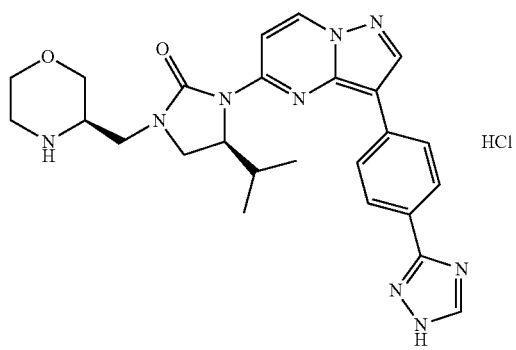 [SMILES: CC(C)[C@H]1CN(C[C@@H]2COCCN2)C(=O)N1c1ccn2ncc(-c3ccc(-c4nc[nH]n4)cc3)c2n1 ; Cl]

(S)-3-(3-(4-(1H-1,2,4-triazol-3-yl)phenyl)pyrazolo[1,5-a]pyrimidin-5-yl)-4-isopropyl-1-((R)-morpholin-3-ylmethyl)imidazolidin-2-one hydrochloride Step 1: To a stirred solution of (R)-tert-butyl 3-(hydroxymethyl)morpholine-4-carboxylate (0.650 g, 2.99 mmol) in dichloromethane (10 mL) was added Et3N (1.25 mL, 8.98 mmol). MeSO2Cl (0.35 mL, 4.5 mmol) was added dropwise at 0° C. under N2 and the reaction mixture was stirred at 0° C. for 1 hour. The reaction was diluted with dichloromethane, washed with saturated aqueous NaHCO3 and brine, dried and concentrated. The residue was purified by silica gel chromatography (1:1 hexane/EtOAc) to give (S)-tert-butyl 3-((methylsulfonyloxy)methyl)morpholine-4-carboxylate (0.720 g, 81%) as a white solid.

Step 2: (R)-tert-butyl 3-(((S)-4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)morpholine-4-carboxylate (24 mg, 17%) was prepared by the procedure described in Example 38, Step 1, substituting (S)-tert-butyl 3-((methylsulfonyl-oxy)methyl)morpholine-4-carboxylate for tert-butyl 4-(bromomethyl)piperidine-1-carboxylate. LCMS (APCI+) m/z 719 [M+H]+.

Step 3: (S)-3-(3-(4-(1H-1,2,4-triazol-3-yl)phenyl)pyrazolo[1,5-a]pyrimidin-5-yl)-4-isopropyl-1-((R)-morpholin-3-ylmethyl)imidazolidin-2-one hydrochloride (21 mg, 64%) was prepared by the procedure described in Example 38, Step 2, from (R)-tert-butyl 3-(((S)-4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)morpholine-4-carboxylate. LCMS (APCI+) m/z 488.3 [M+H]+.

Example 42

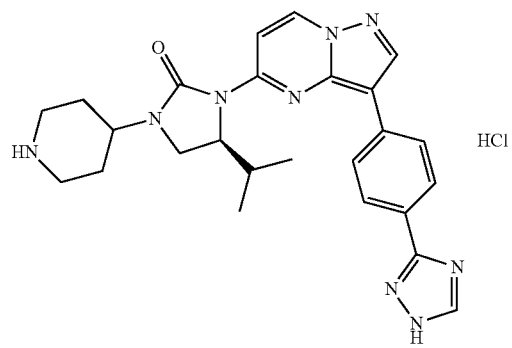 [SMILES: CC(C)[C@H]1CN(C2CCNCC2)C(=O)N1c1ccn2ncc(-c3ccc(-c4nc[nH]n4)cc3)c2n1 ; Cl]

(S)-3-(3-(4-(1H-1,2,4-triazol-3-yl)phenyl)pyrazolo[1,5-a]pyrimidin-5-yl)-4-isopropyl-1-(piperidin-4-yl)imidazolidin-2-one hydrochloride Step 1: (S)-tert-butyl 4-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)piperidine-1-carboxylate (18 mg, 19%) was prepared by the procedure described in Example 38, Step 1, substituting tert-butyl 4-(methylsulfonyloxy)piperidine-1-carboxylate for tert-butyl 4-(bromomethyl)piperidine-1-carboxylate. LCMS (APCI+) m/z 702.8 [M+H]+.

Step 2: (S)-3-(3-(4-(1H-1,2,4-triazol-3-yl)phenyl)pyrazolo[1,5-a]pyrimidin-5-yl)-4-isopropyl-1-(piperidin-4-yl)imidazolidin-2-one hydrochloride (9 mg, 74%) was prepared by the procedure described in Example 38, Step 2, from (S)-tert-butyl 4-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)piperidine-1-carboxylate. LCMS (APCI+) m/z 472 [M+H]+.

Example 43

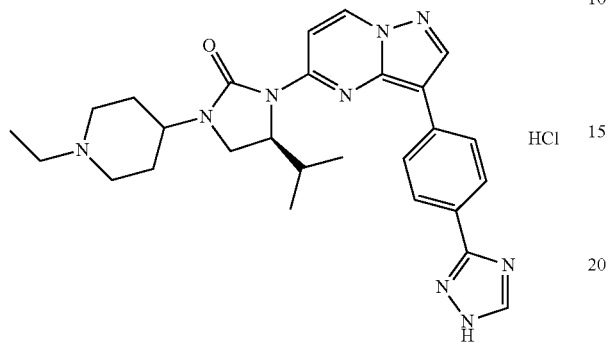

(S)-3-(3-(4-(1H-1,2,4-triazol-3-yl)phenyl)pyrazolo[1,5-a]pyrimidin-5-yl)-1-(1-ethylpiperidin-4-yl)-4-isopropylimidazolidin-2-one hydrochloride Prepared by the procedure described in Example 22, substituting (S)-3-(3-(4-(1H-1,2,4-triazol-3-yl)phenyl)pyrazolo[1,5-a]pyrimidin-5-yl)-4-isopropyl-1-(piperidin-4-yl)imidazolidin-2-one (Example 42) for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one, and substituting acetaldehyde for formaldehyde (3 mg, 53%). LCMS (APCI+) m/z 500.8 [M+H]+.

Example 44

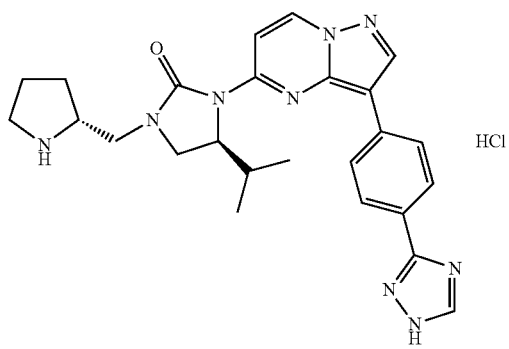 [SMILES: CC(C)[C@H]1CN(C[C@H]2CCCN2)C(=O)N1c1ccn2ncc(-c3ccc(-c4nc[nH]n4)cc3)c2n1 ; Cl]

(S)-3-(3-(4-(1H-1,2,4-triazol-3-yl)phenyl)pyrazolo[1,5-a]pyrimidin-5-yl)-4-isopropyl-1-((R)-pyrrolidin-2-ylmethyl)imidazolidin-2-one hydrochloride Step 1: (R)-tert-butyl 2-(((S)-4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)pyrrolidine-1-carboxylate (30 mg, 28%) was prepared by the procedure described in Example 38, Step 1, substituting (R)-tert-butyl 2-((methylsulfonyloxy)methyl)pyrrolidine-1-carboxylate for tert-butyl 4-(bromomethyl)piperidine-1-carboxylate. LCMS (APCI+) m/z 702.8 [M+H]+.

Step 2: (S)-3-(3-(4-(1H-1,2,4-triazol-3-yl)phenyl)pyrazolo[1,5-a]pyrimidin-5-yl)-4-isopropyl-1-((R)-pyrrolidin-2-ylmethyl)imidazolidin-2-one hydrochloride (8 mg, 74%) was prepared by the procedure described in Example 38, Step 2, from (R)-tert-butyl 2-(((S)-4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)pyrrolidine-1-carboxylate. LCMS (APCI+) m/z 472.3 [M+H]+.

Example 45

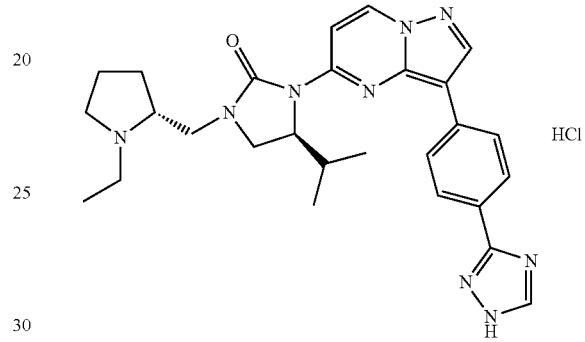

(S)-3-(3-(4-(1H-1,2,4-triazol-3-yl)phenyl)pyrazolo[1,5-a]pyrimidin-5-yl)-1-(((R)-1-ethylpyrrolidin-2-yl)methyl)-4-isopropylimidazolidin-2-one hydrochloride Prepared by the procedure described in Example 22, substituting (S)-3-(3-(4-(1H-1,2,4-triazol-3-yl)phenyl)pyrazolo[1,5-a]pyrimidin-5-yl)-4-isopropyl-1-((R)-pyrrolidin-2-ylmethyl)imidazolidin-2-one for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one, and substituting acetaldehyde for formaldehyde (6 mg, 88%). LCMS (APCI+) m/z 500.8 [M+H]+.

Example 46

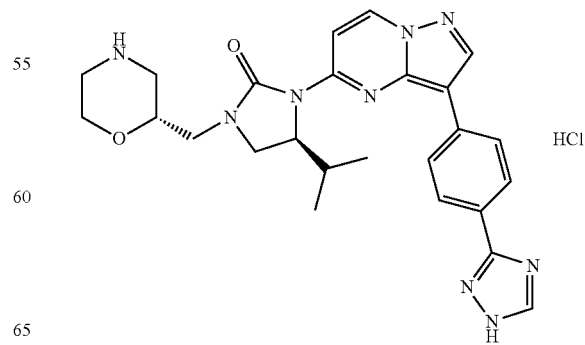

(S)-3-(3-(4-(1H-1,2,4-triazol-3-yl)phenyl)pyrazolo[1,5-a]pyrimidin-5-yl)-4-isopropyl-1-((R)-morpholin-2-ylmethyl)imidazolidin-2-one hydrochloride Step 1: (R)-tert-butyl 2-((methylsulfonyloxy)methyl)morpholine-4-carboxylate (0.795 g, 97%) was prepared by the procedure described in Example 41, Step 1, substituting (R)-tert-butyl 2-(hydroxymethyl)morpholine-4-carboxylate for (R)-tert-butyl 3-(hydroxymethyl)morpholine-4-carboxylate.

Step 2: (S)-tert-butyl 2-(((S)-4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl) morpholine-4-carboxylate (62 mg, 45%) was prepared by the procedure described in Example 38, Step 1, substituting (R)-tert-butyl 2-((methylsulfonyloxy)methyl)morpholine-4-carboxylate for tert-butyl 4-(bromomethyl)piperidine-1-carboxylate. LCMS (APCI+) m/z 718.8 [M+H]+.

Step 3: (S)-3-(3-(4-(1H-1,2,4-triazol-3-yl)phenyl)pyrazolo[1,5-a]pyrimidin-5-yl)-4-isopropyl-1-((R)-morpholin-2-ylmethyl)imidazolidin-2-one hydrochloride (31 mg, 74%) was prepared by the procedure described in Example 38, Step 2, from (S)-tert-butyl 2-(((S)-4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)methyl)morpholine-4-carboxylate. LCMS (APCI+) m/z 488.7 [M+H]+.

Example 47

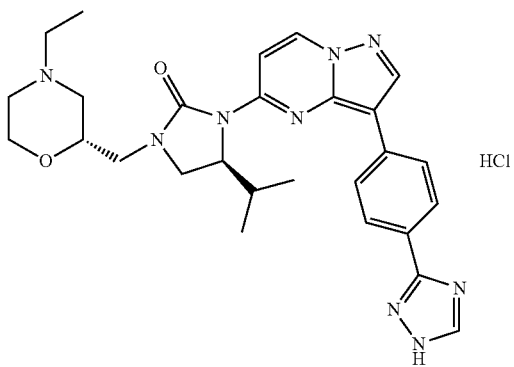 [SMILES: CCN1CCO[C@@H](CN2C[C@H](C(C)C)N(c3ccn4ncc(-c5ccc(-c6nc[nH]n6)cc5)c4n3)C2=O)C1 ; Cl]

(S)-3-(3-(4-(1H-1,2,4-triazol-3-yl)phenyl)pyrazolo[1,5-a]pyrimidin-5-yl)-1-(((R)-4-ethylmorpholin-2-yl)methyl)-4-isopropylimidazolidin-2-one hydrochloride Prepared by the procedure described in Example 22, substituting (S)-3-(3-(4-(1H-1,2,4-triazol-3-yl)phenyl)pyrazolo[1,5-a]pyrimidin-5-yl)-4-isopropyl-1-((R)-morpholin-2-ylmethyl)imidazolidin-2-one for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one, and substituting acetaldehyde for formaldehyde (6 mg, 38%). LCMS (APCI+) m/z 516.8 [M+H]+.

Example 48

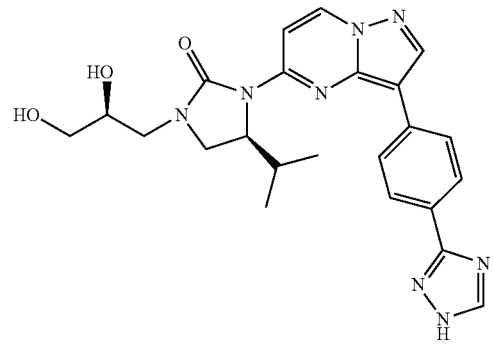 [SMILES: CC(C)[C@H]1CN(C[C@H](O)CO)C(=O)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-1-((S)-2,3-dihydroxypropyl)-4-isopropylimidazolidin-2-one Step 1: (S)-1-(((S)-2,2-dimethyl-1,3-dioxolan-4-yl)methyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (14 mg, 42%) was prepared by the procedure described in Example 38, Step 1, substituting (R)-(2,2-dimethyl-1,3-dioxolan-4-yl)methyl methanesulfonate for tert-butyl 4-(bromomethyl)piperidine-1-carboxylate. LCMS (APCI+) m/z 633.8 [M+H]+.

Step 2: (S)-3-(3-(4-(1H-1,2,4-triazol-3-yl)phenyl)pyrazolo[1,5-a]pyrimidin-5-yl)-1-((S)-2,3-dihydroxypropyl)-4-isopropylimidazolidin-2-one (5 mg, 49%) was prepared by the procedure described in Example 15, Step 6, from (S)-1-(((S)-2,2-dimethyl-1,3-dioxolan-4-yl)methyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one. LCMS (APCI+) m/z 463.7 [M+H]+.

Example 49

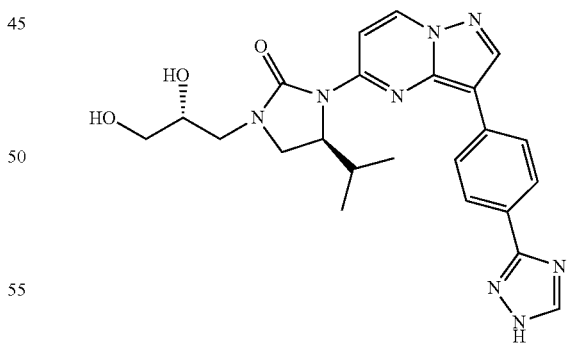

(S)-3-(3-(4-(1H-1,2,4-triazol-3-yl)phenyl)pyrazolo[1,5-a]pyrimidin-5-yl)-1-((R)-2,3-dihydroxypropyl)-4-isopropylimidazolidin-2-one Step 1: (S)-3-(3-bromopyrazolo[1,5-a]pyrimidin-5-yl)-1-(((R)-2,2-dimethyl-1,3-dioxolan-4-yl)methyl)-4-isopropylimidazolidin-2-one (99 mg, 98%) was prepared by the procedure described in Example 38, Step 1, substituting (S)-1-

(3-bromopyrazolo[1,5-a]pyrimidin-5-yl)-5-isopropylimidazolidin-2-one for (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one, and substituting (S)-(2,2-dimethyl-1,3-dioxolan-4-yl)methyl methanesulfonate for tert-butyl 4-(bromomethyl)piperidine-1-carboxylate. LCMS (APCI+) m/z 438, 440 [M+H]+.

Step 2: (S)-1-(((R)-2,2-dimethyl-1,3-dioxolan-4-yl)methyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one (36 mg, 38%) was prepared by the procedure described in Example 25, Step 4, from (S)-3-(3-bromopyrazolo[1,5-a]pyrimidin-5-yl)-1-(((R)-2,2-dimethyl-1,3-dioxolan-4-yl)methyl)-4-isopropylimidazolidin-2-one. LCMS (APCI+) m/z 633.7 [M+H]+.

Step 3: (S)-3-(3-(4-(1H-1,2,4-triazol-3-yl)phenyl)pyrazolo[1,5-a]pyrimidin-5-yl)-1-((R)-2,3-dihydroxypropyl)-4-isopropylimidazolidin-2-one (17 mg, 65%) was prepared by the procedure described in Example 15, Step 6, from (S)-1-(((R)-2,2-dimethyl-1,3-dioxolan-4-yl)methyl)-4-isopropyl-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one. LCMS (APCI+) m/z 463.7 [M+H]+.

Example 50

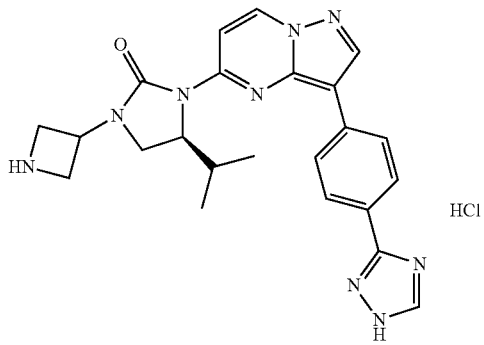 [SMILES: CC(C)[C@H]1CN(C2CNC2)C(=O)N1c1ccn2ncc(-c3ccc(-c4nc[nH]n4)cc3)c2n1 ; Cl]

(S)-3-(3-(4-(1H-1,2,4-triazol-3-yl)phenyl)pyrazolo[1,5-a]pyrimidin-5-yl)-1-(azetidin-3-yl)-4-isopropylimidazolidin-2-one hydrochloride Step 1: (S)-tert-butyl 3-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)azetidine-1-carboxylate (32 mg, 25%) was prepared by the procedure described in Example 38, Step 1, substituting tert-butyl 3-iodoazetidine-1-carboxylate for tert-butyl 4-(bromomethyl)piperidine-1-carboxylate. LCMS (APCI+) m/z 674.7 [M+H]+.

Step 2: (S)-3-(3-(4-(1H-1,2,4-triazol-3-yl)phenyl)pyrazolo[1,5-a]pyrimidin-5-yl)-1-(azetidin-3-yl)-4-isopropylimidazolidin-2-one hydrochloride (6 mg, 90%) was prepared by the procedure described in Example 38, Step 2, from (S)-tert-butyl 3-(4-isopropyl-2-oxo-3-(3-(4-(1-((2-(trimethylsilyl)ethoxy)methyl)-1H-1,2,4-triazol-3-yl)phenyl)pyrazolo[1,5-a]pyrimidin-5-yl)imidazolidin-1-yl)azetidine-1-carboxylate. LCMS (APCI+) m/z 444.3 [M+H]+.

Example 51

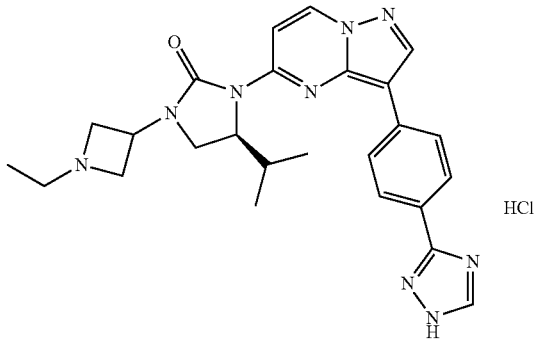 [SMILES: CCN1CC(N2C[C@H](C(C)C)N(c3ccn4ncc(-c5ccc(-c6nc[nH]n6)cc5)c4n3)C2=O)C1 ; Cl]

(S)-3-(3-(4-(1H-1,2,4-triazol-3-yl)phenyl)pyrazolo[1,5-a]pyrimidin-5-yl)-1-(1-ethylazetidin-3-yl)-4-isopropylimidazolidin-2-one hydrochloride Prepared by the procedure described in Example 22, substituting (S)-3-(3-(4-(1H-1,2,4-triazol-3-yl)phenyl)pyrazolo[1,5-a]pyrimidin-5-yl)-1-(azetidin-3-yl)-4-isopropylimidazolidin-2-one for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one, and substituting acetaldehyde for formaldehyde (6 mg, 87%). LCMS (APCI+) m/z 472.3 [M+H]+.

Example 52

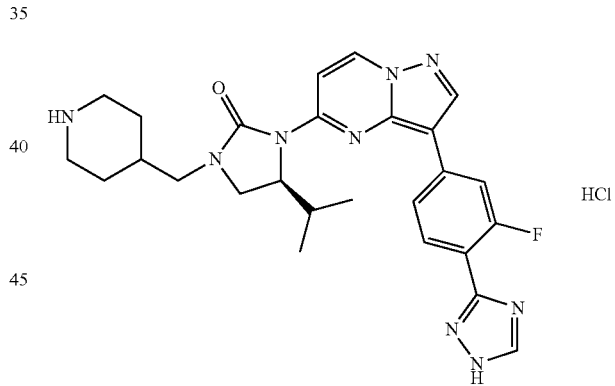

(S)-3-(3-(3-fluoro-4-(1H-1,2,4-triazol-3-yl)phenyl)pyrazolo[1,5-a]pyrimidin-5-yl)-4-isopropyl-1-(piperidin-4-ylmethyl)imidazolidin-2-one hydrochloride Step 1: (S)-tert-butyl 4-((3-(3-bromopyrazolo[1,5-a]pyrimidin-5-yl)-4-isopropyl-2-oxoimidazolidin-1-yl)methyl)piperidine-1-carboxylate (160 mg, 83%) was prepared by the procedure described in Example 38, Step 1, substituting (S)-1-(3-bromopyrazolo[1,5-a]pyrimidin-5-yl)-5-isopropylimidazolidin-2-one for (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one. LCMS (APCI+) m/z 521, 523 [M+H]+.

Step 2: A mixture of (S)-tert-butyl 4-((3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyl-2-oxoimidazolidin-1-yl)methyl)piperidine-1-carboxylate and tert-butyl 4-(((4S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyl-2-oxo imidazolidin-1-yl)methyl)piperidine-1-carboxylate (31 mg, 28%) was prepared by the procedure described in Example 25, Step 4, using (S)-tert-butyl 4-((3-(3-bromopyrazolo[1,5-a]pyrimidin-5-yl)-4-isopropyl-2-oxoimidazolidin-1-yl)methyl)piperidine-1-carboxylate and 5-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole. LCMS (APCI+) m/z 634.8 [M+H]+.

Step 3: (S)-3-(3-(3-fluoro-4-(1H-1,2,4-triazol-3-yl)phenyl)pyrazolo[1,5-a]pyrimidin-5-yl)-4-isopropyl-1-(piperidin-4-ylmethyl)imidazolidin-2-one hydrochloride (6 mg, 85%) was prepared by the procedure described in Example 38, Step 2, from a mixture of (S)-tert-butyl 4-((3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyl-2-oxoimidazolidin-1-yl)methyl) piperidine-1-carboxylate and tert-butyl 4-(((4S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyl-2-oxoimidazolidin-1-yl)methyl)piperidine-1-carboxylate. LCMS (APCI+) m/z 504.4 [M+H]+.

Example 53

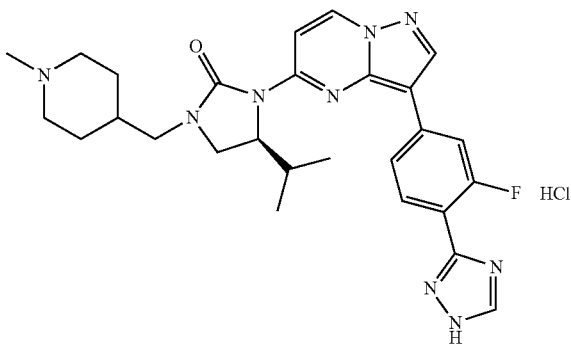 [SMILES: CC(C)[C@H]1CN(CC2CCN(C)CC2)C(=O)N1c1ccn2ncc(-c3ccc(-c4nc[nH]n4)c(F)c3)c2n1 ; Cl]

(S)-3-(3-(4-(1H-1,2,4-triazol-3-yl)phenyl)pyrazolo[1,5-a]pyrimidin-5-yl)-1-(1-ethylazetidin-3-yl)-4-isopropylimidazolidin-2-one hydrochloride Prepared by the procedure described in Example 22, substituting (S)-3-(3-(3-fluoro-4-(1H-1,2,4-triazol-3-yl)phenyl)pyrazolo[1,5-a]pyrimidin-5-yl)-4-isopropyl-1-(piperidin-4-ylmethyl)imidazolidin-2-one for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one (5 mg, 65%). LCMS (APCI+) m/z 518.4 [M+H]+.

Example 54

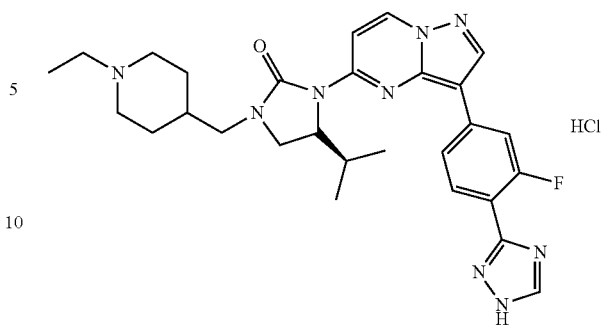

(S)-1-((1-ethylpiperidin-4-yl)methyl)-3-(3-(3-fluoro-4-(1H-1,2,4-triazol-3-yl)phenyl)pyrazolo[1,5-a]pyrimidin-5-yl)-4-isopropylimidazolidin-2-one hydrochloride Prepared by the procedure described in Example 22, substituting (S)-3-(3-(3-fluoro-4-(1H-1,2,4-triazol-3-yl)phenyl)pyrazolo[1,5-a]pyrimidin-5-yl)-4-isopropyl-1-(piperidin-4-ylmethyl)imidazolidin-2-one for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one, and substituting acetaldehyde for formaldehyde (4 mg, 59%). LCMS (APCI+) m/z 532.4 [M+H]+.

Example 55

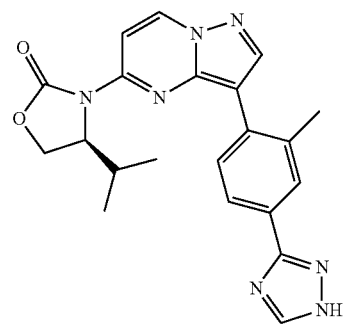 [SMILES: Cc1cc(-c2nc[nH]n2)ccc1-c1cnn2ccc(N3C(=O)OC[C@@H]3C(C)C)nc12]

(S)-4-isopropyl-3-(3-(2-methyl-4-(1H-1,2,4-triazol-3-yl)phenyl)pyrazolo[1,5-a]pyrimidin-5-yl)oxazolidin-2-one Step 1: 4-Bromo-3-methylbenzamide (1.782 g, 90%) was prepared by the procedure described in Example 23, Step 1, substituting 4-bromo-3-methylbenzoic acid (2.00 g, 9.30 mmol) for 4-bromo-3-chlorobenzoic acid, to produce an off-white solid which was carried on without further purification.

Step 2: (E)-4-Bromo-N-((dimethylamino)methylene)-3-methylbenzamide (0.648 g, 29%) was prepared by the procedure described in Example 5, Step 1, substituting 4-bromo-3-methylbenzamide (1.780 g, 8.315 mmol) for 4-bromobenzamide, to produce a light tan solid which was carried on without further purification.

Step 3: 3-(4-Bromo-3-methylphenyl)-1H-1,2,4-triazole (0.559 g, 99%) was prepared by the procedure described in Example 5, Step 2, using (E)-4-bromo-N-((dimethylamino)methylene)-3-methylbenzamide (0.641 g, 2.38 mmol), to produce a white solid which was carried on without further purification.

Step 4: 3-(4-Bromo-3-methylphenyl)-1-((2-(trimethylsilyl)ethoxy)methyl)-1H-1,2,4-triazole and 5-(4-bromo-3-methylphenyl)-1-((2-(trimethylsilyl)ethoxy)methyl)-1H-1,2,4-triazole (0.791 g, 92%) were prepared by the procedure described in Example 1, Step 6, substituting 3-(4-bromo-3-methylphenyl)-1H-1,2,4-triazole (0.556 g, 2.34 mmol) for 2-(4-bromophenyl)-1H-imidazole, to produce a mixture of two regioisomers as a colorless oil.

Step 5: A mixture of 3-(3-methyl-4-(4,4,5,5-tetramethyl-1,3,2-dioxaborolan-2-yl)phenyl)-1-((2-(trimethylsilyl)ethoxy)methyl)-1H-1,2,4-triazole and 5-(3-methyl-4-(4,4,5,5-tetramethyl-1,3,2-dioxaborolan-2-yl)phenyl)-1-((2-(trimethylsilyl)ethoxy)methyl)-1H-1,2,4-triazole (0.511 g, 91%) were prepared by the procedure described in Example 1, Step 7, using a mixture of 3-(4-bromo-3-methylphenyl)-1-((2-(trimethylsilyl)ethoxy)methyl)-1H-1,2,4-triazole and 5-(4-bromo-3-methylphenyl)-1-((2-(trimethylsilyl)ethoxy)methyl)-1H-1,2,4-triazole (0.496 g, 1.35 mmol), to produce a mixture of two regioisomers as an orange oil.

Step 6: A mixture of (4S)-4-isopropyl-3-(3-(2-methyl-4-(1-((2-(trimethylsilyl)ethoxy)methyl)-1H-1,2,4-triazol-3-yl)phenyl)pyrazolo[1,5-a]pyrimidin-5-yl) oxazolidin-2-one and (4S)-4-isopropyl-3-(3-(2-methyl-4-(1-((2-(trimethylsilyl)ethoxy)methyl)-1H-1,2,4-triazol-5-yl)phenyl)pyrazolo[1,5-a]pyrimidin-5-yl)oxazolidin-2-one (0.503 g, 107%) were prepared by the procedure described in Example 1, Step 8, using a mixture of 3-(3-methyl-4-(4,4,5,5-tetramethyl-1,3,2-dioxaborolan-2-yl)phenyl)-1-((2-(trimethylsilyl)ethoxy)methyl)-1H-1,2,4-triazole and 5-(3-methyl-4-(4,4,5,5-tetramethyl-1,3,2-dioxaborolan-2-yl)phenyl)-1-((2-(trimethylsilyl)ethoxy)methyl)-1H-1,2,4-triazole (0.496 g, 1.19 mmol), to produce a mixture of two regioisomers as a yellow oil.

Step 7: (4S)-4-isopropyl-3-(3-(2-methyl-4-(1H-1,2,4-triazol-3-yl)phenyl)pyrazolo[1,5-a]pyrimidin-5-yl)oxazolidin-2-one (0.250 g, 80%) was prepared by the procedure described in Example 1, Step 9, using a mixture of (4S)-4-isopropyl-3-(3-(2-methyl-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (4S)-4-isopropyl-3-(3-(2-methyl-4-(1-((2-(trimethylsilyl)ethoxy)methyl)-1H-1,2,4-triazol-5-yl)phenyl)pyrazolo[1,5-a]pyrimidin-5-yl)oxazolidin-2-one (0.414 g, 0.776 mmol), to produce a yellow solid. LCMS (APCI+) m/z 404.6 [M+H]$^+$; $^1$H-NMR (400 MHz, CDCl$_3$) δ 11.07 (broad s, 1H), 8.61 (d, J=7.8 Hz, 1H), 8.22 (m, 2H), 8.03 (d, J=7.8 Hz, 1H), 7.99 (s, 1H), 7.88 (d, J=7.7 Hz, 1H), 7.72 (d, J=8.1 Hz, 1H), 4.84-4.80 (m, 1H), 4.38-4.30 (m, 2H), 2.72-2.64 (m, 1H), 2.51 (s, 3H), 0.94 (d, J=7.0 Hz, 3H), 0.88 (d, J=6.8 Hz, 3H).

Example 56

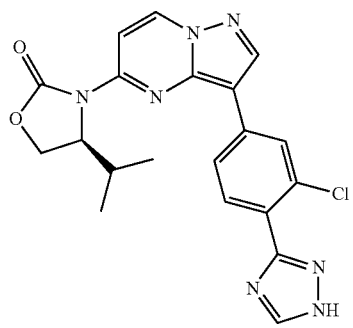 [SMILES: CC(C)[C@H]1COC(=O)N1c1ccn2ncc(-c3ccc(-c4nc[nH]n4)c(Cl)c3)c2n1]

(S)-3-(3-(3-chloro-4-(1H-1,2,4-triazol-3-yl)phenyl)pyrazolo[1,5-a]pyrimidin-5-yl)-4-isopropyloxazolidin-2-one Step 1: 4-Bromo-2-chlorobenzamide (2.224 g, 112%) was prepared by the procedure described in Example 23, Step 1, substituting 4-bromo-2-chlorobenzoic acid (2.00 g, 8.49 mmol) for 4-bromo-3-chlorobenzoic acid, to produce a white solid which was carried on without further purification.

Step 2: (E)-4-Bromo-2-chloro-N-((dimethylamino)methylene)benzamide (2.029 g, 83%) was prepared by the procedure described in Example 5, Step 1, using 4-bromo-2-chlorobenzamide (1.989 g, 8.48 mmol), to produce an amber oil which was carried on without further purification.

Step 3: 5-(4-Bromo-2-chlorophenyl)-1H-1,2,4-triazole (1.620 g, 112%) was prepared by the procedure described in Example 5, Step 2, using (E)-4-bromo-2-chloro-N-((dimethylamino)methylene)benzamide (1.616 g, 5.58 mmol), to produce a light gray which was carried on without further purification.

Step 4: 3-(4-Bromo-2-chlorophenyl)-1-((2-(trimethylsilyl)ethoxy)methyl)-1H-1,2,4-triazole and 5-(4-bromo-2-chlorophenyl)-1-((2-(trimethylsilyl)ethoxy)methyl)-1H-1,2,4-triazole (1.752 g, 96%) were prepared by the procedure described in Example 1, Step 6, using 5-(4-bromo-2-chlorophenyl)-1H-1,2,4-triazole (1.220 g, 4.72 mmol), to produce a mixture of two regioisomers as a light orange oil.

Step 5: 3-(2-Chloro-4-(4,4,5,5-tetramethyl-1,3,2-dioxaborolan-2-yl)phenyl)-1-((2-(trimethylsilyl)ethoxy)methyl)-1H-1,2,4-triazole and 5-(2-chloro-4-(4,4,5,5-tetramethyl-1,3,2-dioxaborolan-2-yl)phenyl)-1-((2-(trimethylsilyl)ethoxy)methyl)-1H-1,2,4-triazole (0.360 g, 61%) were prepared by the procedure described in Example 1, Step 7, using a mixture of 3-(4-bromo-2-chlorophenyl)-1-((2-(trimethylsilyl)ethoxy)methyl)-1H-1,2,4-triazole and 5-(4-bromo-2-chlorophenyl)-1-((2-(trimethylsilyl)ethoxy)methyl)-1H-1,2,4-triazole (0.525 g, 1.35 mmol), to produce a mixture of two regioisomers as a yellow oil.

Step 6: (S)-3-(3-(3-Chloro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (S)-3-(3-(3-chloro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.356 g, 109%) were prepared by the procedure described in Example 1, Step 8, using a mixture of 3-(2-chloro-4-(4,4,5,5-tetramethyl-1,3,2-dioxaborolan-2-yl)phenyl)-1-((2-(trimethylsilyl)ethoxy)methyl)-1H-1,2,4-triazole and 5-(2-chloro-4-(4,4,5,5-tetramethyl-1,3,2-dioxaborolan-2-yl)phenyl)-1-((2-(trimethylsilyl)ethoxy)methyl)-1H-1,2,4-triazole (0.347 g, 0.796 mmol), to produce a mixture of two regioisomers as a yellow oil.

Step 7: (S)-3-(3-(3-Chloro-4-(1H-1,2,4-triazol-3-yl)phenyl)pyrazolo[1,5-a]pyrimidin-5-yl)-4-isopropyloxazolidin-2-one (0.051 g, 25%) was prepared by the procedure described in Example 1, Step 9, using a mixture of (S)-3-(3-(3-chloro-4-(1-((2-(trimethylsilyl)ethoxy)methyl)-1H-1,2,4-triazol-3-yl)phenyl)pyrazolo[1,5-a]pyrimidin-5-yl)-4-isopropyloxazolidin-2-one and (S)-3-(3-(3-chloro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.270 g, 0.487 mmol), to produce a yellow solid. LCMS (APCI+) m/z 424.6 [M+H]$^+$; $^1$H-NMR (400 MHz, DMSO-d$_6$) δ 14.21 (broad s, 1H), 9.13 (d, J=7.8 Hz, 1H), 8.83 (s, 1H), 8.67 (s, 1H), 8.39 (m, 1H), 8.09 (m, 1H), 7.95-7.82 (m, 2H), 4.96-4.92 (m, 1H), 4.56-4.50 (m, 2H), 2.80-2.76 (m, 1H), 1.07 (d, J=7.1 Hz, 3H), 0.86 (d, J=6.8 Hz, 3H).

Example 57

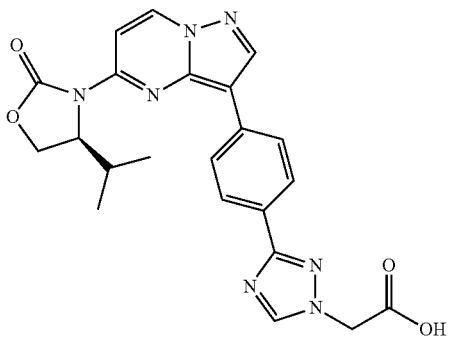 [SMILES: CC(C)[C@H]1COC(=O)N1c1ccn2ncc(-c3ccc(-c4ncn(CC(=O)O)n4)cc3)c2n1]

(S)-2-(3-(4-(5-(4-isopropyl-2-oxooxazolidin-3-yl)pyrazolo[1,5-a]pyrimidin-3-yl)phenyl)-1H-1,2,4-triazol-1-yl)acetic acid Step 1: (S)-tert-butyl 2-(3-(4-(5-(4-isopropyl-2-oxooxazolidin-3-yl)pyrazolo[1,5-a]pyrimidin-3-yl)phenyl)-1H-1,2,4-triazol-1-yl)acetate (66 mg, 64%) was prepared by the procedure described in Example 8, Step 1, substituting tert-butyl 2-chloroacetate for di-tert-butyl chloromethyl phosphate. LCMS (APCI+) m/z 504.5 [M+H]⁺.

Step 2: To a stirred solution of (S)-tert-butyl 2-(3-(4-(5-(4-isopropyl-2-oxooxazolidin-3-yl)pyrazolo[1,5-a]pyrimidin-3-yl)phenyl)-1H-1,2,4-triazol-1-yl)acetate (66 mg, 0.13 mmol) in DCM (1 mL) was added dropwise TFA (1 mL) at 0° C. under N₂. The reaction mixture was stirred at ambient temperature overnight. The solvents were evaporated in vacuo. The residue was dissolved in saturated aqueous NaHCO₃ solution and washed with Ether. The aqueous layer was acidified by slow addition of 1N HCl. The mixture was extracted with EtOAc. The combined organic layers were washed with brine, dried and concentrated to give (S)-2-(3-(4-(5-(4-isopropyl-2-oxooxazolidin-3-yl)pyrazolo[1,5-a]pyrimidin-3-yl)phenyl)-1H-1,2,4-triazol-1-yl)acetic acid (48 mg, 82%). LCMS (APCI+) m/z 448.3 [M+H]⁺.

Example 58

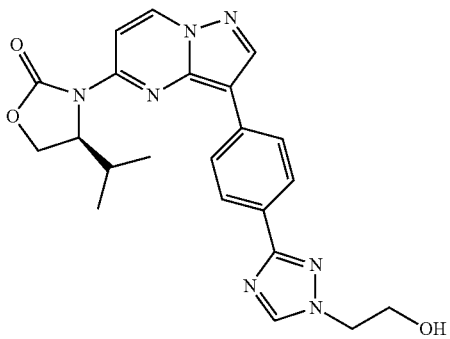 [SMILES: CC(C)[C@H]1COC(=O)N1c1ccn2ncc(-c3ccc(-c4ncn(CCO)n4)cc3)c2n1]

(S)-3-(3-(4-(1-(2-hydroxyethyl)-1H-1,2,4-triazol-3-yl)phenyl)pyrazolo[1,5-a]pyrimidin-5-yl)-4-isopropyloxazolidin-2-one To a mixture of (S)-3-(3-(4-(1H-1,2,4-triazol-3-yl)phenyl)pyrazolo[1,5-a]pyrimidin-5-yl)-4-isopropyloxazolidin-2-one (50 mg, 0.13 mmol), Cs₂CO₃ (46 mg, 0.14 mmol) and DMF (2 mL) was added 2-bromoethanol (19 mg, 0.15 mmol). The reaction mixture was heated at 80° C. for 7 hours. After cooling, the reaction mixture was partitioned between EtOAc and water. The aqueous layer was extracted with EtOAc. The combined organic layers were washed with water and brine, dried and concentrated to give a crude mixture of (S)-3-(3-(4-(1-(2-hydroxyethyl)-1H-1,2,4-triazol-3-yl)phenyl)pyrazolo[1,5-a]pyrimidin-5-yl)-4-isopropyloxazolidin-2-one and (S)-3-(3-(4-(1-(2-hydroxyethyl)-1H-1,2,4-triazol-5-yl)phenyl)pyrazolo[1,5-a]pyrimidin-5-yl)-4-isopropyloxazolidin-2-one. The crude was purified by reverse phase preparative HPLC (5%-95% acetonitrile/water). (S)-3-(3-(4-(1-(2-hydroxyethyl)-1H-1,2,4-triazol-3-yl)phenyl)pyrazolo[1,5-a]pyrimidin-5-yl)-4-isopropyloxazolidin-2-one (41 mg, 74%) was isolated as the major product. LCMS (APCI+) m/z 434.6 [M+H]⁺.

Example 59

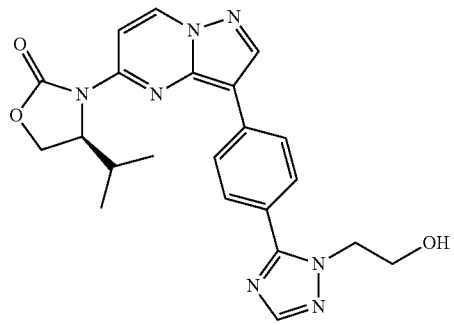 [SMILES: CC(C)[C@H]1COC(=O)N1c1ccn2ncc(-c3ccc(-c4ncnn4CCO)cc3)c2n1]

(S)-3-(3-(4-(1-(2-hydroxyethyl)-1H-1,2,4-triazol-5-yl)phenyl)pyrazolo[1,5-a]pyrimidin-5-yl)-4-isopropyloxazolidin-2-one A crude mixture of (S)-3-(3-(4-(1-(2-hydroxyethyl)-1H-1,2,4-triazol-3-yl)phenyl)pyrazolo[1,5-a]pyrimidin-5-yl)-4-isopropyloxazolidin-2-one and S)-3-(3-(4-(1-(2-hydroxyethyl)-1H-1,2,4-triazol-5-yl)phenyl)pyrazolo[1,5-a]pyrimidin -5-yl)-4-isopropyloxazolidin-2-one was prepared as described in Example 58. (S)-3-(3-(4-(1-(2-hydroxyethyl)-1H-1,2,4-triazol-5-yl)phenyl)pyrazolo[1,5-a]pyrimidin -5-yl)-4-isopropyloxazolidin-2-one (6 mg, 11%) was isolated as the minor product by reverse phase preparative HPLC (5%-95% acetonitrile/water) as described in Example 58. LCMS (APCI+) m/z 434.6 [M+H]⁺.

Example 60

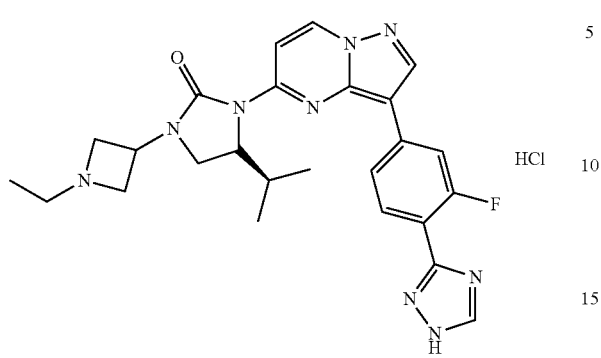

(S)-1-(1-ethylazetidin-3-yl)-3-(3-(3-fluoro-4-(1H-1,2,4-triazol-3-yl)phenyl)pyrazolo[1,5-a]pyrimidin-5-yl)-4-isopropylimidazolidin-2-one hydrochloride Step 1: (S)-tert-butyl 3-(3-(3-bromopyrazolo[1,5-a]pyrimidin-5-yl)-4-isopropyl-2-oxoimidazolidin-1-yl)azetidine-1-carboxylate (60 mg, 41%) was prepared by the procedure described in Example 25, Step 5, substituting tert-butyl 3-iodoazetidine-1-carboxylate for 2-bromoethoxy)(tert-butyl)dimethylsilane, and substituting (S)-1-(3-bromopyrazolo[1,5-a]pyrimidin-5-yl)-5-isopropylimidazolidin-2-one for (S)-5-isopropyl-1-(3-(4-(1-((2-(trimethylsilyl)ethoxy)methyl)-1H-1,2,4-triazol-3-yl)phenyl)pyrazolo[1,5-a]pyrimidin-5-yl)imidazolidin-2-one. LCMS (APCI+) m/z 423, 425 [M-Bu$^t$+H]$^+$.

Step 2: tert-butyl 3-((4S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyl-2-oxoimidazolidin-1-yl)azetidine-1-carboxylate (22 mg, 48%) was prepared by the procedure described in Example 25, Step 4, using (S)-tert-butyl 34343-bromopyrazolo[1,5-a]pyrimidin-5-yl)-4-isopropyl-2-oxoimidazolidin-1-yl)azetidine-1-carboxylate and 5-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole. LCMS (APCI+) m/z 692.1 [M+H]$^+$.

Step 3: A mixture of tert-butyl 3-((4S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyl-2-oxoimidazolidin-1-yl)azetidine-1-carboxylate (22 mg, 0.032 mmol) and 1:2 EtOH/6N aqueous HCl (1 mL) was heated at reflux for 2 hours. After cooling, the reaction mixture was basified by slow addition of saturated aqueous NaHCO$_3$ solution. The mixture was extracted with 10% MeOH in DCM. The combined extracts were washed with brine, dried and concentrated. The residue was purified by column chromatography (20% 7N ammonia in MeOH/dichloromethane) to give (S)-1-(azetidin-3-yl)-3-(3-(3-fluoro-4-(1H-1,2,4-triazol-3-yl)phenyl)pyrazolo[1,5-a]pyrimidin-5-yl)-4-isopropylimidazolidin-2-one (12 mg, 82%) as a pale yellow solid. LCMS (APCI+) m/z 462.2 [M+H]$^+$.

Step 4: (S)-1-(1-ethylazetidin-3-yl)-3-(3-(3-fluoro-4-(1H-1,2,4-triazol-3-yl)phenyl)pyrazolo[1,5-a]pyrimidin-5-yl)-4-isopropylimidazolidin-2-one hydrochloride (5 mg, 37%) was prepared by the procedure described in Example 22, using (S)-1-(azetidin-3-yl)-3-(3-(3-fluoro-4-(1H-1,2,4-triazol-3-yl)phenyl)pyrazolo[1,5-a]pyrimidin-5-yl)-4-isopropylimidazolidin-2-one and substituting acetaldehyde. LCMS (APCI+) m/z 490.2 [M+H]$^+$.

Example 61

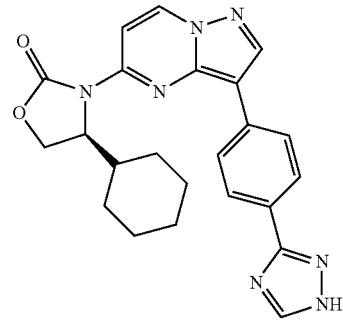 [SMILES: O=C1OC[C@H](C2CCCCC2)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-cyclohexyloxazolidin-2-one Step 1: Diphosgene (0.704 mL, 6.05 mmol) was added dropwise to a stirred suspension of (S)-2-amino-2-cyclohexylethanol (1.02 g, 7.12 mmol), Et$_3$N (6.95 mL, 49.9 mmol) and activated charcoal (40 mg) in THF (20 mL) at 0° C. under N$_2$. The reaction mixture was heated at 50° C. overnight. After cooling, the suspension was filtered through Celite. To the filtrate was added sat. aq. NaHCO$_3$ solution. The mixture was extracted with EtOAc. The combined organic layers were washed with brine, dried and concentrated. The residue was purified by silica gel flash column chromatography (1:1 hexane/EtOAc) to give (S)-4-cyclohexyloxazolidin-2-one (0.900 g, 75%) as a white solid.

Step 2: (S)-3-(3-bromopyrazolo[1,5-a]pyrimidin-5-yl)-4-cyclohexyloxazolidin-2-one (0.285 g, 73%) was prepared by the procedure described in Example 1, Step 4, substituting (S)-4-cyclohexyloxazolidin-2-one for (S)-4-isopropyloxazolidin-2-one. LCMS (APCI+) m/z 365, 367 [M+H]$^+$.

Step 3: (S)-4-cyclohexyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (73 mg, 95%) was prepared by the procedure described in Example 1, Step 8, using (S)-3-(3-bromopyrazolo[1,5-a]pyrimidin-5-yl)-4-cyclohexyloxazolidin-2-one. LCMS (APCI+) m/z 560.6 [M+H]$^+$.

Step 4: (S)-3-(3-(4-(1H-1,2,4-triazol-3-yl)phenyl)pyrazolo[1,5-a]pyrimidin-5-yl)-4-cyclohexyloxazolidin-2-one (29 mg, 52%) was prepared by the procedure described in Example 26, using (S)-4-cyclohexyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one. LCMS (APCI+) m/z 430.6 [M+H]$^+$.

Example 62

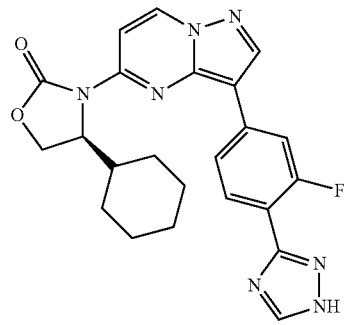

(S)-4-cyclohexyl-3-(3-(3-fluoro-4-(1H-1,2,4-triazol-3-yl)phenyl)pyrazolo[1,5-a]pyrimidin-5-yl)oxazolidin-2-one Step 1: (4S)-4-Cyclohexyl-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one (52 mg, 82%) was prepared by the procedure described in Example 1, Step 8, substituting (S)-3-(3-bromopyrazolo[1,5-a]pyrimidin-5-yl)-4-cyclohexyloxazolidin-2-one for (S)-3-(3-bromopyrazolo[1,5-a]pyrimidin-5-yl)-4-isopropyloxazolidin-2-one, and substituting 5-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole for 2-(4-(4,4,5,5-tetramethyl-1,3,2-dioxaborolan-2-yl)phenyl)-1-((2-(trimethylsilyl)ethoxy)methyl)-1H-imidazole. LCMS (APCI+) m/z 578.5 [M+H]+.

Step 2: (S)-4-cyclohexyl-3-(3-(3-fluoro-4-(1H-1,2,4-triazol-3-yl)phenyl)pyrazolo[1,5-a]pyrimidin-5-yl)oxazolidin-2-one (35 mg, 87%) was prepared by the procedure described in Example 1, Step 9, using (4S)-4-cyclohexyl-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one. LCMS (APCI+) m/z 448.7 [M+H]+.

Example 63

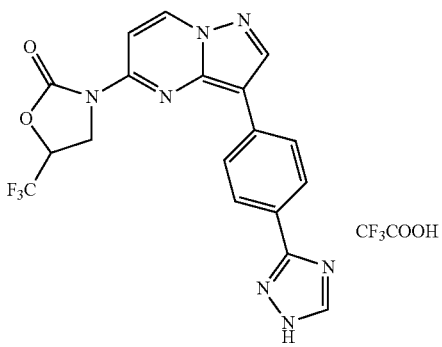 [SMILES: O=C1OC(C(F)(F)F)CN1c1ccn2ncc(-c3ccc(-c4nc[nH]n4)cc3)c2n1 ; "CF3COOH"]

3-(3-(4-(1H-1,2,4-triazol-3-yl)phenyl)pyrazolo[1,5-a]pyrimidin-5-yl)-5-(trifluoromethyl)oxazolidin-2-one trifluoroacetate 3-(3-(4-(1H-1,2,4-triazol-3-yl)phenyl)pyrazolo[1,5-a]pyrimidin-5-yl)-5-(trifluoromethyl)oxazolidin-2-one (3.3 mg, 10%) as the TFA salt was made from 5-(trifluoromethyl)oxazolidin-2-one according to the method of Example 1, Step 4, and substituting 3-(4-(4,4,5,5-tetramethyl-1,3,2-dioxaborolan-2-yl)phenyl)-1-((2-(trimethylsilyl)ethoxy)methyl)-1H-1,2,4-triazole for 2-(4-(4,4,5,5-tetramethyl-1,3,2-dioxaborolan-2-yl)phenyl)-1-((2-(trimethylsilyl)ethoxy)methyl)-1H-imidazole in Example 1, Step 8. LCMS (APCI+) m/z 416 [M+H]+.

Example 64

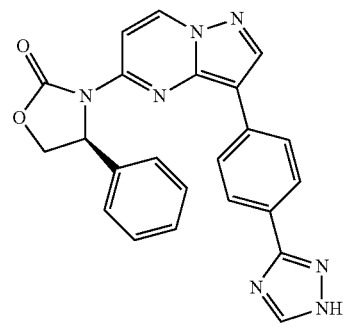 [SMILES: O=C1OC[C@H](c2ccccc2)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-phenyloxazolidin-2-one Step 1: To a solution of (S)-4-phenyloxazolidin-2-one (0.737 g, 4.517 mmol) in DMF was added sodium hydride (0.189 g, 4.73 mmol) and the reaction stirred at ambient temperature for 45 minutes. 3-Bromo-5-chloropyrazolo[1,5-a]pyrimidine (1.00 g, 4.302 mmol) was added and the reaction stirred at ambient temperature for 3 hours. The reaction mixture was poured into water and the water layer extracted with ether. The combined organic layers were washed with brine, dried over MgSO4 and concentrated in vacuo. The crude material was purified by normal phase chromatography using 2% EtOAc/DCM as the eluent to yield (S)-3-(3-bromopyrazolo[1,5-a]pyrimidin-5-yl)-4-phenyloxazolidin-2-one (1.233 g, 3.433 mmol, 79.80% yield).

Step 2: To a solution of (S)-3-(3-bromopyrazolo[1,5-a]pyrimidin-5-yl)-4-phenyloxazolidin-2-one (0.7 g, 1.9 mmol) in dioxane bubbled with nitrogen was added sodium carbonate (2.0 M, 4.9 mL, 9.7 mmol) and 3-(4-(4,4,5,5-tetramethyl-1,3,2-dioxaborolan-2-yl)phenyl)-1-((2-(trimethylsilyl)ethoxy)methyl)-1H-1,2,4-triazole (1.0 g, 2.5 mmol), and the reaction was degassed with nitrogen for 30 minutes. XPHOS (0.093 g, 0.19 mmol) and Pd2dba3 (0.089 g, 0.097 mmol) were added to the mixture and the reaction was stirred for 2 hours at 80° C. The reaction was poured into water and the aqueous layer extracted with EtOAc. The organic layer was washed with brine, dried over MgSO4 and concentrated in vacuo. The crude material purified by normal phase chromatography using 25% EtOAc/DCM as the eluent to yield (S)-4-phenyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.80 g, 1.4 mmol, 74% yield).

Step 3: To the solid (S)-4-phenyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.80 g, 1.4 mmol) was added TFA (20 mL) and the reaction stirred at room temperature for 3 hours. The reaction was concentrated and the residue slurried in methanol/acetonitrile (20 mL 1:1) and water (20 mL) added and the reaction stirred at ambient temperature for 1 hour. The organic solvents were removed in vacuo and the water layer basified to about pH 7 using a solution of saturated NaHCO3. The aqueous layer was then stirred for 5 minutes. The solids were filtered and dried in vacuo. The solids were then taken up in water and stirred for 2 hours. The solids were filtered and dried in vacuo. The solids were next slurried in methanol while nitrogen was bubbled through the solution for 2 hours. The slurry was concentrated to about 20 mL, and the solids filtered and dried in vacuo to give (S)-3-(3-(4-(1H-1,2,4-triazol-3-yl)phenyl)pyrazolo[1,5-a]pyrimidin-5-yl)-4-phenyloxazolidin-2-one (0.19 g, 0.45 mmol, 31% yield). LCMS (APCI+) m/z 424 [M+H]+.

Example 65

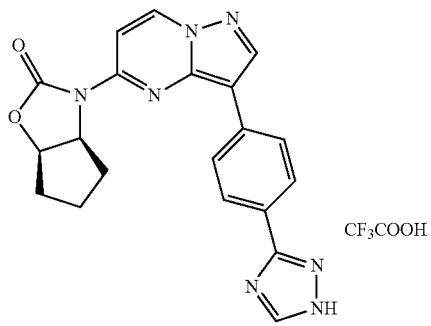 [SMILES: O=C1O[C@@H]2CCC[C@@H]2N1c1ccn2ncc(-c3ccc(-c4nc[nH]n4)cc3)c2n1 ; "CF3COOH"]

(3aS,6aR)-3-(3-(4-(1H-1,2,4-triazol-3-yl)phenyl)pyrazolo[1,5-a]pyrimidin-5-yl)hexahydro-2H-cyclopenta[d]oxazol-2-one trifluoroacetate Step 1: To a solution of (1R,2S)-2-aminocyclopentanol (1.0 g, 9.9 mmol) as the HCl salt in water (50 mL) was added potassium hydroxide (3.9 g, 69 mmol) and the slurry stirred until all the material was in solute ion. To the reaction was added THF (100 mL) and the reaction was cooled to 0° C., followed by bis(trichloromethyl) carbonate (2.9 g, 9.9 mmol) as a solid and the reaction stirred at 0° C. for 2 hours. The reaction was poured into EtOAc and the layers were separated. The organic layer was washed with 1N HCl, 1N NaOH and brine, dried over MgSO$_4$ and concentrated in vacuo. The material was purified by silica gel chromatography using 20% EtOAc/DCM as the eluent to yield (3aS,6aR)-hexahydro-2H-cyclopenta[d]oxazol-2-one (0.30 g, 2.4 mmol, 24% yield).

Step 2: (3aS,6aR)-3-(3-(4-(1H-1,2,4-triazol-3-yl)phenyl)pyrazolo[1,5-a]pyrimidin-5-yl)hexahydro-2H-cyclopenta[d]oxazol-2-one (45 mg, 60%) as the TFA salt was made according to the method of Example 1, Step 4, substituting (3aS,6aR)-hexahydro-2H-cyclopenta[d]oxazol-2-one for (S)-4-isopropyloxazolidin-2-one and substituting 3-(4-(4,4,5,5-tetramethyl-1,3,2-dioxaborolan-2-yl)phenyl)-1-((2-(trimethylsilyl)ethoxy)methyl)-1H-1,2,4-triazole for 2-(4-(4,4,5,5-tetramethyl-1,3,2-dioxaborolan-2-yl)phenyl)-1-((2-(trimethylsilyl)ethoxy)methyl)-1H-imidazole in Example 1, Step 8. LCMS (APCI+) m/z 388 [M+H]$^+$.

Example 66

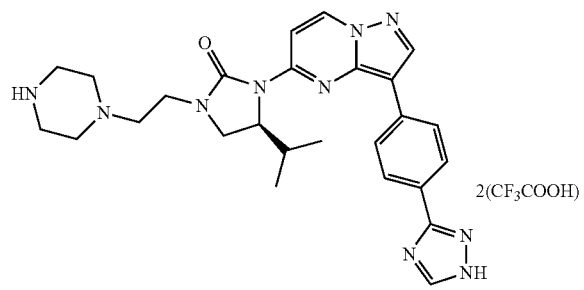 [SMILES: CC(C)[C@H]1CN(CCN2CCNCC2)C(=O)N1c1ccn2ncc(-c3ccc(-c4nc[nH]n4)cc3)c2n1 ; "2(CF3COOH)"]

(S)-3-(3-(4-(1H-1,2,4-triazol-3-yl)phenyl)pyrazolo[1,5-a]pyrimidin-5-yl)-4-isopropyl-1-(2-(piperazin-1-yl)ethyl)imidazolidin-2-one bis-trifluoroacetate (S)-3-(3-(4-(1H-1,2,4-triazol-3-yl)phenyl)pyrazolo[1,5-a]pyrimidin-5-yl)-4-isopropyl-1-(2-(piperazin-1-yl)ethyl)imidazolidin-2-one (7.1 mg, 34%) as the bis TFA salt was made according to the method of Example 30, Step 2, substituting N-Boc piperidine for (R)-3-fluoropyrrolidine hydrochloride. LCMS (APCI+) m/z 501 [M+H]$^+$.

Example 67

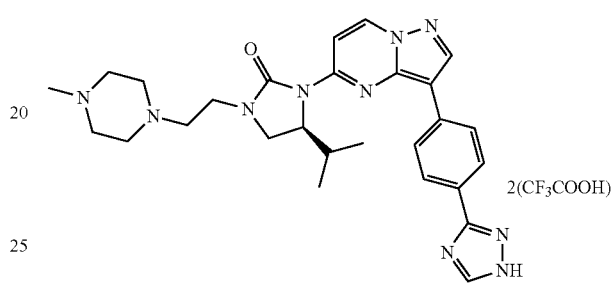

(S)-3-(3-(4-(1H-1,2,4-triazol-3-yl)phenyl)pyrazolo[1,5-a]pyrimidin-5-yl)-4-isopropyl-1-(2-(4-methylpiperazin-1-yl)ethyl)imidazolidin-2-one bis-trifluoroacetate (S)-3-(3-(4-(1H-1,2,4-triazol-3-yl)phenyl)pyrazolo[1,5-a]pyrimidin-5-yl)-4-isopropyl-1-(2-(4-methylpiperazin-1-yl)ethyl)imidazolidin-2-one (8.6 mg, 30%) as the bis TFA salt was made according to the method of Example 30, Step 2, substituting N-methyl piperidine for (R)-3-fluoropyrrolidine hydrochloride. LCMS (APCI+) m/z 515 [M+H]$^+$.

Example 68

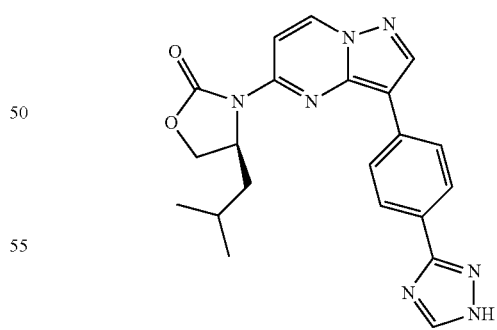

(S)-3-(3-(4-(1H-1,2,4-triazol-3-yl)phenyl)pyrazolo[1,5-a]pyrimidin-5-yl)-4-isobutyloxazolidin-2-one (S)-3-(3-(4-(1H-1,2,4-triazol-3-yl)phenyl)pyrazolo[1,5-a]pyrimidin-5-yl)-4-isobutyloxazolidin-2-one (0.0069 g, 18%) was made according to the method of Example 65, Step 1, substituting (S)-2-amino-4-methylpentan-1-ol for (1R,2S)-2-aminocyclopentanol. LCMS (APCI+) m/z 404 [M+H]⁺.

Example 69

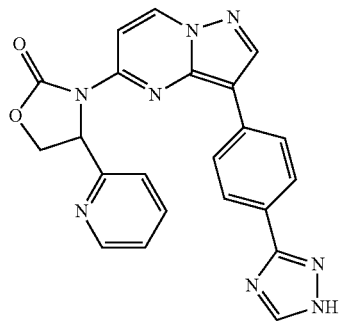 [SMILES: O=C1OCC(c2ccccn2)N1c1ccn2ncc(-c3ccc(-c4nc[nH]n4)cc3)c2n1]

3-(3-(4-(1H-1,2,4-triazol-3-yl)phenyl)pyrazolo[1,5-a]pyrimidin-5-yl)-4-(pyridin-2-yl)oxazolidin-2-one 3-(3-(4-(1H-1,2,4-triazol-3-yl)phenyl)pyrazolo[1,5-a]pyrimidin-5-yl)-4-(pyridin-2-yl)oxazolidin-2-one (0.0055 g, 72%) was made according to the method of Example 65, Step 1, substituting 2-amino-2-(pyridin-2-yl)ethanol bis hydrochloride for (1R,2S)-2-aminocyclopentanol. LCMS (APCI+) m/z 425 [M+H]⁺.

Example 70

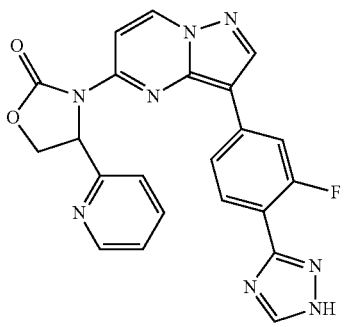 [SMILES: O=C1OCC(c2ccccn2)N1c1ccn2ncc(-c3ccc(-c4nc[nH]n4)c(F)c3)c2n1]

3-(3-(3-fluoro-4-(1H-1,2,4-triazol-3-yl)phenyl)pyrazolo[1,5-a]pyrimidin-5-yl)-4-(pyridin-2-yl)oxazolidin-2-one Step 1: To a solution of 2-amino-2-(pyridin-2-yl)ethanol (3.8 g, 28 mmol) (as the bis HCl salt) in water (50 mL) cooled to 0° C. was added potassium hydroxide (11 g, 19 mmol) followed by THF (50 mL) and the reaction stirred for 20 minutes at 0° C., followed by addition of bis(trichloromethyl)carbonate (8.2 g, 28 mmol) as the solid and stirring at 0° C. for 2 hours. The reaction was next poured into water and extracted with EtOAc and the combined organic layers were washed with 1N NaOH, brine, dried over MgSO₄ and concentrated in vacuo. The crude material was purified by normal phase chromatography using EtOAc as eluent to yield 4-(pyridin-2-yl)oxazolidin-2-one (1.4 g, 8.5 mmol, 31% yield).

Step 2: To a solution of 4-(pyridin-2-yl)oxazolidin-2-one (1.4 g, 8.5 mmol) in DMF was added sodium hydride (0.34 g, 8.5 mmol) and the reaction stirred at ambient temperature for 30 minutes, followed by addition of 3-bromo-5-chloropyrazolo[1,5-a]pyrimidine (1.8 g, 7.7 mmol) and the reaction stirred for 2 hours. The reaction was next poured into water and extracted into ether. The combined organic layers were washed with brine, dried over MgSO₄ and concentrated in vacuo. The crude material was purified by normal phase chromatography using 10% EtOAc/DCM as eluent to yield 3-bromo-5-chloropyrazolo[1,5-a]pyrimidine (1.8 g, 7.7 mmol).

Step 3: To a solution of 3-(3-chloropyrazolo[1,5-a]pyrimidin-5-yl)-4-(pyridin-2-yl)oxazolidin-2-one (0.42 g, 1.3 mmol) in dioxanes was added sodium carbonate solution (2.0 M, 3.3 ml, 6.7 mmol) and 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.61 g, 1.5 mmol) and the reaction bubbled with nitrogen for 30 minutes, followed by the addition of XPHOS (0.63 g, 1.3 mmol) and Pd₂dba₃ (1.2 g, 1.3 mmol), and the reaction stirred at 80° C. for 3 hours. The reaction was poured into water and extracted into EtOAc. The combined organic layers were washed with brine, dried over MgSO₄ and concentrated in vacuo. The crude material was purified by normal phase chromatography using a gradient eluent from 25% EtOAc in hexane to EtOAc to yield 3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(pyridin-2-yl)oxazolidin-2-one (0.36 g, 0.63 mmol, 47% yield).

Step 4: To the solid 3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(pyridin-2-yl)oxazolidin-2-one (0.36 g, 0.63 mmol) was added TFA (20 mL) and the reaction stirred at ambient temperature for 2 hours. The reaction was concentrated in vacuo and the material slurried in 1:1 methanol/acetonitrile (20 mL) with 10 mL of water, then stirred for 2 hours at ambient temperature. The reaction was concentrated in vacuo and the water layer basified to about pH 7 by the addition of saturated NaHCO₃. The solids were filtered and washed with water. The solids were then slurried in 1:1 methanol/acetonitrile (20 mL) with 10 mL of water, and the organic solvents were removed in vacuo (3×). The residue was slurried in 1:1 methanol/acetonitrile (5 mL) with 10 mL of water and the solid filtered and washed with water to yield 3-(3-(3-fluoro-4-(1H-1,2,4-triazol-3-yl)phenyl)pyrazolo[1,5-a]pyrimidin-5-yl)-4-(pyridin-2-yl)oxazolidin-2-one (0.30 g, 0.68 mmol, 108% yield). LCMS (APCI+) m/z 443 [M+H]⁺.

Example 71

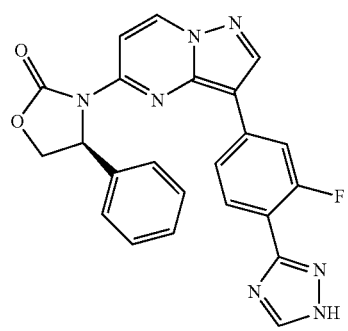 [SMILES: O=C1OC[C@H](c2ccccc2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-phenyloxazolidin-2-one Step 1: To a solution of (S)-3-(3-bromopyrazolo[1,5-a]pyrimidin-5-yl)-4-phenyloxazolidin-2-one (0.20 g, 0.56 mmol), 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.35 g, 0.84 mmol) and sodium carbonate (2.0 M, 1.4 ml, 2.8 mmol) in dioxanes (30 mL) was degassed with nitrogen for 30 minutes. $Pd_2$ $dba_3$ (70 mg) and XPHOS (70 mg) were added and the reaction was heated to 80° C. for 4 hours. The reaction was poured into EtOAc and the layers separated. The organic layer was washed with water, brine, dried over $MgSO_4$ and concentrated in vacuo. The crude material was purified by normal phase chromatography, using 25% EtOAc/DCM as the eluent to give (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-phenyloxazolidin-2-one as a solid (0.30 g, 0.52 mmol, 94% yield).

Step 2: To the solid (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-phenyloxazolidin-2-one (0.30 g, 0.525 mmol) was added TFA (10 mL) and the reaction stirred for 2 hours at ambient temperature. The reaction was concentrated in vacuo and the material was slurried in water (5 mL) with acetonitrile/methanol (10 mL, 1:1) and stirred for 3 hours. The slurry was filtered and the solids were dried in vacuo. The solids were then taken up in water and the water layer was basified with a solution of saturated $NaHCO_3$, and the solids were filtered. The solids were again slurried in water, then filtered and concentrated. The residue was slurried in water/acetonitrile/methanol (30 mL total) and nitrogen was bubbled through the solution to drive complete deprotection. The slurry was filtered and the isolated solids were taken up in acetonitrile (3 mL) and heated to reflux, then cooled. The mixture was filtered and concentrated in vacuo to yield (S)-3-(3-(3-fluoro-4-(1H-1,2,4-triazol-3-yl)phenyl)pyrazolo[1,5-a]pyrimidin-5-yl)-4-phenyloxazolidin-2-one (0.0589 g, 0.133 mmol, 25.4% yield) as the free base. LCMS (APCI+) m/z 442 $[M+H]^+$.

Example 72

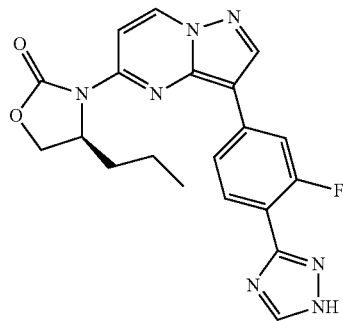 [SMILES: CCC[C@H]1COC(=O)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-propyloxazolidin-2-one Step 1: A solution of triphosgene (0.431 g, 1.45 mmol) in THF (5 mL) was added dropwise to a stirred solution of (S)-2-aminopentan-1-ol (0.500 g, 4.85 mmol) and $Et_3N$ (1.49 mL, 10.7 mmol) in THF (22 mL) at 0° C. under $N_2$. The reaction mixture was stirred at ambient temperature for 2 hours. After cooling, the suspension was filtered through GF/F paper and concentrated in vacuo. The residue was taken up in EtOAc and washed with 10% HCl, dried and concentrated to give (S)-4-propyloxazolidin-2-one (0.348 g, 55%) as a clear oil.

Step 2: To a solution of 3-bromo-5-chloropyrazolo[1,5-a]pyrimidine (5.30 g, 22.8 mmol) and (S)-4-propyloxazolidin-2-one (0.354 g, 2.74 mmol) in dry DMF (10 mL) at ambient temperature was added sodium hydride (0.110 g, 2.74 mmol) and the solution was stirred for 18 hours. Saturated aqueous $NH_4Cl$ solution was added and the solids were collected by filtration. Purification of the crude material by normal phase column chromatography, eluting with 1-10% EtOAc/dichloromethane afforded 0.372 g (63%) of (S)-3-(3-bromopyrazolo[1,5-a]pyrimidin-5-yl)-4-propyloxazolidin-2-one as a yellow solid.

Step 3: To a sealed tube were added (S)-3-(3-bromopyrazolo[1,5-a]pyrimidin-5-yl)-4-propyloxazolidin-2-one (0.100 g, 0.308 mmol), 3-(4-(4,4,5,5-tetramethyl-1,3,2-dioxaborolan-2-yl)phenyl)-1-((2-(trimethylsilyl)ethoxy)methyl)-1H-1,2,4-triazole (0.160 g, 0.400 mmol), in dioxane (1.6 mL) and 2.0 M $Na_2CO_3$ (0.461 ml, 0.923 mmol). The mixture was degassed by bubbling $N_2$ through the solution. $Pd_2$ $dba_3$ (0.0141 g, 0.0154 mmol) and dicyclohexyl(2',4',6'-triisopropylbiphenyl-2-yl)phosphine (0.0147 g, 0.0308 mmol) were added and the vessel was sealed under a $N_2$ atmosphere. The mixture was heated at 90° C. for 18 hours. The reaction mixture was cooled to ambient temperature, filtered through GF/F paper, diluted with $H_2O$ and separated, and the aqueous layer was further extracted with EtOAc. The combined organic extracts were washed with brine, dried and concentrated. Purification of the crude material by normal phase chromatography, eluting with 1-25% EtOAc/dichloromethane, provided (S)-4-propyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one as a bright yellow-orange foamy solid (0.115 g, 72%). LCMS (APCI+) m/z 520 $[M+H]^+$.

Step 4: A mixture of (S)-4-propyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.039 g, 0.075 mmol) in DCM (0.4 mL) was treated with trifluoroacetic acid (0.4 mL) at ambient temperature. The mixture was stirred for 18 hours. The solvent was concentrated and the residue was partitioned between EtOAc and aqueous saturated $NaHCO_3$. The aqueous layer was further extracted with EtOAc. The combined organic extracts were washed with brine, dried, concentrated and purified by column chromatography (1-5% 20% 7N ammonia in MeOH/dichloromethane) to give (S)-3-(3-(4-(1H-1,2,4-triazol-3-yl)phenyl)pyrazolo[1,5-a]pyrimidin-5-yl)-4-propyloxazolidin-2-one (0.018 g, 62%) as a beige solid. LCMS (APCI+) m/z 390 $[M+H]^+$.

Example 73

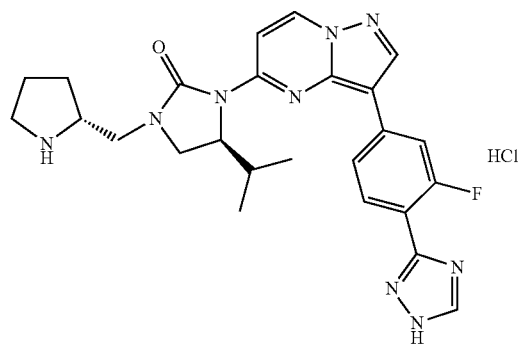 [SMILES: CC(C)[C@H]1CN(C[C@H]2CCCN2)C(=O)N1c1ccn2ncc(-c3ccc(-c4nc[nH]n4)c(F)c3)c2n1 ; Cl]

(S)-3-(3-(3-fluoro-4-(1H-1,2,4-triazol-3-yl)phenyl) pyrazolo[1,5-a]pyrimidin-5-yl)-4-isopropyl-1-((R)-pyrrolidin-2-ylmethyl)imidazolidin-2-one hydrochloride Step 1: (R)-tert-butyl 2-(((S)-3-(3-bromopyrazolo[1,5-a]pyrimidin-5-yl)-4-isopropyl-2-oxoimidazolidin-1-yl)methyl)pyrrolidine-1-carboxylate (94 mg, 50%) was prepared by the procedure described in Example 38, Step 1, using (S)-1-(3-bromopyrazolo[1,5-a]pyrimidin-5-yl)-5-isopropylimidazolidin-2-one and (R)-tert-butyl 2-((methylsulfonyloxy)methyl)pyrrolidine-1-carboxylate.

Step 2: A mixture of ((R)-tert-butyl 2-(((S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyl-2-oxoimidazolidin-1-yl)methyl)pyrrolidine-1-carboxylate and (2R)-tert-butyl 2-(((4S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyl-2-oxo imidazolidin-1-yl)methyl)pyrrolidine-1-carboxylate (69 mg, 52%) was prepared by the procedure described in Example 6, Step 6, using (R)-tert-butyl 2-(((S)-3-(3-bromopyrazolo[1,5-a]pyrimidin-5-yl)-4-isopropyl-2-oxoimidazolidin-1-yl)methyl)pyrrolidine-1-carboxylate.

Step 3: (S)-3-(3-(3-fluoro-4-(1H-1,2,4-triazol-3-yl)phenyl)pyrazolo[1,5-a]pyrimidin-5-yl)-4-isopropyl-1-((R)-pyrrolidin-2-ylmethyl)imidazolidin-2-one hydrochloride (6 mg, 75%) was prepared by the procedure described in Example 38, Step 2, from a mixture of ((R)-tert-butyl 2-(((S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-isopropyl-2-oxoimidazolidin-1-yl)methyl)pyrrolidine-1-carboxylate and (2R)-tert-butyl 2-(((4S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-isopropyl-2-oxo imidazolidin-1-yl)methyl)pyrrolidine-1-carboxylate. LCMS (APCI+) m/z 490.7 [M+H]+.

Example 74

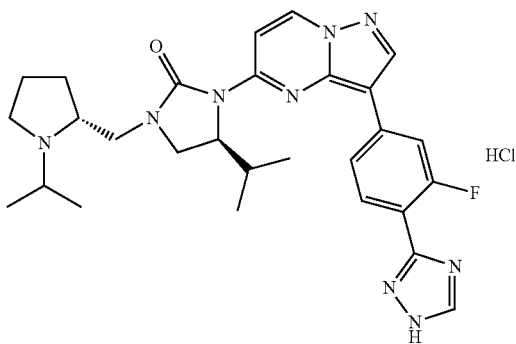 [SMILES: CC(C)[C@H]1CN(C[C@H]2CCCN2C(C)C)C(=O)N1c1ccn2ncc(-c3ccc(-c4nc[nH]n4)c(F)c3)c2n1 ; Cl]

(S)-3-(3-(3-fluoro-4-(1H-1,2,4-triazol-3-yl)phenyl) pyrazolo[1,5-a]pyrimidin-5-yl)-4-isopropyl-1-(((R)-1-isopropylpyrrolidin-2-yl)methyl)imidazolidin-2-one hydrochloride Prepared by the procedure described in Example 22, substituting (S)-3-(3-(3-fluoro-4-(1H-1,2,4-triazol-3-yl)phenyl)pyrazolo[1,5-a]pyrimidin-5-yl)-4-isopropyl-1-((R)-pyrrolidin-2-ylmethyl)imidazolidin-2-one for (S)-3-(3-(4-(1H-imidazol-2-yl)phenyl)pyrazolo[1,5-a]pyrimidin-5-yl)-4-isopropyl-1-(piperidin-4-ylmethyl)imidazolidin-2-one, and substituting acetone for formaldehyde (5 mg, 43%). LCMS (APCI+) m/z 532.8 [M+H]

Example 75

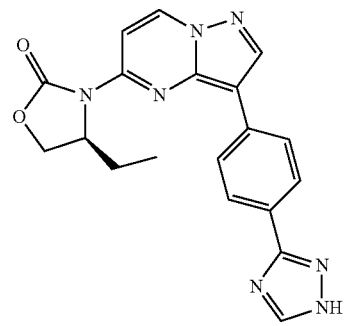 [SMILES: CC[C@H]1COC(=O)N1c1ccn2ncc(-c3ccc(-c4nc[nH]n4)cc3)c2n1]

(S)-3-(3-(4-(1H-1,2,4-triazol-3-yl)phenyl)pyrazolo [1,5-a]pyrimidin-5-yl)-4-ethyloxazolidin-2-one Step 1: A 5 mL THF solution containing triphosgene (0.499 g, 1.68 mmol) was added dropwise to a cold 22 mL THF solution containing (S)-2-aminobutan-1-ol (0.530 mL, 5.61 mmol) and triethylamine (1.72 mL, 12.3 mmol). A thick white precipitate formed immediately. Reaction was allowed to warm up to ambient temperature and stirred for 3 hours. The solids were filtered, concentrated, taken in EtOAc and washed with 10% HCl, dried (phase separator silicone treated filter paper), concentrated and purified on silica gel (1-2% MeOH in DCM) to provide (S)-4-ethyloxazolidin-2-one (0.263 g, 41% yield).

Step 2: To a solution of 3-bromo-5-chloropyrazolo[1,5-a]pyrimidine (0.375 g, 1.61 mmol) and (S)-4-ethyloxazolidin-2-one (0.279 g, 2.42 mmol) in DMF (10 mL) was added sodium hydride (0.0968 g, 2.42 mmol) at ambient temperature. The mixture was stirred for 18 hours. Saturated aqueous NH$_4$Cl was added and the solids were collected by filtration. Purification of the crude material by column chromatography (1-10% EtOAc in DCM) provided (S)-3-(3-bromopyrazolo[1,5-a]pyrimidin-5-yl)-4-ethyloxazolidin-2-one (0.282 g, 56% yield) as a pale yellow solid.

Step 3: To a sealed tube was added (S)-3-(3-bromopyrazolo[1,5-a]pyrimidin-5-yl)-4-ethyloxazolidin-2-one (0.100 g, 0.321 mmol), 3-(4-(4,4,5,5-tetramethyl-1,3,2-dioxaborolan-2-yl)phenyl)-1-((2-(trimethylsilyl)ethoxy)methyl)-1H-1,2,4-triazole (0.168 g, 0.418 mmol) and 2.0 M Na$_2$CO$_3$ (0.482 mL, 0.964 mmol) in dioxane (1.6 mL). The mixture was degassed by bubbling N$_2$ through the solution. Pd$_2$ dba$_3$ (0.0147 g, 0.0161 mmol), and dicyclohexyl(2',4',6'-triisopropylbiphenyl-2-yl)phosphine (0.0153 g, 0.0321 mmol) were added and the vessel was sealed under a N$_2$ atmosphere. The mixture was heated at 90° C. for 18 hours. The reaction mixture was cooled to ambient temperature, filtered through glass fiber filter paper, concentrated and purified on silica gel (1-55% EtOAc in DCM) to provide (S)-4-ethyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.076 g, 47% yield) as a yellow gum.

Step 4: A mixture of (S)-4-ethyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.024 g, 0.047 mmol) in DCM (1 mL) was treated with trifluoroacetic acid (0.4 mL) at ambient temperature. The mixture was stirred for 18 hours. The solvent was concentrated and the residue partitioned between EtOAc and aqueous satd. NaHCO₃. The aqueous layer was further extracted with EtOAc. The combined organic extracts were washed with brine, dried (phase separator silicone treated filter paper), concentrated and purified on silica gel (1-5% 7N ammonia in MeOH/dichloromethane) to give (S)-3-(3-(4-(1H-1,2,4-triazol-3-yl)phenyl)pyrazolo[1,5-a]pyrimidin-5-yl)-4-ethyloxazolidin-2-one (0.008 g, 45%) as a beige solid. MS (APCI+) m/z 376 [M+H]⁺.

Example 76

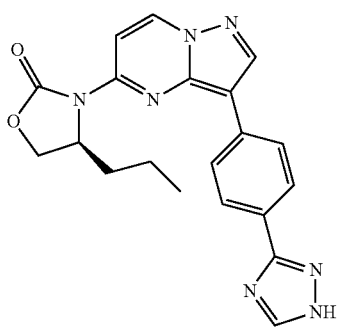 [SMILES: CCC[C@H]1COC(=O)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-propyloxazolidin-2-one Step 1: (S)-4-propyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.115 g, 72% yield) was prepared by the procedure described in Example 75, Step 3, substituting (S)-3-(3-bromopyrazolo[1,5-a]pyrimidin-5-yl)-4-propyloxazolidin-2-one for (S)-3-(3-bromopyrazolo[1,5-a]pyrimidin-5-yl)-4-ethyloxazolidin-2-one.

Step 2: (S)-3-(3-(4-(1H-1,2,4-triazol-3-yl)phenyl)pyrazolo[1,5-a]pyrimidin-5-yl)-4-propyloxazolidin-2-one (0.018 g, 62% yield) was prepared by the procedure described in Example 75, Step 4, using (S)-4-propyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.039 g, 0.075 mmol) to produce a beige residue. MS (APCI+) m/z 390 [M+H]⁺.

Example 77

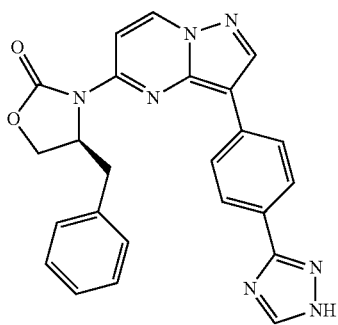 [SMILES: O=C1OC[C@H](Cc2ccccc2)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-benzyloxazolidin-2-one Step 1: (S)-4-benzyl-3-(3-bromopyrazolo[1,5-a]pyrimidin-5-yl)oxazolidin-2-one (0.32 g, 99% yield) was prepared by the procedure described in Example 75, Step 2, substituting (S)-4-benzyloxazolidin-2-one for (S)-4-ethyloxazolidin-2-one.

Step 2: (S)-4-benzyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.089 g, 58% yield) was prepared by the procedure described in Example 75, Step 3, substituting (S)-4-benzyl-3-(3-bromopyrazolo[1,5-a]pyrimidin-5-yl)oxazolidin-2-one for (S)-3-(3-bromopyrazolo[1,5-a]pyrimidin-5-yl)-4-ethyloxazolidin-2-one.

Step 3: (S)-3-(3-(4-(1H-1,2,4-triazol-3-yl)phenyl)pyrazolo[1,5-a]pyrimidin-5-yl)-4-benzyloxazolidin-2-one (0.037 g, 54% yield) was prepared by the procedure described in Example 75, Step 4, using (S)-4-benzyl-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.089 g, 0.16 mmol) to produce a beige residue. MS (APCI+) m/z 438 [M+H]⁺.

Example 78

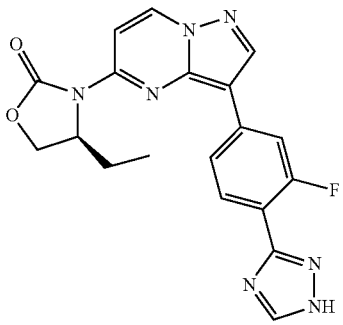 [SMILES: CC[C@H]1COC(=O)N1c1ccn2ncc(-c3ccc(-c4nc[nH]n4)c(F)c3)c2n1]

(S)-4-ethyl-3-(3-(3-fluoro-4-(1H-1,2,4-triazol-3-yl)phenyl)pyrazolo[1,5-a]pyrimidin-5-yl)oxazolidin-2-one Step 1: (S)-4-ethyl-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.023 g, 34% yield) was prepared by the procedure described in Example 76, Step 1 substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole for 3-(4-(4,4,5,5-tetramethyl-1,3,2-dioxaborolan-2-yl)phenyl)-1-((2-(trimethylsilyl)ethoxy)methyl)-1H-1,2,4-triazole.

Step 2: (S)-4-ethyl-3-(3-(3-fluoro-4-(1H-1,2,4-triazol-3-yl)phenyl)pyrazolo[1,5-a]pyrimidin-5-yl)oxazolidin-2-one (0.008 g, 46% yield) was prepared by the procedure described in Example 75, Step 4, using ((S)-4-ethyl-3-(3-(3-fluoro-4-(1-((2-(trim-ethylsilyl)ethoxy)methyl)-1H-1,2,4-triazol-3-yl)phenyl)pyrazolo[1,5-a]pyrimidin-5-yl) oxazolidin-2-one (0.023 g, 0.044 mmol) to produce a beige residue. MS (APCI+) m/z 394 [M+H]⁺.

Example 79

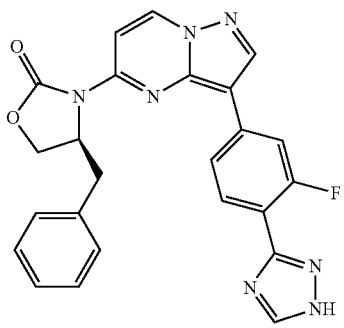 [SMILES: O=C1OC[C@H](Cc2ccccc2)N1c1ccn2ncc(-c3ccc(-c4nc[nH]n4)c(F)c3)c2n1]

(S)-4-benzyl-3-(3-(3-fluoro-4-(1H-1,2,4-triazol-3-yl)phenyl)pyrazolo[1,5-a]pyrimidin-5-yl)oxazolidin-2-one Step 1: (S)-4-benzyl-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one) (0.015 g, 24% yield) was prepared by the procedure described in Example 77, Step 2, substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole for 3-(4-(4,4,5,5-tetramethyl-1,3,2-dioxaborolan-2-yl)phenyl)-1-((2-(trimethylsilyl)ethoxy)methyl)-1H-1,2,4-triazole.

Step 2: (S)-4-benzyl-3-(3-(3-fluoro-4-(1H-1,2,4-triazol-3-yl)phenyl)pyrazolo[1,5-a]pyrimidin-5-yl)oxazolidin-2-one (0.006 g, 6% yield) was prepared by the procedure described in Example 75, Step 4, using (S)-4-benzyl-3-(3-(3-fluoro-4-(1-((2-(tri-methylsilyl)ethoxy)methyl)-1H-1,2,4-triazol-3-yl)phenyl)pyrazolo[1,5-a]pyrimidin-5-yl)oxazolidin-2-one (0.030 g, 0.051 mmol)) to produce a beige residue. MS (APCI+) m/z 456 [M+H]+.

Example 80

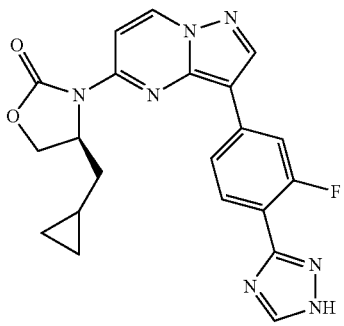 [SMILES: O=C1OC[C@H](CC2CC2)N1c1ccn2ncc(-c3ccc(-c4nc[nH]n4)c(F)c3)c2n1]

(S)-4-(cyclopropylmethyl)-3-(3-(3-fluoro-4-(1H-1,2,4-triazol-3-yl)phenyl)pyrazolo[1,5-a]pyrimidin-5-yl)oxazolidin-2-one Step 1: (S)-2-amino-3-cyclopropylpropanoic acid (1.0 g, 7.743 mmol) in 1N NaOH (26 mL) was treated with benzyl chlorofomate (1.326 mL, 9.291 mmol) and stirred at ambient temperature overnight. This mixture was extracted with DCM, organics discarded, aqueous layer acidified with concentrated HCl and extracted with DCM. The combined organic layer was dried (phase separator silicone treated filter paper) and solvent concentrated to afford (S)-2-(benzyloxycarbonylamino)-3-cyclopropylpropanoic acid (1.18 g, 58% yield) as a white gum.

Step 2: A solution of (S)-2-(benzyloxycarbonylamino)-3-cyclopropylpropanoic acid (0.292 g, 1.11 mmol) in THF (2 mL) was cooled to 0° C. and treated with borane-THF complex (1.44 mL, 1.44 mmol). The mixture was stirred at ambient temperature for 4 hours and then treated with 1N HCl until bubbling ceased. After stirring at ambient temperature overnight, the organic solvent was concentrated. The residue is treated with EtOAc, aqueous phase removed, organic phase washed with 1N NaOH, dried (phase separator silicone treated filter paper), concentrated to provide (S)-benzyl 1-cyclopropyl-3-hydroxypropan-2-ylcarbamate (0.156 g, 56% yield) as a white gum.

Step 3: To a stirred solution of (S)-benzyl 1-cyclopropyl-3-hydroxypropan-2-ylcarbamate (0.734 g, 2.94 mmol) in DMF (15 mL) was added sodium hydride (0.177 g, 4.42 mmol) at 0° C. The mixture was then stirred at ambient temperature for 30 minutes. The solvent was concentrated and the residue distributed between water and EtOAc. The combined organic extracts were dried (phase separator silicone treated filter paper), concentrated to provide (S)-4-(cyclopropylmethyl)oxazolidin-2-one (0.318 g, 76% yield) as a clear oil.

Step 4: (S)-3-(3-bromopyrazolo[1,5-a]pyrimidin-5-yl)-4-(cyclopropylmethyl) oxazolidin-2-one (0.073 g, 25% yield) was prepared by the procedure described in Example 75, Step 2, using (S)-4-(cyclopropylmethyl)oxazolidin-2-one for (S)-4-ethyloxazolidin-2-one.

Step 5: (S)-4-(cyclopropylmethyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.090 g, 76% yield) was prepared by the procedure described in Example 77, Step 2, using 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole for 3-(4-(4,4,5,5-tetramethyl-1,3,2-dioxaborolan-2-yl)phenyl)-1-((2-(trimethylsilyl)ethoxy)methyl)-1H-1,2,4-triazole.

Step 6: (S)-4-(cyclopropylmethyl)-3-(3-(3-fluoro-4-(1H-1,2,4-triazol-3-yl)phenyl)pyrazolo[1,5-a]pyrimidin-5-yl)oxazolidin-2-one (0.023 g, 33% yield) was prepared by the procedure described in Example 75, Step 4, using (S)-4-(cyclopropylmethyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.090 g, 0.16 mmol). MS (APCI+) m/z 420 [M+H]+.

Example 81

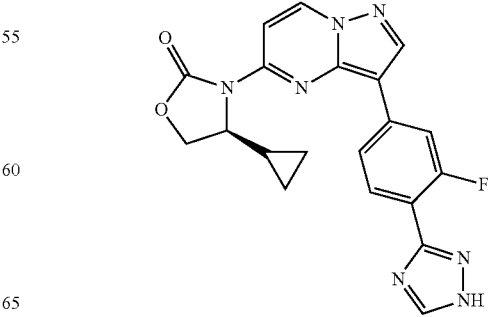

(S)-4-cyclopropyl-3-(3-(3-fluoro-4-(1H-1,2,4-triazol-3-yl)phenyl)pyrazolo[1,5-a]pyrimidin-5-yl)oxazolidin-2-one Step 1: (S)-2-(benzyloxycarbonylamino)-2-cyclopropylacetic acid (1.5 g, 69% yield) was prepared by the procedure described in Example 80, Step 1, using (S)-2-amino-2-cyclopropylacetic acid.

Step 2: (S)-benzyl 1-cyclopropyl-2-hydroxyethylcarbamate (0.176 g, 48% yield) was prepared by the procedure described in Example 80, Step 2, using (S)-2-(benzyloxycarbonylamino)-2-cyclopropylacetic acid.

Step 3: (S)-4-cyclopropyloxazolidin-2-one (0.206, 100% yield) was prepared by the procedure described in Example 80, Step 3, using (S)-benzyl 1-cyclopropyl-2-hydroxyethylcarbamate.

Step 4: (S)-3-(3-bromopyrazolo[1,5-a]pyrimidin-5-yl)-4-cyclopropyloxazolidin-2-one (0.094 g, 30% yield) was prepared by the procedure described in Example 80, Step 4, using (S)-4-cyclopropyloxazolidin-2-one.

Step 5: (S)-4-cyclopropyl-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.030 g, 20% yield) was prepared by the procedure described in Example 80, Step 5, using (S)-3-(3-bromopyrazolo[1,5-a]pyrimidin-5-yl)-4-cyclopropyloxazolidin-2-one.

Step 6: (S)-4-cyclopropyl-3-(3-(3-fluoro-4-(1H-1,2,4-triazol-3-yl)phenyl)pyrazolo[1,5-a]pyrimidin-5-yl)oxazolidin-2-one (0.008 g, 81% yield) was prepared by the procedure described in Example 80, Step 6, using (S)-4-cyclopropyl-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.013 g, 0.024 mmol). MS (APCI+) m/z 406 [M+H]$^+$.

Example 82

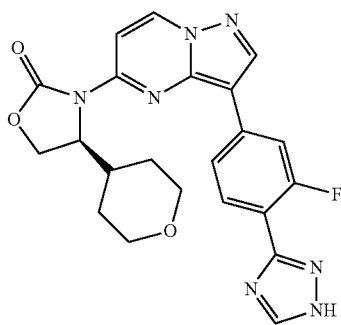 [SMILES: O=C1OC[C@H](C2CCOCC2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(tetrahydro-2H-pyran-4-yl)oxazolidin-2-one Step 1: (S)-2-(benzyloxycarbonylamino)-2-(tetrahydro-2H-pyran-4-yl)acetic acid (0.620 g, 68% yield) was prepared by the procedure described in Example 80, Step 1, using (S)-2-amino-2-(tetrahydro-2H-pyran-4-yl)acetic acid.

Step 2: (S)-benzyl 2-hydroxy-1-(tetrahydro-2H-pyran-4-yl)ethylcarbamate (0.246 g, 42% yield) was prepared by the procedure described in Example 80, Step 2, using (S)-2-(benzyloxycarbonylamino)-2-(tetrahydro-2H-pyran-4-yl)acetic acid.

Step 3: (S)-4-(tetrahydro-2H-pyran-4-yl)oxazolidin-2-one (0.099 g, 66% yield) was prepared by the procedure described in Example 80, Step 3, using (S)-benzyl 2-hydroxy-1-(tetrahydro-2H-pyran-4-yl)ethylcarbamate.

Step 4: (S)-3-(3-bromopyrazolo[1,5-a]pyrimidin-5-yl)-4-(tetrahydro-2H-pyran-4-yl)oxazolidin-2-one (0.030 g, 21% yield) was prepared by the procedure described in Example 80, Step 4, using (S)-4-(tetrahydro-2H-pyran-4-yl)oxazolidin-2-one.

Step 5: (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(tetrahydro-2H-pyran-4-yl)oxazolidin-2-one (0.027 g, 57% yield) was prepared by the procedure described in Example 80, Step 5, using (S)-3-(3-bromopyrazolo[1,5-a]pyrimidin-5-yl)-4-(tetrahydro-2H-pyran-4-yl)oxazolidin-2-one.

Step 6: (S)-3-(3-(3-fluoro-4-(1H-1,2,4-triazol-3-yl)phenyl)pyrazolo[1,5-a]pyrimidin-5-yl)-4-(tetrahydro-2H-pyran-4-yl)oxazolidin-2-one (0.003 g, 17% yield) was prepared by the procedure described in Example 80, Step 6, using (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(tetrahydro-2H-pyran-4-yl)oxazolidin-2-one (0.023 g, 0.040 mmol). MS (APCI+) m/z 450 [M+H]$^+$.

Example 83

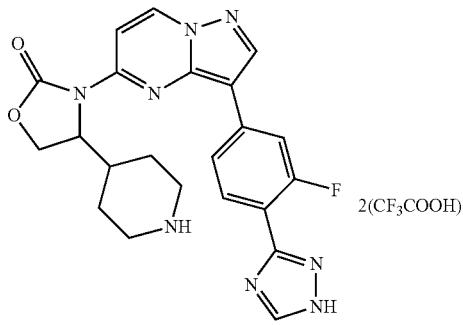 [SMILES: O=C1OCC(C2CCNCC2)N1c1ccn2ncc(-c3ccc(-c4nc[nH]n4)c(F)c3)c2n1]

3-(3-(3-fluoro-4-(1H-1,2,4-triazol-3-yl)phenyl)pyrazolo[1,5-a]pyrimidin-5-yl)-4-(piperidin-4-yl)oxazolidin-2-one bis-trifluoroacetate Step 1: A solution of 2-amino-2-(1-(tert-butoxycarbonyl)piperidin-4-yl)acetic acid (1.0 g, 3.87 mmol) in THF (20 mL) was added 1N NaOH (14 mL, 28.0 mmol) and di-tert-butyl dicarbonate (0.887 g, 4.06 mmol) and stirred at ambient temperature overnight. The mixture was treated with 2N HCl, extracted twice with EtOAc, dried (phase separator silicone treated filter paper) and concentrated to provide 2-(1-(tert-butoxycarbonyl)piperidin-4-yl)-2-(tert-butoxycarbonylamino)acetic acid (1.03 g, 74% yield) as a white foam.

Step 2: tert-Butyl 4-(1-(tert-butoxycarbonylamino)-2-hydroxyethyl)piperidine-1-carboxylate (0.422 g, 43% yield) was prepared by the procedure described in Example 80, Step 2, using 2-(1-(tert-butoxycarbonyl)piperidin-4-yl)-2-(tert-butoxycarbonylamino)acetic acid.

Step 3: tert-Butyl 4-(2-oxooxazolidin-4-yl)piperidine-1-carboxylate (0.099 g, 79% yield) was prepared by the procedure described in Example 80, Step 3, using tert-butyl 4-(1-(tert-butoxycarbonylamino)-2-hydroxyethyl)piperidine-1-carboxylate.

Step 4: tert-Butyl 4-(3-(3-bromopyrazolo[1,5-a]pyrimidin-5-yl)-2-oxooxazolidin-4-yl)piperidine-1-carboxylate (0.034 g, 21% yield) was prepared by the procedure described in Example 80, Step 4, using tert-butyl 4-(2-oxooxazolidin-4-yl)piperidine-1-carboxylate.

Step 5: (S)-tert-Butyl 4-(3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-2-oxooxazolidin-4-yl)piperidine-1-carboxylate (0.018 g, 36% yield) was prepared by the procedure described in Example 80, Step 5, using tert-butyl 4-(3-(3-bromopyrazolo[1,5-a]pyrimidin-5-yl)-2-oxooxazolidin-4-yl)piperidine-1-carboxylate.

Step 6: A solution of tert-butyl 4-(3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-2-oxooxazolidin-4-yl)piperidine-1-carboxylate (0.012 g, 0.018 mmol) in DCM (0.2 mL) was treated with TFA (0.1 mL) at ambient temperature. Stirring was continued for 2 hours. The reaction was concentrated in vacuo and azeotroped with ether (3×). The residue was triturated in ether and collected by filtration to give 3-(3-(3-fluoro-4-(1H-1,2,4-triazol-3-yl)phenyl)pyrazolo[1,5-a]pyrimidin-5-yl)-4-(piperidin-4-yl)oxazolidin-2-one bis-trifluoroace-tate (0.0052 g, 66% yield). MS (APCI+) m/z 449 [M+H]+.

Example 84

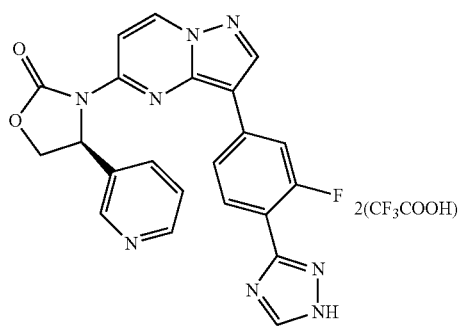 [SMILES: O=C1OC[C@H](c2cccnc2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(pyridin-3-yl)oxazolidin-2-one bis-trifluoroacetate Step 1: A mixture of 2-(tert-butyldimethylsilyloxy)acetaldehyde (54.64 mL, 258.2 mmol) in DCM (500 mL) was treated with (S)-2-methylpropane-2-sulfinamide (34.42 g, 284.0 mmol), followed by copper sulfate (103.0 g, 645.4 mmol) at ambient temperature. After stirring for 48 hours, the mixture was filtered through Celite and washed with DCM. The mixture was concentrated and purified on silica gel (10-30% EtOAc in hexane) to provide (S,E)-N-(2-(tert-butyldimethylsilyloxy)ethylidene)-2-methylpropane-2-sulfinamide (67.3 g, 94% yield).

Step 2: To a solution of toluene (50 mL) cooled to −78° C. was added 2.5 M butyllithium in hexanes (6.31 mL, 15.1 mmol) and the reaction mixture was stirred until the temperature returned to −78° C. 3-Bromopyridine (1.88 g, 11.9 mmol) in toluene (5 mL) was added to the reaction mixture a rate such that the temperature never went above −65° C., and then the reaction was stirred at −78° C. for 1 hour. (S,E)-N-(2-(tert-Butyldimethylsilyloxy)ethylidene)-2-methylpropane-2-sulfinamide (3.00 g, 10.8 mmol) in toluene (1 mL) was added to the reaction mixture at a rate such that the temperature did not exceed −70° C., and then the reaction was stirred at −78° C. for 2 hours. To the −78° C. solution was added brine and the mixture partitioned between ETOAc/water. The organic layer was washed with brine, dried (phase separator silicone treated filter paper), concentrated and purified on silica gel (15-80% EtOAc in DCM) to provide (S)—N—((S)-2-(tert-butyldimethylsilyloxy)-1-(pyridin-3-yl)ethyl)-2-methylpropane-2-sulfinamide (0.862 g, 22% yield) as a yellow oil.

Step 3: A mixture of (S)—N—((S)-2-(tert-butyldimethylsilyloxy)-1-(pyridin-3-yl)ethyl)-2-methylpropane-2-sulfinamide (0.2 g, 1.77 mmol) in MeOH (9 mL) was treated with 4N hydrogen chloride (2.21 mL, 8.85 mmol) at 0° C. The mixture was allowed to warm up to ambient temperature and stirred for 1 hour. The mixture was concentrated and the residue treated with aqueous saturated NaHCO3/EtOAc. The organic layer was dried (phase separator silicone treated filter paper), concentrated. The residue was purified on silica gel (2-10% 7N ammonia in MeOH in DCM) to provide (S)-2-amino-2-(pyridin-3-yl)ethanol dihydrochloride (0.060 g, 16% yield) as a beige solid.

Step 4: To a solution of (S)-2-amino-2-(pyridin-3-yl)ethanol hydrochloride (0.255 g, 1.46 mmol) in water (2 mL) was added potassium hydroxide (0.573 g, 10.2 mmol) and the reaction stirred until complete dissolution occurred, followed by addition of THF (3 mL) and the reaction cooled to 0° C. To the reaction was next added triphosgene (0.433 g, 1.46 mmol) and the reaction allowed to warm up to ambient temperature and stirred for 18 hours. The reaction was concentrated and the adjusted to about pH 8 with 3N NaOH, and concentrated. The residue was purified on silica gel (2-10% 7N ammonia in MeOH in DCM) to provide (S)-4-(pyridin-3-yl)oxazolidin-2-one (0.054 g, 23% yield) as a beige solid.

Step 5: (S)-3-(3-Bromopyrazolo[1,5-a]pyrimidin-5-yl)-4-(pyridin-3-yl) oxazolidin-2-one (0.042 g, 39% yield) was prepared by the procedure described in Example 75, Step 2, using (S)-4-(pyridin-3-yl)oxazolidin-2-one for (S)-4-ethyloxazolidin-2-one.

Step 6: (S)-3-(3-(3-Fluoro-4-(1-((2-(trimethylsilyl)ethoxy)methyl)-1H-1,2,4-triazol-3-yl)phenyl)pyrazolo[1,5-a]pyrimidin-5-yl)-4-(pyridin-3-yl)oxazolidin-2-one (0.011 g, 16% yield) was prepared by the procedure described in Example 77, Step 2, substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole for 3-(4-(4,4,5,5-tetramethyl-1,3,2-dioxaborolan-2-yl)phenyl)-1-((2-(trimethylsilyl)ethoxy)methyl)-1H-1,2,4-triazole.

Step 7: (S)-3-(3-(3-Fluoro-4-(1H-1,2,4-triazol-3-yl)phenyl)pyrazolo[1,5-a]pyrimidin-5-yl)-4-(pyridin-3-yl)oxazolidin-2-one bis(2,2,2-trifluoroacetate) (0.012 g, 92% yield) was prepared by the procedure described in Example 83, Step 6, using (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(pyridin-3-yl)oxazolidin-2-one (0.011 g, 0.019 mmol). LCMS (APCI+) m/z 443 [M+H]+.

Example 85

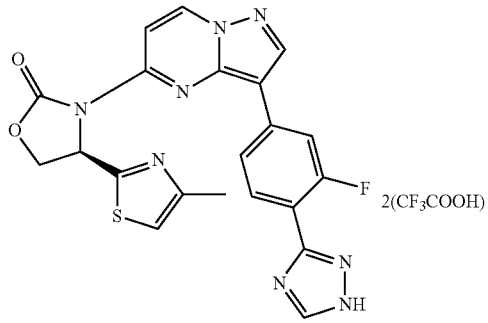 [SMILES: Cc1csc([C@H]2COC(=O)N2c2ccn3ncc(-c4ccc(-c5nc[nH]n5)c(F)c4)c3n2)n1]

(R)-3-(3-(3-fluoro-4-(1H-1,2,4-triazol-3-yl)phenyl)pyrazolo[1,5-a]pyrimidin-5-yl)-4-(4-methylthiazol-2-yl)oxazolidin-2-one bis(2,2,2-trifluoroacetate)

Step 1: Following the procedure of Example 84, Step 2 and using 2-bromo-4-methylthiazole in place of 3-bromopyridine, (S)—N—((R)-2-(tert-butyldimethylsilyloxy)-1-(4-methylthiazol-2-yl)ethyl)-2-methylpropane-2-sulfinamide (0.970 g, 36% yield) was isolated as a major product.

Step 2: (R)-2-amino-2-(4-methylthiazol-2-yl)ethanol hydrochloride (0.503 g, 100% yield) was prepared by the procedure described in Example 84, Step 3, using (S)—N—((R)-2-(tert-butyldimethylsilyloxy)-1-(4-methylthiazol-2-yl)ethyl)-2-methylpropane-2-sulfinamide.

Step 3: (S)-4-(4-methylthiazol-2-yl)oxazolidin-2-one (0.329 g, 69% yield) was prepared by the procedure described in Example 84, Step 4, using (R)-2-amino-2-(4-methylthiazol-2-yl)ethanol hydrochloride.

Step 4: (R)-3-(3-bromopyrazolo[1,5-a]pyrimidin-5-yl)-4-(4-methylthiazol-2-yl)oxazolidin-2-one (0.228 g, 37% yield) was prepared by the procedure described in Example 84, Step 5, using (S)-4-(4-methylthiazol-2-yl)oxazolidin-2-one.

Step 5: (R)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(4-methylthiazol-2-yl)oxazolidin-2-one (0.033 g, 42% yield) was prepared by the procedure described in Example 84, Step 6, using (R)-3-(3-bromopyrazolo[1,5-a]pyrimidin-5-yl)-4-(4-methylthiazol-2-yl)oxazolidin-2-one.

Step 6: (R)-3-(3-(3-fluoro-4-(1H-1,2,4-triazol-3-yl)phenyl)pyrazolo[1,5-a]pyrimidin-5-yl)-4-(4-methylthiazol-2-yl)oxazolidin-2-one bis(2,2,2-trifluoroacetate) (0.010 g, 72% yield) was prepared by the procedure described in Example 83, Step 6, using (R)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(4-methylthiazol-2-yl)oxazolidin-2-one (0.012 g, 0.020 mmol). LCMS (APCI+) m/z 463 [M+H]+.

Example 86

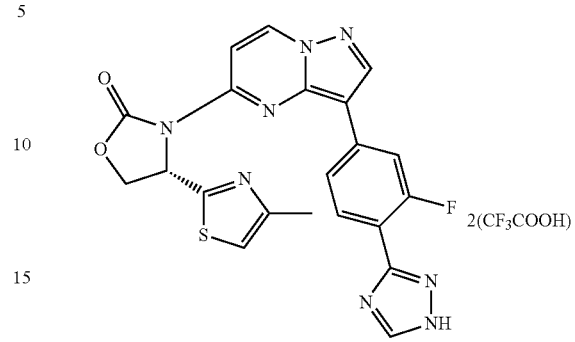

(S)-3-(3-(3-fluoro-4-(1H-1,2,4-triazol-3-yl)phenyl)pyrazolo[1,5-a]pyrimidin-5-yl)-4-(4-methylthiazol-2-yl)oxazolidin-2-one bis(2,2,2-trifluoroacetate)

Step 1: Following the procedure of Example 84, Step 2 and using 2-bromo-4-methylthiazole in place of 3-bromopyridine, (S)—N((S)-2-(tert-butyldimethylsilyloxy)-1-(4-methylthiazol-2-yl)ethyl)-2-methylpropane-2-sulfinamide (0.584 g, 22% yield) was isolated as a minor product.

Step 2: (S)-2-amino-2-(4-methylthiazol-2-yl)ethanol hydrochloride (0.301 g, 100% yield) was prepared by the procedure described in Example 84, Step 3, using (S)—N—(S)-2-(tert-butyldimethylsilyloxy)-1-(4-methylthiazol-2-yl)ethyl)-2-methylpropane-2-sulfinamide.

Step 3: (R)-4-(4-methylthiazol-2-yl)oxazolidin-2-one (0.182 g, 56% yield) was prepared by the procedure described in Example 84, Step 4, using (S)-2-amino-2-(4-methylthiazol-2-yl)ethanol hydrochloride.

Step 4: (S)-3-(3-bromopyrazolo[1,5-a]pyrimidin-5-yl)-4-(4-methylthiazol-2-yl)oxazolidin-2-one (0.122 g, 36% yield) was prepared by the procedure described in Example 84, Step 5, using (R)-4-(4-methylthiazol-2-yl)oxazolidin-2-one.

Step 5: (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(4-methylthiazol-2-yl)oxazolidin-2-one (0.122 g, 36% yield) was prepared by the procedure described in Example 84, Step 6, using (S)-3-(3-bromopyrazolo[1,5-a]pyrimidin-5-yl)-4-(4-methylthiazol-2-yl)oxazolidin-2-one.

Step 6: (S)-3-(3-(3-fluoro-4-(1H-1,2,4-triazol-3-yl)phenyl)pyrazolo[1,5-a]pyrimidin-5-yl)-4-(4-methylthiazol-2-yl)oxazolidin-2-one bis(2,2,2-trifluoroacetate) (0.010 g, 66% yield) was prepared by the procedure described in Example 83, Step 6, using (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(4-methylthiazol-2-yl)oxazolidin-2-one (0.050 g, 0.13 mmol). LCMS (APCI+) m/z 463 [M+H]+.

Example 87

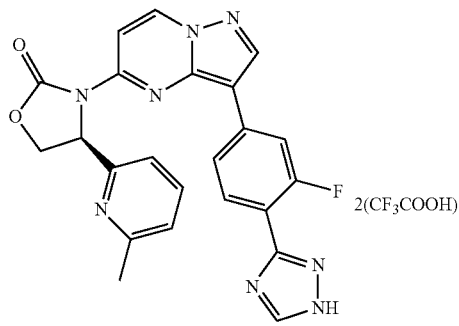 [SMILES: Cc1cccc([C@H]2COC(=O)N2c2ccn3ncc(-c4ccc(-c5nc[nH]n5)c(F)c4)c3n2)n1]

(S)-3-(3-(3-fluoro-4-(1H-1,2,4-triazol-3-yl)phenyl)
pyrazolo[1,5-a]pyrimidin-5-yl)-4-(6-methylpyridin-
2-yl)oxazolidin-2-one bis(2,2,2-trifluoroacetate)

Step 1: (S)—N—((S)-2-(tert-butyldimethylsilyloxy)-1-(6-methylpyridin-2-yl)ethyl)-2-methylpropane-2-sulfinamide (0.521 g, 20% yield) was prepared by the procedure described in Example 84, Step 2, using 2-bromo-6-methylpyridine.

Step 2: (S)-2-amino-2-(6-methylpyridin-2-yl)ethanol dihydrochloride (0.316 g, 99% yield) was prepared by the procedure described in Example 84, Step 3, using (S)—N—((S)-2-(tert-butyldimethylsilyloxy)-1-(6-methylpyridin-2-yl)ethyl)-2-methylpropane-2-sulfinamide.

Step 3: (S)-4-(6-methylpyridin-2-yl)oxazolidin-2-one (0.207 g, 83% yield) was prepared by the procedure described in Example 84, Step 4, using (S)-2-amino-2-(6-methylpyridin-2-yl)ethanol dihydrochloride.

Step 4: (S)-3-(3-bromopyrazolo[1,5-a]pyrimidin-5-yl)-4-(6-methylpyridin-2-yl)oxazolidin-2-one (0.135 g, 35% yield) was prepared by the procedure described in Example 84, Step 5, using (S)-4-(6-methylpyridin-2-yl)oxazolidin-2-one.

Step 5: (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(6-methylpyridin-2-yl)oxazolidin-2-one (0.042 g, 67% yield) was prepared by the procedure described in Example 84, Step 6, using (S)-3-(3-bromopyrazolo[1,5-a]pyrimidin-5-yl)-4-(6-methylpyridin-2-yl)oxazolidin-2-one.

Step 6: (S)-3-(3-(3-fluoro-4-(1H-1,2,4-triazol-3-yl)phenyl)pyrazolo[1,5-a]pyrimidin-5-yl)-4-(6-methylpyridin-2-yl)oxazolidin-2-one bis(2,2,2-trifluoroacetate) (0.005 g, 21% yield) was prepared by the procedure described in Example 83, Step 6, using (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(6-methylpyridin-2-yl)oxazolidin-2-one (0.020 g, 0.034 mmol). LCMS (APCI+) m/z 457 [M+H]$^+$.

Example 88

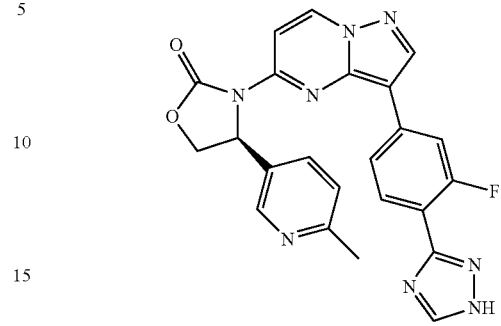

(S)-3-(3-(3-fluoro-4-(1H-1,2,4-triazol-3-yl)phenyl)
pyrazolo[1,5-a]pyrimidin-5-yl)-4-(6-methylpyridin-
3-yl)oxazolidin-2-one Step 1: Following the procedure of Example 84, Step 2 and using 5-bromo-2-methylpyridine in place of 3-bromopyridine, (S)—N—((S)-2-(tert-butyldimethylsilyloxy)-1-(6-methylpyridin-3-yl)ethyl)-2-methylpropane-2-sulfinamide (1.15 g, 29% yield) was isolated as a major isomer product.

Step 2: (S)-2-amino-2-(6-methylpyridin-3-yl)ethanol dihydrochloride (0.653 g, 98% yield) was prepared by the procedure described in Example 84, Step 3, using (S)—N—((S)-2-(tert-butyldimethylsilyloxy)-1-(6-methylpyridin-3-yl)ethyl)-2-methylpropane-2-sulfinamide.

Step 3: (S)-4-(6-methylpyridin-3-yl)oxazolidin-2-one (0.387 g, 75% yield) was prepared by the procedure described in Example 84, Step 4, using (S)-2-amino-2-(6-methylpyridin-3-yl)ethanol dihydrochloride.

Step 4: (S)-3-(3-bromopyrazolo[1,5-a]pyrimidin-5-yl)-4-(6-methylpyridin-3-yl)oxazolidin-2-one (0.233 g, 40% yield) was prepared by the procedure described in Example 84, Step 5, using (S)-4-(6-methylpyridin-3-yl)oxazolidin-2-one.

Step 5: (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(6-methylpyridin-3-yl)oxazolidin-2-one (0.005 g, 6% yield) was prepared by the procedure described in Example 84, Step 6, using (S)-3-(3-bromopyrazolo[1,5-a]pyrimidin-5-yl)-4-(6-methylpyridin-3-yl)oxazolidin-2-one.

Step 6: (S)-3-(3-(3-fluoro-4-(1H-1,2,4-triazol-3-yl)phenyl)pyrazolo[1,5-a]pyrimidin-5-yl)-4-(6-methylpyridin-3-yl)oxazolidin-2-one (0.0015 g, 64% yield) was prepared by the procedure described in Example 75, Step 4, using (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(6-methylpyridin-3-yl)oxazolidin-2-one (0.003 g, 0.0051 mmol). LCMS (APCI+) m/z 457 [M+H]$^+$.

Example 89

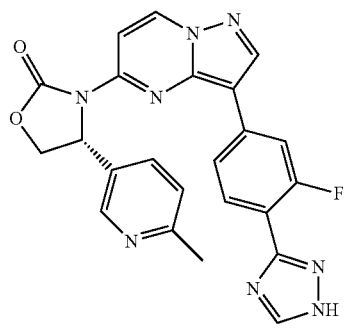 [SMILES: Cc1ccc([C@@H]2COC(=O)N2c2ccn3ncc(-c4ccc(-c5nc[nH]n5)c(F)c4)c3n2)cn1]

(R)-3-(3-(3-fluoro-4-(1H-1,2,4-triazol-3-yl)phenyl)pyrazolo[1,5-a]pyrimidin-5-yl)-4-(6-methylpyridin-3-yl)oxazolidin-2-one Step 1: Following the procedure of Example 84, Step 2 and using 5-bromo-2-methylpyridine in place of 3-bromopyridine, (R)—N—((S)-2-(tert-butyldimethylsilyloxy)-1-(6-methylpyridin-3-yl)ethyl)-2-methylpropane-2-sulfinamide (0.316 g, 8% yield) was isolated as a minor product.

Step 2: (R)-2-amino-2-(6-methylpyridin-3-yl)ethanol dihydrochloride (0.190 g, 98% yield) was prepared by the procedure described in Example 84, Step 3, using (R)—N—((S)-2-(tert-butyldimethylsilyloxy)-1-(6-methylpyridin-3-yl)ethyl)-2-methylpropane-2-sulfinamide.

Step 3: (R)-4-(6-methylpyridin-3-yl)oxazolidin-2-one (0.051 g, 34% yield) was prepared by the procedure described in Example 84, Step 4, using (R)-2-amino-2-(6-methylpyridin-3-yl)ethanol dihydrochloride.

Step 4: (R)-3-(3-bromopyrazolo[1,5-a]pyrimidin-5-yl)-4-(6-methylpyridin-3-yl)oxazolidin-2-one (0.029 g, 24% yield) was prepared by the procedure described in Example 84, Step 5, using (R)-4-(6-methylpyridin-3-yl)oxazolidin-2-one.

Step 5: (R)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(6-methylpyridin-3-yl)oxazolidin-2-one (0.010 g, 22% yield) was prepared by the procedure described in Example 84, Step 6, using (R)-3-(3-bromopyrazolo[1,5-a]pyrimidin-5-yl)-4-(6-methylpyridin-3-yl)oxazolidin-2-one.

Step 6: (R)-3-(3-(3-fluoro-4-(1H-1,2,4-triazol-3-yl)phenyl)pyrazolo[1,5-a]pyrimidin-5-yl)-4-(6-methylpyridin-3-yl)oxazolidin-2-one (0.005 g, 64% yield) was prepared by the procedure described in Example 75, Step 4, using (R)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(6-methylpyridin-3-yl)oxazolidin-2-one (0.010 g, 0.017 mmol). LCMS (APCI+) m/z 457 [M+H]+.

Example 90

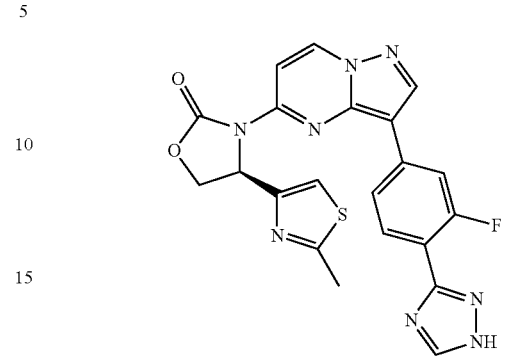

(S)-3-(3-(3-fluoro-4-(1H-1,2,4-triazol-3-yl)phenyl)pyrazolo[1,5-a]pyrimidin-5-yl)-4-(2-methylthiazol-4-yl)oxazolidin-2-one Step 1: (S)—N#S)-2-(tert-butyldimethylsilyloxy)-1-(2-methylthiazol-4-yl)ethyl)-2-methylpropane-2-sulfinamide (0.748 g, 37% yield) was prepared by the procedure described in Example 84, Step 2, using 4-bromo-2-methylthiazole.

Step 2: (S)-2-Amino-2-(2-methylthiazol-4-yl)ethanol hydrochloride (0.244 g, 63% yield) was prepared by the procedure described in Example 84, Step 3, using (S)—N—((S)-2-(tert-butyldimethylsilyloxy)-1-(2-methylthiazol-4-yl)ethyl)-2-methylpropane-2-sulfinamide.

Step 3: (S)-4-(2-Methylthiazol-4-yl)oxazolidin-2-one (0.119 g, 52% yield) was prepared by the procedure described in Example 84, Step 4, using (S)-2-amino-2-(2-methylthiazol-4-yl)ethanol hydrochloride.

Step 4: (S)-3-(3-Bromopyrazolo[1,5-a]pyrimidin-5-yl)-4-(2-methylthiazol-4-yl)oxazolidin-2-one (0.74 g, 32% yield) was prepared by the procedure described in Example 84, Step 5, using (S)-4-(2-methylthiazol-4-yl)oxazolidin-2-one.

Step 5: (S)-3-(3-(3-Fluoro-4-(1-((2-(trimethylsilyl)ethoxy)methyl)-1H-1,2,4-triazol-3-yl)phenyl)pyrazolo[1,5-a]pyrimidin-5-yl)-4-(2-methylthiazol-4-yl)oxazolidin-2-one (0.026 g, 23% yield) was prepared by the procedure described in Example 84, Step 6, using (S)-3-(3-bromopyrazolo[1,5-a]pyrimidin-5-yl)-4-(2-methylthiazol-4-yl)oxazolidin-2-one.

Step 6: (S)-3-(3-(3-Fluoro-4-(1H-1,2,4-triazol-3-yl)phenyl)pyrazolo[1,5-a]pyrimidin-5-yl)-4-(2-methylthiazol-4-yl)oxazolidin-2-one (0.005 g, 26% yield) was prepared by the procedure described in Example 75, Step 4, using (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(2-methylthiazol-4-yl)oxazolidin-2-one (0.025 g, 0.042 mmol). LCMS (APCI+) m/z 463 [M+H]+.

Example 91

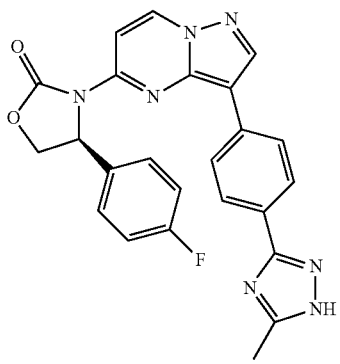 [SMILES: Cc1nc(-c2ccc(-c3cnn4ccc(N5C(=O)OC[C@@H]5c5ccc(F)cc5)nc34)cc2)n[nH]1]

(S)-4-(4-fluorophenyl)-3-(3-(4-(5-methyl-1H-1,2,4-triazol-3-yl)phenyl)pyrazolo[1,5-a]pyrimidin-5-yl)oxazolidin-2-one Step 1: To a sealed tube was added (S)-3-(3-bromopyrazolo[1,5-a]pyrimidin-5-yl)-4-(4-fluorophenyl)oxazolidin-2-one (Preparation A; 0.200 g, 0.530 mmol), 4-(tert-butoxycarbonyl)phenyl boronic acid (0.177 g, 0.795 mmol) and 2.0 M $Na_2CO_3$ (0.795 mL, 1.59 mmol) in dioxane (1 mL). The mixture was degassed by bubbling $N_2$ through the solution. $Pd_2 dba_3$ (0.0486 g, 0.053 mmol), and dicyclohexyl(2',4',6'-triisopropylbiphenyl-2-yl)phosphine (0.0253 g, 0.053 mmol) were added and the vessel was sealed under a $N_2$ atmosphere. The mixture was heated at 90° C. for 18 hours. The reaction mixture was cooled to ambient temperature, filtered through glass fiber filter paper, concentrated and purified on silica gel (10-100% ether in DCM) giving (S)-tert-butyl 4-(5-(4-(4-fluorophenyl)-2-oxooxazolidin-3-yl)pyrazolo[1,5-a]pyrimidin-3-yl)benzoate (0.148 g, 59% yield).

Step 2: A solution of (S)-tert-butyl 4-(5-(4-(4-fluorophenyl)-2-oxooxazolidin-3-yl)pyrazolo[1,5-a]pyrimidin-3-yl)benzoate (0.148 g, 0.312 mmol) in DCM (1.5 mL) was treated with trifluoroacetic acid (0.7 mL) at ambient temperature and stirring continued for 3 hours. The solvent was concentrated and the residue taken in water, neutralized with 1N NaOH carefully and suspended solids collected by filtration to afford (S)-4-(5-(4-(4-fluorophenyl)-2-oxooxazolidin-3-yl)pyrazolo[1,5-a]pyrimidin-3-yl)₆ enzoic acid (0.081 g, 62% yield).

Step 3: 1-Ethyl-3-(3-dimethylaminopropyl) carbodiimide (0.1031 g, 0.5378 mmol) was added to a mixture of (S)-4-(5-(4-(4-fluorophenyl)-2-oxooxazolidin-3-yl)pyrazolo[1,5-a]pyrimidin-3-yl)benzoic acid (0.075 g, 0.1793 mmol) and hydroxybenzotriazole (0.073 g, 0.5378 mmol) in DMF (0.6 mL) at ambient temperature. After stirring for 10 minutes, hydrazine monohydrate (0.02609 mL, 0.5378 mmol), followed by triethylamine (0.07496 mL, 0.5378 mmol) were added. The mixture was stirred at ambient temperature for 4 hours, diluted with EtOAc, washed with aqueous saturated $NH_4Cl$, brine, dried (phase separator silicone treated filter paper), concentrated and purified on silica gel (2-8% MeOH in DCM) to provide (S)-4-(5-(4-(4-fluorophenyl)-2-oxooxazolidin-3-yl)pyrazolo[1,5-a]pyrimidin-3-yl)benzohydrazide (0.061 g, 79% yield) as a clear oil.

Step 4: To a stirred suspension of (S)-4-(5-(4-(4-fluorophenyl)-2-oxooxazolidin-3-yl)pyrazolo[1,5-a]pyrimidin-3-yl)benzohydrazide (0.062 g, 0.14 mmol) in 2:1 THF-DMF (1.5 mL) was added triethylamine (0.026 mL, 0.19 mmol), followed by ethyl acetimidate hydrochloride (0.021 g, 0.17 mmol) at 0° C. The mixture was allowed to warm up to ambient temperature and stirring continued at 60° C. for 5 hours. The mixture was poured into water, neutralized with 1N HCl, extracted with EtOAc, dried (phase separator silicone treated filter paper) and concentrated to give (S)-4-(5-(4-(4-fluorophenyl)-2-oxooxazolidin-3-yl)pyrazolo[1,5-a]pyrimidin-3-yl)-N'-(1-iminoethyl)benzohydrazide (0.049 g, 72% yield) as a yellow oil.

Step 5: A suspension of (S)-4-(5-(4-(4-fluorophenyl)-2-oxooxazolidin-3-yl)pyrazolo[1,5-a]pyrimidin-3-yl)-N'-(1-iminoethyl)benzohydrazide (0.049 g, 0.104 mmol) in 1:1 DCM-acetonitrile (10 mL) was treated with carbon tetrachloride (0.040 mL, 0.414 mmol), triethylamine (0.1442 mL, 1.035 mmol) and triphenylphosphine (0.1086 g, 0.414 mmol) at ambient temperature. The mixture was heated at 50° C. for 2 hours. After cooing to ambient temperature, the mixture was treated with EtOAc, washed with water, dried (phase separator silicone treated filter paper), concentrated and purified on silica gel (2-5% MeOH in DCM) to provide (S)-4-(4-fluorophenyl)-3-(3-(4-(5-methyl-4H-1,2,4-triazol-3-yl)phenyl)pyrazolo[1,5-a]pyrimidin-5-yl)oxazolidin-2-one (0.003 g, 6% yield) as a yellow oil. LCMS (APCI+) m/z 456 $[M+H]^+$.

Example 92

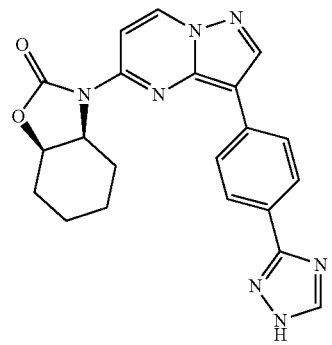 [SMILES: O=C1O[C@@H]2CCCC[C@@H]2N1c1ccn2ncc(-c3ccc(-c4nc[nH]n4)cc3)c2n1]

(3aS,7aR)-3-(3-(4-(1H-1,2,4-triazol-3-yl)phenyl)pyrazolo[1,5-a]pyrimidin-5-yl)hexahydrobenzo[d]oxazol-2(3H)-one Step 1: To a stirred suspension of (1S,2S)-(+)-2-aminocyclohexanol hydrochloride (1.04 g, 6.86 mmol) in DCM (20 mL) was added triethylamine (2.39 mL, 17.1 mmol). A solution of di-tert-butyl dicarbonate (1.80 g, 8.23 mmol) in DCM (15 mL) was added dropwise. The reaction mixture was stirred at ambient temperature for 2 hours. The reaction was diluted with DCM and washed successively with 1N HCl, saturated aqueous $NaHCO_3$ and brine, dried and concentrated. The residue was purified by column chromatography (hexane/EtOAc, 1:1) to give tert-butyl (1S,2S)-2-hydroxycyclohexylcarbamate (1.30 g, 88%).

Step 2: To a solution of tert-butyl (1S,2S)-2-hydroxycyclohexylcarbamate (1.30 g, 6.04 mmol), 4-nitrobenzoic acid (1.11 g, 6.64 mmol), triphenylphosphine (1.74 g, 6.64 mmol) in THF (30 mL) was added diethylazo dicarboxylate (1.05 ml, 6.64 mmol) and the resulting solution was stirred at ambient temperature overnight. The reaction mixture was diluted with ethyl acetate and washed with brine. The organic layer was dried and concentrated to give an orange oil that was purified by column chromatography (hexanes/ethyl acetate, 8:1) to give (1R,2S)-2-(tert-butoxycarbonylamino)cyclohexyl 4-nitrobenzoate (1.95 g, 89%).

Step 3: To a stirred solution of (1R,2S)-2-(tert-butoxycarbonylamino)cyclohexyl 4-nitrobenzoate (1.95 g, 5.35 mmol) in THF (50 mL) was added a solution of 1N LiOH (9.63 mL, 9.63 mmol) at 0° C. The reaction mixture was stirred at ambient temperature for 6 hours and then partitioned between EtOAc and water. The organic layer was washed with brine, dried and concentrated. The residue was purified by column chromatography (EtOAc/hexane, 1:1) to give tert-butyl (1S, 2R)-2-hydroxycyclohexylcarbamate (1.15 g, 100%).

Step 4: To a stirred solution of tert-butyl (1S,2R)-2-hydroxycyclohexylcarbamate (1.15 g, 5.34 mmol) in THF (40 mL) was added NaH (60%, 0.32 g, 8.0 mmol) at 0° C. The reaction mixture was stirred at ambient temperature overnight. Saturated aqueous NH$_4$Cl solution was added to quench the reaction. The mixture was partitioned between EtOAc and water. The aqueous layer was extracted with EtOAc. The combined organic layers were washed with brine, dried and concentrated. The residue was purified by column chromatography (EtOAc/hexanes, 2:1) to give (3aS, 7aR)-hexahydrobenzo[d]oxazol-2(3H)-one (0.50 g, 66%) as a white solid.

Step 5: (3aS,7aR)-3-(3-bromopyrazolo[1,5-a]pyrimidin-5-yl)hexahydrobenzo[d]oxazol-2(3H)-one (0.231 g, 64%) was prepared by the procedure described in Example 1, Step 4, using (3aS,7aR)-hexahydrobenzo[d]oxazol-2(3H)-one for (S)-4-isopropyloxazolidin-2-one.

Step 6: (3aS,7aR)-3-(3-(4-(1-((2-(trimethylsilyl)ethoxy)methyl)-1H-1,2,4-triazol-3-yl)phenyl)pyrazolo[1,5-a]pyrimidin-5-yl)hexahydrobenzo[d]oxazol-2(3H)-one (39 mg, 50%) was prepared by the procedure described in Example 1, Step 8, using (3aS,7aR)-3-(3-bromopyrazolo[1,5-a]pyrimidin-5-yl)hexahydrobenzo[d]oxazol-2(3H)-one.

Step 7: (3aS,7aR)-3-(3-(4-(1H-1,2,4-triazol-3-yl)phenyl)pyrazolo[1,5-a]pyrimidin-5-yl)hexahydrobenzo[d]oxazol-2 (3H)-one (17 mg, 58%) was prepared by the procedure described in Example 1, Step 9, using (3aS,7aR)-3-(3-(4-(1-((2-(trimethylsilyl)ethoxy)methyl)-1H-1,2,4-triazol-3-yl)phenyl)pyrazolo[1,5-a]pyrimidin-5-yl)hexahydrobenzo[d]oxazol-2(3H)-one. LCMS (APCI+) m/z 402.5 [M+H]$^+$.

Example 93

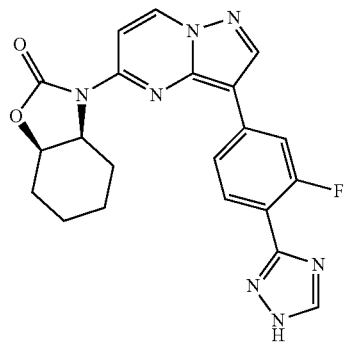 [SMILES: O=C1O[C@@H]2CCCC[C@@H]2N1c1ccn2ncc(-c3ccc(-c4nc[nH]n4)c(F)c3)c2n1]

(3aS,7aR)-3-(3-(3-fluoro-4-(1H-1,2,4-triazol-3-yl)phenyl)pyrazolo[1,5-a]pyrimidin-5-yl)hexahydrobenzo[d]oxazol-2(3H)-one Step 1: (3aS,7aR)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)hexahydrobenzo[d]oxazol-2(3H)-one (17 mg, 52%) was prepared by the procedure described in Example 1, Step 8, using (3aS,7aR)-3-(3-bromopyrazolo[1,5-a]pyrimidin-5-yl)hexahydrobenzo[d]oxazol-2(3H)-one and 5-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole.

Step 2: (3aS,7aR)-3-(3-(3-fluoro-4-(1H-1,2,4-triazol-3-yl)phenyl)pyrazolo[1,5-a]pyrimidin-5-yl)hexahydrobenzo[d]oxazol-2(3H)-one (9 mg, 69%) was prepared by the procedure described in Example 1, Step 9, using (3aS,7aR)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)hexahydrobenzo[d]oxazol-2(3H)-one. LCMS (APCI+) m/z 420.5 [M+H]$^+$.

Example 94

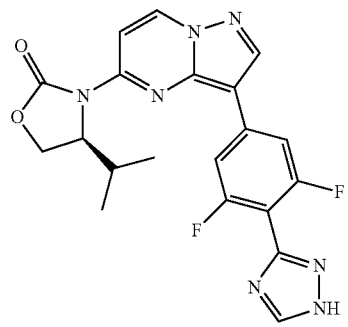 [SMILES: CC(C)[C@H]1COC(=O)N1c1ccn2ncc(-c3cc(F)c(-c4nc[nH]n4)c(F)c3)c2n1]

(S)-3-(3-(3,5-difluoro-4-(1H-1,2,4-triazol-3-yl)phenyl)pyrazolo[1,5-a]pyrimidin-5-yl)-4-isopropyloxazolidin-2-one Step 1: 4-bromo-2,6-difluorobenzamide (4.92 g, 86%) was prepared by the procedure described in Example 6, Step 1, using 4-bromo-2,6-difluorobenzonitrile for 4-bromo-2-fluorobenzonitrile.

Step 2: (E)-4-bromo-N-((dimethylamino)methylene)-2,6-difluorobenzamide (5.50 g, 91%) was prepared by the procedure described in Example 5, Step 1, using 4-bromo-2,6-difluorobenzamide.

Step 3: 3-(4-bromo-2,6-difluorophenyl)-1H-1,2,4-triazole (3.28 g, 67%) was prepared by the procedure described in Example 5, Step 2, using (E)-4-bromo-N-((dimethylamino)methylene)-2,6-difluorobenzamide.

Step 4: 5-(4-bromo-2,6-difluorophenyl)-1-((2-(trimethylsilyl)ethoxy)methyl)-1H-1,2,4-triazole (0.93 g, 41%) were prepared by the procedure described in Example 1, Step 6, using 3-(4-bromo-2,6-difluorophenyl)-1H-1,2,4-triazole.

Step 5: 5-(2,6-difluoro-4-(4,4,5,5-tetramethyl-1,3,2-dioxaborolan-2-yl)phenyl)-1-((2-(trimethylsilyl)ethoxy)methyl)-1H-1,2,4-triazole (0.58 g, 56%) was prepared by the procedure described in Example 1, Step 7, using -(4-bromo-2,6-difluorophenyl)-1-((2-(trimethylsilyl)ethoxy)methyl)-1H-1,2,4-triazole.

Step 6: (S)-3-(3-(3,5-difluoro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one (0.126 g, 86%) were prepared by the procedure described in Example 1, Step 8, using 5-(2,6-difluoro-4-(4,4,5,5-tetramethyl-1,3,2-dioxaborolan-2-yl)phenyl)-1-((2-(trimethylsilyl)ethoxy)methyl)-1H-1,2,4-triazole.

Step 7: (S)-3-(3-(3,5-difluoro-4-(1H-1,2,4-triazol-3-yl)phenyl)pyrazolo[1,5-a]pyrimidin-5-yl)-4-isopropyloxazolidin-2-one (0.088 g, 91%) was prepared by the procedure described in Example 1, Step 9, using (S)-3-(3-(3,5-difluoro-4-(1-((2-(trimethylsilyl)ethoxy)methyl)-1H-1,2,4-triazol-5-yl)phenyl)pyrazolo[1,5-a]pyrimidin-5-yl)-4-isopropyloxazolidin-2-one. LCMS (APCI+) m/z 426.6 [M+H]+.

Example 95

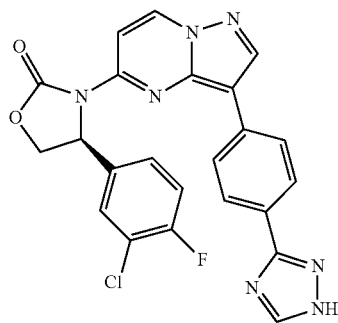 [SMILES: O=C1OC[C@H](c2ccc(F)c(Cl)c2)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-(3-chloro-4-fluorophenyl)oxazolidin-2-one Step 1: (S)-3-(3-bromopyrazolo[1,5-a]pyrimidin-5-yl)-4-(3-chloro-4-fluorophenyl)oxazolidin-2-one (0.153 g, 43%) was prepared by the procedures described in Example 70, Step 1 and Step 2, using (S)-2-amino-2-(3-chloro-4-fluorophenyl)ethanol hydrochloride in Step 1.

Step 2: (S)-4-(3-chloro-4-fluorophenyl)-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.088 g, 60%) were prepared by the procedure described in Example 1, Step 8, using (S)-3-(3-bromopyrazolo[1,5-a]pyrimidin-5-yl)-4-(3-chloro-4-fluorophenyl)oxazolidin-2-one.

Step 3: (S)-3-(3-(4-(1H-1,2,4-triazol-3-yl)phenyl)pyrazolo[1,5-a]pyrimidin-5-yl)-4-(3-chloro-4-fluorophenyl)oxazolidin-2-one (0.051 g, 74%) was prepared by the procedure described in Example 1, Step 9, using (S)-4-(3-chloro-4-fluorophenyl)-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one. LCMS (APCI+) m/z 476, 478 [M+H]+.

Example 96

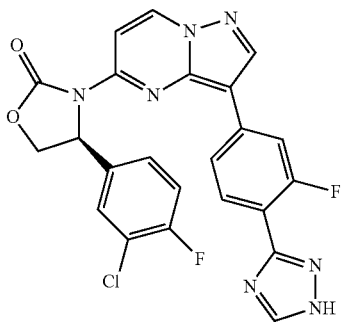

(S)-4-(3-chloro-4-fluorophenyl)-3-(3-(3-fluoro-4-(1H-1,2,4-triazol-3-yl)phenyl)pyrazolo[1,5-a]pyrimidin-5-yl)oxazolidin-2-one Step 1: A mixture of (S)-4-(3-chloro-4-fluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-(3-chloro-4-fluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one (31 mg, 68%) was prepared by the procedure described in Example 6, Step 6, using (S)-3-(3-bromopyrazolo[1,5-a]pyrimidin-5-yl)-4-(3-chloro-4-fluorophenyl)oxazolidin-2-one.

Step 2: (S)-4-(3-chloro-4-fluorophenyl)-3-(3-(3-fluoro-4-(1H-1,2,4-triazol-3-yl)phenyl)pyrazolo[1,5-a]pyrimidin-5-yl)oxazolidin-2-one (19 mg, 77%) was prepared by the procedure described in Example 1, Step 9, using a mixture of (S)-4-(3-chloro-4-fluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-(3-chloro-4-fluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one. LCMS (APCI+) m/z 495, 497 [M+H]+.

Example 97

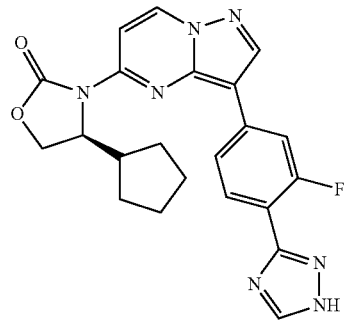 [SMILES: O=C1OC[C@H](C2CCCC2)N1c1ccn2ncc(-c3ccc(-c4nc[nH]n4)c(F)c3)c2n1]

(S)-4-cyclopentyl-3-(3-(3-fluoro-4-(1H-1,2,4-triazol-3-yl)phenyl)pyrazolo[1,5-a]pyrimidin-5-yl)oxazolidin-2-one Step 1: To a stirred solution of (S)-2-amino-2-cyclopentylacetic acid (1.00 g, 6.98 mmol) in THF (20 mL) was added dropwise a solution of LiAlH$_4$ in THF (1.0 M, 10.5 mL, 10.5 mmol) at 0° C. under N$_2$. The reaction was allowed to warm to ambient temperature and heated at reflux overnight. After cooling, the reaction mixture was cooled to 0° C. and carefully quenched by dropwise addition of water (0.4 mL) followed by 15% NaOH solution (0.4 mL) and water (1.2 mL). The mixture was stirred at ambient temperature for 15 minutes and filtered through Celite. The filtrate was concentrated to give crude (S)-2-amino-2-cyclopentylethanol, which was used in the next step without further purification.

Step 2: (S)-4-cyclopentyloxazolidin-2-one (0.42 g, 39% for two steps) was prepared by the procedure described in Example 65, Step 1, using (S)-2-amino-2-cyclopentylethanol.

Step 3: (S)-3-(3-bromopyrazolo[1,5-a]pyrimidin-5-yl)-4-cyclopentyloxazoli-din-2-one (0.159 g, 53%) was prepared by the procedure described in Example 1, Step 4, using (S)-4-cyclopentyloxazolidin-2-one for (S)-4-isopropyloxazolidin-2-one.

Step 4: A mixture of (S)-4-cyclopentyl-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl) oxazolidin-2-one and (S)-4-cyclopentyl-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one (26 mg, 28%) was prepared by the procedure described in Example 6, Step 6, using (S)-3-(3-bromopyrazolo[1,5-a]pyrimidin-5-yl)-4-cyclopentyloxazolidin-2-one.

Step 5: (S)-4-cyclopentyl-3-(3-(3-fluoro-4-(1H-1,2,4-triazol-3-yl)phenyl)pyrazolo[1,5-a]pyrimidin-5-yl)oxazolidin-2-one (10 mg, 50%) was prepared by the procedure described in Example 1, Step 9, using a mixture of (S)-4-cyclopentyl-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-cyclopentyl-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one. LCMS (APCI+) m/z 434.6 [M+H]⁺.

Example 98

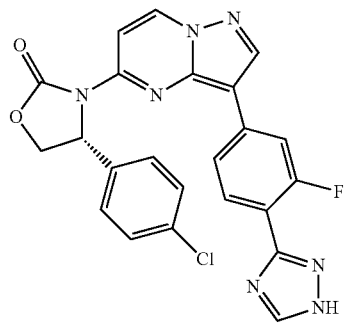 [SMILES: O=C1OC[C@@H](c2ccc(Cl)cc2)N1c1ccn2ncc(-c3ccc(-c4nc[nH]n4)c(F)c3)c2n1]

(R)-4-(4-chlorophenyl)-3-(3-(3-fluoro-4-(1H-1,2,4-triazol-3-yl)phenyl)pyrazolo[1,5-a]pyrimidin-5-yl)oxazolidin-2-one Step 1: (R)-3-(3-bromopyrazolo[1,5-a]pyrimidin-5-yl)-4-(4-chlorophenyl) oxazolidin-2-one (0.170 g, 50%) was prepared by the procedures described in Example 70, Step 1 and Step 2, using (R)-2-amino-2-(4-chlorophenyl)ethanol hydrochloride in Step 1.

Step 2: (R)-4-(4-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.102 g, 66%) were prepared by the procedure described in Example 70, Step 3, using (R)-3-(3-bromopyrazolo[1,5-a]pyrimidin-5-yl)-4-(4-chlorophenyl)oxazolidin-2-one.

Step 3: (R)-4-(4-chlorophenyl)-3-(3-(3-fluoro-4-(1H-1,2,4-triazol-3-yl)phenyl)pyrazolo[1,5-a]pyrimidin-5-yl)oxazolidin-2-one (0.067 g, 84%) was prepared by the procedure described in Example 1, Step 9, using (R)-4-(4-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one. LCMS (APCI+) m/z 476.6, 478.6 [M+H]⁺.

Example 99

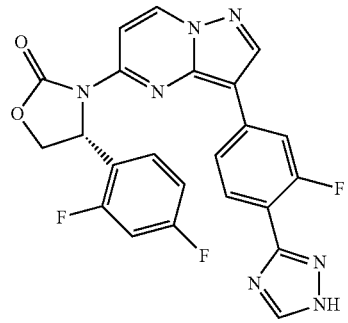 [SMILES: O=C1OC[C@@H](c2ccc(F)cc2F)N1c1ccn2ncc(-c3ccc(-c4nc[nH]n4)c(F)c3)c2n1]

(R)-4-(2,4-difluorophenyl)-3-(3-(3-fluoro-4-(1H-1,2,4-triazol-3-yl)phenyl)pyrazolo[1,5-a]pyrimidin-5-yl)oxazolidin-2-one Step 1: To a first flask was added magnesium turnings (197 mg, 8.11 mmol) and THF (7 mL). A 2.0 M solution of isopropyl magnesium chloride in THF (16 µL, 0.032 mmol) was added followed by 1-bromo-2,4-difluorobenzene (0.10 mL). The temperature of the reaction mixture raised to 30° C. Additional 1-bromo-2,4-difluorobenzene (0.91 mL) was added dropwise at such a rate that the internal temperature did not exceed 32° C. After addition, the reaction mixture was stirred at 26-28° C. for 30 minutes. To a second flask was added (S,E)-N-(2-(tert-butyldimethylsilyloxy)ethylidene)-2-methylpropane-2-sulfinamide (1.50 g, 5.41 mmol) and toluene (32 mL) under N₂. The reaction mixture was cooled to −78° C. The Grignard reagent prepared in the first flask was slowly transferred to the reaction mixture in the second flask using a syringe. The reaction was allowed to slowly warm up to 0° C. The reaction was quenched by the addition of saturated aqueous NH₄Cl solution. The organic layer was separated. The aqueous layer was extracted with EtOAc. The combined organic layer was washed with brine, dried and concentrated. The residue was purified by column chromatography (hexane/EtOAc, 6:1) to give (S)—N—((R)-2-(tert-butyldimethylsilyloxy)-1-(2,4-difluorophenyl)ethyl)-2-methylpropane-2-sulfinamide (1.14 g, 54%) as a white solid.

Step 2: To a mixture of (S)—N—((R)-2-(tert-butyldimethylsilyloxy)-1-(2,4-difluorophenyl)ethyl)-2-methylpropane-2-sulfinamide (1.08 g, 2.76 mmol) in MeOH (8 mL) was added 4N HCl in dioxane (6.9 mL, 28 mmol) at 0° C. under N₂. The reaction mixture was stirred at 0° C. for 4 hours. The solvents were evaporated in vacuo to give (R)-2-amino-2-(2,4-difluorophenyl)ethanol hydrochloride (0.58 g, 100%) as a white solid, which was used in the next step without further purification.

Step 3: To a stirred mixture of (R)-2-amino-2-(2,4-difluorophenyl)ethanol hydrochloride (0.58 g, 2.8 mmol) in THF (18 mL) was added Et₃N (1.2 mL, 8.9 mmol). The reaction mixture was cooled in an ice bath under N₂. A solution of triphosgene (0.33 g, 1.1 mmol) in THF (10 mL) was added. The reaction was allowed to warm to ambient temperature and stirred for 2 hours. The reaction mixture was partitioned between EtOAc and saturated aqueous NaHCO₃. The aqueous layer was extracted with EtOAc. The combined organic layers were washed with brine, dried and concentrated. The residue was purified by column chromatography (EtOAc/hexane, 1:1) to give (R)-4-(2,4-difluorophenyl)oxazolidin-2-one (0.50 g, 91%).

Step 4: (R)-3-(3-bromopyrazolo[1,5-a]pyrimidin-5-yl)-4-(2,4-difluorophenyl)oxazolidin-2-one (0.290 g, 57%) was prepared by the procedure described in Example 1, Step 4, using (R)-4-(2,4-difluorophenyl)oxazolidin-2-one for (S)-4-isopropyloxazolidin-2-one.

Step 5: A mixture of (R)-4-(2,4-difluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl) oxazolidin-2-one and (R)-4-(2,4-difluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one (25 mg, 41%) was prepared by the procedure described in Example 6, Step 6, using (R)-3-(3-bromopyrazolo[1,5-a]pyrimidin-5-yl)-4-(2,4-difluorophenyl)oxazolidin-2-one.

Step 6: (R)-4-(2,4-difluorophenyl)-3-(3-(3-fluoro-4-(1H-1,2,4-triazol-3-yl)phenyl)pyrazolo[1,5-a]pyrimidin-5-yl)oxazolidin-2-one (16 mg, 81%) was prepared by the procedure described in Example 1, Step 9, using a mixture of (R)-4-(2,4-difluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (R)-4-(2,4-difluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one. LCMS (APCI+) m/z 478.2 [M+H]$^+$.

Example 100

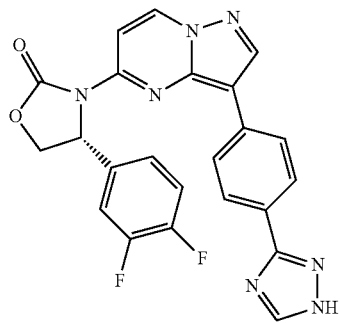 [SMILES: O=C1OC[C@@H](c2ccc(F)c(F)c2)N1c1ccn2ncc(-c3ccc(-c4nc[nH]n4)cc3)c2n1]

(R)-3-(3-(4-(1H-1,2,4-triazol-3-yl)phenyl)pyrazolo[1,5-a]pyrimidin-5-yl)-4-(3,4-difluorophenyl)oxazolidin-2-one Step 1: (S)—N—((R)-2-(tert-butyldimethylsilyloxy)-1-(3,4-difluorophenyl)ethyl)-2-methylpropane-2-sulfinamide (0.620 g, 62%) was prepared by the procedure described in Example 99, Step 1, substituting 4-bromo-1,2-difluorobenzene for 1-bromo-2,4-difluorobenzene.

Step 2: (R)-2-amino-2-(3,4-difluorophenyl)ethanol hydrochloride (0.33 g, 100%) was prepared by the procedure described in Example 99 Step 2, using (S)—N—((R)-2-(tert-butyldimethylsilyloxy)-1-(3,4-difluorophenyl)ethyl)-2-methylpropane-2-sulfinamide.

Step 3: (R)-4-(3,4-difluorophenyl)oxazolidin-2-one (0.28 g, 89%) was prepared by the procedure described in Example 99, Step 3, using (R)-2-amino-2-(3,4-difluorophenyl)ethanol hydrochloride.

Step 4: (R)-3-(3-bromopyrazolo[1,5-a]pyrimidin-5-yl)-4-(3,4-difluorophenyl) oxazolidin-2-one (0.237 g, 45%) was prepared by the procedure described in Example 1, Step 4, substituting (R)-4-(3,4-difluorophenyl)oxazolidin-2-one for (S)-4-isopropyloxazolidin-2-one.

Step 5: (R)-4-(3,4-difluorophenyl)-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.016 g, 27%) were prepared by the procedure described in Example 1, Step 8, using (R)-3-(3-bromopyrazolo[1,5-a]pyrimidin-5-yl)-4-(3,4-difluorophenyl)oxazolidin-2-one.

Step 6: (R)-3-(3-(4-(1H-1,2,4-triazol-3-yl)phenyl)pyrazolo[1,5-a]pyrimidin-5-yl)-4-(3,4-difluorophenyl)oxazolidin-2-one (8 mg, 64%) was prepared by the procedure described in Example 1, Step 9, using (R)-4-(3,4-difluorophenyl)-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one. LCMS (APCI+) m/z 460.2 [M+H]$^+$.

Example 101

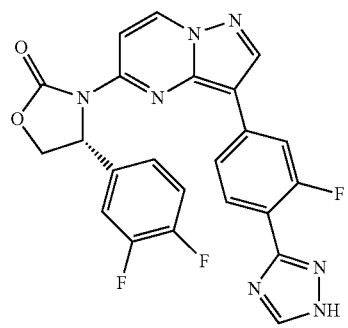 [SMILES: O=C1OC[C@@H](c2ccc(F)c(F)c2)N1c1ccn2ncc(-c3ccc(-c4nc[nH]n4)c(F)c3)c2n1]

(R)-4-(3,4-difluorophenyl)-3-(3-(3-fluoro-4-(1H-1,2,4-triazol-3-yl)phenyl)pyrazolo[1,5-a]pyrimidin-5-yl)oxazolidin-2-one Step 1: A mixture of (R)-4-(3,4-difluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (R)-4-(3,4-difluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one (45 mg, 73%) was prepared by the procedure described in Example 6, Step 6, using (R)-3-(3-bromopyrazolo[1,5-a]pyrimidin-5-yl)-4-(3,4-difluorophenyl)oxazolidin-2-one.

Step 2: (R)-4-(3,4-difluorophenyl)-3-(3-(3-fluoro-4-(1H-1,2,4-triazol-3-yl)phenyl)pyrazolo[1,5-a]pyrimidin-5-yl)oxazolidin-2-one (16 mg, 81%) was prepared by the procedure described in Example 1, Step 9, using a mixture of (R)-4-(3,4-difluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (R)-4-(3,4-difluorophenyl)-3-(3-(3-fluoro-4-(1-((2-(trimethylsilyl)ethoxy)methyl)-1H-1,2,4-triazol-5-yl)phenyl)pyrazolo [1,5-a]pyrimidin-5-yl)oxazolidin-2-one. LCMS (APCI+) m/z 478.2 [M+H]$^+$.

Example 102

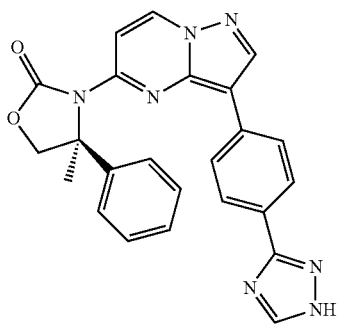 [SMILES: C[C@]1(c2ccccc2)COC(=O)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-methyl-4-phenyloxazolidin-2-one Step 1: (S)-4-methyl-4-phenyloxazolidin-2-one (0.354 g, 65%) was prepared by the procedure described in Example 99, Step 3, using (S)-2-amino-2-phenylpropan-1-ol hydrochloride.

Step 2: (S)-3-(3-bromopyrazolo[1,5-a]pyrimidin-5-yl)-4-methyl-4-phenyloxazolidin-2-one (0.088 g, 12%) was prepared by the procedure described in Example 1, Step 4, substituting (S)-4-methyl-4-phenyloxazolidin-2-one for (S)-4-isopropyloxazolidin-2-one.

Step 3: A mixture of (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-methyl-4-phenyloxa-zolidin-2-one and (S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-methyl-4-phenyloxa-zolidin-2-one (25 mg, 32%) was prepared by the procedure described in Example 6, Step 6, using (S)-3-(3-bromopyrazolo[1,5-a]pyrimidin-5-yl)-4-methyl-4-phenyloxazolidin-2-one.

Step 4: (S)-3-(3-(3-fluoro-4-(1H-1,2,4-triazol-3-yl)phenyl)pyrazolo[1,5-a]pyrimidin-5-yl)-4-methyl-4-phenyloxazolidin-2-one (17 mg, 75%) was prepared by the procedure described in Example 1, Step 9, using a mixture of (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-methyl-4-phenyloxazolidin-2-one and (S)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-4-methyl-4-phenyloxa-zolidin-2-one. LCMS (APCI+) m/z 456.2 [M+H]+.

Example 103

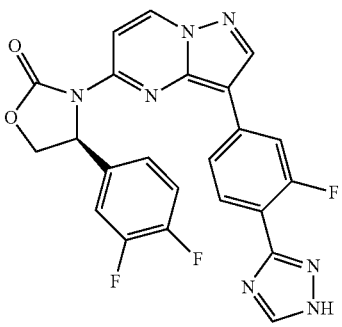 [SMILES: O=C1OC[C@H](c2ccc(F)c(F)c2)N1c1ccn2ncc(-c3ccc(-c4nc[nH]n4)c(F)c3)c2n1]

(S)-4-(3,4-difluorophenyl)-3-(3-(3-fluoro-4-(1H-1,2,4-triazol-3-yl)phenyl)pyrazolo[1,5-a]pyrimidin-5-yl)oxazolidin-2-one Step 1: (R)—N—((S)-2-(tert-butyldimethylsilyloxy)-1-(3,4-difluorophenyl)ethyl)-2-methylpropane-2-sulfinamide (4.12 g, 65%) was prepared by the procedure described in Example 99, Step 1, using 4-bromo-1,2-difluorobenzene and (R,E)-N-(2-(tert-butyldimethylsilyloxy)ethylidene)-2-methylpropane-2-sulfinamide.

Step 2: (S)-2-amino-2-(3,4-difluorophenyl)ethanol hydrochloride (2.21 g, 100%) was prepared by the procedure described in Example 99 Step 2, using (R)—N—((S)-2-(tert-butyldimethylsilyloxy)-1-(3,4-difluorophenyl)ethyl)-2-methylpropane-2-sulfinamide.

Step 3: (S)-4-(3,4-difluorophenyl)oxazolidin-2-one (1.86 g, 89%) was prepared by the procedure described in Example 99, Step 3, using (S)-2-amino-2-(3,4-difluorophenyl)ethanol hydrochloride.

Step 4: (S)-3-(3-bromopyrazolo[1,5-a]pyrimidin-5-yl)-4-(3,4-difluorophenyl)oxazolidin-2-one (0.240 g, 47%) was prepared by the procedure described in Example 1, Step 4, substituting (S)-4-(3,4-difluorophenyl)oxazolidin-2-one for (S)-4-isopropyloxazolidin-2-one.

Step 5: A mixture of (S)-4-(3,4-difluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-(3,4-difluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one (52 mg, 85%) was prepared by the procedure described in Example 6, Step 6, using (S)-3-(3-bromopyrazolo[1,5-a]pyrimidin-5-yl)-4-(3,4-difluorophenyl)oxazolidin-2-one.

Step 6: (S)-4-(3,4-difluorophenyl)-3-(3-(3-fluoro-4-(1H-1,2,4-triazol-3-yl)phenyl)pyrazolo[1,5-a]pyrimidin-5-yl)oxazolidin-2-one (30 mg, 73%) was prepared by the procedure described in Example 1, Step 9, using a mixture of (S)-4-(3,4-difluorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one and (S)-4-(3,4-difluorophenyl)-3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)oxazolidin-2-one. LCMS (APCI+) m/z 478.2 [M+H]+.

Example 104

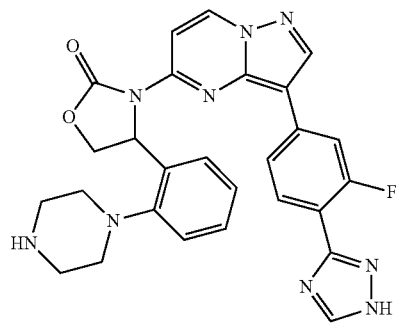 [SMILES: O=C1OCC(c2ccccc2N2CCNCC2)N1c1ccn2ncc(-c3ccc(-c4nc[nH]n4)c(F)c3)c2n1]

3-(3-(3-fluoro-4-(1H-1,2,4-triazol-3-yl)phenyl)pyrazolo[1,5-a]pyrimidin-5-yl)-4-(2-(piperazin-1-yl)phenyl)oxazolidin-2-one Step 1: To a stirred solution of 2-amino-2-(2-bromophenyl)acetic acid (4.89 g, 21.3 mmol) in THF (50 mL) was added dropwise a solution of LiAlH$_4$ in THF (1.0 M, 42.5 mL, 42.5 mmol) at 0° C. under N$_2$. The reaction was allowed to warm to ambient temperature and stirred for 4 hours. The reaction mixture was cooled to 0° C. and carefully quenched by dropwise addition of water (1.7 mL) followed by 15% NaOH solution (1.7 mL) and water (5.1 mL). The mixture was stirred at ambient temperature for 15 minutes and filtered through Celite. The filtrate was concentrated to give crude 2-amino-2-(2-bromophenyl)ethanol, which was used in the next step without further purification.

Step 2: 4-(2-bromophenyl)oxazolidin-2-one (0.67 g, 28% for two steps) was prepared by the procedure described in Example 99 Step 3, using 2-amino-2-(2-bromophenyl)ethanol.

Step 3: A mixture of 4-(2-bromophenyl)oxazolidin-2-one (497 mg, 2.05 mmol), 1H-pyrrole-2-carboxylic acid (137 mg, 1.23 mmol), tert-butyl piperazine-1-carboxylate (765 mg, 4.11 mmol), copper(I) iodide (117 mg, 0.616 mmol) and K$_3$PO$_4$ (1.74 g, 8.21 mmol) in DMSO (15 mL) was heated at 90° C. for 8 hours. After cooling, the reaction mixture was partitioned between EtOAc and water. The aqueous layer was extracted with EtOAc. The combined organic layers were washed with brine, dried and concentrated. The residue was purified by column chromatography (hexane/EtOAc, 1:1) to give tert-butyl 4-(2-(2-oxooxazolidin-4-yl)phenyl)piperazine-1-carboxylate (462 mg, 65%).

Step 4: tert-butyl 4-(2-(3-(3-bromopyrazolo[1,5-a]pyrimidin-5-yl)-2-oxooxazolidin-4-yl)phenyl)piperazine-1-carboxylate (0.360 g, 51%) was prepared by the procedure described in Example 1, Step 4, substituting tert-butyl 4-(2-(2-oxooxazolidin-4-yl)phenyl)piperazine-1-carboxylate for (S)-4-isopropyloxazolidin-2-one.

Step 5: A mixture of tert-butyl 4-(2-(3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-2-oxooxazolidin-4-yl)phenyl)piperazine-1-carboxylate and tert-butyl 4-(2-(3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-2-oxooxazolidin-4-yl)phenyl)piperazine-1-carboxylate (120 mg, 66%) was prepared by the procedure described in Example 6, Step 6, using tert-butyl 4-(2-(3-(3-bromopyrazolo[1,5-a]pyrimidin-5-yl)-2-oxooxazolidin-4-yl)phenyl)piperazine-1-carboxylate.

Step 6: 3-(3-(3-fluoro-4-(1H-1,2,4-triazol-3-yl)phenyl)pyrazolo[1,5-a]pyrimidin-5-yl)-4-(2-(piperazin-1-yl)phenyl)oxazolidin-2-one (36 mg, 43%) was prepared by the procedure described in Example 1, Step 9, using a mixture of tert-butyl 4-(2-(3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-2-oxooxazolidin-4-yl)phenyl)piperazine-1-carboxylate and tert-butyl 4-(2-(3-(3-(3-fluoro-4-(1-((2-(trimethylsilyl)ethoxy)methyl)-1H-1,2,4-triazol-5-yl)phenyl)pyrazolo[1,5-a]pyrimidin-5-yl)-2-oxooxazolidin-4-yl)phenyl)piperazine-1-carboxylate. LCMS (APCI+) m/z 526.1 [M+H]$^+$.

Example 105

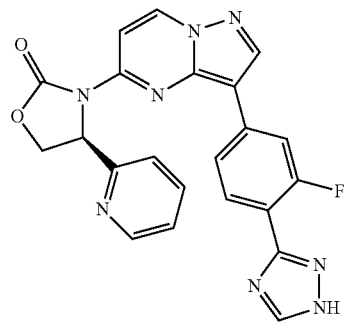 [SMILES: O=C1OC[C@H](c2ccccn2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(5-fluoropyridin-2-yl)oxazolidin-2-one Step 1: To a solution of toluene (500 mL) at −78° C. was added butyl lithium (1.6 M in hexanes, 75.6 ml, 121 mmol) at a rate such that the internal temperature did not exceed −50° C. To this solution was added 2-bromo-5-fluoropyridine (23.2 g, 132 mmol) in toluene (200 mL) at a rate such that the internal temperature did not exceed −68° C. The reaction was stirred at −78° C. for 1 hour. To the reaction was added (S,E)-N-(2-(tert-butyldimethylsilyloxy)ethylidene)-2-methylpropane-2-sulfinamide (30.5 g, 110 mmol) in toluene (200 mL) at a rate such that the internal temperature did exceed −68° C. The reaction was again stirred at −78° C. for 1 hour. To the reaction was added 200 mL of water and the layers separated. The toluene solution was washed with water (200 mL), brine (200 mL), dried over MgSO$_4$ and concentrated in vacuo. The crude material was chromatographed using 4:1 hexanes/ethyl acetate as eluent to yield (S)—N—((S)-2-(tert-butyldimethylsilyloxy)-1-(5-fluoropyridin-2-yl)ethyl)-2-methylpropane-2-sulfinamide (20 g, 48%).

Step 2: To a solution of (S)—N—((S)-2-(tert-butyldimethylsilyloxy)-1-(5-fluoropyridin-2-yl)ethyl)-2-methylpropane-2-sulfinamide (16 g, 43 mmol) in methanol (300 mL) was added hydrogen chloride (53 mL, 210 mmol) (4M in dioxanes) and the reaction stirred at room temperature for 2 hours. The reaction was concentrated in vacuo and the material taken up in water (200 mL) and washed with dichloromethane (200 mL) to give (S)-2-amino-2-(5-fluoropyridin-2-yl)ethanol bis-hydrochloride (9.8 g, 43 mmol) as a solution in water. The solution was used crude in the next reaction.

Step 3: To the solution of (S)-2-amino-2-(5-fluoropyridin-2-yl)ethanol bis-hydrochloride (9.8 g, 43 mmol) in water (200 mL) cooled to 0° C. was added potassium hydroxide (24 g, 430 mmol) followed by THF (200 mL) and the reaction stirred until the temperature reached 0° C. To the reaction was added bis(trichloromethyl) carbonate (13 g, 43 mmol) (in THF, 200 mL) dropwise such that the internal temperature did not exceed 7° C., and the reaction was stirred for 2 hours. The reaction was diluted with ethyl acetate and the aqueous layer made basic with NaOH (1M). The organic layer was washed with brine, dried over MgSO$_4$ and concentrated in vacuo. The crude material was chromatographed using a gradient of 50% DCM/EtOAc to EtOAc as eluent to yield (S)-4-(5-fluoropyridin-2-yl)oxazolidin-2-one (4.3 g, 24 mmol, 55% yield).

Step 4: To a solution of (S)-4-(5-fluoropyridin-2-yl)oxazolidin-2-one (4.3 g, 24 mmol) in DMF (75 mL) was added sodium hydride (0.94 g, 24 mmol) in portions and the reaction stirred for 15 minutes at room temperature, followed by the addition of 3-bromo-5-chloropyrazolo[1,5-a]pyrimidine (5.5 g, 24 mmol) in a solution of DMF (50 mL) and the reaction was stirred for an additional 1 hour. The reaction was poured into water (400 mL) and extracted into ether (400 mL). The water layer was separated and washed with ether (200 mL). The combined organic layers were washed with water (100 mL) and brine (200 mL), dried over MgSO$_4$ and concentrated in vacuo. The crude material was chromatographed using 15% EtOAc/DCM as eluent to yield (S)-3-(3-bromopyrazolo[1,5-a]pyrimidin-5-yl)-4-(5-fluoropyridin-2-yl)oxazolidin-2-one (6.7 g, 18 mmol, 75% yield).

Step 5: To a solution of (S)-3-(3-bromopyrazolo[1,5-a]pyrimidin-5-yl)-4-(5-fluoropyridin-2-yl)oxazolidin-2-one (6.7 g, 18 mmol) and 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (11 g, 27 mmol) in dioxane (150 mL) was added sodium carbonate (44 ml, 89 mmol) (2 M in water) and the reaction mixture bubbled with nitrogen gas for 30 minutes, followed by addition of 750 mg each of Pd$_2$dba$_3$ and X-phos, and the reaction heated to 80° C. while the nitrogen purge continued. The reaction was poured into water (150 mL) and extracted with ethyl acetate (400 mL). The organic layer was washed with water (100 mL), brine (100 mL), dried over MgSO$_4$ and concentrated in vacuo. The material was chromatographed using a gradient of 70% EtOAc/DCM to EtOAc as eluent to yield (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(5-fluoropyridin-2-yl)oxazolidin-2-one (5.8 g, 9.8 mmol, 55% yield).

Step 6: To the solid (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(5-fluoropyridin-2-yl)oxazolidin-2-one (5.8 g, 9.8 mmol) was added TFA (40 mL) and the reaction stirred at ambient temperature for 2 hours. The reaction was concentrated in vacuo and the residue was dissolved in acetonitrile/methanol (1:1, 70 mL). Water (30 mL) was added and the mixture was stirred at ambient temperature for 3 hours. The aqueous layer was made basic with NaHCO$_3$ (saturated solution) and the organic layer was removed in vacuo. The solid that formed was filtered and dried in vacuo. The solid was taken up in acetone (100 mL) and water added (500 mL) slowly. After complete addition, the slurry was stirred for 1 hour at ambient temperature. The slurry was filtered and the solid dried in vacuo for 36 hours to yield (S)-3-(3-(3-fluoro-4-(1H-1,2,4-triazol-3-yl)phenyl)pyrazolo[1,5-a]pyrimidin-5-yl)-4-(5-fluoropyridin-2-yl)oxazolidin-2-one (3.4 g, 7.4 mmol, 75% yield). LCMS (APCI+) m/z 461 [M+H]$^+$.

Example 106

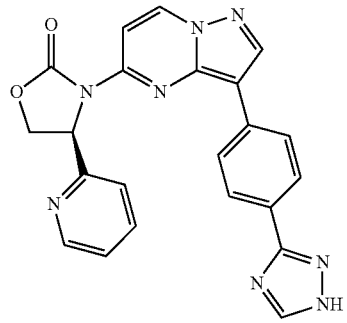 [SMILES: O=C1OC[C@H](c2ccccn2)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-(pyridin-2-yl)oxazolidin-2-one Racemic 3-(3-(4-(1H-1,2,4-triazol-3-yl)phenyl)pyrazolo[1,5-a]pyrimidin-5-yl)-4-(pyridin-2-yl)oxazolidin-2-one (Example 69) was dissolved in hot ethanol (10 mg/3 mL) and 1.5 ml of the solution injected (8 injections total) onto a 2.2 cm×250 mm Chiral Tech OD-H column using 35% ethanol/65% hexanes as eluent with a 21 mL/minute flow rate. Peak 1 was isolated to provide (S)-3-(3-(4-(1H-1,2,4-triazol-3-yl)phenyl)pyrazolo[1,5-a]pyrimidin-5-yl)-4-(pyridin-2-yl)oxazolidin-2-one (19.2 mg). LCMS (APCI+) m/z 425 [M+H]$^+$.

Example 107

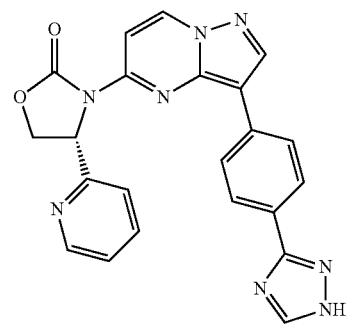 [SMILES: O=C1OC[C@@H](c2ccccn2)N1c1ccn2ncc(-c3ccc(-c4nc[nH]n4)cc3)c2n1]

(R)-3-(3-(4-(1H-1,2,4-triazol-3-yl)phenyl)pyrazolo[1,5-a]pyrimidin-5-yl)-4-(pyridin-2-yl)oxazolidin-2-one Racemic 3-(3-(4-(1H-1,2,4-triazol-3-yl)phenyl)pyrazolo[1,5-a]pyrimidin-5-yl)-4-(pyridin-2-yl)oxazolidin-2-one (Example 69) was dissolved in hot ethanol (10 mg/3 mL) and 1.5 mL of the solution injected (8 injections total) onto a 2.2 cm×250 mm Chiral Tech OD-H column using 35% ethanol/65% hexanes as eluent with a 21 mL/minute flow rate. Peak 2 was isolated to give (R)-3-(3-(4-(1H-1,2,4-triazol-3-yl)phenyl)pyrazolo[1,5-a]pyrimidin-5-yl)-4-(pyridin-2-yl)oxazolidin-2-one (19.8 mg). LCMS (APCI+) m/z 425 [M+H]$^+$.

Example 108

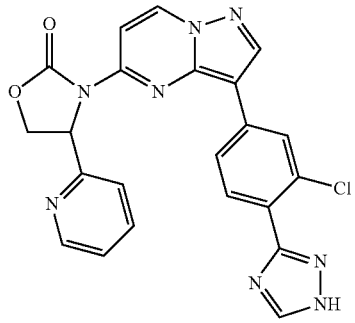 [SMILES: O=C1OCC(c2ccccn2)N1c1ccn2ncc(-c3ccc(-c4nc[nH]n4)c(Cl)c3)c2n1]

3-(3-(3-chloro-4-(1H-1,2,4-triazol-3-yl)phenyl)pyrazolo[1,5-a]pyrimidin-5-yl)-4-(pyridin-2-yl)oxazolidin-2-one 3-(3-(3-chloro-4-(1H-1,2,4-triazol-3-yl)phenyl)pyrazolo[1,5-a]pyrimidin-5-yl)-4-(pyridin-2-yl)oxazolidin-2-one (0.177 g, 0.388 mmol) was made substituting 2-amino-2-(pyridin-2-yl)ethanol hydrochloride for (S)-2-amino-2-(5-fluoropyridin-2-yl)ethanol bis-hydrochloride in Example 105, Step 3 and substituting 3-(2-chloro-4-(4,4,5,5-tetramethyl-1,3,2-dioxaborolan-2-yl)phenyl)-1-((2-(trimethylsilyl)ethoxy)methyl)-1H-1,2,4-triazole for 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole in Example 105, Step 5. LCMS (APCI+) m/z 459, 461 [M+H]+.

Example 109

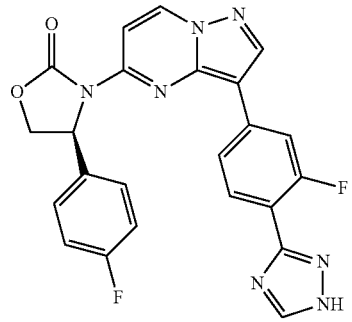 [SMILES: O=C1OC[C@H](c2ccc(F)cc2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(4-fluorophenyl)oxazolidin-2-one (S)-3-(3-(3-fluoro-4-(1H-1,2,4-triazol-3-yl)phenyl)pyrazolo[1,5-a]pyrimidin-5-yl)-4-(4-fluorophenyl)oxazolidin-2-one (0.050 g, 0.11 mmol) was made substituting (S)-2-amino-2-(4-fluorophenyl)ethanol hydrochloride for (S)-2-amino-2-(5-fluoropyridin-2-yl)ethanol bis-hydrochloride in Example 105, step 3. LCMS (APCI+) m/z 460 [M+H]+.

Example 110

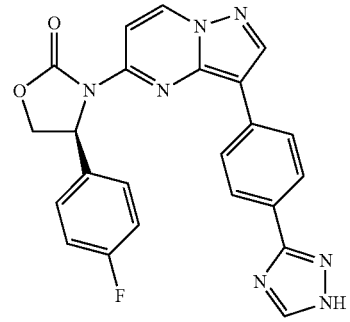 [SMILES: O=C1OC[C@H](c2ccc(F)cc2)N1c1ccn2ncc(-c3ccc(-c4nc[nH]n4)cc3)c2n1]

(S)-3-(3-(4-(1H-1,2,4-triazol-3-yl)phenyl)pyrazolo[1,5-a]pyrimidin-5-yl)-4-(4-fluorophenyl)oxazolidin-2-one (S)-3-(3-(4-(1H-1,2,4-triazol-3-yl)phenyl)pyrazolo[1,5-a]pyrimidin-5-yl)-4-(4-fluorophenyl)oxazolidin-2-one (0.0853 g, 0.193 mmol) was made substituting (S)-2-amino-2-(4-fluorophenyl)ethanol hydrochloride for (S)-2-amino-2-(5-fluoropyridin-2-yl)ethanol bis hydrochloride in Example 105, Step 3 and substituting 3-(4-(4,4,5,5-tetramethyl-1,3,2-dioxaborolan-2-yl)phenyl)-1-((2-(trimethylsilyl)ethoxy)methyl)-1H-1,2,4-triazole for 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole in Example 105, Step 5. LCMS (APCI+) m/z 442 [M+H]+.

Example 111

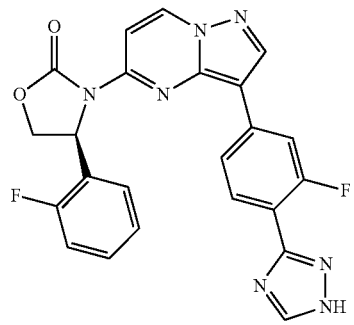 [SMILES: O=C1OC[C@H](c2ccccc2F)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(2-fluorophenyl)oxazolidin-2-one (S)-3-(3-(3-fluoro-4-(1H-1,2,4-triazol-3-yl)phenyl)pyrazolo[1,5-a]pyrimidin-5-yl)-4-(2-fluorophenyl)oxazolidin-2-one (0.061 g, 0.13 mmol) was made substituting (S)-2-amino-2-(2-fluorophenyl)ethanol hydrochloride for (S)-2-amino-2-(5-fluoropyridin-2-yl)ethanol bis-hydrochloride in Example 105, step 3. LCMS (APCI+) m/z 460 [M+H]+.

Example 112

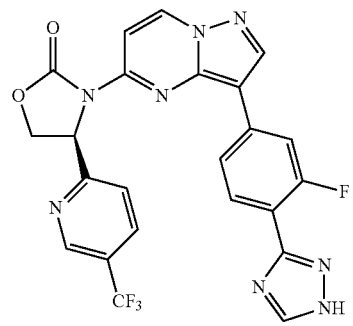 [SMILES: O=C1OC[C@H](c2ccc(C(F)(F)F)cn2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(5-(trifluoromethyl)pyridin-2-yl)oxazolidin-2-one (S)-3-(3-(3-fluoro-4-(1H-1,2,4-triazol-3-yl)phenyl)pyrazolo[1,5-a]pyrimidin-5-yl)-4-(5-(trifluoromethyl)pyridin-2-yl)oxazolidin-2-one (0.0084 g, 0.016 mmol) was made substituting 2-bromo-5-(trifluoromethyl)pyridine for 2-bromo-5-fluoro pyridine in Example 105, step 1. LCMS (APCI+) m/z 511 [M+H]+.

Example 113

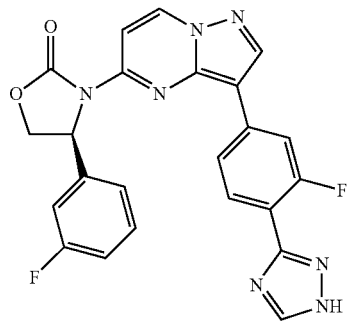 [SMILES: O=C1OC[C@H](c2cccc(F)c2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(3-fluorophenyl)oxazolidin-2-one (S)-3-(3-(3-fluoro-4-(1H-1,2,4-triazol-3-yl)phenyl)pyrazolo[1,5-a]pyrimidin-5-yl)-4-(3-fluorophenyl)oxazolidin-2-one (0.023 g, 0.049 mmol) was made substituting (S)-2-amino-2-(3-fluorophenyl)ethanol hydrochloride for (S)-2-amino-2-(5-fluoropyridin-2-yl)ethanol bis-hydrochloride in Example 105, step 3. LCMS (APCI+) m/z 460 [M+H]+.

Example 114

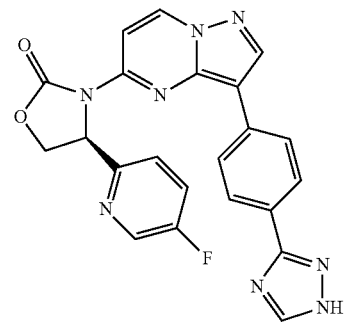

(S)-3-(3-(4-(1H-1,2,4-triazol-3-yl)phenyl)pyrazolo[1,5-a]pyrimidin-5-yl)-4-(5-fluoropyridin-2-yl)oxazolidin-2-one Step 1: (S)-4-(5-fluoropyridin-2-yl)-3-(3-(4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.043 g, 57%) were prepared by the procedure described in Example 1, Step 8, using (S)-3-(3-bromopyrazolo[1,5-a]pyrimidin-5-yl)-4-(5-fluoropyridin-2-yl)oxazolidin-2-one.

Step 2: (S)-3-(3-(4-(1H-1,2,4-triazol-3-yl)phenyl)pyrazolo[1,5-a]pyrimidin-5-yl)-4-(5-fluoropyridin-2-yl)oxazolidin-2-one (28 mg, 84%) was prepared by the procedure described in Example 1, Step 9, using (S)-3-(3-bromopyrazolo[1,5-a]pyrimidin-5-yl)-4-(5-fluoropyridin-2-yl)oxazolidin-2-one. LCMS (APCI+) m/z 443.5 [M+H]+.

Example 115

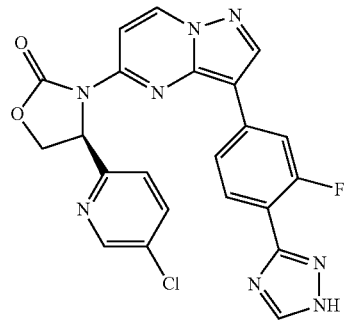 [SMILES: O=C1OC[C@H](c2ccc(Cl)cn2)N1c1ccn2ncc(-c3ccc(-c4nc[nH]n4)c(F)c3)c2n1]

(S)-4-(5-chloropyridin-2-yl)-3-(3-(3-fluoro-4-(1H-1,2,4-triazol-3-yl)phenyl)pyrazolo[1,5-a]pyrimidin-5-yl)oxazolidin-2-one (S)-4-(5-chloropyridin-2-yl)-3-(3-(3-fluoro-4-(1H-1,2,4-triazol-3-yl)phenyl)pyrazolo[1,5-a]pyrimidin-5-yl)oxazolidin-2-one (0.109 g, 0.229 mmol) was made substituting 2-bromo-5-(chlororo)pyridine for 2-bromo-5-fluoropyridine in Example 105, step 1. LCMS (APCI+) m/z 477, 479 [M+H]+.

Example 116

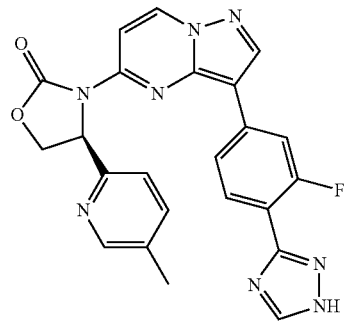 [SMILES: Cc1ccc([C@H]2COC(=O)N2c2ccn3ncc(-c4ccc(-c5nc[nH]n5)c(F)c4)c3n2)nc1]

(S)-3-(3-(3-fluoro-4-(1H-1,2,4-triazol-3-yl)phenyl)pyrazolo[1,5-a]pyrimidin-5-yl)-4-(5-methylpyridin-2-yl)oxazolidin-2-one (S)-3-(3-(3-fluoro-4-(1H-1,2,4-triazol-3-yl)phenyl)pyrazolo[1,5-a]pyrimidin-5-yl)-4-(5-methylpyridin-2-yl)oxazolidin-2-one (0.035 g, 0.077 mmol) was made substituting 2-bromo-5-methylpyridine for 2-bromo-5-fluoropyridine in Example 105, Step 1. LCMS (APCI+) m/z 457 [M+H]+.

Example 117

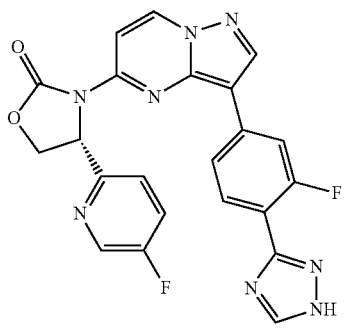 [SMILES: O=C1OC[C@@H](c2ccc(F)cn2)N1c1ccn2ncc(-c3ccc(-c4nc[nH]n4)c(F)c3)c2n1]

(R)-3-(3-(3-fluoro-4-(1H-1,2,4-triazol-3-yl)phenyl) pyrazolo[1,5-a]pyrimidin-5-yl)-4-(5-fluoropyridin-2-yl)oxazolidin-2-one Prepared according to the method of Example 105, with the exception that (R)—N#S)-2-(tert-butyldimethylsilyloxy)-1-(5-fluoropyridin-2-yl)ethyl)-2-methylpropane-2-sulfinamide was isolated in Step 1. LCMS (APCI+) m/z 461 [M+H]+.

Example 118

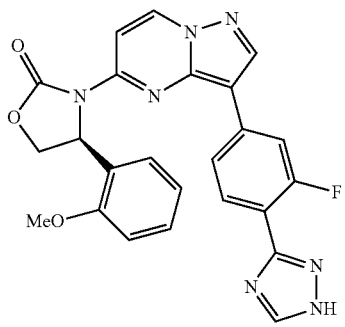 [SMILES: COc1ccccc1[C@H]1COC(=O)N1c1ccn2ncc(-c3ccc(-c4nc[nH]n4)c(F)c3)c2n1]

(S)-3-(3-(3-fluoro-4-(1H-1,2,4-triazol-3-yl)phenyl) pyrazolo[1,5-a]pyrimidin-5-yl)-4-(2-methoxyphenyl) oxazolidin-2-one Step 1: (S)-4-(2-Methoxyphenyl)oxazolidin-2-one was prepared according to the method of Example 72, Step 1, substituting (S)-2-aminopentan-1-ol with (S)-2-amino-2-(2-methoxyphenyl)ethanol to provide 0.58 g (quantitative) of the desired product as a yellow solid.

Step 2: (S)-3-(3-bromopyrazolo[1,5-a]pyrimidin-5-yl)-4-(2-methoxyphenyl) oxazolidin-2-one was prepared according to the method of Example 72, Step 2, to provide 0.103 g (31%) of the desired product as a yellow solid.

Step 3: To a round bottom flask were added (S)-3-(3-bromopyrazolo[1,5-a]pyrimidin-5-yl)-4-(2-methoxyphenyl)oxazolidin-2-one (0.103 g, 0.265 mmol), 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.144 g, 0.344 mmol), dioxane (2 mL) and 2.0 M Na₂CO₃ (0.40 mL, 0.80 mmol). The mixture was degassed by bubbling N₂ through the solution. Pd₂ dba₃ (0.012 g, 0.013 mmol) and dicyclohexyl(2',4',6'-triisopropylbiphenyl-2-yl)phosphine (0.013 g, 0.027 mmol) were added, and the mixture was heated at 80° C. overnight. The reaction mixture was cooled to ambient temperature, diluted with H₂O, and extracted thoroughly with EtOAc and DCM. The combined organic extracts were washed with brine, dried, and concentrated. Purification of the crude material on silica, eluting with 70% EtOAc/hexanes, to provide (S)-3-(3-(3-fluoro-4-(1-((2-(trimethylsilyl)ethoxy)methyl)-1H-1,2,4-triazol-3-yl)phenyl) pyrazolo[1,5-a]pyrimidin-5-yl)-4-(2-methoxyphenyl)oxazolidin-2-one as a bright yellow solid (0.0848 g, 53%). MS (APCI+) m/z 601 [M+H]+.

Step 4: A mixture of (S)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(2-methoxyphenyl) oxazolidin-2-one (0.0424 g, 0.071 mmol) in DCM (1 mL) was treated with trifluoroacetic acid (0.5 mL) at ambient temperature. The mixture was stirred for 18 hours. The solvent was concentrated and the residue was partitioned between EtOAc and saturated aqueous NaHCO₃. The aqueous layer was further extracted with EtOAc and DCM. The combined organic extracts were washed with brine, dried, and concentrated, and the crude material was purified by column chromatography (silica, 10% MeOH/dichloromethane) to afford the title compound (0.011 g, 33%) as a yellow solid. MS (APCI+) m/z 472 [M+H]+.

Example 119

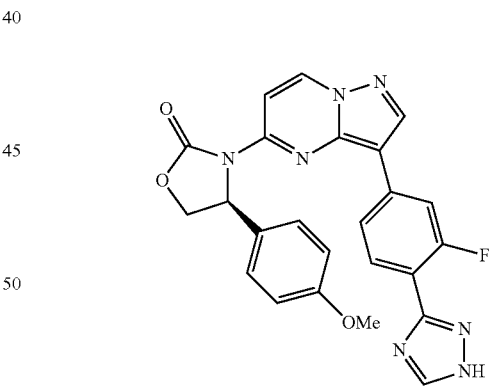

(S)-3-(3-(3-fluoro-4-(1H-1,2,4-triazol-3-yl)phenyl) pyrazolo[1,5-a]pyrimidin-5-yl)-4-(4-methoxyphenyl) oxazolidin-2-one The title compound was prepared according to the procedures for the preparation of Example 118 (Steps 1-4), substituting (S)-2-amino-2-(2-methoxyphenyl)ethanol with (S)-2-amino-2-(4-methoxyphenyl)ethanol in Step 1 to provide 0.029 g as a yellow solid. MS (APCI+) m/z 472 [M+H]+.

Example 120

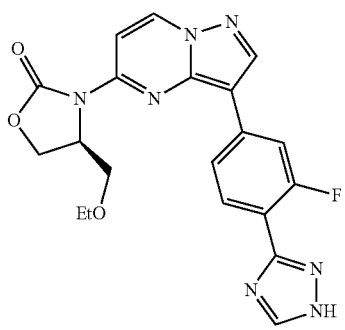 [SMILES: CCOC[C@H]1COC(=O)N1c1ccn2ncc(-c3ccc(-c4nc[nH]n4)c(F)c3)c2n1]

(S)-4-(ethoxymethyl)-3-(3-(3-fluoro-4-(1H-1,2,4-triazol-3-yl)phenyl)pyrazolo[1,5-a]pyrimidin-5-yl)oxazolidin-2-one Step 1: A mixture of sodium hydride (354 mg, 8.86 mmol) and iodoethane (0.90 ml, 11.2 mmol) in anhydrous THF (22 mL) was chilled to 0° C. A solution of (S)-(2-phenyl-4,5-dihydrooxazol-4-yl)methanol (785 mg, 4.43 mmol) (Synthesis, 1993, 2, 250-262; using D-, instead of L-serine as a starting material) in 10 ml anhydrous THF was then added dropwise to the reaction mixture. The resulting mixture was allowed to warm to ambient temperature, and stirred overnight. After addition of water, the mixture was extracted with EtOAc. The combined organic extracts were dried and concentrated to afford (S)-4-(ethoxymethyl)-2-phenyl-4,5-dihydrooxazole as a clear, light-brown oil (0.981 g, 108%), which was used directly in the next step.

Step 2: (S)-4-(ethoxymethyl)-2-phenyl-4,5-dihydrooxazole (909 mg, 4.43 mmol) was dissolved in 25 ml 4.0 M hydrochloric acid. The resulting solution was refluxed for 20 hours. After cooling to ambient temperature the mixture was filtered to remove the benzoic acid. The filtrate was extracted with ether, and the ether layer discarded. The aqueous layer was concentrated to afford (R)-2-amino-3-ethoxypropan-1-ol hydrochloride (425 mg, 62%) as a low-melting reddish solid.

Step 3: (S)-4-(ethoxymethyl)-3-(3-(3-fluoro-4-(1H-1,2,4-triazol-3-yl)phenyl)pyrazolo[1,5-a]pyrimidin-5-yl)oxazolidin-2-one was prepared according to the procedures for the preparation of Example 118 (Steps 1-4), substituting (S)-2-amino-2-(2-methoxyphenyl)ethanol with (R)-2-amino-3-ethoxypropan-1-ol in Step 1. Obtained 0.030 g as a yellow solid. MS (APCI+) m/z 424 [M+H]+.

Example 121

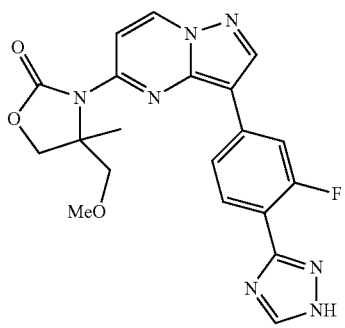 [SMILES: COCC1(C)COC(=O)N1c1ccn2ncc(-c3ccc(-c4nc[nH]n4)c(F)c3)c2n1]

3-(3-(3-fluoro-4-(1H-1,2,4-triazol-3-yl)phenyl)pyrazolo[1,5-a]pyrimidin-5-yl)-4-(methoxymethyl)-4-methyloxazolidin-2-one Step 1: To a chilled (0° C.) solution of 4-(hydroxymethyl)-4-methyloxazolidin-2-one (629 mg, 4.8 mmol) in anhydrous pyridine (4 ml) was added in portions tosyl chloride (1.05 g, 5.5 mmol). The solution was allowed to warm to ambient temperature and stirred under nitrogen for 48 hours. Water (12 mL) was added dropwise to the reaction mixture, and the resulting suspension was stirred at ambient temperature for 5 hours. The solids were isolated, and dried under vacuum to afford (4-methyl-2-oxooxazolidin-4-yl)methyl 4-methylbenzenesulfonate 1.17 g (86%).

Step 2: To a round bottom flask containing (4-methyl-2-oxooxazolidin-4-yl)methyl 4-methylbenzenesulfonate (300 mg, 1.05 mmol) was added under a nitrogen atmosphere 3 ml of sodium methoxide in methanol solution (25% wt). The resulting thick suspension was stirred at ambient temperature for 24 hours, and then heated at 80° C. for 18 hours. The reaction was cooled to ambient temperature, diluted with water, and the pH was adjusted to neutral. The mixture was concentrated, and the resulting solids were extracted with DCM and EtOAc. The combined organic layer was concentrated to afford 4-(methoxymethyl)-4-methyloxazolidin-2-one (129 mg, 85%) as an oil.

Step 3: 3-(3-(3-fluoro-4-(1H-1,2,4-triazol-3-yl)phenyl)pyrazolo[1,5-a]pyrimidin-5-yl)-4-(methoxymethyl)-4-methyloxazolidin-2-one was prepared according to the procedures for the preparation of Example 118 (Steps 1-4), substituting (S)-2-amino-2-(2-methoxyphenyl)ethanol with 2-amino-3-methoxy-2-methylpropan-1-ol in Step 1 to provide 0.030 g as a yellow solid. MS (APCI+) m/z 424 [M+H]+.

Example 122

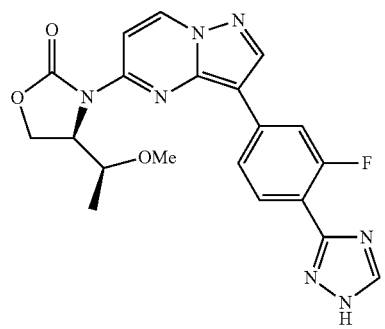 [SMILES: CO[C@@H](C)[C@H]1COC(=O)N1c1ccn2ncc(-c3ccc(-c4nc[nH]n4)c(F)c3)c2n1]

(R)-3-(3-(3-fluoro-4-(1H-1,2,4-triazol-3-yl)phenyl)pyrazolo[1,5-a]pyrimidin-5-yl)-4-((S)-1-methoxyethyl)oxazolidin-2-one Step 1: To a solution of (2S,3S)-2-amino-3-methoxybutanoic acid (250 mg, 1.88 mmol) in anhydrous THF was added lithium aluminum hydride solution (1.0 M in THF, 3.8 mL, 3.8 mmol) under a nitrogen atmosphere. The resulting solution was refluxed for 10 hours, cooled to ambient temperature and stirred overnight, and refluxed for another three hours. The cooled mixture was diluted with THF, and anhydrous sodium sulfate was added. The supernatant was decanted, and treated again with anhydrous sodium sulfate.

The THF extract was concentrated and dried under vacuum to afford (2R,3S)-2-amino-3-methoxybutan-1-ol as a white solid (167 mg, 75%).

Step 2: (R)-3-(3-(3-fluoro-4-(1H-1,2,4-triazol-3-yl)phenyl)pyrazolo[1,5-a]pyrimidin-5-yl)-4-((S)-1-methoxyethyl)oxazolidin-2-one was prepared according to the procedures for the preparation of Example 118 (Steps 1-4), substituting (S)-2-amino-2-(2-methoxyphenyl)ethanol with (2R,3S)-2-amino-3-methoxybutan-1-ol in Step 1. Obtained 0.010 g as a yellow solid. $^1$H NMR (CDCl$_3$) δ 8.62 (d, 1H), 8.43 (s, 1H), 8.25 (t, 1H), 8.08 (d, 1H), 8.06 (s, 1H), 8.0 (d, 1H), 7.94 (d, 1H), 4.87 (d, 1H), 4.65 (dd, 1H), 4.44 (t, 1H), 4.26 (q, 1H), 3.26 (s, 3H), 1.27 (d, 3H).

Example 123

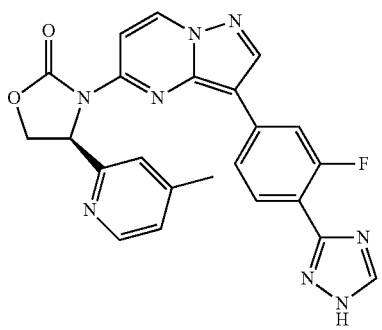 [SMILES: Cc1ccnc([C@H]2COC(=O)N2c2ccn3ncc(-c4ccc(-c5nc[nH]n5)c(F)c4)c3n2)c1]

(S)-3-(3-(3-fluoro-4-(1H-1,2,4-triazol-3-yl)phenyl)pyrazolo[1,5-a]pyrimidin-5-yl)-4-(4-methylpyridin-2-yl)oxazolidin-2-one Step 1: To a chilled (−78° C.) solution of n-butyllithium (2.5 M, 3.5 mL) in anhydrous toluene (30 mL) was added a solution of 2-bromo-4-methylpyridine (1.49 g, 8.65 mmol) at a rate such that the reaction temperature did not exceed −65° C. The resulting viscous mixture was stirred at −78° C. for 2.5 hours. To the reaction was next added a solution of (S,E)-N-(2-(tert-butyldimethylsilyloxy)ethylidene)-2-methylpropane-2-sulfinamide (2.0 g, 7.21 mmol), such that the reaction temperature did not exceed −70° C. The reaction was stirred at −78° C. for an additional three hours. Saturated aqueous sodium sulfate solution was added, the mixture was warmed up to ambient temperature, and extracted with EtOAc. The combined organic extracts were dried and concentrated. Chromatography on silica (30% EtOAc-DCM as eluant) afforded 1.10 g (41%) of (S)—N4S)-2-(tert-butyldimethylsilyloxy)-1-(4-methylpyridin-2-yl)ethyl)-2-methylpropane-2-sulfinamide as a clear, viscous oil.

Step 2: (S)—N—((S)-2-(tert-butyldimethylsilyloxy)-1-(4-methylpyridin-2-yl)ethyl)-2-methylpropane-2-sulfinamide (1.10 g, 2.97 mmol) was dissolved in MeOH (15 ml), and treated with 3.7 ml of a 4.0 M hydrogen chloride solution in dioxane. The reaction was stirred at ambient temperature for 2 hours, concentrated to dryness, and stored under high vacuum overnight to provide 0.71 g (106%) of crude (S)-2-amino-2-(4-methylpyridin-2-yl)ethanol dihydrochloride which was used directly in the next step.

Step 3: (S)-3-(3-(3-fluoro-4-(1H-1,2,4-triazol-3-yl)phenyl)pyrazolo[1,5-a]pyrimidin-5-yl)-4-(4-methylpyridin-2-yl)oxazolidin-2-one was prepared according to the procedures for the preparation of Example 118 (Steps 1-4), substituting (S)-2-amino-2-(2-methoxyphenyl)ethanol with (S)-2-amino-2-(4-methylpyridin-2-yl)ethanol in Step 1 to provide 4 mg of the title compound as a yellow solid. MS (APCI+) m/z 457 [M+H]$^+$.

Example 124

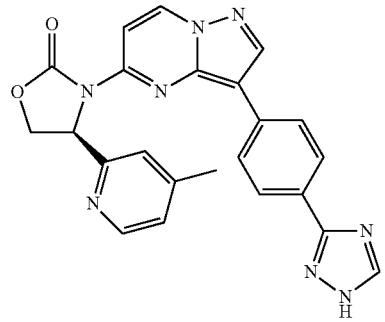 [SMILES: Cc1ccnc([C@H]2COC(=O)N2c2ccn3ncc(-c4ccc(-c5nc[nH]n5)cc4)c3n2)c1]

(S)-3-(3-(4-(1H-1,2,4-triazol-3-yl)phenyl)pyrazolo[1,5-a]pyrimidin-5-yl)-4-(4-methylpyridin-2-yl)oxazolidin-2-one The title compound was prepared according to the procedures for the preparation of Example 123, substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole with 3-(4-(4,4,5,5-tetramethyl-1,3,2-dioxaborolan-2-yl)phenyl)-1-((2-(trimethylsilyl)ethoxy)methyl)-1H-1,2,4-triazole in the penultimate step to provide 16 mg of the title compound as a yellow solid. MS (APCI+) m/z 438 [M+H]$^+$.

Example 125

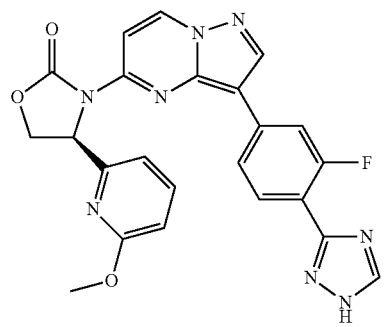 [SMILES: COc1cccc([C@H]2COC(=O)N2c2ccn3ncc(-c4ccc(-c5nc[nH]n5)c(F)c4)c3n2)n1]

(S)-3-(3-(3-fluoro-4-(1H-1,2,4-triazol-3-yl)phenyl)pyrazolo[1,5-a]pyrimidin-5-yl)-4-(4-methylpyridin-2-yl)oxazolidin-2-one Step 1: (S)-2-amino-2-(4-methylpyridin-2-yl)ethanol (240 mg, 46%) was prepared by the procedures described in Example 123 (Steps 1-2), substituting 2-bromo-4-methylpyridine with 2-bromo-6-methoxypyridine in the first step.

Step 2: (S)-3-(3-(3-fluoro-4-(1H-1,2,4-triazol-3-yl)phenyl)pyrazolo[1,5-a]pyrimidin-5-yl)-4-(4-methylpyridin-2-yl)oxazolidin-2-one was prepared according to the procedures for the preparation of Example 118 (Steps 1-4), substituting (S)-2-amino-2-(2-methoxyphenyl)ethanol with (S)-2-amino-2-(6-methoxypyridin-2-yl)ethanol in Step 1 to provide 22.5 mg of the title compound as a yellow solid. MS (APCI+) m/z 473 [M+H]+.

Example 126

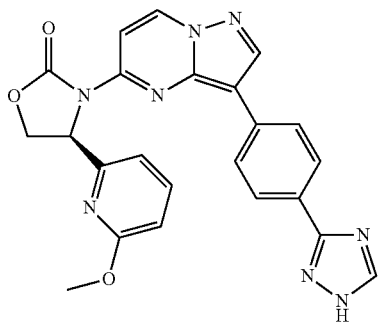 [SMILES: COc1cccc([C@H]2COC(=O)N2c2ccn3ncc(-c4ccc(-c5nc[nH]n5)cc4)c3n2)n1]

(S)-3-(3-(4-(1H-1,2,4-triazol-3-yl)phenyl)pyrazolo[1,5-a]pyrimidin-5-yl)-4-(6-methoxypyridin-2-yl)oxazolidin-2-one Prepared according to the method of Example 125, substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole with 3-(4-(4,4,5,5-tetramethyl-1,3,2-dioxaborolan-2-yl)phenyl)-1-((2-(trimethylsilyl)ethoxy)methyl)-1H-1,2,4-triazole in the penultimate step to provide 7 mg of the title compound as a yellow solid. MS (APCI+) m/z 455 [M+H]+.

Example 127

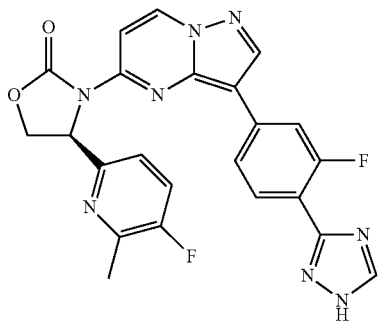 [SMILES: Cc1nc([C@H]2COC(=O)N2c2ccn3ncc(-c4ccc(-c5nc[nH]n5)c(F)c4)c3n2)ccc1F]

(S)-3-(3-(3-fluoro-4-(1H-1,2,4-triazol-3-yl)phenyl)pyrazolo[1,5-a]pyrimidin-5-yl)-4-(5-fluoro-6-methylpyridin-2-yl)oxazolidin-2-one Step 1: (S)-2-amino-2-(5-fluoro-6-methylpyridin-2-yl)ethanol (200 mg, 46%) was prepared by the procedures described in Example 123 (Steps 1-2), substituting 2-bromo-4-methylpyridine with 6-bromo-3-fluoro-2-methylpyridine in the first step.

Step 2: (S)-3-(3-(3-fluoro-4-(1H-1,2,4-triazol-3-yl)phenyl)pyrazolo[1,5-a]pyrimidin-5-yl)-4-(5-fluoro-6-methylpyridin-2-yl)oxazolidin-2-one was prepared according to the procedures for the preparation of Example 118 (Steps 1-4), substituting (S)-2-amino-2-(2-methoxyphenyl)ethanol with (S)-2-amino-2-(5-fluoro-6-methylpyridin-2-yl)ethanol in Step 1 to provide 11.2 mg of the title compound as a yellow solid. MS (APCI+) m/z 475 [M+H]+.

Example 128

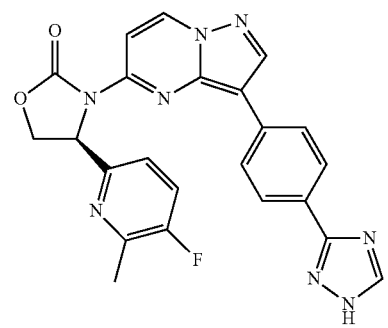 [SMILES: Cc1nc([C@H]2COC(=O)N2c2ccn3ncc(-c4ccc(-c5nc[nH]n5)cc4)c3n2)ccc1F]

(S)-3-(3-(4-(1H-1,2,4-triazol-3-yl)phenyl)pyrazolo[1,5-a]pyrimidin-5-yl)-4-(5-fluoro-6-methylpyridin-2-yl)oxazolidin-2-one Prepared according to the method of Example 127, substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole with 3-(4-(4,4,5,5-tetramethyl-1,3,2-dioxaborolan-2-yl)phenyl)-1-((2-(trimethylsilyl)ethoxy)methyl)-1H-1,2,4-triazole in the penultimate step to provide 15 mg of the title compound as a yellow solid. $^1$H NMR (CDCl$_3$) δ 8.57 (d, 1H), 8.29 (d, 2H), 8.02 (m, 3H), 7.77 (d, 2H), 7.23 (m, 2H), 5.86 (dd, 1H), 4.78 (t, 1H), 4.40 (dd, 1H), 2.48 (s, 3H).

Example 129

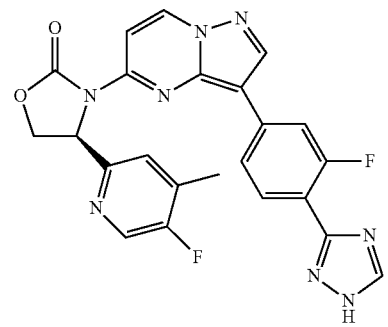 [SMILES: Cc1cc([C@H]2COC(=O)N2c2ccn3ncc(-c4ccc(-c5nc[nH]n5)c(F)c4)c3n2)ncc1F]

(S)-3-(3-(3-fluoro-4-(1H-1,2,4-triazol-3-yl)phenyl)pyrazolo[1,5-a]pyrimidin-5-yl)-4-(5-fluoro-4-methylpyridin-2-yl)oxazolidin-2-one Step 1: (S)-2-Amino-2-(5-fluoro-4-methylpyridin-2-yl)ethanol (150 mg, 59%) was prepared according to the method of Example 123, Steps 1-2, substituting 2-bromo-4-methylpyridine with 2-bromo-5-fluoro-4-methylpyridine in the first step.

Step 2: (S)-3-(3-(3-Fluoro-4-(1H-1,2,4-triazol-3-yl)phenyl)pyrazolo[1,5-a]pyrimidin-5-yl)-4-(5-fluoro-4-methylpyridin-2-yl)oxazolidin-2-one was prepared according to the method of Example 118, Steps 1-4, substituting (S)-2-amino-2-(2-methoxyphenyl)ethanol with (S)-2-amino-2-(5-fluoro-4-methylpyridin-2-yl)ethanol in Step 1 to provide 12 mg of the title compound as a yellow solid. MS (APCI+) m/z 475 [M+H]+.

Example 130

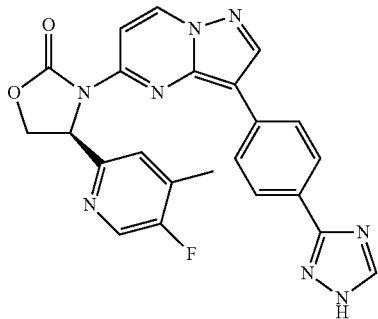 [SMILES: Cc1cc([C@H]2COC(=O)N2c2ccn3ncc(-c4ccc(-c5nc[nH]n5)cc4)c3n2)ncc1F]

(S)-3-(3-(4-(1H-1,2,4-triazol-3-yl)phenyl)pyrazolo[1,5-a]pyrimidin-5-yl)-4-(5-fluoro-4-methylpyridin-2-yl)oxazolidin-2-one Prepared according to the method of Example 129, substituting 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole with 3-(4-(4,4,5,5-tetramethyl-1,3,2-dioxaborolan-2-yl)phenyl)-1-((2-(trimethylsilyl)ethoxy)methyl)-1H-1,2,4-triazole in the penultimate step to provide 7.9 mg of the title compound as a yellow solid. $^1$H NMR (CDCl$_3$) δ 8.57 (d, 1H), 8.28 (m, 3H), 8.04 (m, 3H), 7.78 (d, 2H), 7.21 (d, 1H), 5.9 (d, 1H), 4.79 (t, 1H), 4.40 (dd, 1H), 2.12 (s, 3H).

Example 131

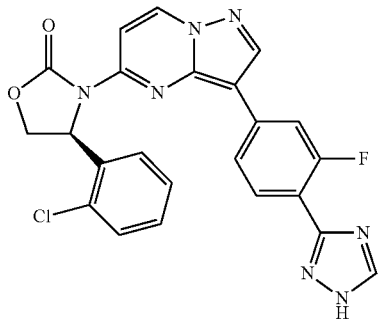 [SMILES: O=C1OC[C@H](c2ccccc2Cl)N1c1ccn2ncc(-c3ccc(-c4nc[nH]n4)c(F)c3)c2n1]

(S)-4-(2-chlorophenol)-3-(3-(3-fluoro-4-(1H-1,2,4-triazol-3-yl)phenyl)pyrazolo[1,5-a]pyrimidin-5-yl)oxazolidin-2-one Step 1: To a solution of (S)-2-amino-2-(2-chlorophenyl)ethanol hydrochloride (500 mg, 2.40 mmol) in water (12 mL) at 0° C. was added potassium hydroxide (809 mg, 14.4 mmol) followed by THF (12 mL) and the reaction was stirred at 0° C. for 20 minutes. Bis(trichloromethyl) carbonate (713 mg, 2.40 mmol) was added and the reaction was stirred at 0° C. for 2 hours. The reaction was poured into EtOAc and the organic phase washed with 1N HCl, 1N NaOH and brine. The organic layer was dried over MgSO$_4$, filtered and concentrated to provide (S)-4-(2-chlorophenyl)oxazolidin-2-one (265 mg, 55.8% yield) as an oil which solidified upon standing.

Step 2: To (S)-4-(2-chlorophenyl)oxazolidin-2-one (265 mg, 1.34 mmol) in DMF (10 mL) was added sodium hydride (59.0 mg, 1.48 mmol) and the reaction was stirred at ambient temperature for 1 hour. 3-Bromo-5-chloropyrazolo[1,5-a]pyrimidine (343 mg, 1.48 mmol) was added in one portion and the reaction was stirred at ambient temperature for 18 hours. Ice was added followed by ammonium chloride (aqueous) and the resulting suspension was filtered and washed with water. After drying, (S)-3-(3-bromopyrazolo[1,5-a]pyrimidin-5-yl)-4-(2-chlorophenyl)oxazolidin-2-one (180 mg, 34.1% yield) was isolated as a pale yellow solid.

Step 3: To (S)-3-(3-bromopyrazolo[1,5-a]pyrimidin-5-yl)-4-(2-chlorophenyl) oxazolidin-2-one (50 mg, 0.13 mmol) were added Pd$_2$ dba$_3$ (5.8 mg, 0.0064 mmol), (9,9-dimethyl-9H-xanthene-4,5-diyl)bis(diphenylphosphine) (7.3 mg, 0.013 mmol), 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (69 mg, 0.17 mmol), dioxane (1.2 mL) and 2M Na$_2$CO$_3$ (0.2 mL). The reaction was stirred for 2 hours at 80° C. in a sealed tube. After cooling, EtOAc and water were added. The organic phase was washed with brine and dried over MgSO$_4$. The residue was purified by reverse phase chromatography (SP4, 12M, water/CH$_3$CN 90:10 to 0:100, 20 column volumes) to yield (S)-4-(2-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (24 mg, 31% yield) as a pale yellow solid.

Step 4: To (S)-4-(2-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (20 mg, 0.033 mmol) in DCM (5 mL) was added TFA (1 mL) and the reaction was stirred at ambient temperature for 6 hours. The reaction was concentrated to dryness and the residue dissolved in MeOH/ammonia (7N). After stirring at ambient temperature for 30 minutes, the reaction was concentrated then purified by reverse phase chromatography (SP4, 12M, water/CH$_3$CN 100:0 to 0:100, 20 column volumes) to yield (S)-4-(2-chlorophenyl)-3-(3-(3-fluoro-4-(1H-1,2,4-triazol-3-yl)phenyl)pyrazolo[1,5-a]pyrimidin-5-yl)oxazolidin-2-one (9 mg, 57% yield) as a pale yellow solid. LCMS (APCI+) m/z 476.2 [M+H]+.

Example 132

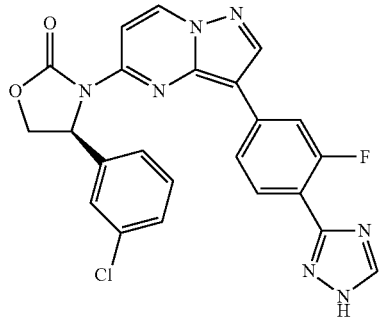 [SMILES: O=C1OC[C@H](c2cccc(Cl)c2)N1c1ccn2ncc(-c3ccc(-c4nc[nH]n4)c(F)c3)c2n1]

(S)-4-(3-chlorophenyl)-3-(3-(3-fluoro-4-(1H-1,2,4-triazol-3-yl)phenyl)pyrazolo[1,5-a]pyrimidin-5-yl)oxazolidin-2-one Step 1: To a solution of (S)-2-amino-2-(3-chlorophenyl)ethanol hydrochloride (500 mg, 2.40 mmol) in water (12 mL) at 0° C. was added potassium hydroxide (809 mg, 14.4 mmol) followed by THF (12 mL) and the reaction was stirred at 0° C. for 20 minutes. Triphosgene (713 mg, 2.40 mmol) was added and the reaction was stirred at 0° C. for 2 hours. The reaction was poured into EtOAc and the organic phase washed with 1N HCl, 1N NaOH and brine. After drying over MgSO₄, concentration yielded (S)-4-(3-chlorophenyl)oxazolidin-2-one (278 mg, 58.5% yield) as an oil.

Step 2: To (S)-4-(3-chlorophenyl)oxazolidin-2-one (278 mg, 1.41 mmol) in DMF (10 mL) was added sodium hydride (56.8 mg, 1.42 mmol) and the reaction was stirred at ambient temperature for 1 hour. 3-bromo-5-chloropyrazolo[1,5-a]pyrimidine (300 mg, 1.29 mmol) was added at once and the reaction was stirred at ambient temperature for 18 hours. Ice was added followed by ammonium chloride (aqueous), and the resulting suspension filtered and washed with water. After drying, (S)-3-(3-bromopyrazolo[1,5-a]pyrimidin-5-yl)-4-(3-chlorophenyl)oxazolidin-2-one (231 mg, 45.5% yield) was isolated as a pale yellow solid.

Step 3: To (S)-3-(3-bromopyrazolo[1,5-a]pyrimidin-5-yl)-4-(3-chlorophenyl)oxazolidin-2-one (100 mg, 0.254 mmol) were added 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (139 mg, 0.330 mmol), Pd₂dba₃ (11.6 mg, 0.0127 mmol), (9,9-dimethyl-9H-xanthene-4,5-diyl)bis(diphenylphosphine) (14.7 mg, 0.0254 mmol), dioxane (1.2 mL) and 2M Na₂CO₃ (0.2 mL). The reaction was stirred for 2 hours at 80° C. in a sealed tube. After cooling, EtOAc and water were added. The organic phase was washed with brine and dried over MgSO₄. The residue was purified by reverse phase chromatography (SP4, 12M, water/CH₃CN 90:10 to 0:100, 20 column volumes) to yield (S)-4-(3-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (67 mg, 43.5% yield) as a pale yellow solid.

Step 4: To (S)-4-(3-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (65 mg, 0.11 mmol) in DCM (5 mL) was added TFA (1 mL) and the reaction was stirred at ambient temperature for 6 hours. The reaction was concentrated to dryness and the residue dissolved in MeOH/ammonia (7N). After stirring at ambient temperature for 30 minutes, the reaction was concentrated then purified by reverse phase chromatography (SP4, 12M, water/CH₃CN 100:0 to 0:100, 20 column volumes) to yield (S)-4-(3-chlorophenyl)-3-(3-(3-fluoro-4-(1H-1,2,4-triazol-3-yl)phenyl)pyrazolo[1,5-a]pyrimidin-5-yl)oxazolidin-2-one (22 mg, 43% yield) as a pale yellow solid. LCMS (APCI+) m/z 476.3 [M+H]⁺.

Example 133

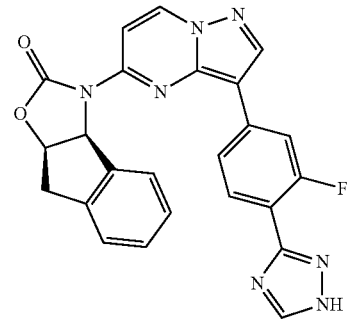 [SMILES: O=C1O[C@@H]2Cc3ccccc3[C@@H]2N1c1ccn2ncc(-c3ccc(-c4nc[nH]n4)c(F)c3)c2n1]

(3aS,8aR)-3-(3-(3-fluoro-4-(1H-1,2,4-triazol-3-yl)phenyl)pyrazolo[1,5-a]pyrimidin-5-yl)-3,3a,8,8a-tetrahydro-2H-indeno[1,2-d]oxazol-2-one Step 1: To a solution of (1S,2R)-1-amino-2,3-dihydro-1H-inden-2-ol (500 mg, 3.35 mmol) in water (20 mL) at 0° C. was added potassium hydroxide (1128 mg, 20.1 mmol) followed by THF (20 mL) and the reaction was stirred at 0° C. for 20 minutes. Bis(trichloromethyl) carbonate (995 mg, 3.35 mmol) was added and the reaction was stirred at 0° C. for 2 hours. The reaction was poured into EtOAc and the organic phase washed with 1N HCl, 1N NaOH and brine. After drying over MgSO₄, concentration yielded (3aS,8aR)-3,3a,8,8a-tetrahydro-2H-indeno[1,2-d]oxazol-2-one (574 mg, 97.8% yield) as a white solid.

Step 2: To 3-bromo-5-chloropyrazolo[1,5-a]pyrimidine (603 mg, 2.59 mmol) in DMF (30 mL) was added sodium hydride (114 mg, 2.85 mmol) and the reaction was stirred at ambient temperature for 1 hour. 3-Bromo-5-chloropyrazolo[1,5-a]pyrimidine (603 mg, 2.59 mmol) was added at once and the reaction was stirred at ambient temperature for 18 hours. Ice was added, followed by ammonium chloride (aqueous), and the resulting suspension filtered and washed with water. After drying, (3aS,8aR)-3-(3-bromopyrazolo[1,5-a]pyrimidin-5-yl)-3,3a,8,8a-tetrahydro-2H-indeno[1,2-d]oxazol-2-one (820 mg, 85.1% yield) was isolated as a pale yellow solid.

Step 3: To (3aS,8aR)-3-(3-bromopyrazolo[1,5-a]pyrimidin-5-yl)-3,3a,8,8a-tetrahydro-2H-indeno[1,2-d]oxazol-2-one (100 mg, 0.269 mmol) were added 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (147 mg, 0.350 mmol), (9,9-dimethyl-9H-xanthene-4,5-diyl)bis(diphenylphosphine) (15.6 mg, 0.0269 mmol), Pd₂dba₃ (12.3 mg, 0.0135 mmol), dioxane (1.2 mL) and 2M Na₂CO₃ (0.2 mL). The reaction was stirred for 2 hours at 80° C. in a sealed tube. After cooling, EtOAc and water were added. The organic phase was washed with brine and dried over MgSO₄. The residue was purified by reverse phase chromatography (SP4, 12M, water/CH₃CN 90:10 to 0:100, 20 column volumes) to yield (3aS,8aR)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-3,3a,8,8a-tetrahydro-2H-indeno[1,2-d]oxazol-2-one (45 mg, 28.6% yield) as a pale yellow solid.

Step 4: To (3aS,8aR)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)-3,3a,8,8a-tetrahydro-2H-indeno[1,2-d]oxazol-2-one (45 mg, 0.077 mmol) in DCM (5 mL) was added TFA (1 mL) and the reaction was stirred at ambient temperature for 6 hours. The reaction was concentrated to dryness and the residue dissolved in MeOH and added to 2N HCl in ether. After concentration, the residue was purified by reverse phase chromatography (SP4, 12M, water/CH$_3$CN 100:0 to 0:100, 20 column volumes) to yield (3aS,8aR)-3-(3-(3-fluoro-4-(1H-1,2,4-triazol-3-yl)phenyl)pyrazolo[1,5-a]pyrimidin-5-yl)-3,3a,8,8a-tetrahydro-2H-indeno[1,2-d]oxazol-2-one (3.5 mg, 10% yield) as a pale yellow solid. LCMS (APCI+) m/z 454.2 [M+H]$^+$.

Example 134

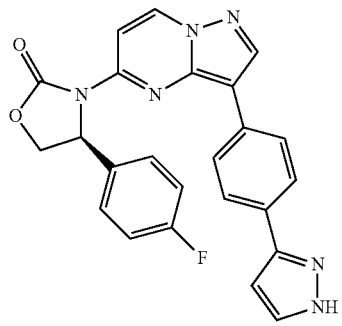 [SMILES: O=C1OC[C@H](c2ccc(F)cc2)N1c1ccn2ncc(-c3ccc(-c4cc[nH]n4)cc3)c2n1]

(S)-3-(3-(4-(1H-pyrazol-3-yl)phenyl)pyrazolo[1,5-a]pyrimidin-5-yl)-4-(4-fluorophenyl)oxazolidin-2-one Step 1: To 3-(4-bromophenyl)-1H-pyrazole (2.0 g, 9.0 mmol) in DMF was added sodium hydride (0.54 g, 13 mmol) (60% in oil) and the reaction was stirred at ambient temperature for 30 minutes. (2-(Chloromethoxy)ethyl)trimethylsilane (4.5 g, 27 mmol) was added and the reaction was stirred overnight. Water was added and the aqueous phase extracted with DCM. The combined organic phases were dried over MgSO$_4$, filtered and concentrated. The crude material was purified by reverse phase chromatography (SP4, 25M, water/CH$_3$CN 60:40 to 0:100, 20 column volumes) to yield 3-(4-bromophenyl)-1-((2-(trimethylsilyl)ethoxy)methyl)-1H-pyrazole (2.4 g, 76% yield) as a clear oil.

Step 2: To 3-(4-bromophenyl)-1-((2-(trimethylsilyl)ethoxy)methyl)-1H-pyrazole (1.0 g, 2.83 mmol) in degassed DMF (10 mL) were added 4,4,4',4',5,5,5',5'-octamethyl-2,2'-bi(1,3,2-dioxaborolane) (1.08 g, 4.25 mmol), potassium acetate (0.972 g, 9.91 mmol) and PdCl$_2$-dppf-dichloromethane (0.116 g, 0.142 mmol). The reaction was stirred at 80° C. for 3 hours in a sealed tube. After cooling down, water was added and the aqueous phase was extracted with DCM. The combined organic phases were dried over MgSO$_4$ and concentrated to an oil which was purified by reverse phase chromatography (SP4, 25 M, water/CH$_3$CN, 100:0 to 0:100, 20 column volumes) to yield 3-(4-(1,5-dimethyl-2,4-dioxa-3-borabicyclo[3.1.0]hexan-3-yl)phenyl)-1-((2-(trimethylsilyl)ethoxy)methyl)-1H-pyrazole (750 mg, 68.9% yield) as a clear oil.

Step 3: To (S)-3-(3-bromopyrazolo[1,5-a]pyrimidin-5-yl)-4-(4-fluorophenyl)oxazolidin-2-one (Preparation A; 100 mg, 0.265 mmol) were added 3-(4-(4,4,5,5-tetramethyl-1,3,2-dioxaborolan-2-yl)phenyl)-1-((2-(trimethylsilyl)ethoxy)methyl)-1H-pyrazole (143 mg, 0.358 mmol), (9,9-dimethyl-9H-xanthene-4,5-diyl) bis(diphenylphosphine) (15.3 mg, 0.0265 mmol), Pd$_2$ dba$_3$ (12.1 mg, 0.0133 mmol) and 2M Na$_2$CO$_3$ (0.2 mL). The reaction was stirred for 2 hours at 80° C. in a sealed tube. After cooling, EtOAc and water were added. The organic phase was washed with brine and dried over MgSO$_4$. The residue was purified by reverse phase chromatography (SP4, 12M, water/CH$_3$CN 90:10 to 0:100, 20 column volumes) to yield (S)-4-(2-chlorophenyl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (24 mg, 31% yield) as a pale yellow solid.

Step 4: To (S)-4-(4-fluorophenyl)-3-(3-(4-(1-((2-(trimethylsilyl)ethoxy)methyl)-1H-pyrazol-3-yl)phenyl)pyrazolo[1,5-a]pyrimidin-5-yl)oxazolidin-2-one (80 mg, 0.14 mmol) in DCM (4 mL) was added TFA (1 mL) and the reaction was stirred for 4 hours at ambient temperature. The reaction was concentrated to dryness, and 7N ammonia in methanol was added to the residue. After concentration to dryness, the residue was purified by reverse phase chromatography (SP4, 12M, water/CH$_3$CN 100:0 to 0:100, 20 column volumes) to yield (S)-3-(3-(4-(1H-pyrazol-3-yl)phenyl)pyrazolo[1,5-a]pyrimidin-5-yl)-4-(4-fluorophenyl)oxazolidin-2-one (35 mg, 57% yield) as a white solid. LCMS (APCI+) m/z 441.2 [M+H]$^+$.

Example 135

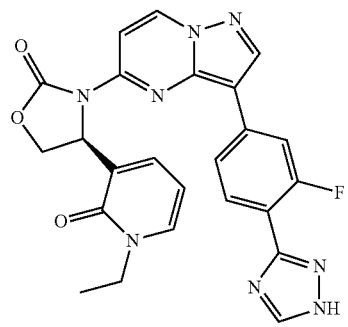 [SMILES: CCn1cccc([C@H]2COC(=O)N2c2ccn3ncc(-c4ccc(-c5nc[nH]n5)c(F)c4)c3n2)c1=O]

(S)-4-(1-ethyl-2-oxo-1,2-dihydropyridin-3-yl)-3-(3-(3-fluoro-4-(1H-1,2,4-triazol-3-yl)phenyl)pyrazolo[1,5-a]pyrimidin-5-yl)oxazolidin-2-one Step 1: A mixture of 3-bromopyridin-2-ol (1.0 g, 5.75 mmol) in DMF (6 mL) was treated with cesium carbonate (1.87 g, 5.75 mmol) and ethyl iodide (1.38 mL, 17.2 mmol). The mixture was heated at 80° C. for 4 hours. The solvent was concentrated and the residue taken in EtOAc, washed with brine, dried (phase separator silicone treated filter paper), concentrated and purified on silica gel (1:2 hexane/ether) to provide 3-bromo-1-ethylpyridin-2(1H)-one (0.905 g, 78% yield) as a yellow oil.

Step 2: (S)—N—((S)-2-(tert-butyldimethylsilyloxy)-1-(1-ethyl-2-oxo-1,2-dihydropyridin-3-yl)ethyl)-2-methylpropane-2-sulfinamide (0.534 g, 31% yield) was prepared by the procedure described in Example 84, Step 2, using 3-bromo-1-ethylpyridin-2(1H)-one.

Step 3: (S)-3-(1-amino-2-hydroxyethyl)-1-ethylpyridin-2(1H)-one (0.107 g, 62% yield) was prepared by the procedure described in Example 84, Step 3, using (S)—N—((S)-2-(tert-butyldimethylsilyloxy)-1-(1-ethyl-2-oxo-1,2-dihydropyridin-3-yl)ethyl)-2-methylpropane-2-sulfinamide.

Step 4: (S)-4-(1-ethyl-2-oxo-1,2-dihydropyridin-3-yl)oxazolidin-2-one (0.045 g, 37% yield) was prepared by the procedure described in Example 84, Step 4, using (S)-3-(1-amino-2-hydroxyethyl)-1-ethylpyridin-2(1H)-one.

Step 5: (S)-3-(3-bromopyrazolo[1,5-a]pyrimidin-5-yl)-4-(1-ethyl-2-oxo-1,2-dihydropyridin-3-yl)oxazolidin-2-one (0.076 g, 58% yield) was prepared by the procedure described in Example 84, Step 5, using (S)-4-(1-ethyl-2-oxo-1,2-dihydropyridin-3-yl)oxazolidin-2-one.

Step 6: (S)-4-(1-ethyl-2-oxo-1,2-dihydropyridin-3-yl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.028 g, 24% yield) was prepared by the procedure described in Example 84, Step 6, using (S)-3-(3-bromopyrazolo[1,5-a]pyrimidin-5-yl)-4-(1-ethyl-2-oxo-1,2-dihydropyridin-3-yl)oxazolidin-2-one.

Step 7: (S)-4-(1-ethyl-2-oxo-1,2-dihydropyridin-3-yl)-3-(3-(3-fluoro-4-(1H-1,2,4-triazol-3-yl)phenyl)pyrazolo[1,5-a]pyrimidin-5-yl)oxazolidin-2-one (0.015 g, 53% yield) was prepared by the procedure described in Example 75, Step 4, using (S)-4-(1-ethyl-2-oxo-1,2-dihydropyridin-3-yl)-3-(3-(3-fluoro-4-(1-((2-(trimethylsilyl)ethoxy)methyl)-1H-1,2,4-triazol-3-yl)phenyl)pyrazolo[1,5-a]pyrimidin-5-yl)oxazolidin-2-one (0.036 g, 0.058 mmol). LCMS (APCI+) m/z 487 [M+H]$^+$.

Example 136

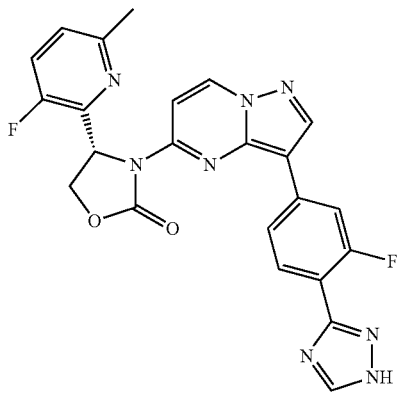 [SMILES: Cc1ccc(F)c([C@H]2COC(=O)N2c2ccn3ncc(-c4ccc(-c5nc[nH]n5)c(F)c4)c3n2)n1]

(S)-3-(3-(3-fluoro-4-(1H-1,2,4-triazol-3-yl)phenyl)pyrazolo[1,5-a]pyrimidin-5-yl)-4-(3-fluoro-6-methylpyridin-2-yl)oxazolidin-2-one Step 1: (S)—N—((S)-2-(tert-butyldimethylsilyloxy)-1-(3-fluoro-6-methylpyridin-2-yl)ethyl)-2-methylpropane-2-sulfinamide (1.93 g, 42% yield) was prepared by the procedure described in Example 84, Step 2, using 2-bromo-3-fluoro-6-methylpyridine.

Step 2: (S)-2-Amino-2-(3-fluoro-6-methylpyridin-2-yl)ethanol dihydrochloride (1.1 g, 93% yield) was prepared by the procedure described in Example 84, Step 3, using (S)—N—((S)-2-(tert-butyldimethylsilyloxy)-1-(3-fluoro-6-methylpyridin-2-yl)ethyl)-2-methylpropane-2-sulfinamide.

Step 3: (S)-4-(3-Fluoro-6-methylpyridin-2-yl)oxazolidin-2-one (0.720 g, 81% yield) was prepared by the procedure described in Example 84, Step 4, using (S)-2-amino-2-(3-fluoro-6-methylpyridin-2-yl)ethanol dihydrochloride.

Step 4: (S)-3-(3-Bromopyrazolo[1,5-a]pyrimidin-5-yl)-4-(3-fluoro-6-methyl-pyridin-2-yl)oxazolidin-2-one (0.107 g, 32% yield) was prepared by the procedure described in Example 84, Step 5, using (S)-4-(3-fluoro-6-methylpyridin-2-yl)oxazolidin-2-one.

Step 5: (S)-3-(3-(3-Fluoro-4-(1-((2-(trimethylsilyl)ethoxy)methyl)-1H-1,2,4-triazol-3-yl)phenyl)pyrazolo[1,5-a]pyrimidin-5-yl)-4-(3-fluoro-6-methylpyridin-2-yl)oxazolidin-2-one (0.014 g, 18% yield) was prepared by the procedure described in Example 84, Step 6, using (S)-3-(3-bromopyrazolo[1,5-a]pyrimidin-5-yl)-4-(3-fluoro-6-methylpyridin-2-yl)oxazolidin-2-one.

Step 6: (S)-3-(3-(3-Fluoro-4-(1H-1,2,4-triazol-3-yl)phenyl)pyrazolo[1,5-a]pyrimidin-5-yl)-4-(3-fluoro-6-methylpyridin-2-yl)oxazolidin-2-one (0.006 g, 54% yield) was prepared by the procedure described in Example 75, Step 4, using (S)-3-(3-(3-fluoro-4-(1-((2-(trimethylsilyl)methyl)-1H-1,2,4-triazol-3-yl)phenyl)pyrazolo[1,5-a]pyrimidin-5-yl)-4-(3-fluoro-6-methylpyridin-2-yl)oxazolidin-2-one (0.014 g, 0.023 mmol). LCMS (APCI+) m/z 475 [M+H]$^+$.

Example 137

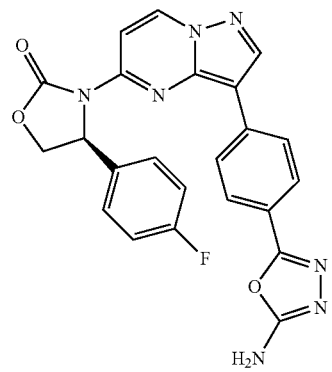 [SMILES: Nc1nnc(-c2ccc(-c3cnn4ccc(N5C(=O)OC[C@@H]5c5ccc(F)cc5)nc34)cc2)o1]

(S)-3-(3-(4-(5-amino-1,3,4-oxadiazol-2-yl)phenyl)pyrazolo[1,5-a]pyrimidin-5-yl)-4-(4-fluorophenyl)oxazolidin-2-one To a suspension of (S)-4-(5-(4-(4-fluorophenyl)-2-oxooxazolidin-3-yl)pyrazolo[1,5-a]pyrimidin-3-yl)benzohydrazide (0.040 g, 0.0925 mmol) in dioxane (4 mL) was added cyanic bromide (0.0216 g, 0.204 mmol) followed by a solution of NaHCO$_3$ (0.00933 g, 0.111 mmol) in water (0.9 mL). The resulting mixture was stirred at ambient temperature overnight, then diluted with EtOAc. The organic layer was washed with brine and water, dried (phase separator silicone treated filter paper) and concentrated. The crude material was purified on silica gel (2-5% MeOH in DCM) to provide (S)-3-(3-(4-(5-amino-1,3,4-oxadiazol-2-yl)phenyl)pyrazolo[1,5-a]pyrimidin-5-yl)-4-(4-fluorophenyl)oxazolidin-2-one (0.0066 g, 16% yield). LCMS (APCI+) m/z 458 [M+H]$^+$.

Example 138

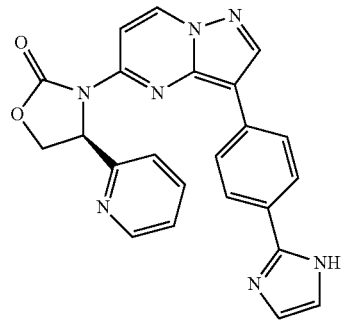 [SMILES: O=C1OC[C@H](c2ccccn2)N1c1ccn2ncc(-c3ccc(-c4ncc[nH]4)cc3)c2n1]

(S)-3-(3-(4-(1H-Imidazol-2-yl)phenyl)pyrazolo[1,5-a]pyrimidin-5-yl)-4-(pyridin-2-yl) oxazolidin-2-one Step 1: (S)-4-(Pyridin-2-yl)-3-(3-(4-(1-((2-(trimethylsilyl)ethoxy)methyl)-1H-imidazol-2-yl)phenyl)pyrazolo[1,5-a]pyrimidin-5-yl)oxazolidin-2-one (42 mg, 55%) was prepared by the procedure described in Example 1, Step 8, substituting (S)-3-(3-bromopyrazolo[1,5-a]pyrimidin-5-yl)-4-(pyridin-2-yl)oxazolidin-2-one for (S)-3-(3-bromopyrazolo[1,5-a]pyrimidin-5-yl)-4-isopropyloxazolidin-2-one.

Step 2: (S)-3-(3-(4-(1H-Imidazol-2-yl)phenyl)pyrazolo[1,5-a]pyrimidin-5-yl)-4-(pyridin-2-yl)oxazolidin-2-one (25 mg, 78%) was prepared by the procedure described in Example 1, Step 9, using (S)-4-(pyridin-2-yl)-3-(3-(4-(1-((2-(trimethylsilyl)ethoxy)methyl)-1H-imidazol-2-yl)phenyl)pyrazolo[1,5-a]pyrimidin-5-yl)oxazolidin-2-one. LCMS (APCI+) m/z 424.2 [M+H]+.

Example 139

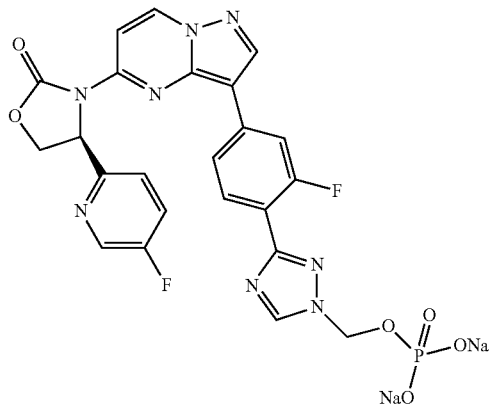

Bis-sodium (S)-(3-(2-fluoro-4-(5-(4-(5-fluoropyridin-2-yl)-2-oxooxazolidin-3-yl)pyrazolo[1,5-a]pyrimidin-3-yl)phenyl)-1H-1,2,4-triazol-1-yl)methyl phosphate Step 1: To a solution of (S)-3-(3-(3-fluoro-4-(1H-1,2,4-triazol-3-yl)phenyl)pyrazolo[1,5-a]pyrimidin-5-yl)-4-(5-fluoropyridin-2-yl)oxazolidin-2-one (0.66 g, 1.4 mmol) in DMF (10 mL) was added cesium carbonate (0.47 g, 1.4 mmol) followed by di-tert-butyl chloromethyl phosphate (1.1 g, 4.3 mmol) and the reaction mixture was stirred overnight at ambient temperature, then diluted with EtOAc (100 mL). The organic layer was washed with water and brine, dried over MgSO₄, filtered and concentrated in vacuo. The crude material was chromatographed twice on silica gel using EtOAc as eluent to yield (S)-di-tert-butyl (3-(2-fluoro-4-(5-(4-(5-fluoropyridin-2-yl)-2-oxooxazolidin-3-yl)pyrazolo[1,5-a]pyrimidin-3-yl)phenyl)-1H-1,2,4-triazol-1-yl)methyl phosphate (0.27 g, 0.40 mmol, 28% yield).

Step 2: To a solution of (S)-di-tert-butyl (3-(2-fluoro-4-(5-(4-(5-fluoropyridin-2-yl)-2-oxooxazolidin-3-yl)pyrazolo[1,5-a]pyrimidin-3-yl)phenyl)-1H-1,2,4-triazol-1-yl) methyl phosphate (0.32 g, 0.469 mmol) in DCM (10 mL) cooled to 0° C. was added TFA (2.5 mL) and the reaction stirred at 0° C. for 2 hours. The reaction was next concentrated in vacuo and azeotroped with DCM/Hexanes (2×50 mL). The material was taken up in water (20 mL). The aqueous layer was made basic (about pH 9) by the addition of saturated NaHCO₃. To this solution was added isopropanol (20 mL), at which point a solid slowly precipitated from the solution. The solid was filtered and dried in vacuo. The material was next taken up in water (10 mL) and isopropanol (8 mL) added slowly at which point a solid formed. The solid was isolated by filtration and dried in vacuo overnight to yield bis-sodium (S)-(3-(2-fluoro-4-(5-(4-(5-fluoropyridin-2-yl)-2-oxooxazolidin-3-yl)pyrazolo[1,5-a]pyrimidin-3-yl)phenyl)-1H-1,2,4-triazol-1-yl) methyl phosphate (0.140 g, 0.228 mmol, 48.6% yield). LCMS (APCI+) m/z 571 [M+H]+.

Example 140

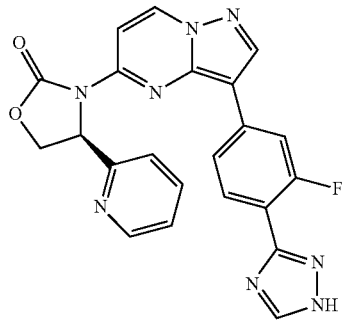 [SMILES: O=C1OC[C@H](c2ccccn2)N1c1ccn2ncc(-c3ccc(-c4nc[nH]n4)c(F)c3)c2n1]

(S)-3-(3-(3-fluoro-4-(1H-1,2,4-triazol-3-yl)phenyl)pyrazolo[1,5-a]pyrimidin-5-yl)-4-(pyridin-2-yl)oxazolidin-2-one Step 1: To a solution of toluene (40 mL) cooled to −78° C. was added butyl lithium (1.6 M in hexanes, 5.57 mL, 13.9 mmol) at a rate such that the internal temperature did not exceed −50° C., and the reaction stirred until the internal temperature returned to −78° C. 2-Bromopyridine (1.20 mL, 12.7 mmol) in toluene (4 mL) was added to the reaction mixture at a rate such that the temperature did not exceed −65° C. The reaction was stirred at −78° C. for 1 hour. To the reaction was added (S,E)-N-(2-(tert-butyldimethylsilyloxy)ethylidene)-2-methylpropane-2-sulfinamide (3.58 g, 13.9 mmol) in toluene (20 mL) at a rate such that the internal temperature did not exceed −60° C. The reaction was stirred at −78° C. for 2 hours. To the −78° C. solution was added brine (50 mL) and the mixture was partitioned between EtOAc/water (300 mL total). The organic layer was washed with brine (50 mL), dried over MgSO₄ and concentrated in vacuo. The crude material was chromatographed using 40% EtOAc/DCM as eluent to yield (S)—N—((S)-2-(tert-butyldimethylsilyloxy)-1-(pyridin-2-yl)ethyl)-2-methylpropane-2-sulfinamide (2.1 g, 46.7%).

Step 2: To a solution of (S)—N4S)-2-(tert-butyldimethylsilyloxy)-1-(pyridin-2-yl)ethyl)-2-methylpropane-2-sulfinamide (2.1 g, 5.9 mmol) in methanol was added hydrogen chloride (7.4 ml, 29 mmol) in dioxanes (4 M) and the reaction was stirred at ambient temperature for 3 hours. The reaction was then concentrated in vacuo and the crude material dried in vacuo to yield (S)-2-amino-2-(pyridin-2-yl)ethanol bis hydrochloride salt (1.23 g, 5.8 mmol) which was used directly in the next step.

Step 3: To a solution of (S)-2-amino-2-(pyridin-2-yl)ethanol bis hydrochloride (0.80 g, 5.8 mmol) in water (50 mL) cooled to 0° C. was added potassium hydroxide (2.6 g, 46 mmol) and the reaction stirred at 0° C. for 15 minutes, followed by the addition of THF (100 mL) and the reaction cooled to 0° C. To the reaction was next added bis(trichloromethyl) carbonate (1.7 g, 5.8 mmol) and the reaction stirred at 0° C. for 2 hours. The reaction was diluted with EtOAc (300 mL) and the layers were separated. The organic layer was washed with water (100 mL) and brine (100 mL), dried over MgSO$_4$ and concentrated in vacuo. The crude material was chromatographed using EtOAc as eluent to yield (S)-4-(pyridin-2-yl)oxazolidin-2-one (0.20 g, 21%).

Step 4: To a solution of (S)-4-(pyridin-2-yl)oxazolidin-2-one (0.20 g, 1.2 mmol) in DMF (20 mL) was added sodium hydride (0.049 g, 1.2 mmol) and the reaction was stirred at ambient temperature for 1 hour. 3-Bromo-5-chloropyrazolo[1,5-a]pyrimidine (0.28 g, 1.2 mmol) was added and the reaction stirred for an additional 1 hour. The reaction was then poured into water (100 mL) and extracted into ether (200 mL). The organic layer was washed with water (100 mL), dried over MgSO$_4$ and concentrated in vacuo. The crude material was chromatographed using 100% DCM to 15% EtOAc/DCM as eluent to yield (S)-3-(3-bromopyrazolo[1,5-a]pyrimidin-5-yl)-4-(pyridin-2-yl)oxazolidin-2-one (0.25 g, 56.8%).

Step 5: To a solution of (S)-3-(3-bromopyrazolo[1,5-a]pyrimidin-5-yl)-4-(pyridin-2-yl)oxazolidin-2-one (0.25 g, 0.69 mmol) in dioxanes (70 mL) purged continuously with nitrogen gas was added 3-(2-fluoro-4-(4,4,5,5-tetramethyl-1,3,2-dioxaborolan-2-yl)phenyl)-1-((2-(trimethylsilyl)ethoxy)methyl)-1H-1,2,4-triazole (0.44 g, 1.0 mmol) and sodium carbonate (1.7 mL, 3.5 mmol) (2M in water). Pd$_2$ dba$_3$ (70 mg) and X-Phos (70 mg) were added, and the reaction mixture was stirred at 80° C. for 3 hours, then diluted with EtOAc (200 mL). The organic layer was washed with water and brine, dried over MgSO$_4$, filtered concentrated in vacuo. The crude material was chromatographed using 50% EtOAc/hexane as eluent to yield (S)-3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(pyridin-2-yl)oxazolidin-2-one (0.090 g, 22.5%).

Step 6: To (S)-3-(3-fluoro-4-(1-((2-(trimethylsilyl)ethoxy)methyl)-1H-1,2,4-triazol-3-yl)phenyl)pyrazolo[1,5-a]pyrimidin-5-yl)-4-(pyridin-2-yl)oxazolidin-2-one (0.090 g, 0.16 mmol) was added TFA (10 mL) and the reaction was stirred at ambient temperature for 2 hours. The reaction was concentrated in vacuo and the resulting material dissolved in MeOH/CH$_3$CN/water (1:1:1, 30 mL total) and stirred for 20 minutes at ambient temperature. The mixture was basified by adding NaHCO$_3$ (saturated aqueous solution) and the solid that formed was isolated by filtration. The solids were slurried in CH$_3$CN/MeOH/water (1:1:5, 40 mL total) and the material filtered and dried in vacuo to yield (S)-3-(3-(3-fluoro-4-(1H-1,2,4-triazol-3-yl)phenyl)pyrazolo[1,5-a]pyrimidin-5-yl)-4-(pyridin-2-yl)oxazolidin-2-one (0.054 g, 77.1%). LCMS (APCI+) m/z 443 [M+H]$^+$.

Example 141

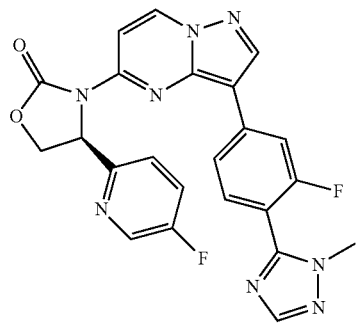 [SMILES: Cn1ncnc1-c1ccc(-c2cnn3ccc(N4C(=O)OC[C@@H]4c4ccc(F)cn4)nc23)cc1F]

S)-3-(3-(3-fluoro-4-(1-methyl-1H-1,2,4-triazol-3-yl)phenyl)pyrazolo[1,5-a]pyrimidin-5-yl)-4-(5-fluoropyridin-2-yl)oxazolidin-2-one (S)-3-(3-(3-fluoro-4-(1-methyl-1H-1,2,4-triazol-5-yl)phenyl)pyrazolo[1,5-a]pyrimidin-5-yl)-4-(5-fluoropyridin-2-yl)oxazolidin-2-one To a stirred solution of (S)-3-(3-(3-fluoro-4-(1H-1,2,4-triazol-3-yl)phenyl)pyrazolo[1,5-a]pyrimidin-5-yl)-4-(5-fluoropyridin-2-yl)oxazolidin-2-one (Example 105, 85 mg, 0.18 mmol) in DMF (2 mL) was added Cs$_2$CO$_3$ (66 mg, 0.20 mmol) and MeI (39 mg, 0.28 mmol) at ambient temperature. The reaction mixture was stirred at ambient temperature for 2 hours, and then partitioned between EtOAc and water. The aqueous layer was extracted with EtOAc. The combined organic layers were washed with brine, dried and concentrated to give a crude mixture of (S)-3-(3-(3-fluoro-4-(1-methyl-1H-1,2,4-triazol-5-yl)phenyl)pyrazolo[1,5-a]pyrimidin-5-yl)-4-(5-fluoropyridin-2-yl)oxazolidin-2-one and (S)-3-(3-(3-fluoro-4-(1-methyl-1H-1,2,4-triazol-3-yl)phenyl)pyrazolo[1,5-a]pyrimidin-5-yl)-4-(5-fluoropyridin-2-yl)oxazolidin-2-one. The residue was purified by silica gel column chromatography (EtOAc) to give (S)-3-(3-(3-fluoro-4-(1-methyl-1H-1,2,4-triazol-5-yl)phenyl)pyrazolo[1,5-a]pyrimidin-5-yl)-4-(5-fluoropyridin-2-yl)oxazolidin-2-one (26 mg, 30% yield) as the less polar product. MS (APCI+) m/z 475 [M+H]$^+$.

Example 1-((2

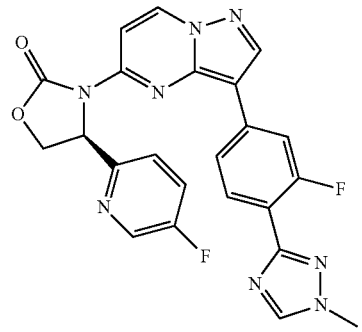 [SMILES: Cn1cnc(-c2ccc(-c3cnn4ccc(N5C(=O)OC[C@@H]5c5ccc(F)cn5)nc34)cc2F)n1]

S)-3-(3-(3-fluoro-4-(1-methyl-1H-1,2,4-triazol-3-yl)phenyl)pyrazolo[1,5-a]pyrimidin-5-yl)-4-(5-fluoropyridin-2-yl)oxazolidin-2-one A crude mixture of (S)-3-(3-(3-fluoro-4-(1-methyl-1H-1,2,4-triazol-5-yl)phenyl)pyrazolo[1,5-a]pyrimidin-5-yl)-4-(5-fluoropyridin-2-yl)oxazolidin-2-one and (S)-3-(3-(3-fluoro-4-(1-methyl-1H-1,2,4-triazol-3-yl)phenyl)pyrazolo[1,5-a]pyrimidin-5-yl)-4-(5-fluoropyridin-2-yl)oxazolidin-2-one was prepared as described in Example 140. The residue was purified by silica gel column chromatography (EtOAc) to give the less polar product (S)-3-(3-(3-fluoro-4-(1-methyl-1H-1,2,4-triazol-5-yl)phenyl)pyrazolo[1,5-a]pyrimidin-5-yl)-4-(5-fluoropyridin-2-yl)oxazolidin-2-one (26 mg, 30% yield). Further elution with 5% MeOH in EtOAc afforded the more polar product (S)-3-(3-(3-fluoro-4-(1-methyl-1H-1,2,4-triazol-3-yl)phenyl)pyrazolo[1,5-a]pyrimidin-5-yl)-4-(5-fluoropyridin-2-yl)oxazolidin-2-one (36 mg, 41% yield). MS (APCI+) m/z 475 [M+H]$^+$.

Example 143

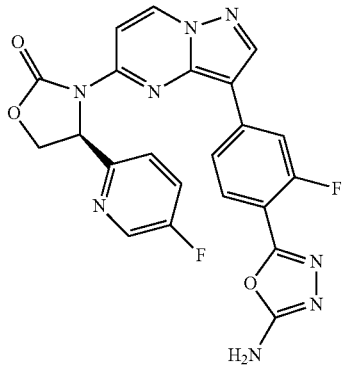 [SMILES: Nc1nnc(-c2ccc(-c3cnn4ccc(N5C(=O)OC[C@@H]5c5ccc(F)cn5)nc34)cc2F)o1]

(S)-3-(3-(4-(5-amino-1,3,4-oxadiazol-2-yl)-3-fluorophenyl)pyrazolo[1,5-a]pyrimidin-5-yl)-4-(5-fluoropyridin-2-yl)oxazolidin-2-one Step 1: To a solution of (S)-3-(3-bromopyrazolo[1,5-a]pyrimidin-5-yl)-4-(5-fluoropyridin-2-yl)oxazolidin-2-one (0.500 g, 1.32 mmol) in dioxane (8 mL) purged continuously with nitrogen gas was added 3-fluoro-4-formylphenylboronic acid (0.333 g, 1.98 mmol) and 2.0 M sodium carbonate aqueous solution (1.98 mL, 3.97 mmol). To the reaction was added Pd$_2$dba$_3$ (0.242 g, 0.264 mmol) and X-Phos (0.126 g, 0.264 mmol) and the reaction stirred at 80° C. for 1 hour. After cooling, the reaction was partitioned between EtOAc and water. The aqueous layer was extracted with EtOAc. The combined organic layers were washed with water and brine, dried, and concentrated under vacuum. The residue was purified by preparative TLC (50% EtOAc/hexane) to give (S)-2-fluoro-4-(5-(4-(5-fluoropyridin-2-yl)-2-oxooxazolidin-3-yl)pyrazolo[1,5-a]pyrimidin-3-yl)benzaldehyde (0.47 g, 84% yield) as a yellow solid.

Step 2: A solution of (S)-2-fluoro-4-(5-(4-(5-fluoropyridin-2-yl)-2-oxooxazolidin-3-yl)pyrazolo[1,5-a]pyrimidin-3-yl)$_b$ enzaldehyde (0.370 g, 0.878 mmol), potassium acetate (0.0948 g, 0.966 mmol) and hydrazinecarboxamide hydrochloride (0.108 g, 0.966 mmol) in 3:1 EtOH/MeOH (6 mL) was stirred at ambient temperature overnight. The solvents were evaporated under vacuum. The residue was purified by preparative TLC (10% MeOH in DCM) to give (S,E)-2-(2-fluoro-4-(5-(4-(5-fluoropyridin-2-yl)-2-oxooxazolidin-3-yl)pyrazolo[1,5-a]pyrimidin-3-yl)benzylidene)hydrazinecarboxamide (0.164 g, 39% yield) as a yellow powder.

Step 3: To a solution of (S,E)-2-(2-fluoro-4-(5-(4-(5-fluoropyridin-2-yl)-2-oxooxazolidin-3-yl)pyrazolo[1,5-a]pyrimidin-3-yl)benzylidene)hydrazinecarboxamide (26 mg, 0.054 mmol) in acetic acid (0.6 mL) was added sodium acetate (44 mg, 0.54 mmol). After complete dissolution of the salt, a dilute solution of Br$_2$ (2.7 μL, 0.054 mmol) in acetic acid was slowly added dropwise in portions. The reaction mixture was stirred at ambient temperature for 1 hour. The reaction mixture was applied directly on a preparative TLC plate. Acetic acid was removed under a stream of air, and the preparative TLC plate was developed with 10% MeOH in DCM to afford (S)-3-(3-(4-(5-amino-1,3,4-oxadiazol-2-yl)-3-fluorophenyl)pyrazolo[1,5-a]pyrimidin-5-yl)-4-(5-fluoropyridin-2-yl)oxazolidin-2-one (7.9 mg, 31% yield) as a yellow solid. MS (APCI+) m/z 477 [M+H]$^+$.

Example 144

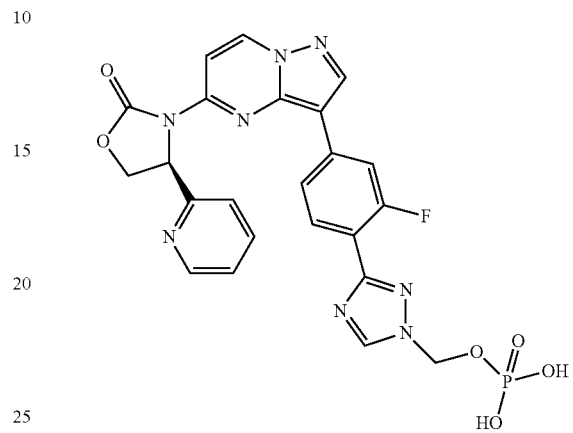

(S)-(3-(2-fluoro-4-(5-(2-oxo-4-(pyridin-2-yl)oxazolidin-3-yl)pyrazolo[1,5-a]pyrimidin-3-yl)phenyl)-1H-1,2,4-triazol-1-yl)methyl dihydrogen phosphate Step 1: (S)-di-tert-butyl (3-(2-fluoro-4-(5-(2-oxo-4-(pyridin-2-yl)oxazolidin-3-yl)pyrazolo[1,5-a]pyrimidin-3-yl)phenyl)-1H-1,2,4-triazol-1-yl)methyl phosphate (50 mg, 2%) was prepared by the procedure described in Example 8, Step 1, substituting (S)-3-(3-(4-(1H-1,2,4-triazol-3-yl)phenyl)pyrazolo[1,5-a]pyrimidin-5-yl)-4-isopropyloxazolidin-2-one with (S)-3-(3-(3-fluoro-4-(1H-1,2,4-triazol-3-yl)phenyl)pyrazolo[1,5-a]pyrimidin-5-yl)-4-(pyridin-2-yl)oxazolidin-2-one.

Step 2: To a stirred solution of (S)-di-tert-butyl (3-(2-fluoro-4-(5-(2-oxo-4-(pyridin-2-yl)oxazolidin-3-yl)pyrazolo[1,5-a]pyrimidin-3-yl)phenyl)-1H-1,2,4-triazol-1-yl)methyl phosphate (50 mg, 0.075 mmol) in DCM (0.5 mL) cooled to 0° C. was added TFA (0.1 mL) and the reaction stirred at 0° C. for 1 hour. The reaction was concentrated under vacuum and azeotroped with DCM/Hexanes. The remaining material was taken up in water. The aqueous layer was made basic (pH 9) by the addition of saturated NaHCO$_3$. HCl (0.1 N) was then slowly added to the solution to adjust the pH to 2. The precipitated solid was collected by filtration, washed with acetone and diethyl ether, and dried under vacuum to give (S)-(3-(2-fluoro-4-(5-(2-oxo-4-(pyridin-2-yl)oxazolidin-3-yl)pyrazolo[1,5-a]pyrimidin-3-yl)phenyl)-1H-1,2,4-triazol-1-yl)methyl dihydrogen phosphate (22 mg, 53% yield) as a yellow solid. $^1$H-NMR (400 MHz, DMSO-d6) δ 9.11 (d, J=7.6 Hz, 1H), 8.79 (s, 1H), 8.73 (s, 1H), 8.52 (d, J=4.0 Hz, 1H), 7.99 (m, 2H), 7.84 (t, J=7.6 Hz, 1H), 7.72 (m, 3H), 7.31 (t, J=6.4 Hz, 1H), 6.06 (d, J=6.0 Hz, 1H), 5.95 (d, J=10.8 Hz, 2H), 4.91 (t, J=8.4 Hz, 1H), 4.32 (dd, J=8.4 Hz, 2.8 Hz, 1H).

What is claimed is:

1. A compound having the general formula I

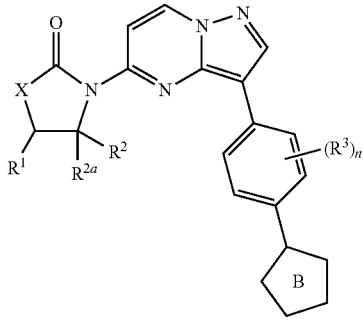

or a salt thereof, wherein:
R¹ is H, (1-6C)alkyl or trifluoromethyl;
R²ᵃ is hydrogen or methyl;
R² is H, (1-6C)alkyl, a 3-6 membered cycloalkyl ring, hetCyc⁴, Ar²CH₂—, (3-6C cycloalkyl)CH₂—, Ar³, hetAr¹, hetAr², (1-3C alkoxy)(1-3C)alkyl, or a 2-oxo-1,2-dihydropyridinyl ring optionally substituted with (1-6C)alkyl;
or R¹ and R² together with the atoms to which they are attached form a 5-6 membered carbocyclic ring optionally fused to a benzo ring;
each R³ is independently selected from halogen and (1-6C)alkyl;
n is 0, 1 or 2;
ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, NH₂, (1-6C hydroxyalkyl)NH—, (HO)₂P(=O)OCH₂—, (1-6C)hydroxyalkyl, and (1-6C alkyl)COOH;
X is O or NR⁴;
R⁴ is H, (1-6C)alkyl, (1-6C)hydroxyalkyl, (1-6C)dihydroxyalkyl, [(1-6C)alkoxy](1-6C)alkyl-, [(1-6C)alkoxy]-[(1-6C)alkoxy]-(1-6C)alkyl-, Ar¹CH₂—, hetCyc¹, hetCyc²(1-2C)alkyl-or hetCyc³(1-2C)alkyl-;
Ar¹ is phenyl optionally substituted with one or more substituents independently selected from (1-6C)alkoxy, halogen, (1-6C)alkyl and CF₃;
hetCyc¹ is a carbon-linked 4-6 membered azacyclic ring optionally substituted with a substituent selected from (1-6C)alkyl;
hetCyc² is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo;
hetCyc³ is a bridged 8-membered heterocyclic ring having a ring nitrogen atom and optionally having a ring oxygen atom;
hetCyc⁴ is a 5-6 membered heterocyclic ring having a ring heteroatom selected from N and O;
Ar² is phenyl optionally substituted with one or more halogen atoms;
Ar³ is phenyl optionally substituted with one or more substituents independently selected from halogen, (1-6C) alkoxy, hetCyc⁵, (1-6C)alkyl and CF₃;
hetCyc⁵ is a 6 membered heterocyclic ring having 1-2 ring nitrogen atoms;
hetAr¹ is pyridyl optionally substituted with one or more substituents independently selected from halogen, CF₃, (1-6C)alkyl and (1-6C)alkoxy; and
hetAr² is a 5-membered heteroaryl having 1-2 ring heteroatoms independently selected from N and S and optionally substituted with (1-6C)alkyl.

2. A compound according to claim 1, wherein:
R¹ is H, (1-6C)alkyl or trifluoromethyl;
R² is H, (1-6C)alkyl, phenyl, pyridyl, or a 5-6 membered cycloalkyl ring;
or R¹ and R² together with the atoms to which they are attached form a 5-6 membered carbocyclic ring;
R²ᵃ is hydrogen;
R³ is halogen or (1-6C)alkyl;
n is 0 or 1;
ring B is a 5-membered heteroaryl ring having 2-3 ring heteroatoms, wherein 2 of said ring heteroatoms are N and the third ring heteroatom when present is selected from N, O and S, wherein ring B is optionally substituted with a substituent selected from (1-6C)alkyl, NH₂, (1-6C hydroxyalkyl)NH—, (HO)₂P(=O)OCH₂—, (1-6C)hydroxyalkyl, and (1-6C alkyl)COOH;
X is O or NR⁴;
R⁴ is H, (1-6C)alkyl, (1-6C)hydroxyalkyl, (1-6C)dihydroxyalkyl, [(1-6C)alkoxy](1 6C)alkyl, [(1-6C) alkoxy]-[(1-6C)alkoxy]-(1-6C)alkyl, Ar¹CH₂—, hetCyc¹, hetCyc²(1-2C)alkyl or hetCyc³(1-2C)alkyl;
Ar¹ is phenyl optionally substituted with (1-6C)alkoxy;
hetCyc¹ is a carbon-linked 4-6 membered azacyclic ring having optionally substituted with a substituent selected from (1-6C)alkyl;
hetCyc² is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo; and
hetCyc³ is a bridged heterocyclic ring having a ring nitrogen atom and optionally having a ring oxygen atom.

3. A compound according to claim 1, wherein X is O.
4. A compound according to claim 1, wherein X is NR⁴.
5. A compound according to claim 4, wherein R⁴ is H.
6. A compound according to claim 4, wherein R⁴ is (1-6C) alkyl.
7. A compound according to claim 4, wherein R⁴ is (2-6C) hydroxyalkyl, (1-6C)dihydroxyalkyl, [(1-6C)alkoxy](1-6C) alkyl, or [(1-6C)alkoxy]-[(1-6C)alkoxy]-(1 -6C)alkyl.
8. A compound according to claim 4, wherein R⁴ is Ar'CH₂—.
9. A compound according to claim 4, wherein R⁴ is hetCyc³ or hetCyc²(1-2C)alkyl-.
10. A compound according to claim 4, wherein R⁴ is hetCyc³(1-2C)alkyl-.
11. A compound according to claim 1, wherein R¹ is hydrogen.
12. A compound according to claim 1, wherein R¹ is (1-6C) alkyl.
13. A compound according to claim 1, wherein R¹ is CF₃.
14. A compound according to claim 1, wherein R² is hydrogen.
15. A compound according to claim 1, wherein R² is (1-6C) alkyl.
16. A compound according to claim 15, wherein R² is methyl, ethyl, isopropyl or isobutyl.
17. A compound according to claim 1, wherein R² is Ar³.

18. A compound according to claim 2, wherein $R^2$ is phenyl.

19. A compound according to claim 1, wherein $R^2$ is a 3-6 membered cycloalkyl ring.

20. A compound according to claim 2, wherein $R^2$ is a 5-6 membered cycloalkyl ring.

21. A compound according to claim 1, wherein $R^2$ is hetAr$^1$.

22. A compound according to claim 2, wherein $R^2$ is pyridyl.

23. A compound according to claim 1, wherein $R^2$ is hetCyc$^4$.

24. A compound according to claim 1, wherein $R^2$ is Ar$^2$CH$_2$—.

25. A compound according to claim 1, wherein $R^2$ is (3-6C cycloalkyl)CH$_2$—.

26. A compound according to claim 1, wherein $R^2$ is (1-3C alkoxy)(1-3C)alkyl.

27. A compound according to claim 1, wherein $R^1$ and $R^2$ together with the atoms to which they are attached form a 5-6-membered carbocyclic ring.

28. A compound according to claim 1, wherein ring B is an imidazolyl, triazolyl, oxadiazolyl, thiadiazolyl or pyrazolyl ring, each of which is optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH.

29. A compound according to claim 1, wherein ring B is an imidazolyl, triazolyl, oxadiazolyl or thiadiazolyl ring, each of which is optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH.

30. A compound according to claim 29, wherein ring B is an imidazoyl ring optionally substituted with a substituent selected from (1-6C)alkyl, NH$_2$, (1-6C hydroxyalkyl)NH—, (HO)$_2$P(=O)OCH$_2$—, (1-6C)hydroxyalkyl, and (1-6C alkyl)COOH.

31. A compound according to claim 29, wherein ring B is triazolyl optionally substituted with a substituent selected from Me, HOCH$_2$CH$_2$—, (HO)$_2$P(=O)OCH$_2$—, and CH$_2$C(=O)H.

32. A compound according to claim 29, wherein ring B is oxadiazolyl optionally substituted with —NHCH$_2$CH$_2$OH or NH$_2$.

33. A compound according to claim 29, wherein ring B is thiadiazolyl optionally substituted with NH$_2$.

34. A compound according to claim 28, wherein ring B is pyrazolyl.

35. A compound according to claim 1, wherein n is 0.

36. A compound according to claim 1, wherein n is 1.

37. A compound according to claim 1, wherein n is 2.

38. A compound according to claim 36, wherein $R^3$ is halogen.

39. A compound according to claim 36, wherein $R^3$ is (1-6C)alkyl.

40. A compound according to claim 1, wherein $R^{2a}$ is hydrogen.

41. A compound according to any claim 1, wherein the $R^2$ group of a compound of Formula I has the absolute configuration shown in Formula Ia:

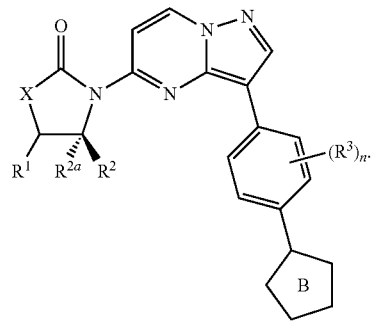

42. A pharmaceutical composition, which comprises a compound of Formula I as defined in claim 1, or a pharmaceutically acceptable salt thereof, and a pharmaceutically acceptable diluent or carrier.

43. A method for inhibiting mTor in a mammal, in need thereof, which comprises administering to said mammal a therapeutically effective amount of a compound of Formula I as defined in claim 1, or a pharmaceutically acceptable salt thereof.

44. A process for the preparation of a compound of claim 1, which comprises:
  (a) coupling a corresponding compound having the formula II

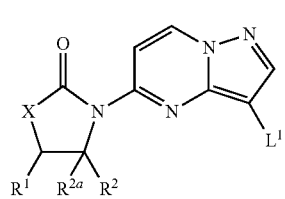

where X, $R^1$, $R^2$ and $R^{2a}$ are as defined for Formula I and $L^1$ is a leaving atom, with a corresponding compound having the formula III

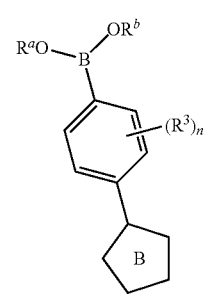

where $R^3$, n and ring B are as defined for Formula I or ring B is an optionally protected derivative thereof, $R^a$ and $R^b$ are H or (1-6C)alkyl, or $R^a$ and $R^b$ together with the atoms to which they are connected form a 5-6 membered ring optionally substituted with 1-4 substituents selected from (1-3C alkyl), wherein said coupling takes place in the presence of a palladium catalyst and base and optionally in the presence of a ligand for the palladium catalyst; or
  (b) for a compound of Formula I where X is O, coupling a corresponding compound having the formula IV

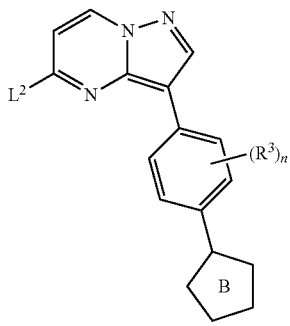

IV where R³, n and ring B are as defined for Formula I, or ring B is a protected derivative thereof, and L² is a leaving group or atom, with a corresponding compound having the formula V

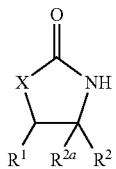

V where X is O and R¹, R² and R²ᵃ are as defined for Formula I, in the presence of a base; or (c) for a compound of Formula I where ring B is a thiadiazolyl ring substituted with NH₂, cyclizing a corresponding compound having the formula VI

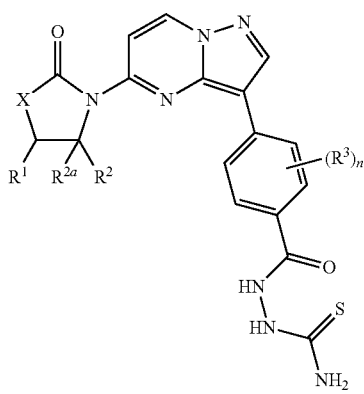

VI where X, R¹, R², R²ᵃ R³ and n are as defined for Formula I and when X is NR⁴ then R⁴ is optionally an amine-protected derivative thereof, in the presence of triphenylphosphine and a base; or (d) for a compound of Formula I where ring B is a triazolyl ring optionally substituted with (1-6C)alkyl, cyclizing a corresponding compound having the formula VII

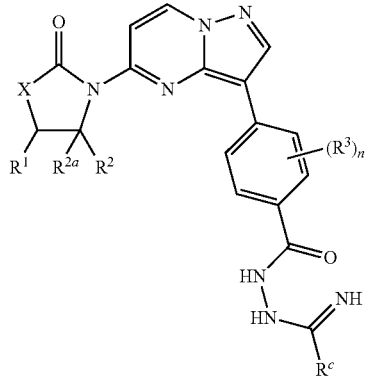

VII where R¹, R^{R2}, R²ᵃ, R³, n, and X are as defined for Formula I and Rᶜ is (1-6C alkyl), and when X is NR⁴ then R⁴ is optionally an amine-protected derivative thereof, in the presence of triphenylphosphine and a base; or (e) for a compound of Formula I where ring B is an oxadiazolyl ring optionally substituted with (1-6C hydroxyalkyl)NH—, cyclizing a corresponding compound having the formula VIII

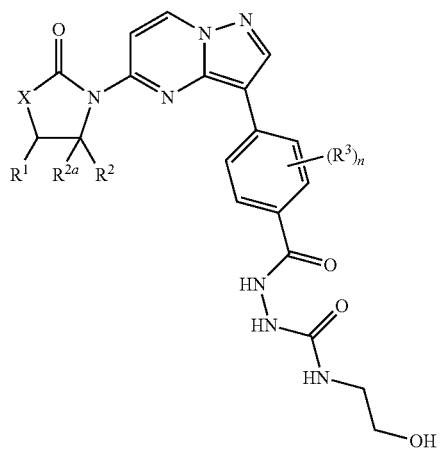

VIII where X, R¹, R²R²ᵃ, R³ and n are as defined for Formula I, and when X is NR⁴ then R⁴ is optionally an amine-protected derivative thereof, in the presence of triphenylphosphine and a base; or (f) for a compound of Formula I where X is NR⁴ and R²ᵃ is hydrogen, cyclizing a corresponding compound of formula IX

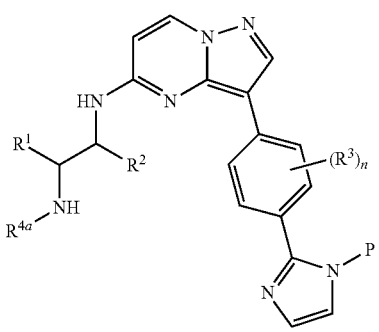

IX where $R^1$, $R^2$, $R^3$ and n are as defined for Formula I and $R^{4a}$ is as defined for $R^4$ or nitrogen-protected derivative thereof, in the presence of a carbonylating reagent, and a base; or (g) for a compound of Formula I where X is $NR^4$ and $R^4$ is hetCyc$^1$, hetCyc$^2$(1-2C)alkyl or hetCyc$^3$(1-2C)alkyl wherein each of hetCyc$^1$, hetCyc$^2$ and hetCyc$^3$ contains a ring nitrogen atom substituted with (1-6C)alkyl, reacting a corresponding compound having the formula X

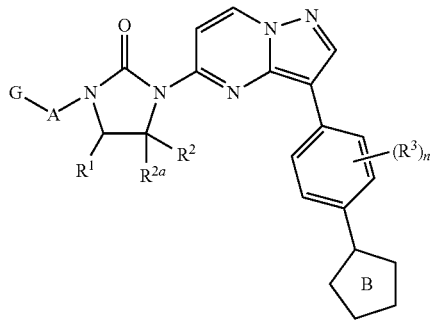

where $R^1$, $R^2$, $R^{2a}$, $R^3$, n and Ring B are as defined for Formula I, A is a bond or (1-2C)alkyl and G is hetCyc$^1$, hetCyc$^2$ or hetCyc$^3$ each of which contains an unsubstituted ring nitrogen atom, with a corresponding compound having the formula (1-5C alkyl)C(=O)H in the presence of a reducing agent; or (h) for a compound of Formula I where X is $NR^4$, coupling a corresponding compound having the formula XI

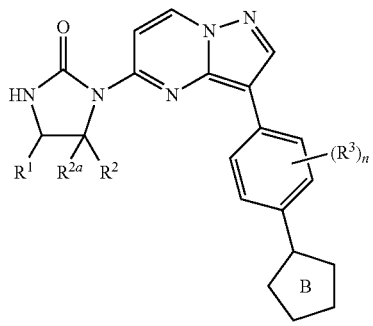

where $R^1$, $R^2$, $R^{2a}$, $R^3$, n and Ring B are as defined for Formula I, with a corresponding compound having the formula $R^4$-$L^3$, where $L^3$ is a leaving group or atom, in the presence of a base;

(i) for a compound of Formula I where X is $NR^4$, and $R^4$ has the formula

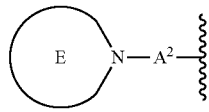

where ring E is a 5-6 membered heterocyclic ring having a ring nitrogen atom and optionally having a second ring heteroatom selected from N and O, wherein said ring is optionally substituted with a substituent selected from (1-6C)alkyl, OH, (1-6C)alkoxy, halogen and oxo, or ring E is a bridged 8-membered heterocyclic ring having a ring nitrogen atom and optionally having a ring oxygen atom, and $A^2$ is (2-3C alkyl), reacting a corresponding compound having the formula XII

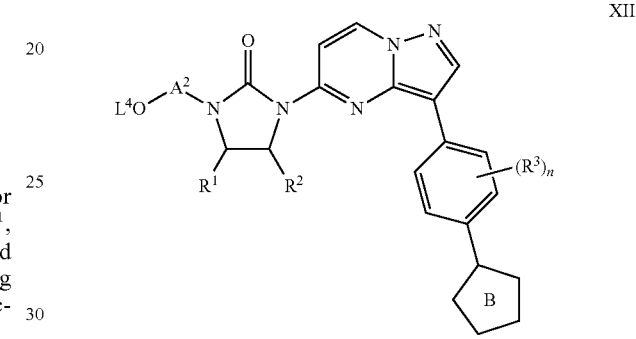

where $R^1$, $R^2$, $R^3$, $A^2$, n and ring B are as defined for Formula I and $L^4$ is a leaving group, with a compound having the formula

where ring $E^2$ is as defined for ring E; or (j) for a compound of Formula I where ring B is an imidazolyl or triazolyl ring substituted with (HO)$_2$P(=O)OCH$_2$—, reacting a corresponding compound where ring B is an unsubstituted imidazolyl or triazolyl ring with di(1-4C alkyl)-chloromethylphosphate in the presence of a base; and optionally removing any protecting groups and forming a salt if desired.

45. The method of claim 43, wherein the mammal is suffering from cancer.

* * * * *